(12) United States Patent
Lee et al.

(10) Patent No.: US 11,641,778 B2
(45) Date of Patent: May 2, 2023

(54) COMPOUND AND ORGANIC LIGHT EMITTING DEVICE COMPRISING SAME

(71) Applicant: LG CHEM, LTD., Seoul (KR)

(72) Inventors: Jungha Lee, Daejeon (KR); Dong Hoon Lee, Daejeon (KR); Jungoh Huh, Daejeon (KR); Seongmi Cho, Daejeon (KR); Dong Uk Heo, Daejeon (KR); Min Woo Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 490 days.

(21) Appl. No.: 16/486,773

(22) PCT Filed: Jul. 10, 2018

(86) PCT No.: PCT/KR2018/007810
§ 371 (c)(1),
(2) Date: Aug. 16, 2019

(87) PCT Pub. No.: WO2019/013526
PCT Pub. Date: Jan. 17, 2019

(65) Prior Publication Data
US 2019/0386227 A1    Dec. 19, 2019

(30) Foreign Application Priority Data
Jul. 10, 2017 (KR) .......................... 10-2017-0087149

(51) Int. Cl.
*C07D 405/14* (2006.01)
*C07D 413/14* (2006.01)
(Continued)

(52) U.S. Cl.
CPC ........ *H01L 51/0073* (2013.01); *C07D 405/14* (2013.01); *C07D 413/14* (2013.01);
(Continued)

(58) Field of Classification Search
CPC ............. H01L 51/0073; H01L 51/0067; H01L 51/0071; H01L 51/5012; H01L 51/5016;
(Continued)

(56) References Cited

U.S. PATENT DOCUMENTS

| | | | |
|---|---|---|---|
| 7,318,966 B2 | 1/2008 | Tominaga et al. | |
| 2008/0265746 A1* | 10/2008 | Yen ..................... | H01L 51/0072 546/88 |

(Continued)

FOREIGN PATENT DOCUMENTS

| | | |
|---|---|---|
| CN | 101440082 | 5/2009 |
| JP | 2009-191232 | 8/2009 |

(Continued)

*Primary Examiner* — Michael Y Sun
(74) *Attorney, Agent, or Firm* — Dentons US LLP

(57) ABSTRACT

Provided are a compound of Chemical Formula 1:

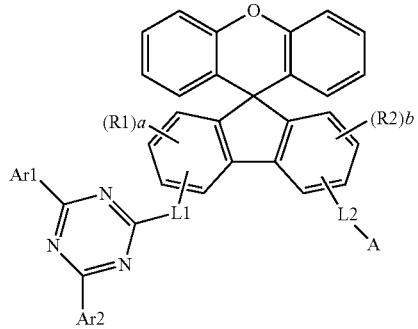

and an organic light emitting device including the same.

12 Claims, 1 Drawing Sheet

(51) Int. Cl.
  *C07D 417/14* (2006.01)
  *C07D 495/04* (2006.01)
  *H01L 51/00* (2006.01)
  *C09K 11/06* (2006.01)
  *H01L 51/50* (2006.01)

(52) U.S. Cl.
  CPC ......... *C07D 417/14* (2013.01); *C07D 495/04* (2013.01); *C09K 11/06* (2013.01); *H01L 51/0067* (2013.01); *H01L 51/0071* (2013.01); C09K 2211/1018 (2013.01); H01L 51/5012 (2013.01); H01L 51/5016 (2013.01); H01L 51/5056 (2013.01); H01L 51/5088 (2013.01); H01L 51/5096 (2013.01)

(58) Field of Classification Search
  CPC ............. H01L 51/5056; H01L 51/5088; H01L 51/5096; H01L 51/0072; H01L 51/0085; H01L 2251/5384; H01L 51/5024; C07D 405/14; C07D 413/14; C07D 417/14; C07D 495/04; C07D 311/96; C09K 11/06; C09K 2211/1018
  See application file for complete search history.

(56) References Cited

U.S. PATENT DOCUMENTS

| | | | |
|---|---|---|---|
| 2015/0115241 A1 | 4/2015 | Zoellner et al. | |
| 2015/0162543 A1* | 6/2015 | Lee | H01L 51/0074 136/263 |
| 2017/0222157 A1* | 8/2017 | Jatsch | H01L 51/0073 |

FOREIGN PATENT DOCUMENTS

| | | | |
|---|---|---|---|
| KR | 10-2015-0002740 | | 1/2015 |
| KR | 1020160049083 | * | 5/2016 |
| KR | 10-2017-0032414 | | 3/2017 |
| KR | 10-2017-0071399 | | 6/2017 |

* cited by examiner

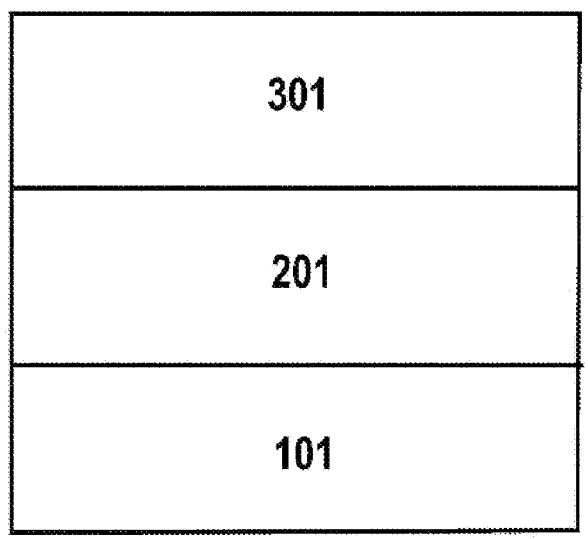

COMPOUND AND ORGANIC LIGHT EMITTING DEVICE COMPRISING SAME

RELATED APPLICATION

This application is a National Stage Application of International Application No. PCT/KR2018/007810 filed on Jul. 10, 2018, which claims priority to and the benefits of Korean Patent Application No. 10-2017-0087149, filed with the Korean Intellectual Property Office on Jul. 10, 2017, the entire contents of which are incorporated herein by reference.

TECHNICAL FIELD

The present specification relates to a compound of Chemical Formula 1 and an organic light emitting device including the same.

BACKGROUND ART

In general, organic light emission refers to a phenomenon in which electrical energy is converted into light energy using an organic material. An organic light emitting device using the phenomenon of organic light emission generally has a structure including an anode, a cathode and an organic material layer interposed therebetween. Here, the organic material layer generally has a structure including a plurality of layers composed of different materials in order to improve efficiency and stability of the organic light emitting device and may, for example, include a hole injection layer, a hole transport layer, a light emitting layer, an electron transport layer, an electron injection layer and the like. In such a structure of the organic light emitting device, when a voltage is applied between two electrodes, holes and electrons are injected into the organic material layer from the anode and the cathode, respectively, and the injected holes and electrons are combined to form excitons. When the excitons fall to the ground state again, light is emitted.

There is a continuous need for development of novel materials for the aforementioned organic light emitting device.

DISCLOSURE

Technical Problem

The present specification is directed to providing a compound with excellent brightness and color purity as well as long lifetime.

Also, the present specification is directed to providing an organic light emitting device including the same.

Technical Solution

One embodiment of the present specification provides a compound of the following Chemical Formula 1:

[Chemical Formula 1]

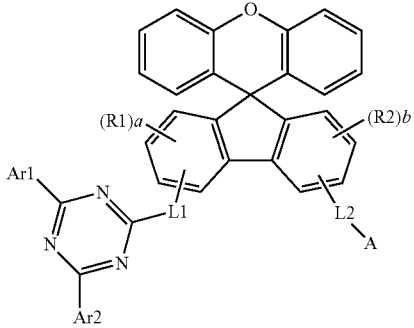

wherein:

R1 and R2 are each independently any one selected from the group consisting of hydrogen, deuterium, a halogen, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryl oxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted aralkylamine group, a substituted or unsubstituted arylamine group, a substituted or unsubstituted arylphosphine group, a substituted or unsubstituted phosphine oxide group, a substituted or unsubstituted aryl group, and a substituted or unsubstituted heterocyclic group including one or more of N, O, S, Si and Se atoms;

a and b are each independently an integer of 1 to 3;

L1 and L2 are each independently a direct bond or a substituted or unsubstituted arylene group;

Ar1 and Ar2 are each independently a substituted or unsubstituted aryl group or a substituted or unsubstituted heterocyclic group; and A is any one compound selected from the following formulae:

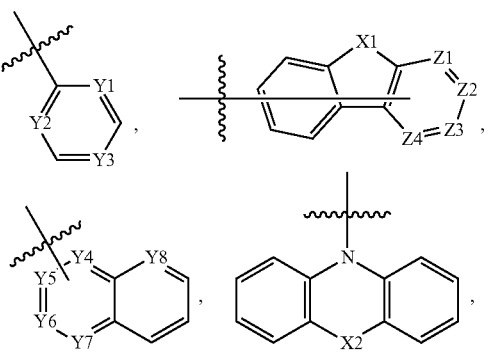

-continued

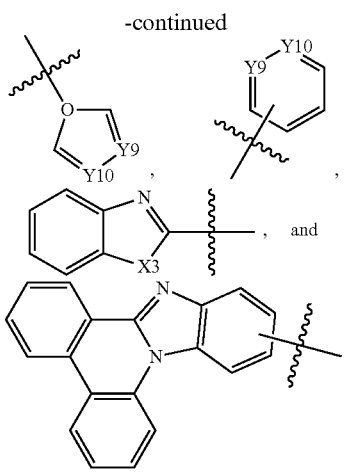

wherein:
X1 is O, S or CR3R4;
X2 is O, NR or S;
X3 is O or S;
Y1 to Y10 are each independently N or CR5;
at least two of Y1 to Y3 are N;
at least two of Y4 to Y8 are N;
at least one of Y9 and Y10 is N; and
at least two of Z1 to Z4 are N and the others are C or CR6,
wherein R and R3 to R6 are each independently any one selected from the group consisting of hydrogen, deuterium a halogen, a nitrile group, a nitro group a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted aralkylamine group, a substituted or unsubstituted arylamine group, a substituted or unsubstituted arylphosphine group, a substituted or unsubstituted phosphine oxide group, a substituted or unsubstituted aryl group, and a substituted or unsubstituted heterocyclic group including one or more of N, O, S, Si and Se atoms; and
each A independently is unsubstituted or is substituted with a substituted or unsubstituted alkyl group, a substituted or unsubstituted aryl group, or a substituted or unsubstituted heterocyclic group.

In addition, another embodiment of the present specification provides an organic light emitting device including: a first electrode; a second electrode facing the first electrode; and at least one organic material layer interposed between the first electrode and the second electrode, wherein the at least one organic material layer contains the compound according to one embodiment of the present specification.

Advantageous Effects

The compound according to an embodiment of the present specification is used as a material for an organic material layer in an organic light emitting device and thus can advantageously improve efficiency, and low driving voltage and lifetime characteristics of the organic light emitting device.

In addition, the compound according to the embodiment of the present specification can be used as a hole injection material, a hole transport material, a hole injection/hole transport material, a light emission material, an electron transport material, or an electron injection material.

DESCRIPTION OF DRAWINGS

FIG. 1 is a sectional view illustrating an organic light emitting device according to an embodiment of the present specification.
101: First electrode
201: Organic material layer
301: Second electrode

MODE FOR DISCLOSURE

Hereinafter, the present specification will be described in more detail.
An embodiment of the present specification provides the compound of Chemical Formula 1 above.
According to the present specification, examples of substituents will be described below, but the specification is not limited thereto.
The term "substituted or unsubstituted" as used herein can mean substituted or unsubstituted with one or more substituents selected from the group consisting of: deuterium, a halogen, a nitrile group, a nitro group, a hydroxyl group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylamine group, an aralkylamine group, an arylamine group, and an arylphosphine group, or substituted or unsubstituted with a substituent linking two or more substituents among the substituents exemplified above. For example, "a substituent linking two or more substituents" can be a biphenyl group. That is, the biphenyl group can be an aryl group or can be construed as being a substituent linking two phenyl groups.

In the present specification, the "adjacent" group can mean a substituent substituting an atom directly linked to an atom substituted with the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

In the present specification, examples of the halogen include fluorine, chlorine, bromine and iodine.

In the present specification, the number of carbon atoms of the carbonyl group is not particularly limited, but is preferably 1 to 40. Specifically, the carbonyl group can be selected from compounds having the following structure, but is not limited thereto:

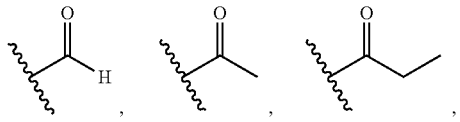

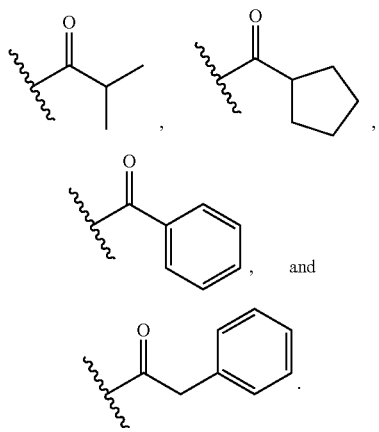

In the present specification, regarding an ester group, the oxygen of the ester group can be substituted with a linear, branched or cyclic alkyl group having 1 to 40 carbon atoms, or an aryl group having 6 to 30 carbon atoms. Specifically, such an ester group can be selected from compounds of the following formulae, but is not limited thereto.

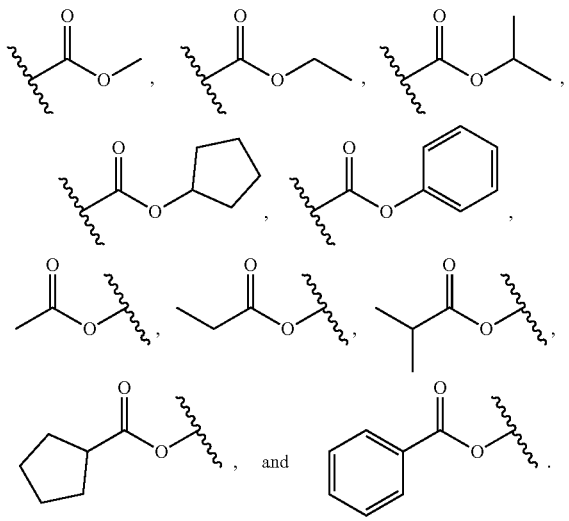

In the present specification, the number of carbon atoms of the imide group is not particularly limited, but is preferably 1 to 25. Specifically, the imide group can be selected from compounds having the following formulae, but is not limited thereto.

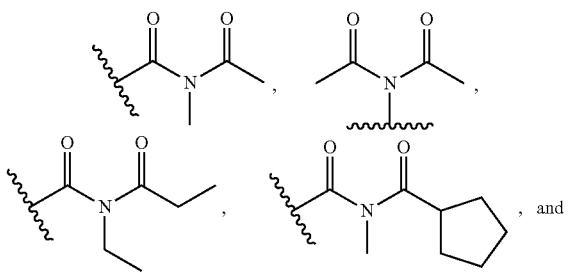

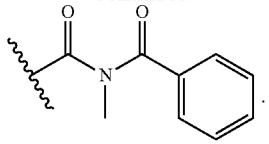

In the present specification, specifically, examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, specifically, examples of the boron group include a trimethylboron group, a triethylboron group, a t-butyldimethylboron group, a triphenylboron group, a phenylboron group and the like, but are not limited thereto.

In the present specification, the alkyl group can be linear or branched, or can include a cycloalkyl group. The number of carbon atoms of the alkyl group is not particularly limited, but is preferably 1 to 40. According to an embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specifically, examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 3,3-dimethyl-butyl, 2-ethylbutyl, heptyl, n-heptyl, 1-methylhexyl, cyclopentylmethyl, cycloheptylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the alkenyl group can be linear or branched, and the number of carbon atoms thereof is not particularly limited, but is preferably 2 to 40. According to an embodiment, the number of carbon atoms of the alkenyl group is 2 to 20. According to another embodiment, the number of carbon atoms of the alkenyl group is 2 to 10. According to another embodiment, the number of carbon atoms of the alkenyl group is 2 to 6. Specifically, examples of the alkenyl group include vinyl, 1-prophenyl, isoprophenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, stilbenyl, styrenyl and the like, but are not limited thereto.

In the present specification, the cycloalkyl group can be included in the alkyl group, and the number of carbon atoms thereof is not particularly limited, but is preferably 3 to 60. According to an embodiment, the number of carbon atoms of the cycloalkyl group is 3 to 30. According to another embodiment, the number of carbon atoms of the cycloalkyl group is 3 to 20. According to another embodiment, the number of carbon atoms of the cycloalkyl group is 3 to 6. Specifically, examples of the cycloalkyl group include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, for example, the arylamine group means a substituted or unsubstituted monocyclic diarylamine group, a substituted or unsubstituted polycyclic diarylamine group, or a substituted or unsubstituted monocyclic and polycyclic diarylamine group.

In the present specification, the aryl group can include a fluorenyl group, and has preferably 6 to 60 carbon atoms, although not particularly limited thereto, and can be a monocyclic aryl group or a polycyclic aryl group. According to an embodiment, the number of carbon atoms of the aryl group is 6 to 30. According to an embodiment, the number of carbon atoms of the aryl group is 6 to 20. When the aryl group is a monocyclic aryl group, it can be a phenyl group, a biphenyl group, a terphenyl group or the like, but is not limited thereto. The polycyclic aryl group can be a naphthyl group, an anthracenyl group, a phenanthryl group, a pyrenyl group, a perylenyl group, a chrysenyl group, a fluorenyl group or the like, but is not limited thereto.

In the present specification, the fluorenyl group can be included in the aryl group. In addition, the fluorenyl group can be substituted and two substituents can bond to each other to form a spiro structure.

When the fluorenyl group is substituted, it can be

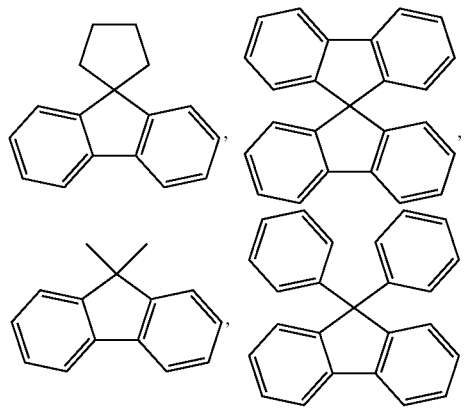

or the like, but is not limited thereto.

In the present specification, the heterocyclic group is a heterocyclic group that includes, as heteroatoms, one or more of N, O, S, Si and Se, and the number of carbon atoms of the heterocyclic group is not particularly limited, but is preferably 2 to 60. Examples of the heterocyclic group include a thiophene group, a furanyl group, a pyrrolyl group, an imidazolyl group, a thiazolyl group, an oxazolyl group, an oxadiazolyl group, a triazolyl group, a pyridyl group, a bipyridyl group, a pyrimidyl group, a triazinyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a phenanthrolinyl group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

In the present specification, the descriptions associated with the aryl group provided above can be applied to an aromatic hydrocarbon ring, except for being divalent.

In the present specification, the descriptions associated with the heterocyclic group provided above can be applied to a heteroring, except for being divalent.

In the present specification, the descriptions associated with the aryl group provided above can be applied to the aryl group of the aryloxy group, the arylthioxy group, the arylsulfoxy group, the arylphosphine group, the aralkyl group, the alkylaryl group, the aralkylamine group, the aralkenyl group and the arylamine group.

In the present specification, the descriptions associated with the alkyl group provided above can be applied to the alkyl group of the alkylthioxy group, the alkylsulfoxy group, the aralkyl group, the alkylaryl group, the aralkylamine group and the alkylamine group.

In the present specification, the descriptions associated with the heterocyclic group provided above can be applied to the heteroaryl group and the heteroaryl group of the heteroarylamine group.

In the present specification, the descriptions associated with the alkenyl group provided above can be applied to the alkenyl of the aralkenyl group.

In the present specification, the descriptions associated with the aryl group provided above can be applied to arylene and alkylarylene, except for being divalent.

In the present specification, the descriptions associated with the heterocyclic group provided above can be applied to heteroarylene except for being divalent.

In the present specification, "bonding to an adjacent group to form a ring" means bonding to an adjacent group to form: a substituted or unsubstituted aliphatic hydrocarbon ring; a substituted or unsubstituted aromatic hydrocarbon ring; a substituted or unsubstituted aliphatic heteroring; or a substituted or unsubstituted aromatic heteroring.

In the present specification, the aliphatic hydrocarbon ring means a non-aromatic ring including only carbon and hydrogen atoms.

In the present specification, examples of the aromatic hydrocarbon ring include a phenyl group, a naphthyl group, an anthracenyl group and the like, but are not limited thereto.

In the present specification, the aliphatic heteroring means an aliphatic ring including one or more heteroatoms.

In the present specification, the aromatic heteroring means an aromatic ring including one or more heteroatoms.

In the present specification, the aliphatic hydrocarbon ring, the aromatic hydrocarbon ring, the aliphatic heteroring and the aromatic heteroring can be monocyclic or polycyclic.

According to an embodiment of the present specification, L1 and L2 are each independently a direct bond; or a substituted or unsubstituted arylene group.

In addition, according to an embodiment of the present specification, L1 and L2 are each independently a direct bond; or a substituted or unsubstituted arylene group having 6 to 30 carbon atoms.

In addition, according to an embodiment of the present specification, L1 and L2 are each independently a direct bond; or a substituted or unsubstituted arylene group having 6 to 20 carbon atoms.

According to an embodiment of the present specification, Ar1 and Ar2 are each independently a substituted or unsubstituted aryl group; or a substituted or unsubstituted heterocyclic group.

In addition, according to an embodiment of the present specification, Ar1 and Ar2 are each independently a substituted or unsubstituted aryl group having 6 to 30 carbon atoms; or a substituted or unsubstituted heterocyclic group having 3 to 30 carbon atoms.

In addition, according to an embodiment of the present specification, Ar1 and Ar2 are each independently a substituted or unsubstituted aryl group having 6 to 20 carbon atoms; or a substituted or unsubstituted heterocyclic group having 3 to 20 carbon atoms.

According to an embodiment of the present specification, A is any one selected from the following formulae:

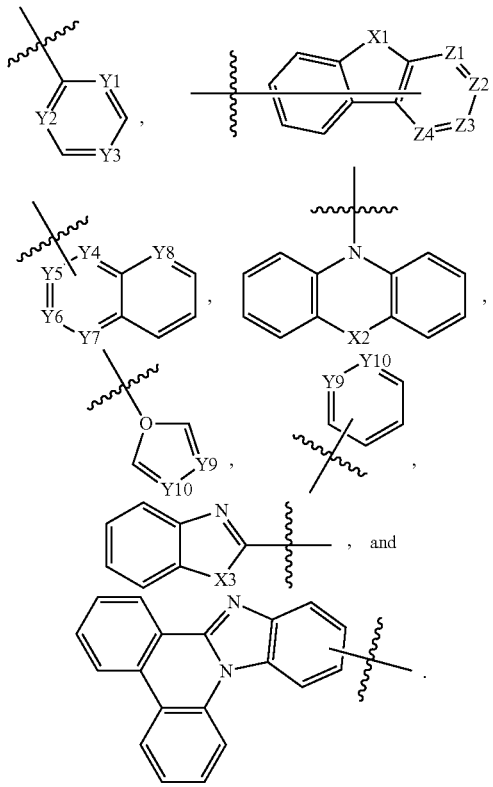

wherein X1 is O, S or CR3R4;
X2 is O, NR or S;
X3 is O or S;
Y1 to Y10 are each independently N or CR5;
at least two of Y1 to Y3 are N;
at least two of Y4 to Y8 are N;
at least one of Y9 and Y10 is N;
at least two of Z1 to Z4 are N and the others are C or CR6,
wherein R and R3 to R6 are each independently any one selected from the group consisting of hydrogen, deuterium, a halogen, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted aralkylamine group, a substituted or unsubstituted arylamine group, a substituted or unsubstituted arylphosphine group, a substituted or unsubstituted phosphine oxide group, a substituted or unsubstituted aryl group, and a substituted or unsubstituted heterocyclic group including one or more of N, O, S, Si and Se atoms; and each A independently is unsubstituted or substituted with a substituted or unsubstituted alkyl group, a substituted or unsubstituted aryl group, or a substituted or unsubstituted heterocyclic group.

According to an embodiment of the present specification, Z1 and Z2 are N.

According to an embodiment of the present specification, Z1 and Z3 are N.

According to an embodiment of the present specification, Z1 and Z4 are N.

According to an embodiment of the present specification, Z2 and Z3 are N.

According to an embodiment of the present specification, Z2 and Z4 are N.

According to an embodiment of the present specification, Z3 and Z4 are N.

According to an embodiment of the present specification, Chemical Formula 1 can be compounds of the following Chemical Formulae 2 to 5:

[Chemical Formula 2]

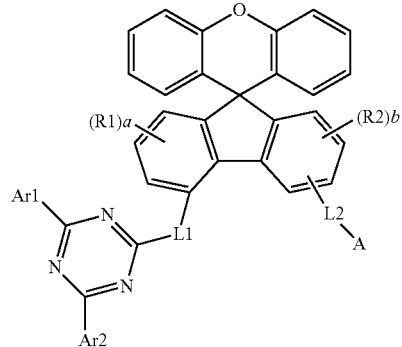

[Chemical Formula 3]

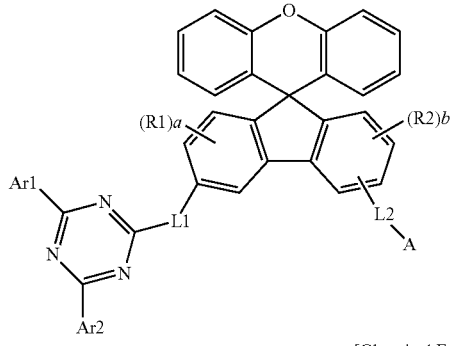

[Chemical Formula 4]

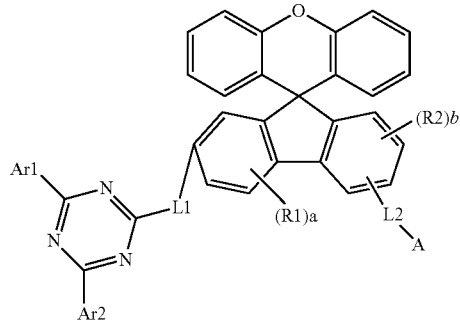

[Chemical Formula 5]

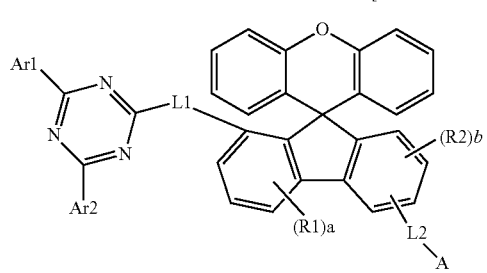

wherein Ar1, Ar2, L1, L2, R1, R2, a and b are as defined above.

According to an embodiment of the present specification, A is any one compound selected from the following formulae:

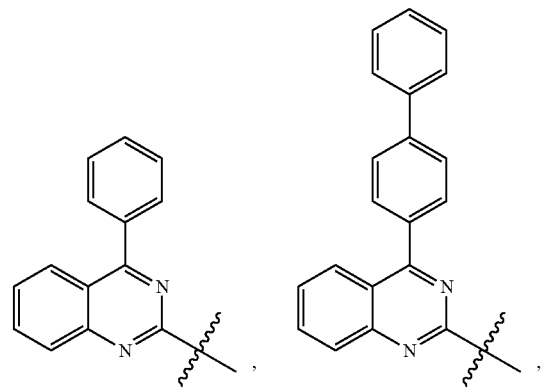

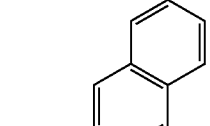

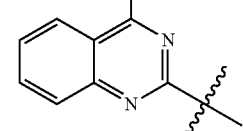

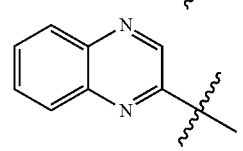

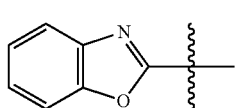

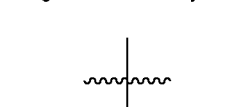

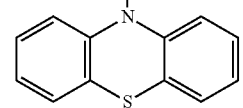

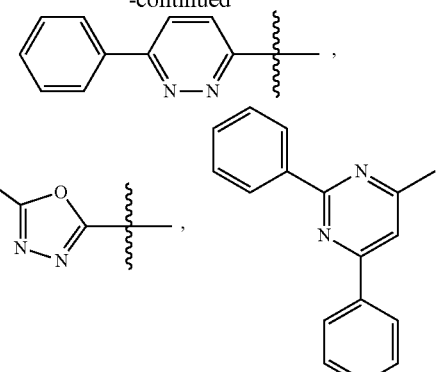

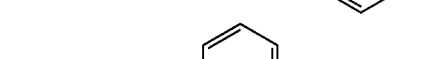
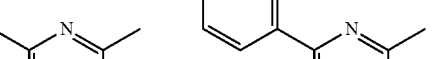
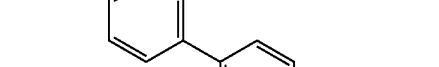
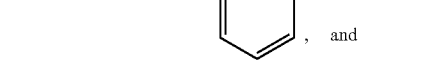
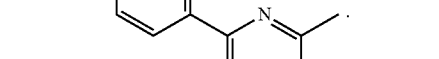
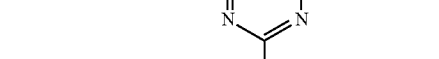
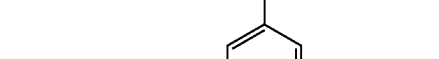
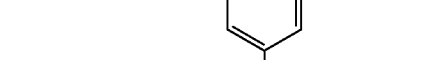
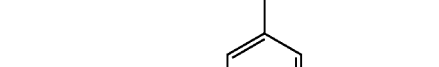
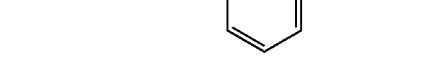
, and
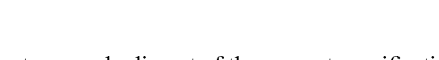
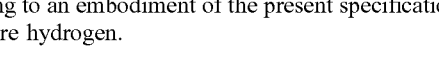
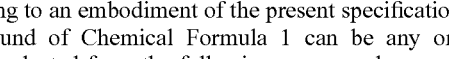
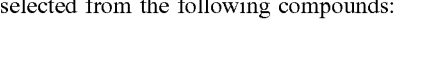

According to an embodiment of the present specification, R1 to R6 are hydrogen.

According to an embodiment of the present specification, the compound of Chemical Formula 1 can be any one compound selected from the following compounds:

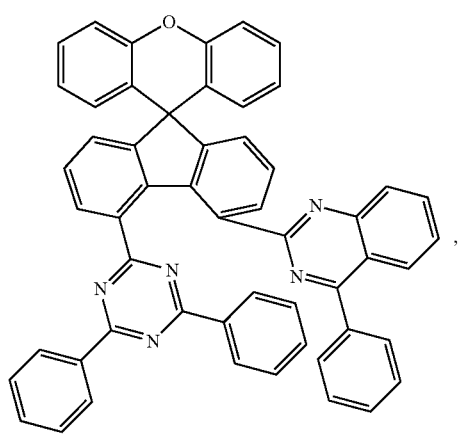
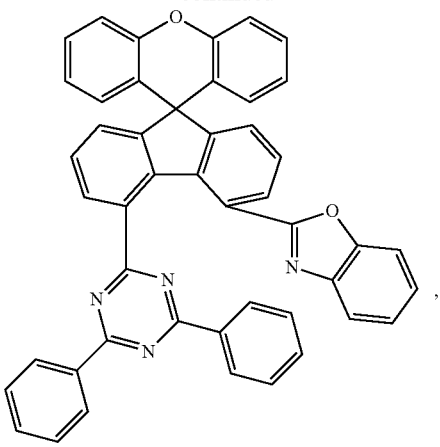
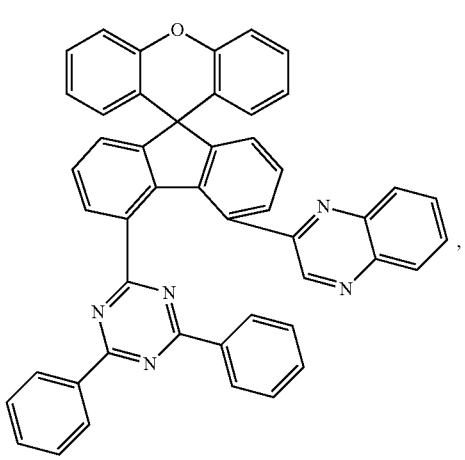
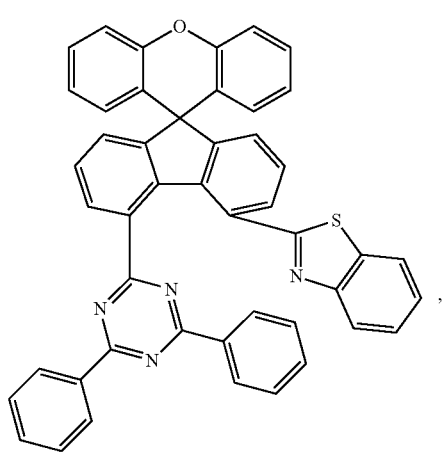
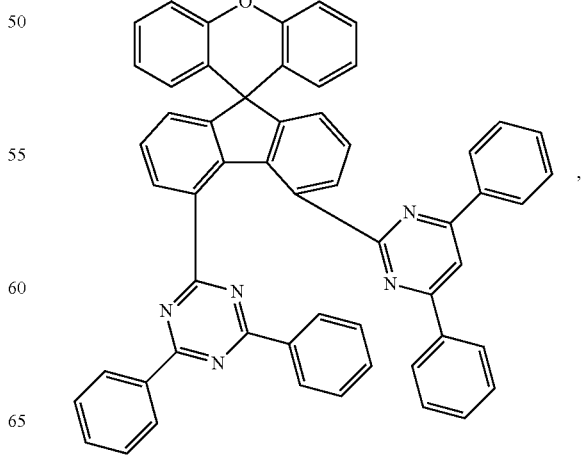

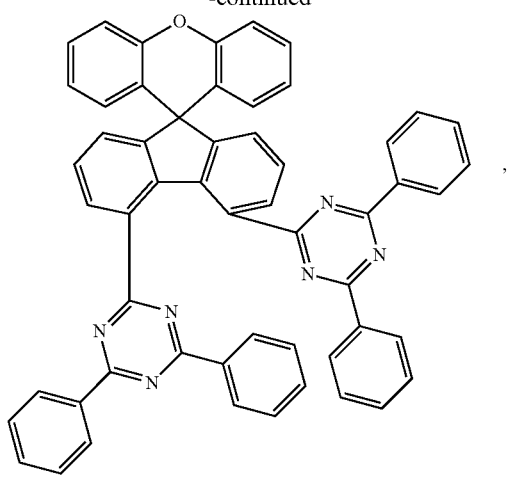
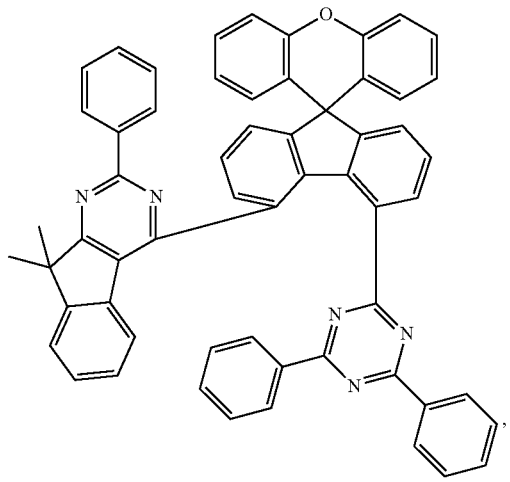
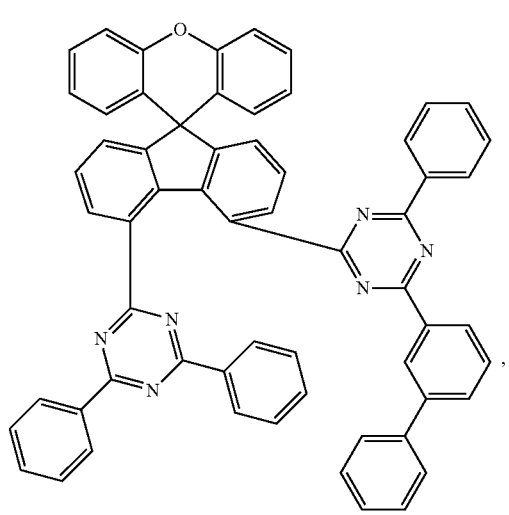
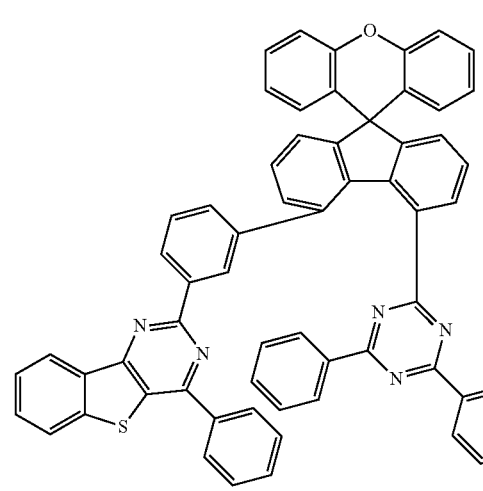
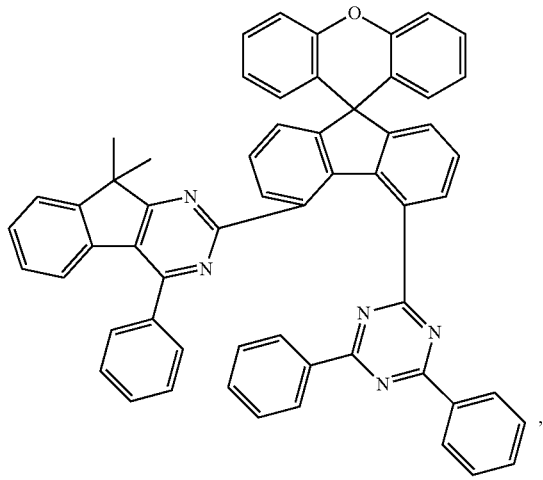
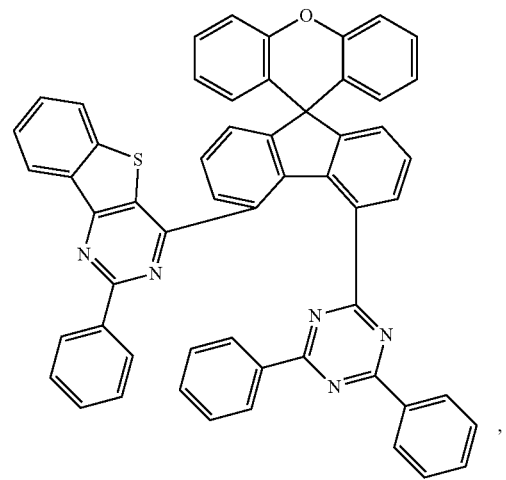

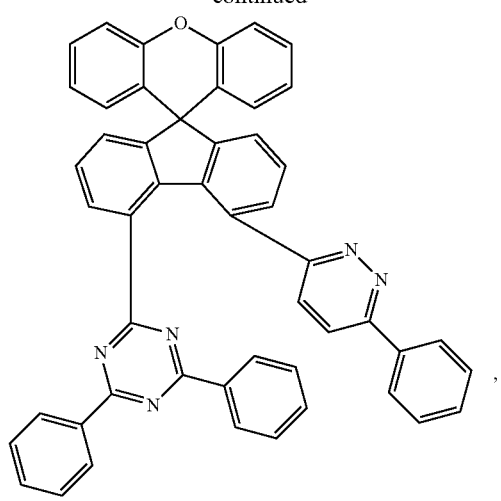
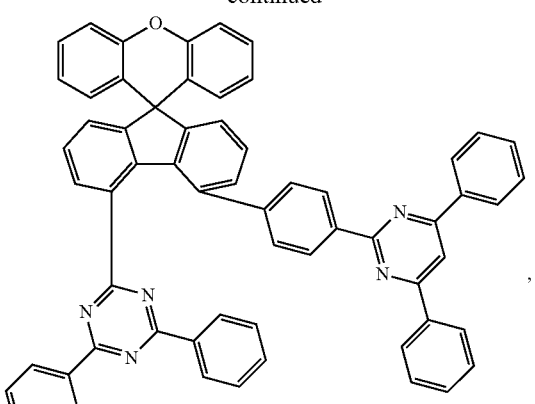
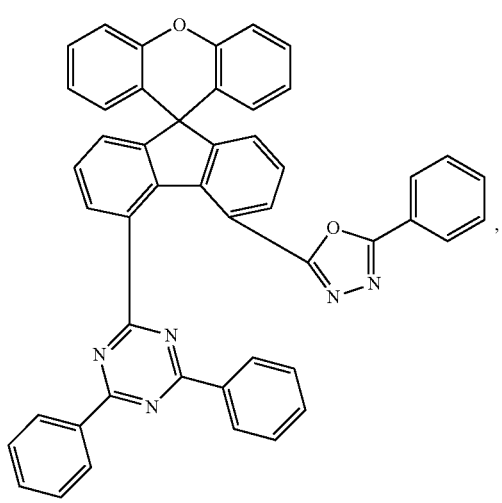
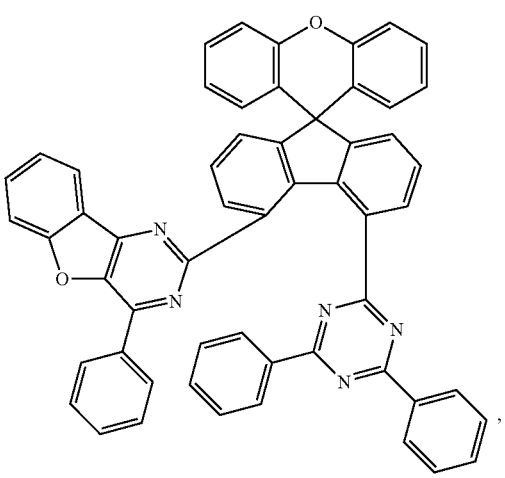
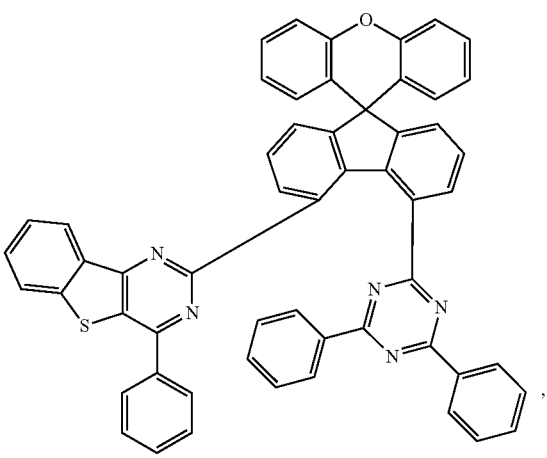

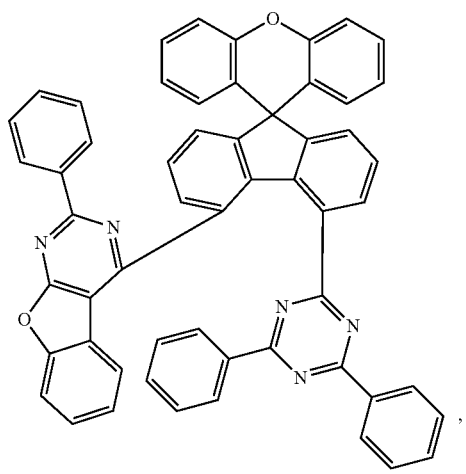
,
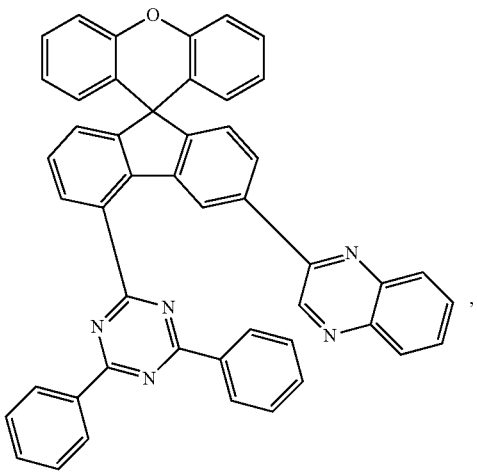
,
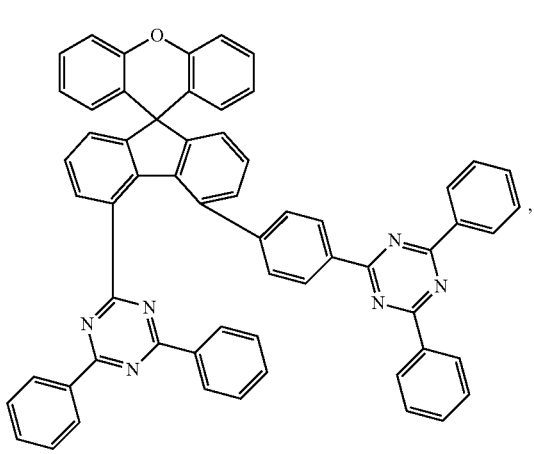
,
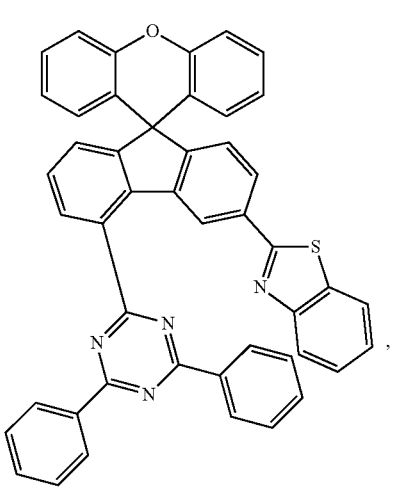
,
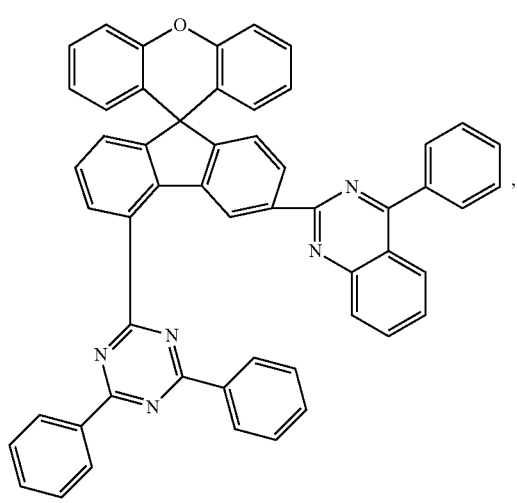
,
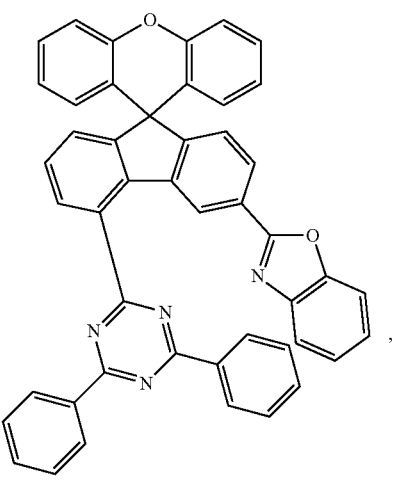
,

21
-continued
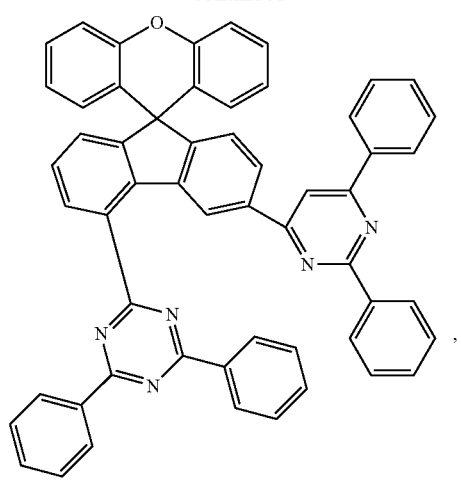
,
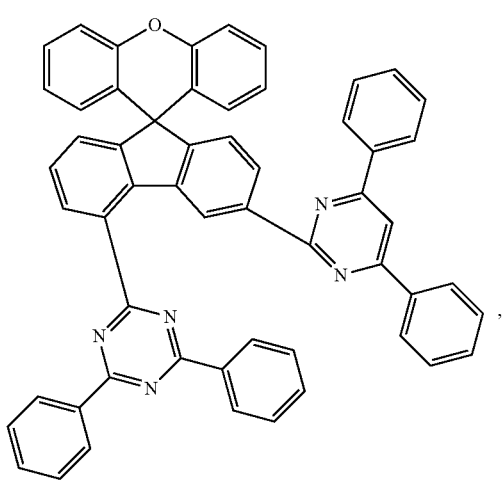
,
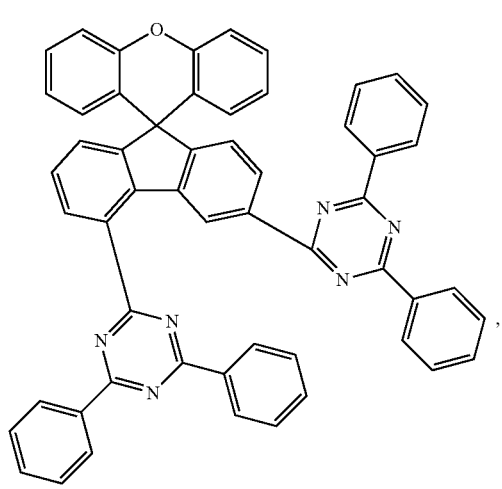
,
22
-continued
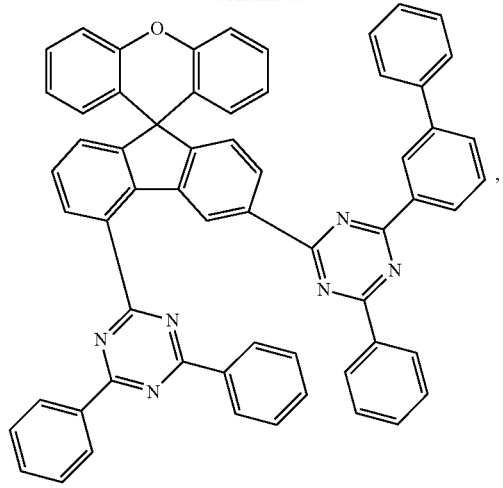
,
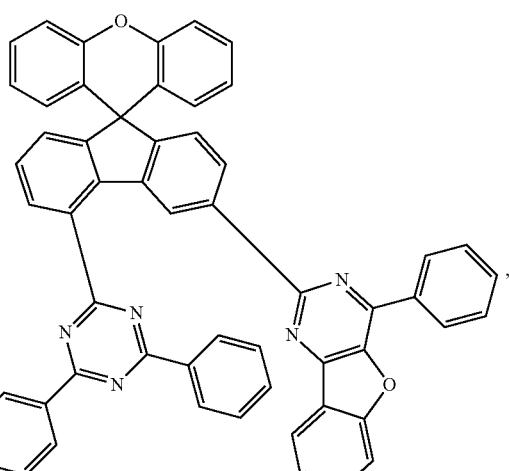
,
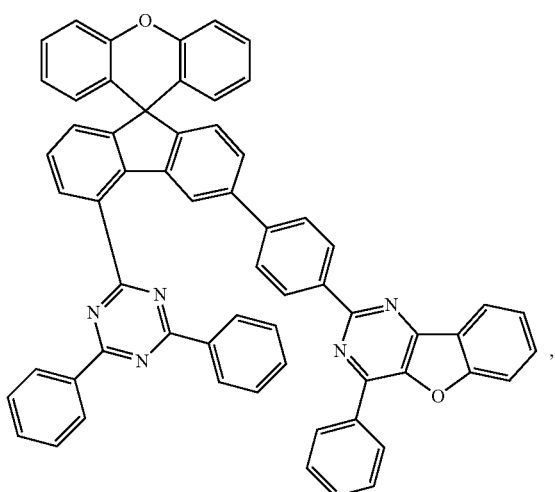
, 23
-continued
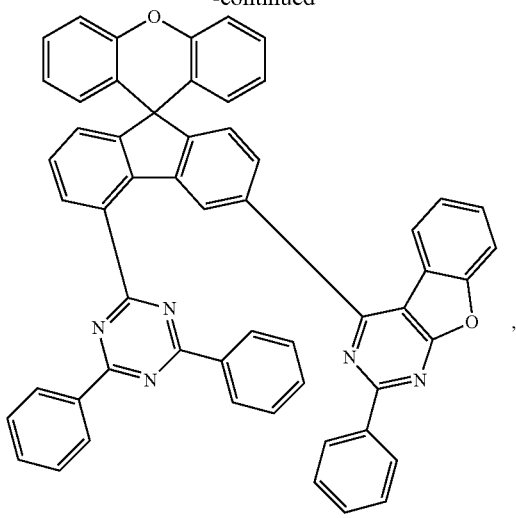
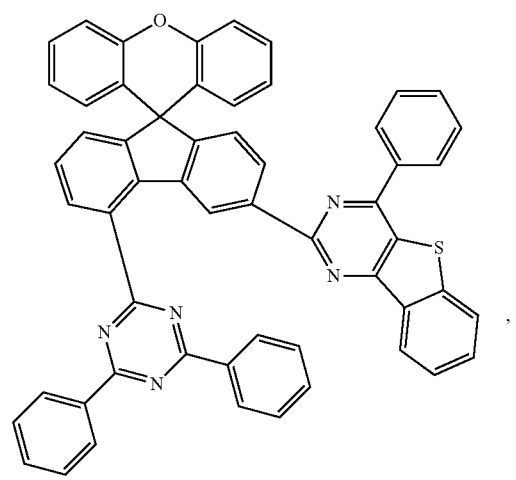
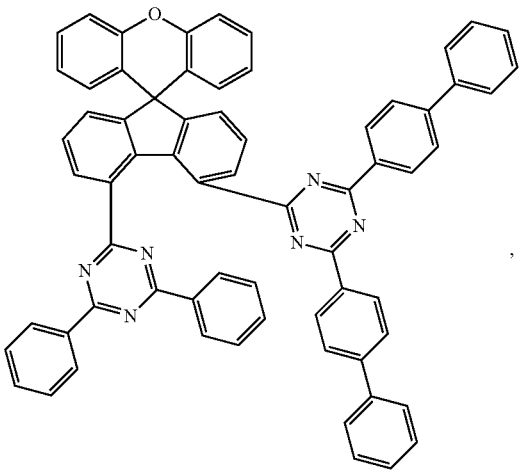
24
-continued
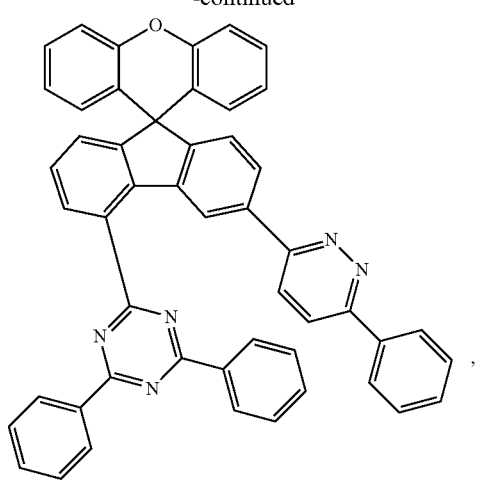
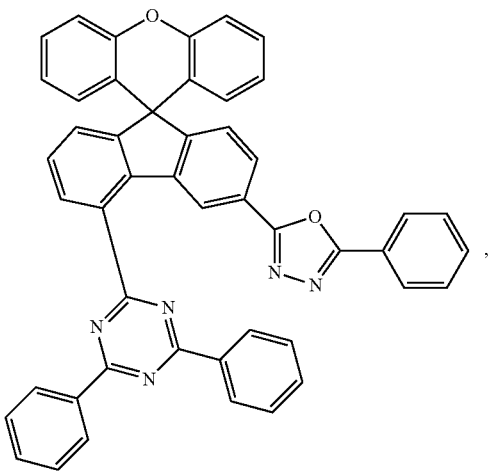
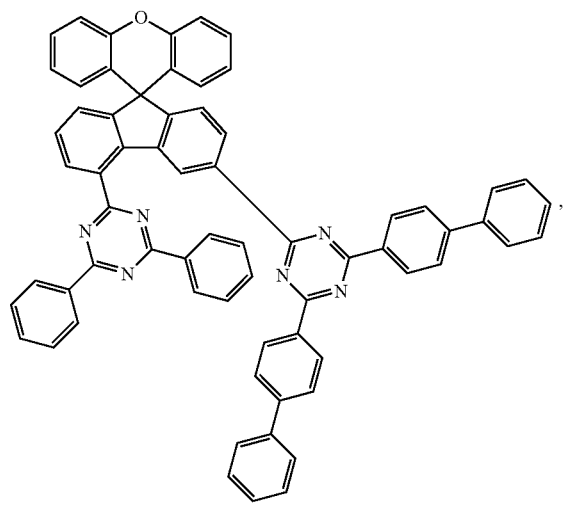

25
-continued
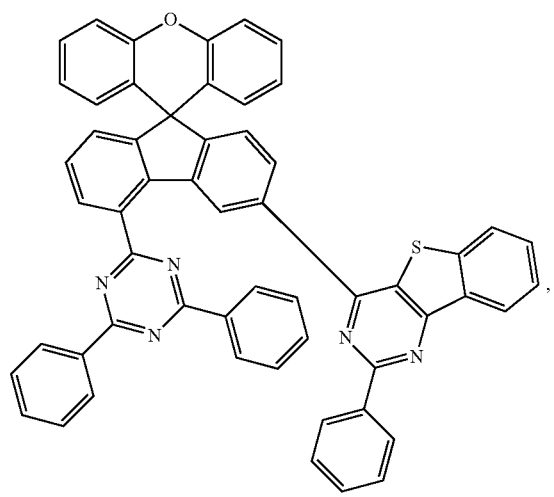
26
-continued
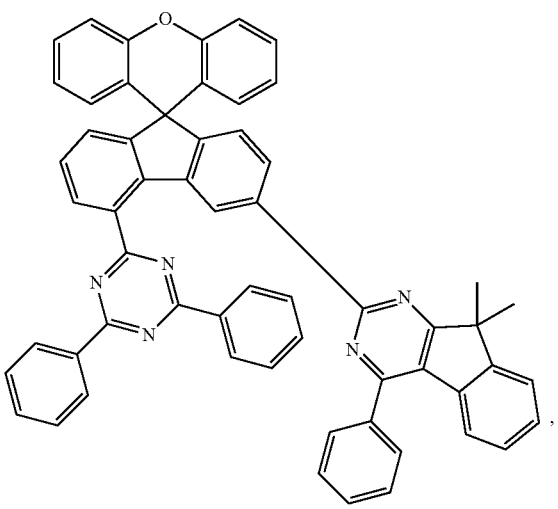
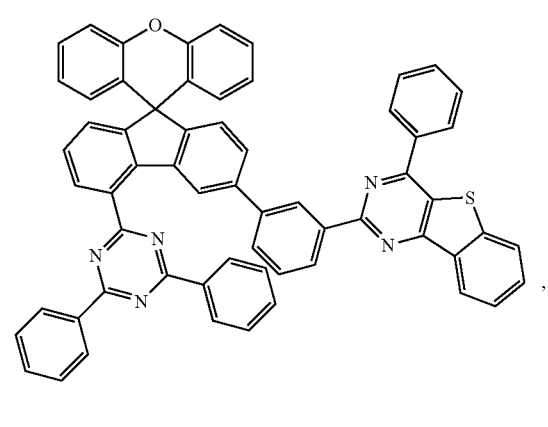
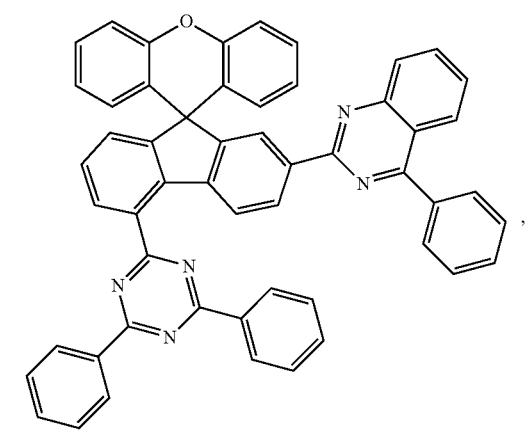
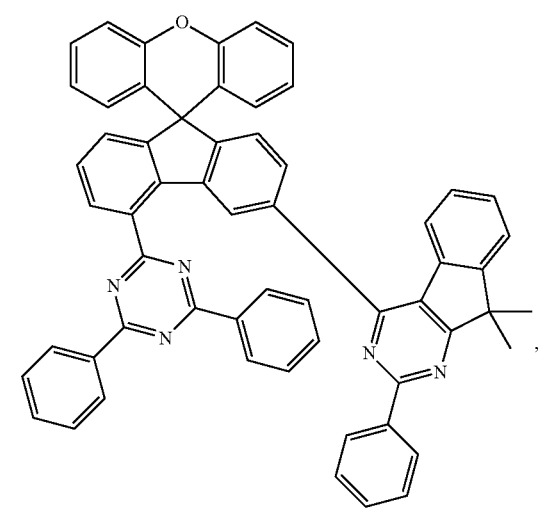

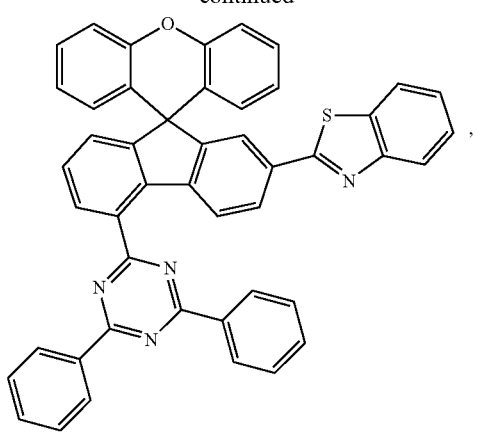
,
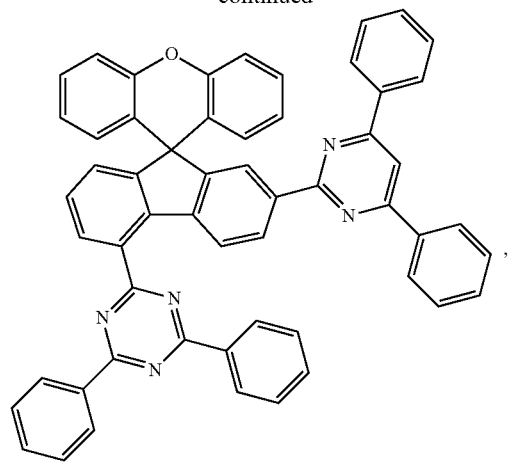
,
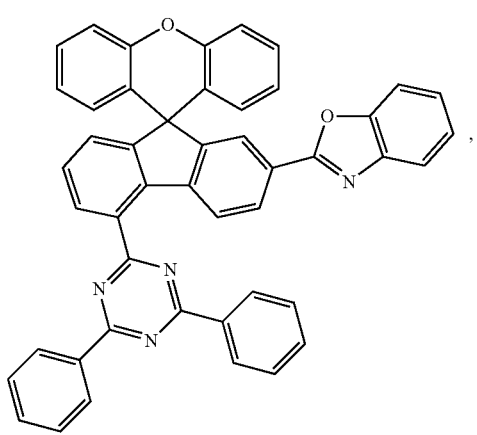
,
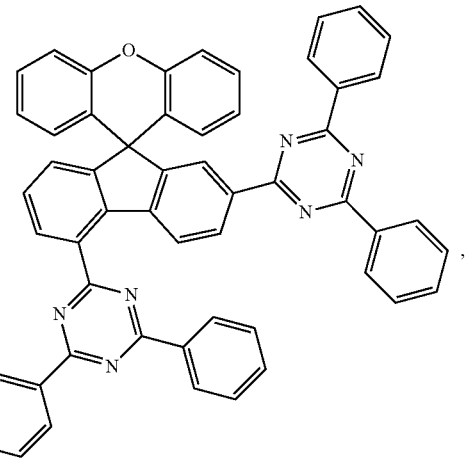
,
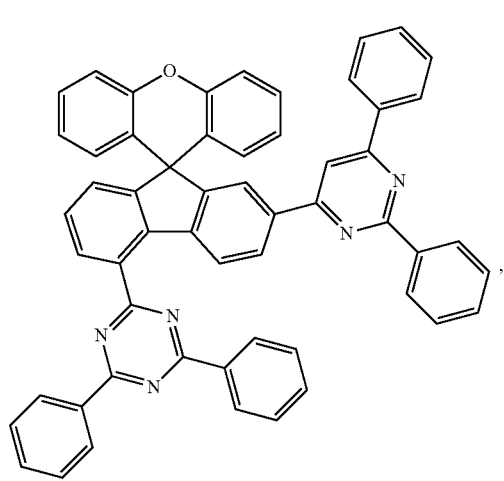
,
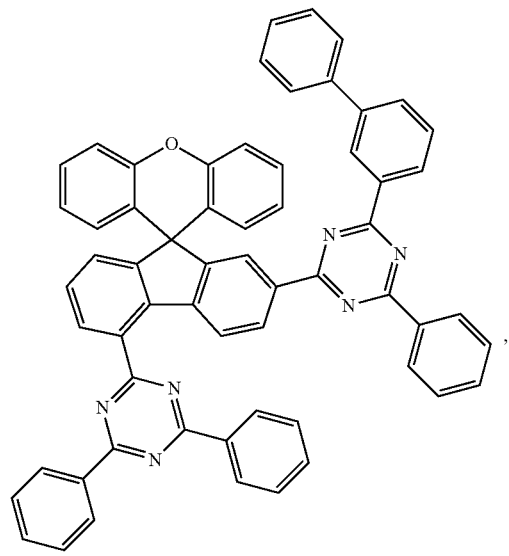
,

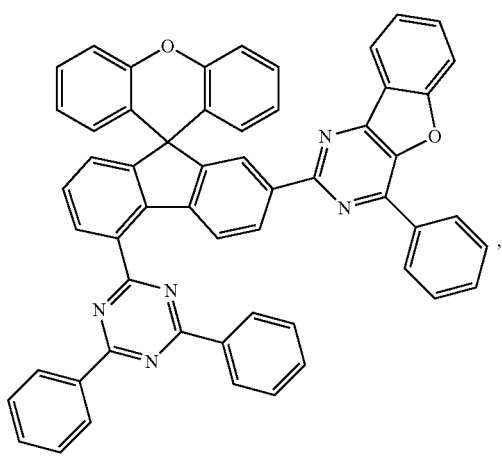
,
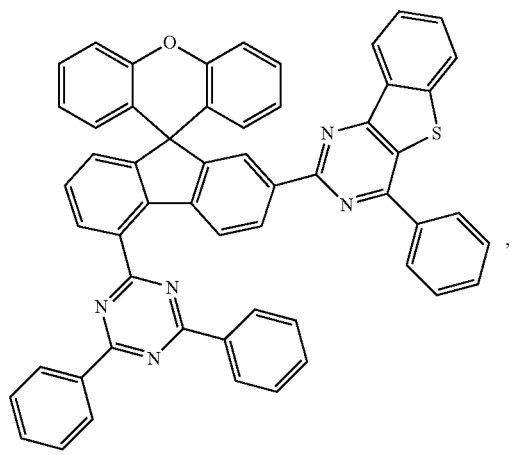
,
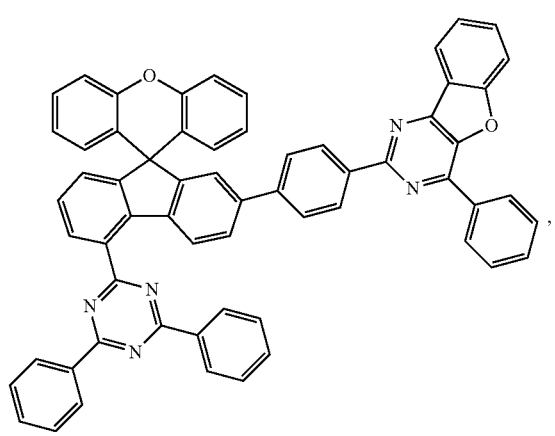
,
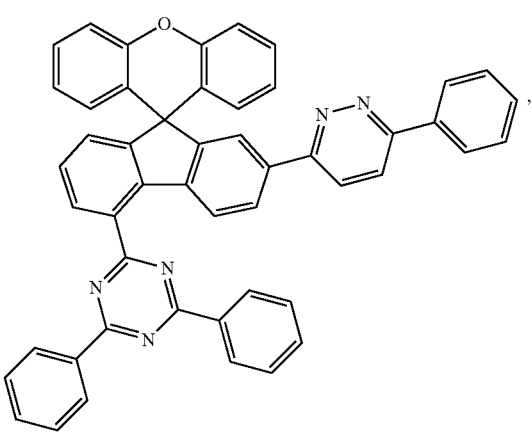
,
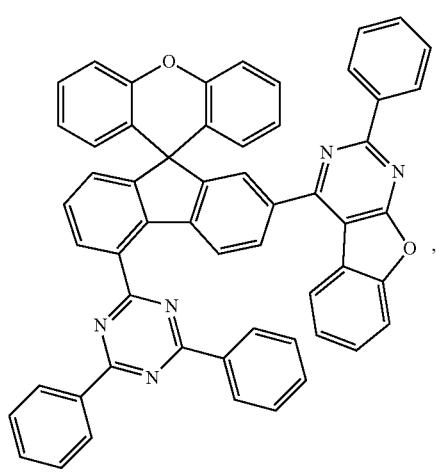
,
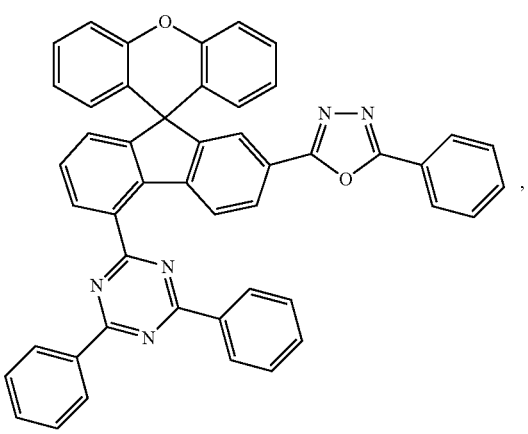
,

31
-continued
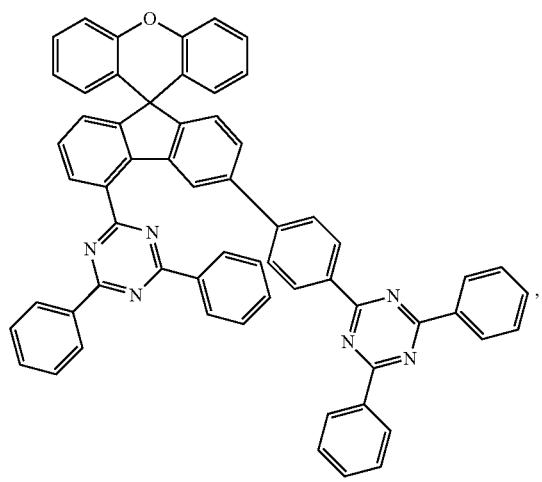
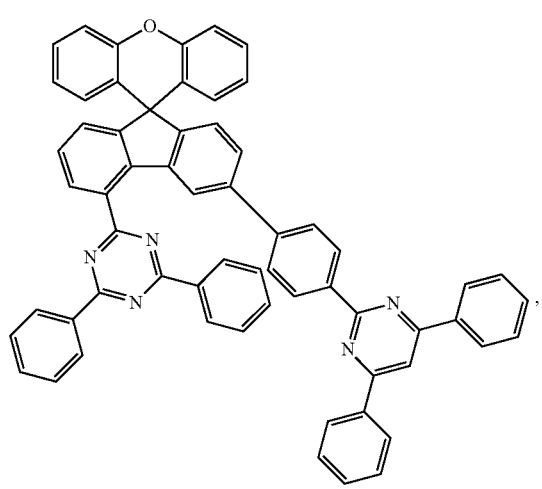
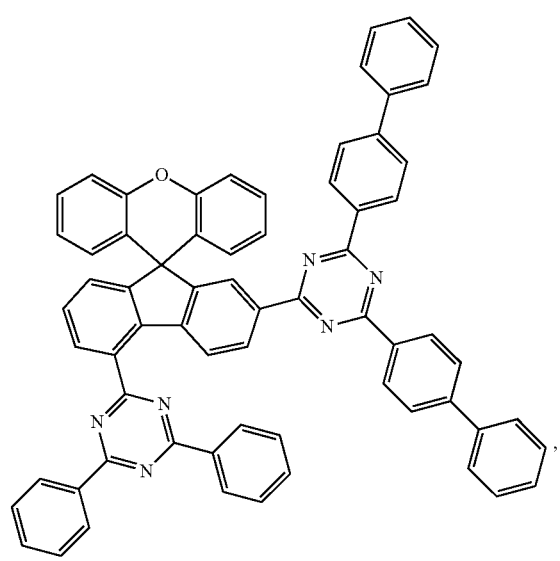
32
-continued
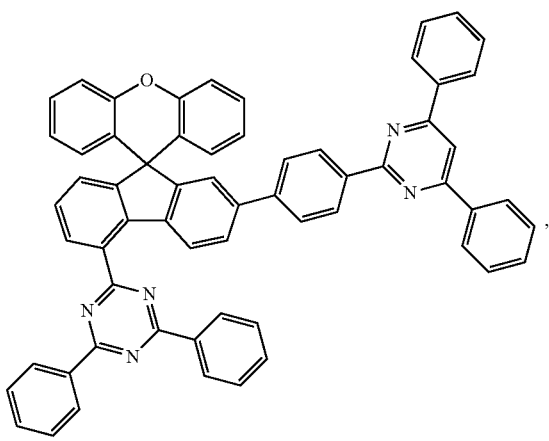
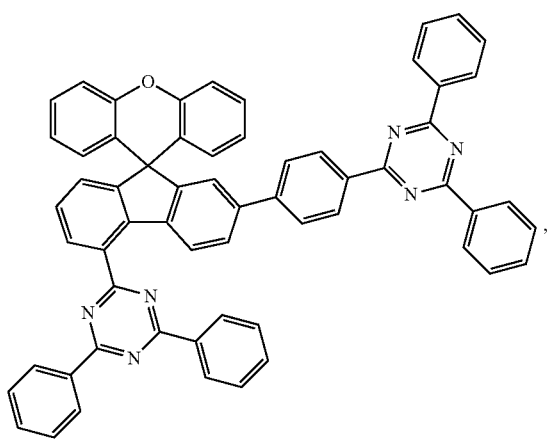
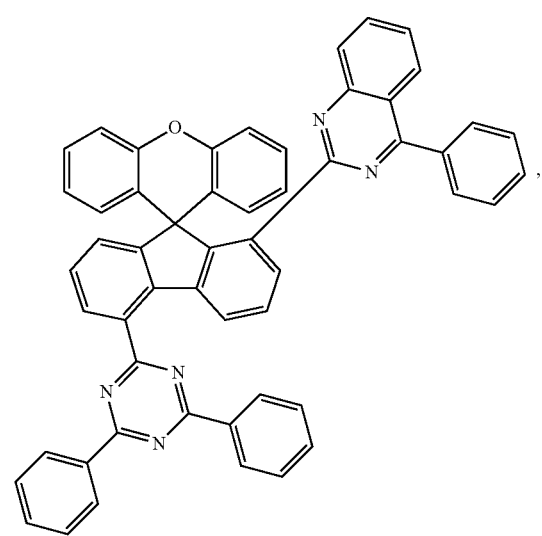

33
-continued
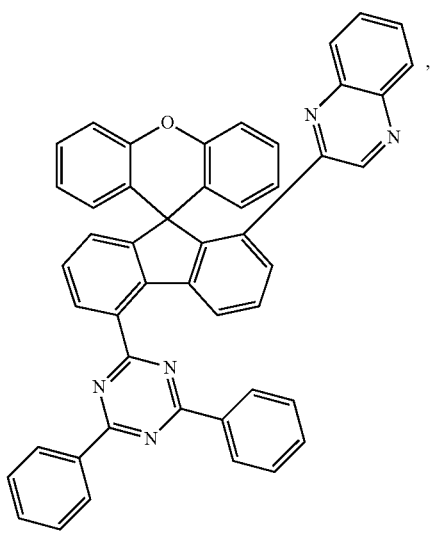
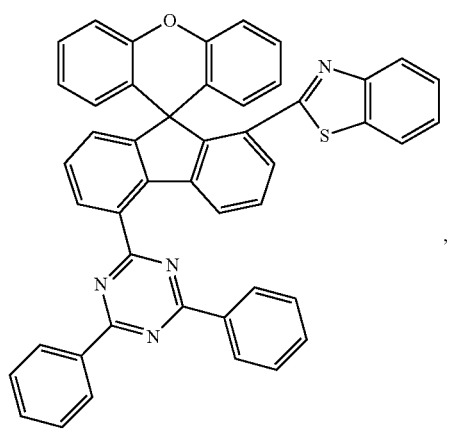
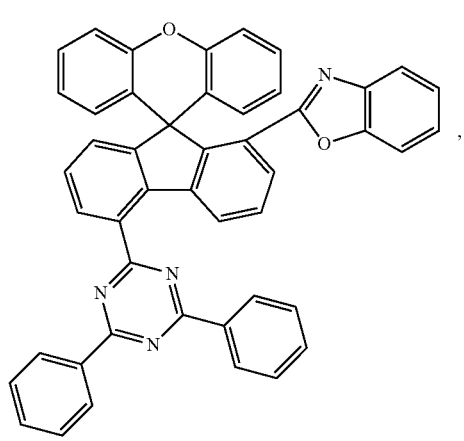
34
-continued
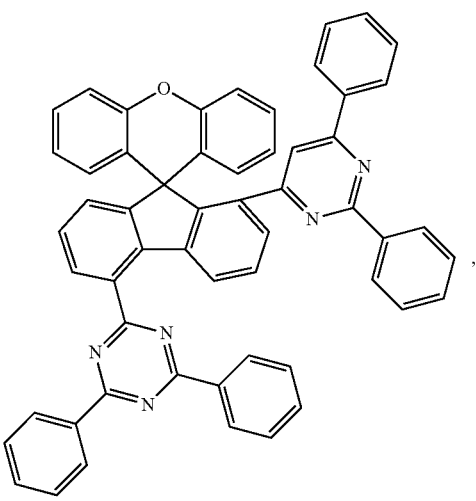
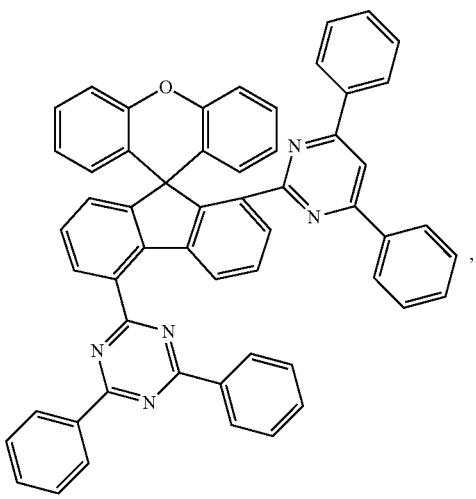
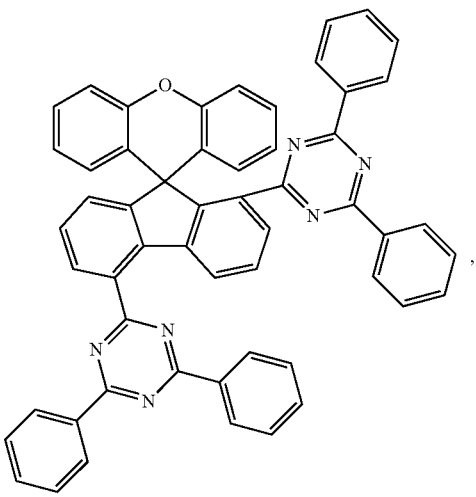

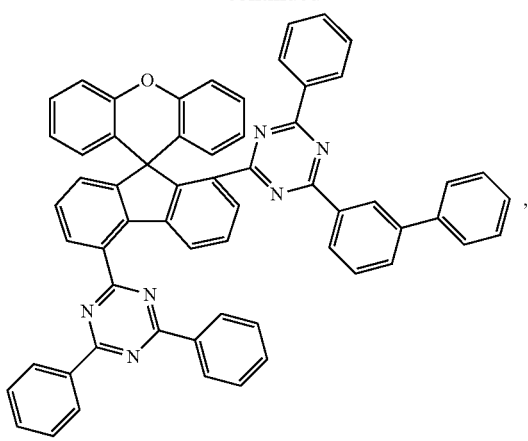
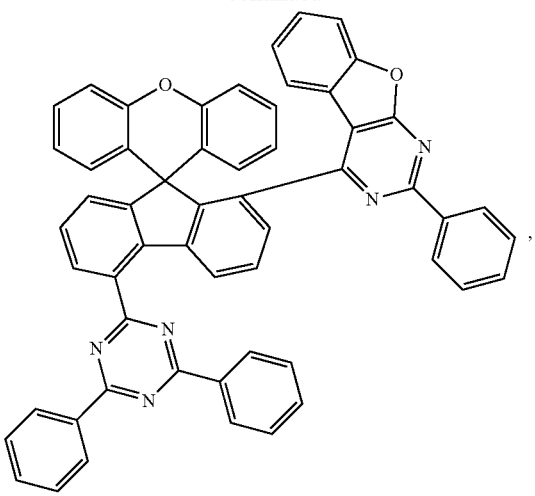
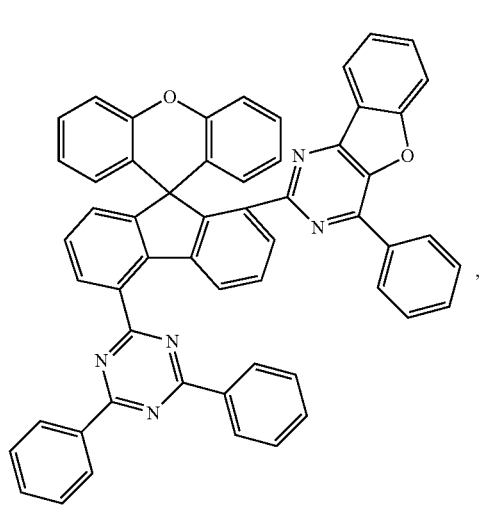
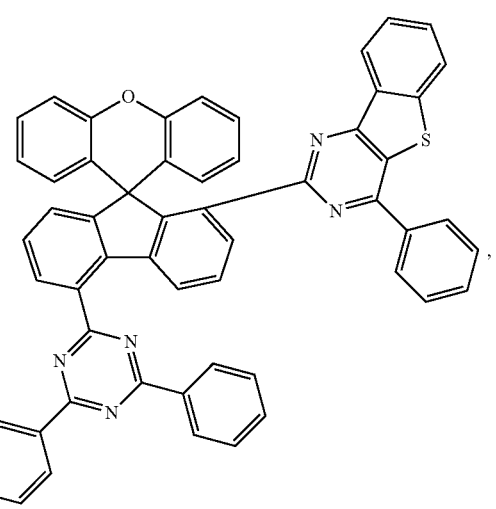
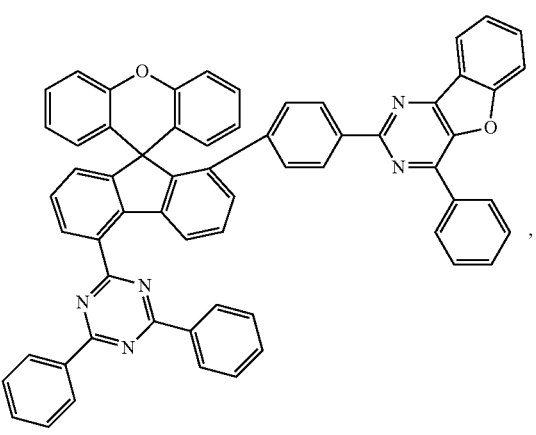

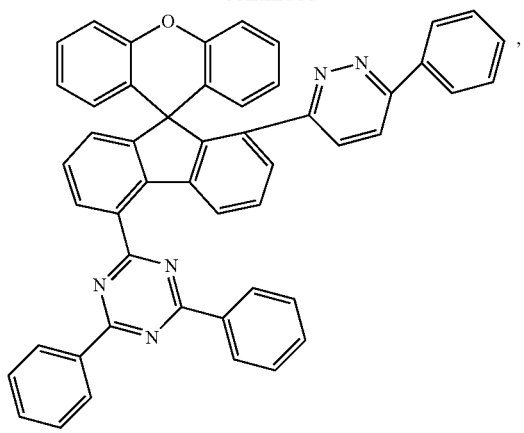
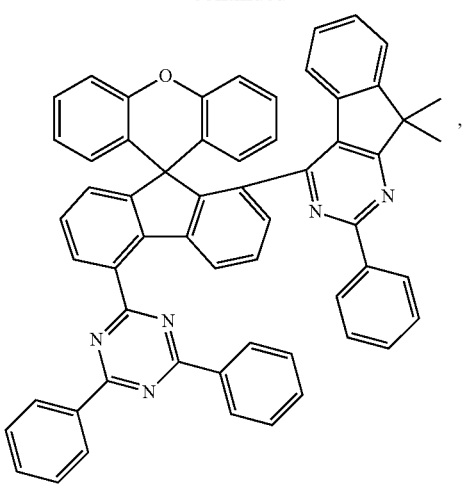

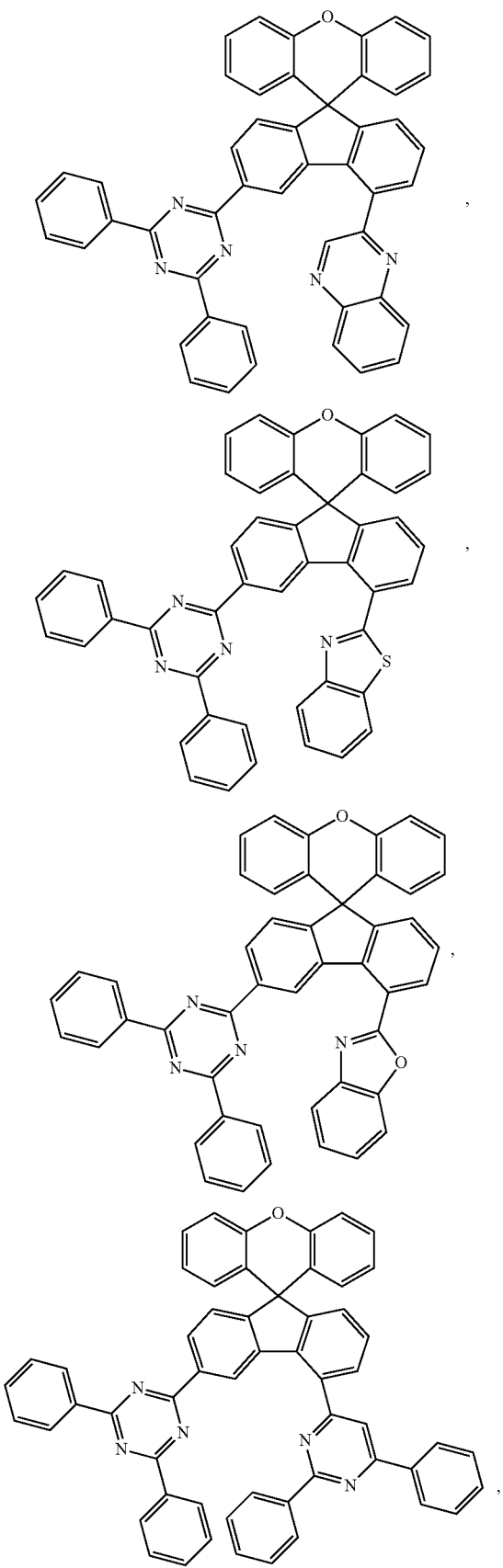
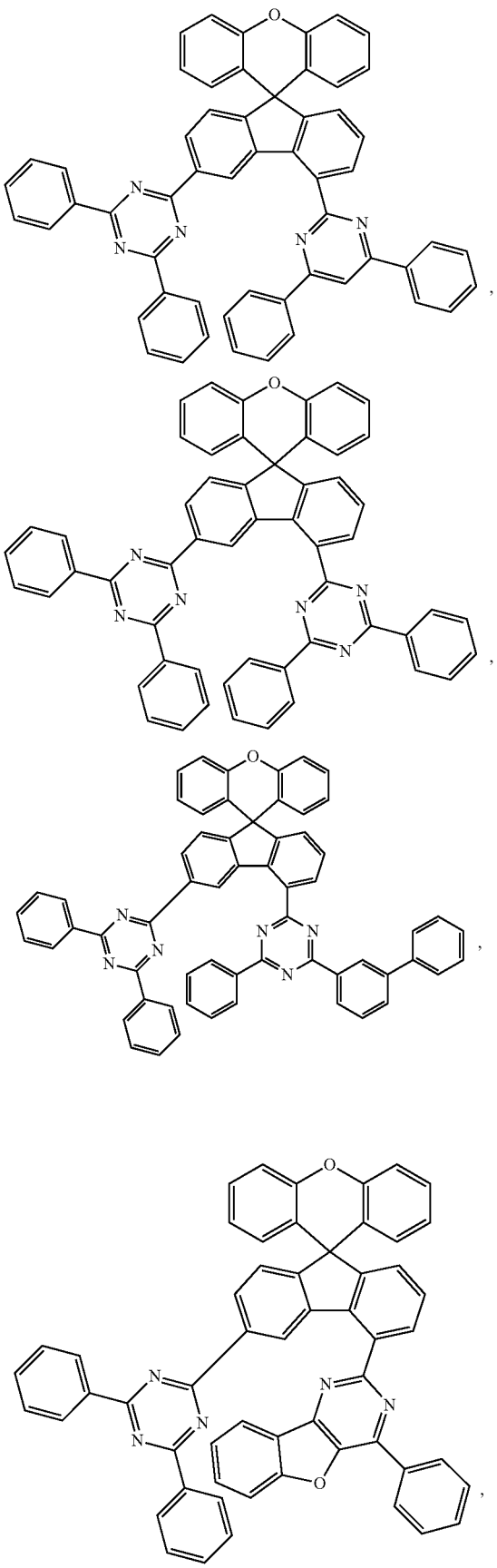

41
-continued
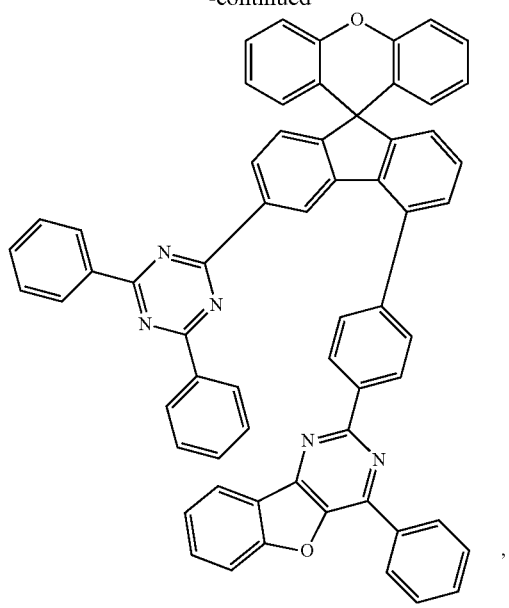
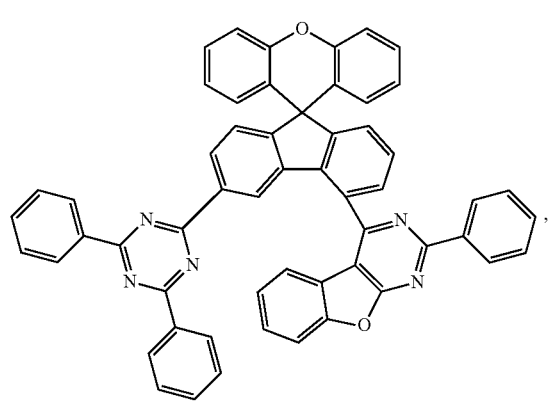
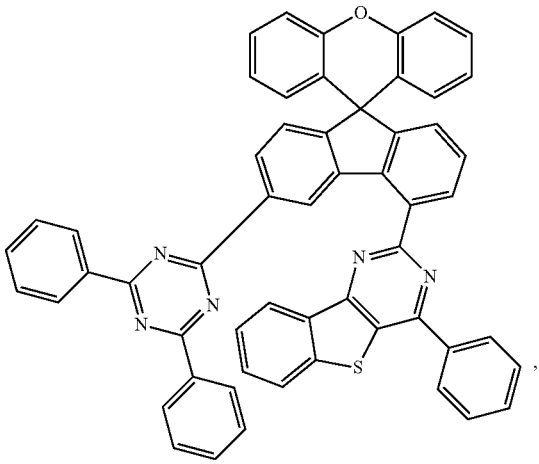
42
-continued
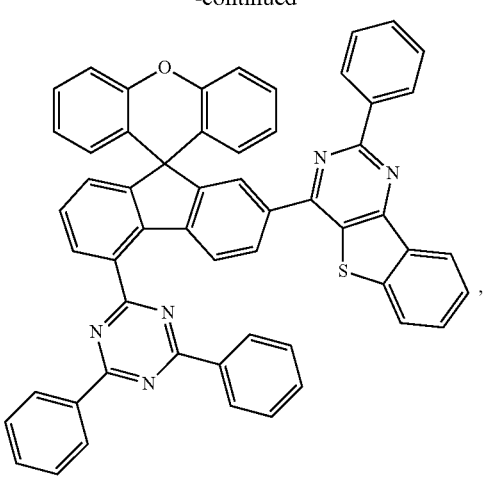
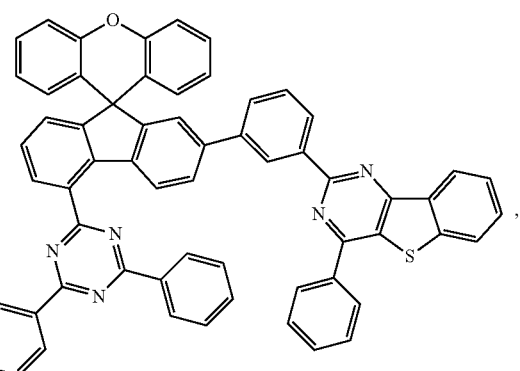
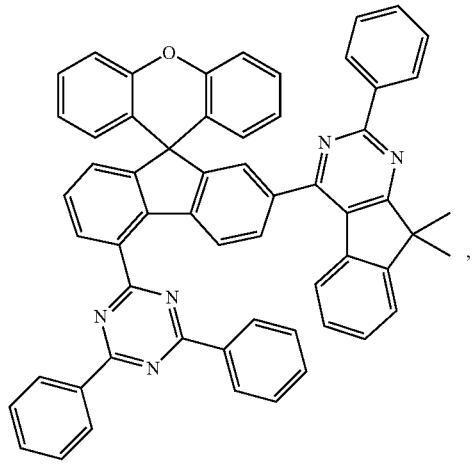

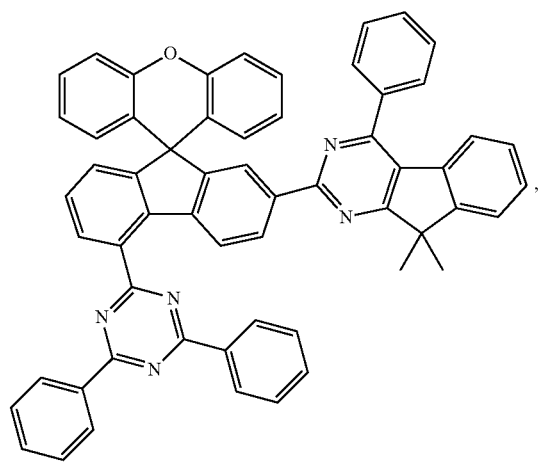
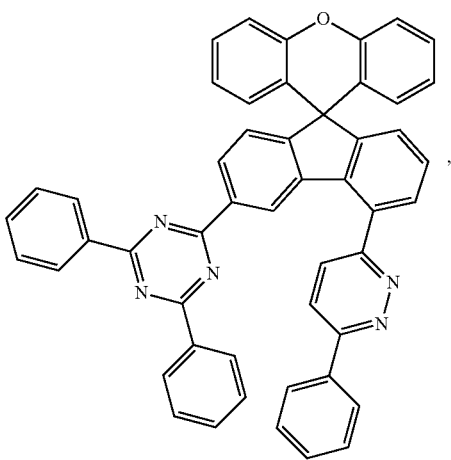
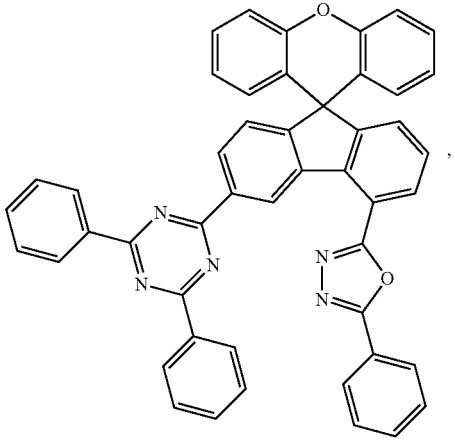
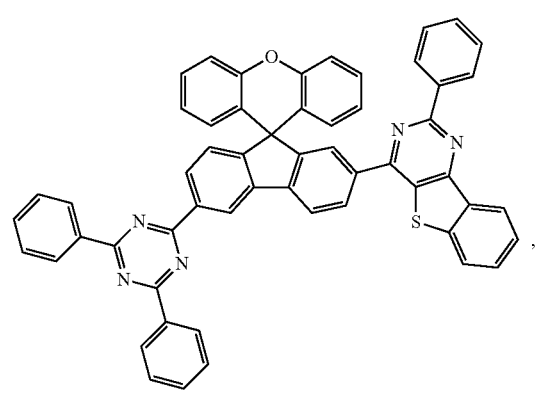
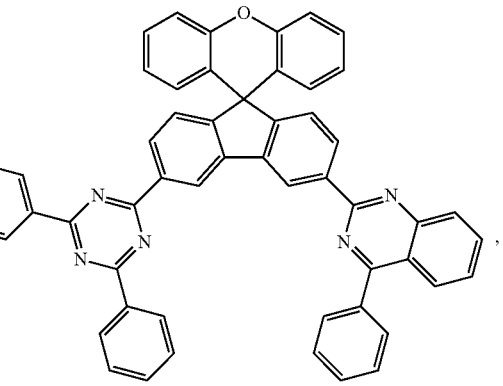
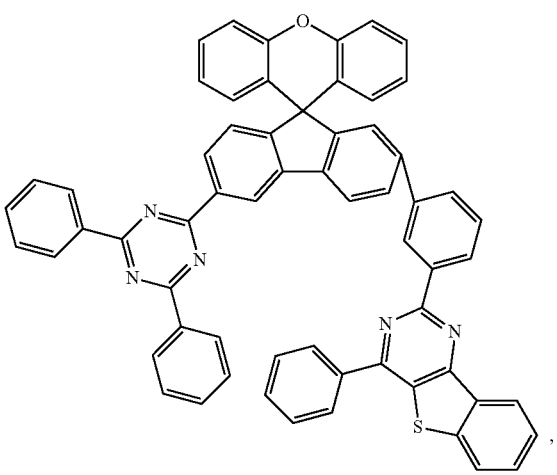
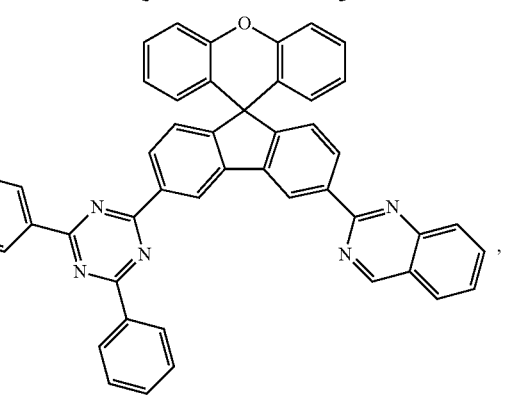

45
-continued
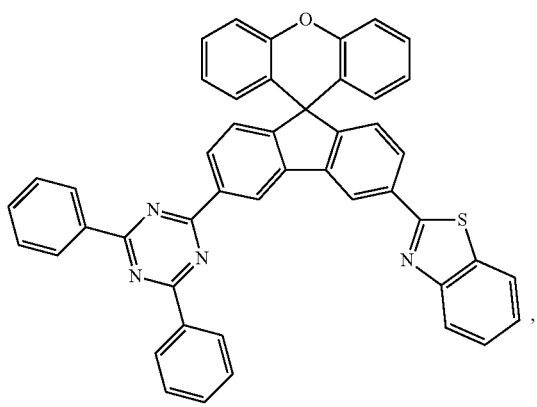
,
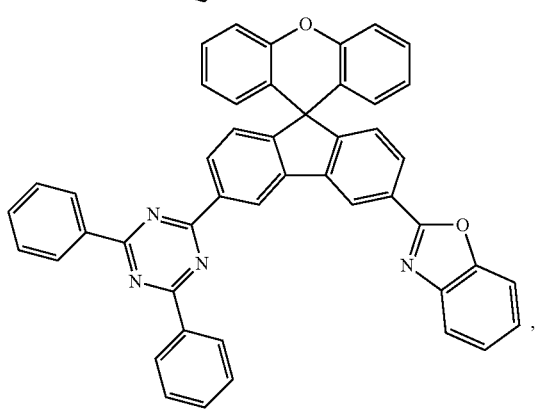
,
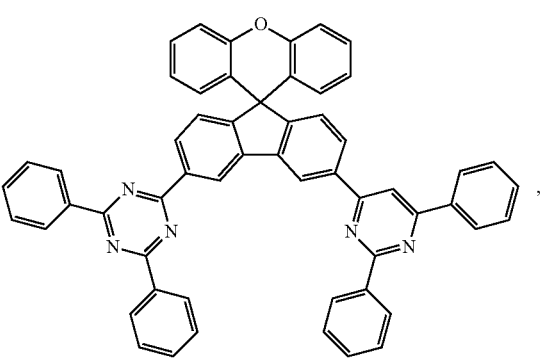
,
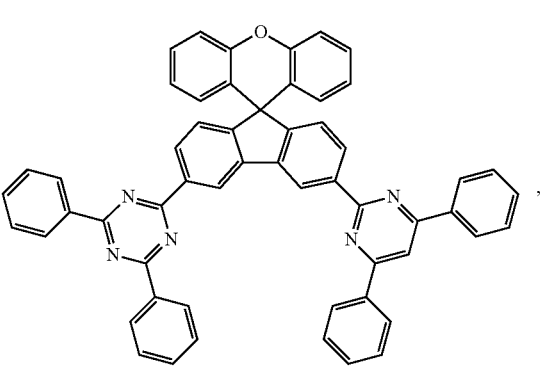
,
46
-continued
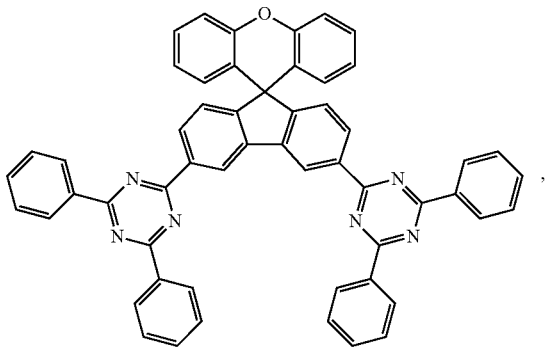
,
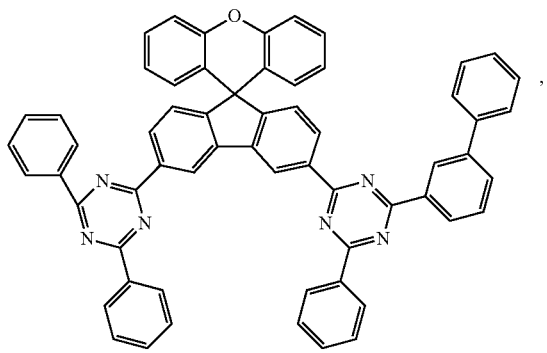
,
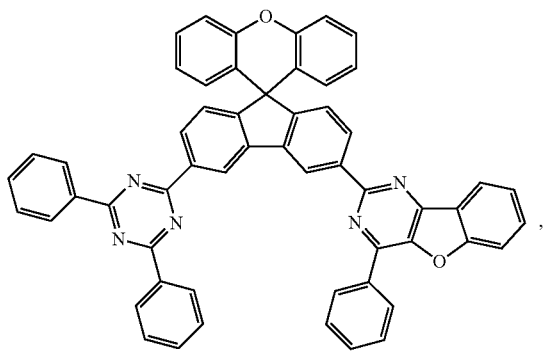
,
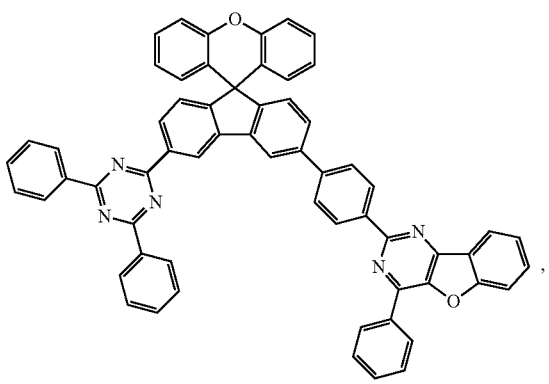
, 47
-continued
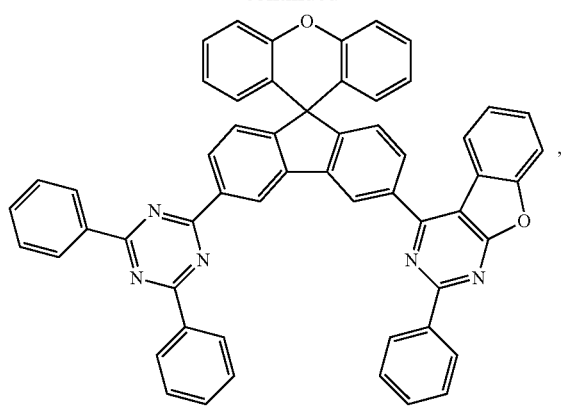
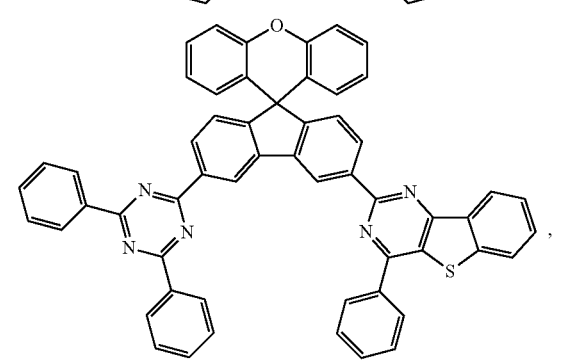
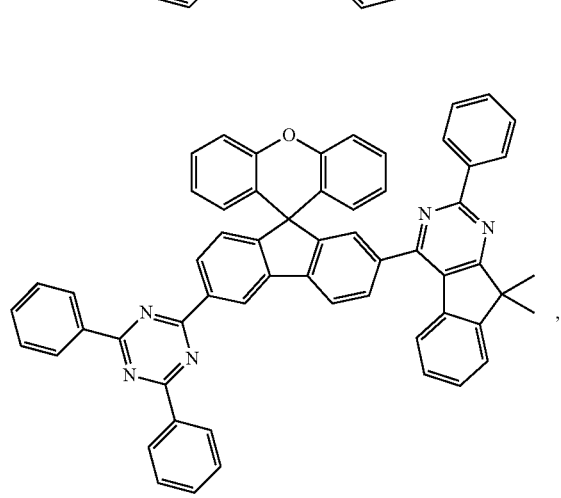
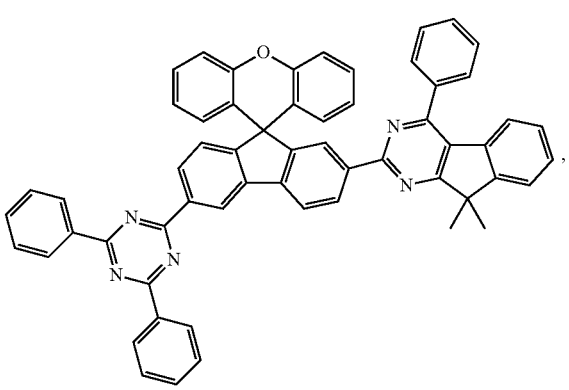
48
-continued
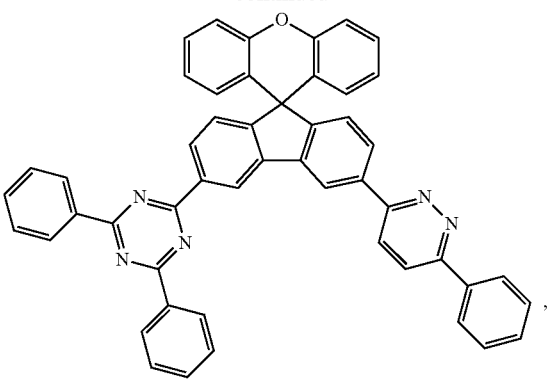
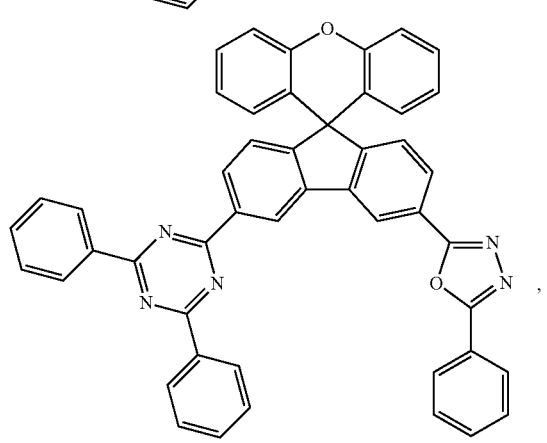
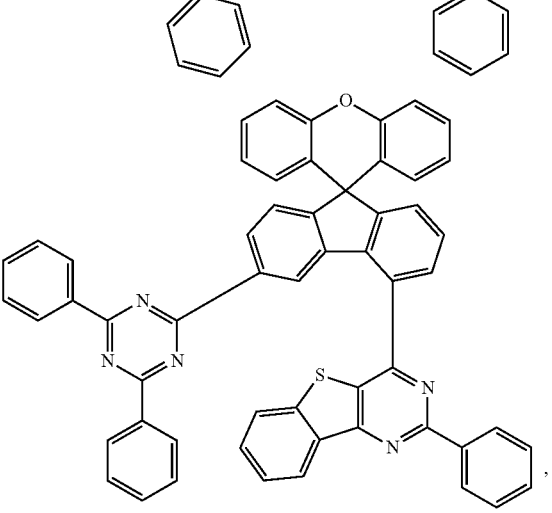
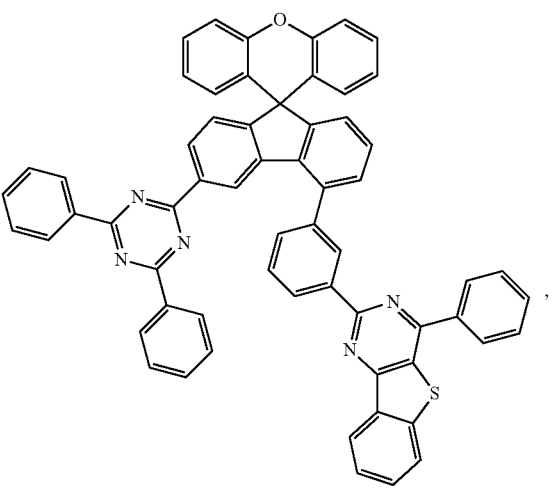

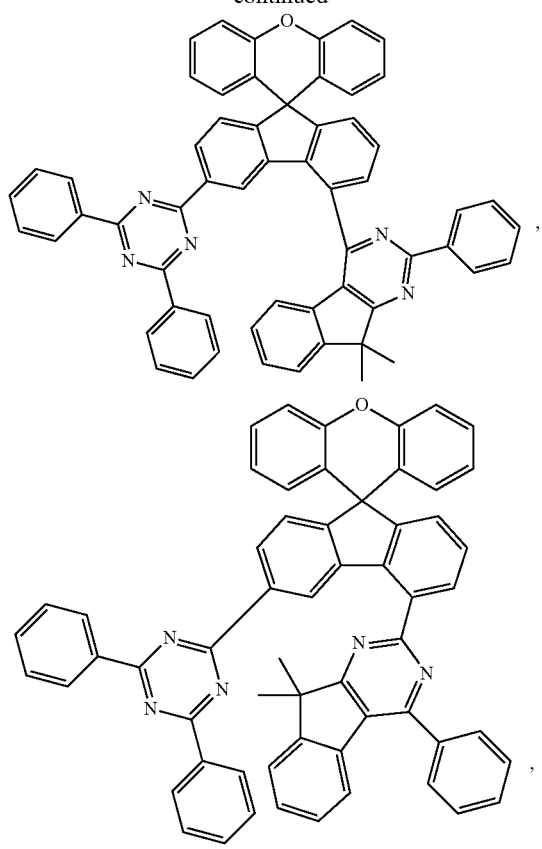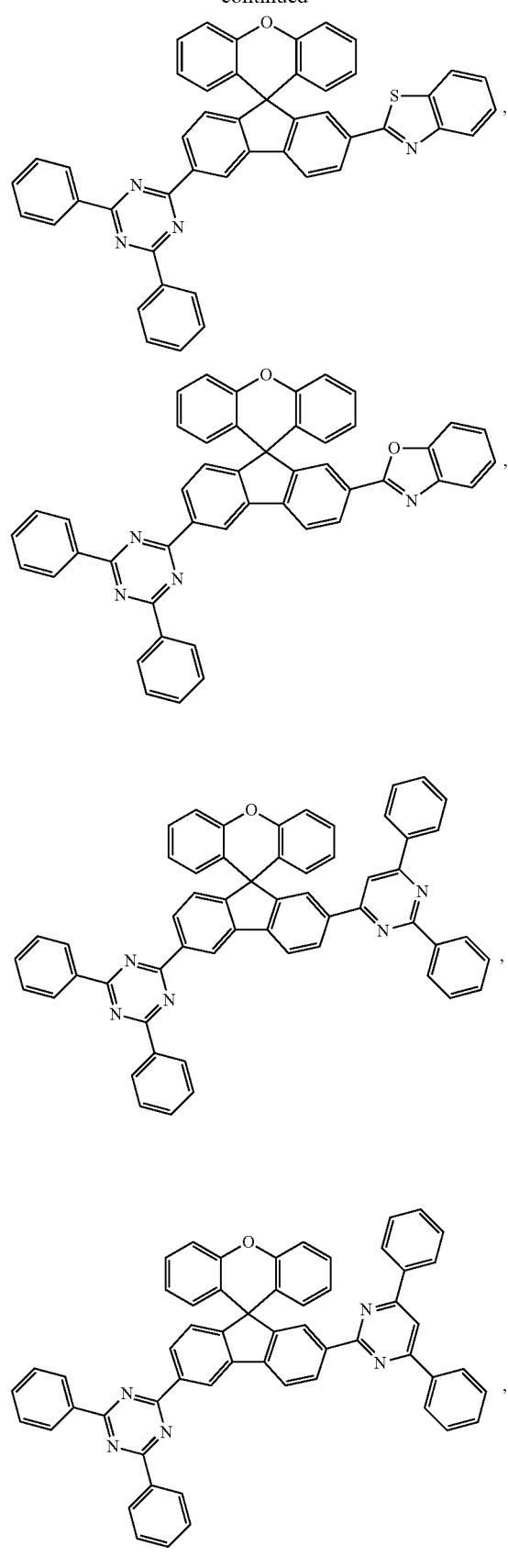

51
-continued
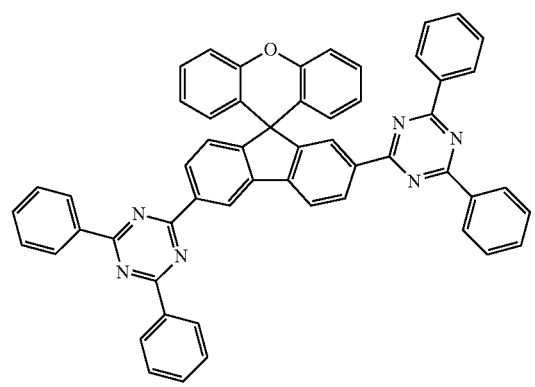
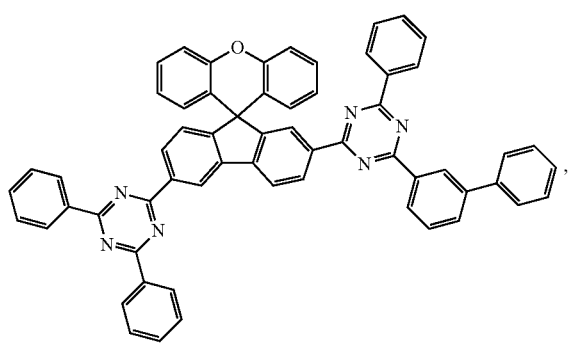
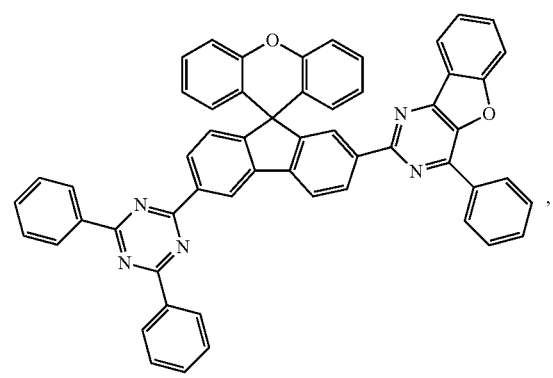
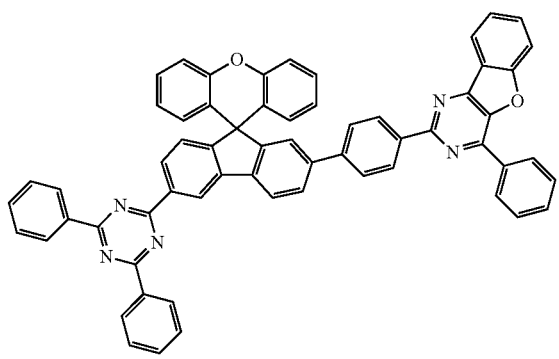
52
-continued
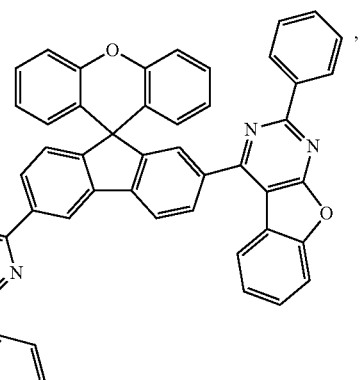
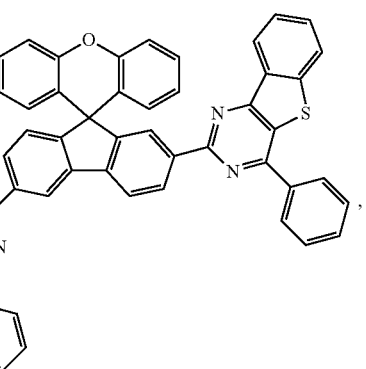
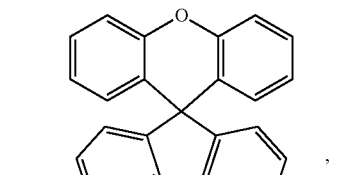
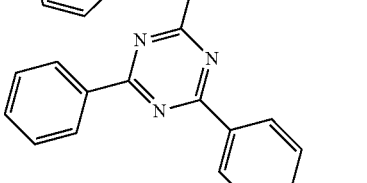

53
-continued
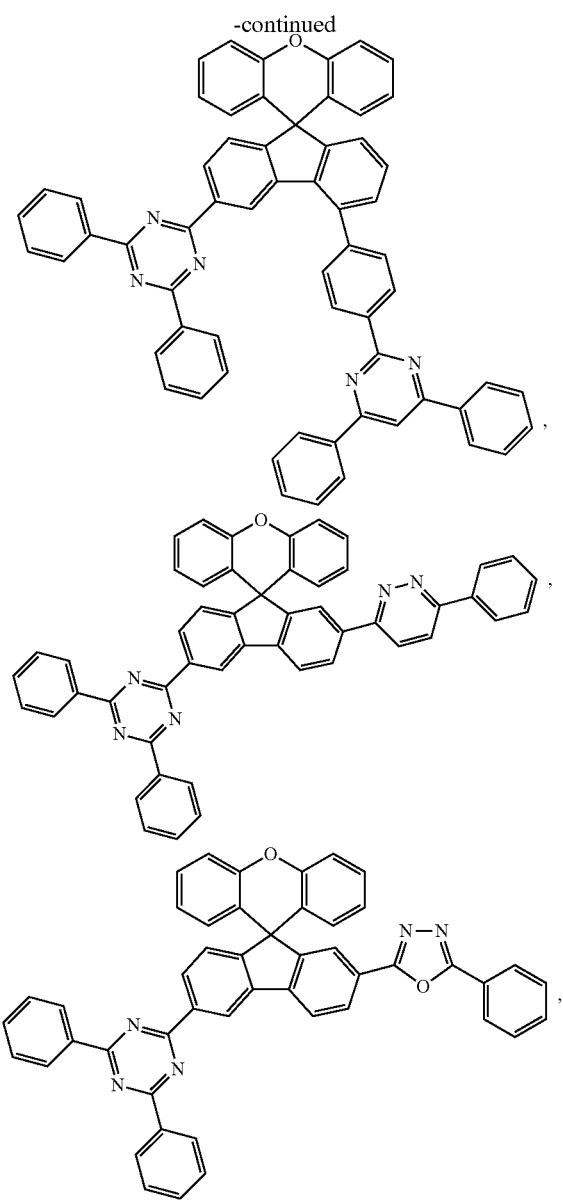
54
-continued
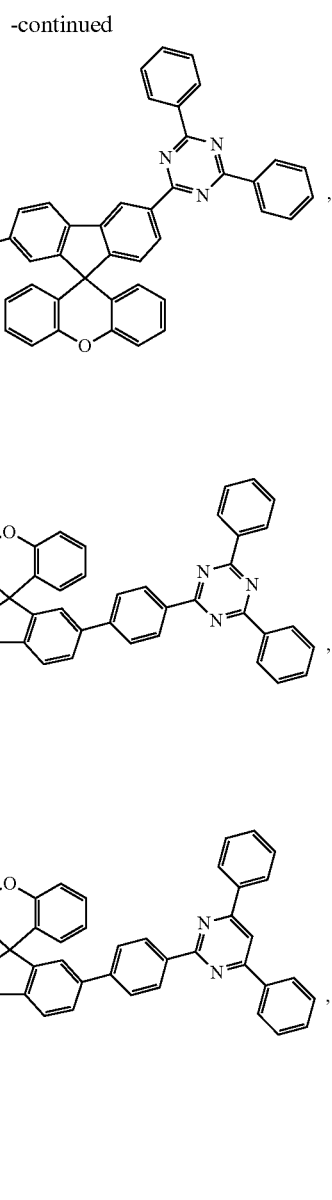
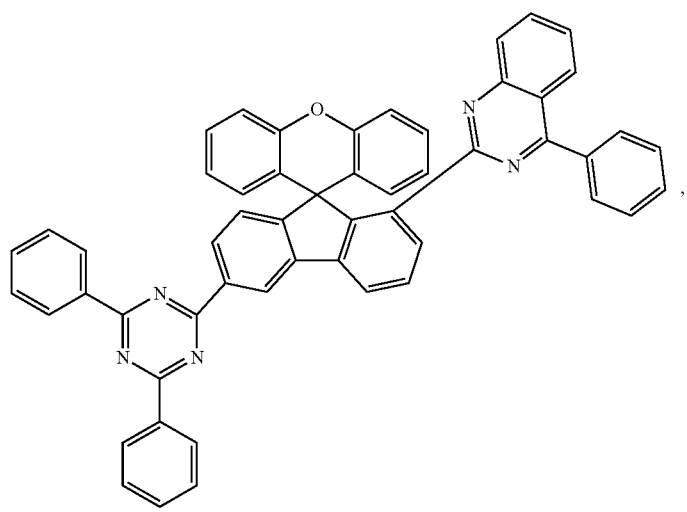

-continued
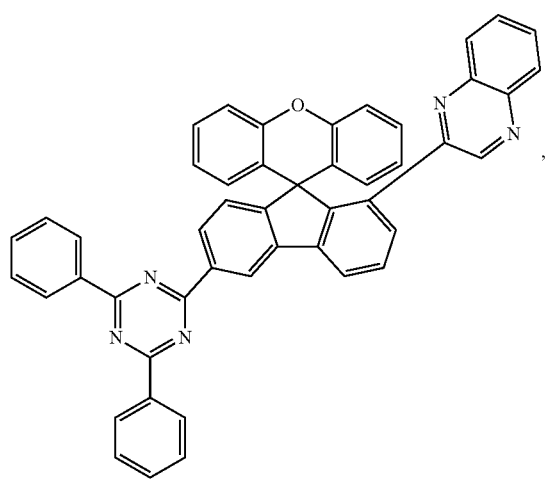
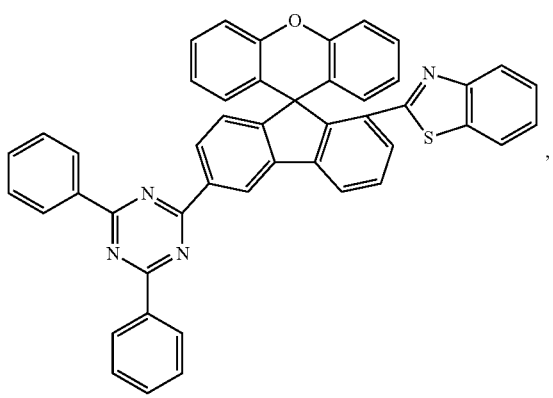
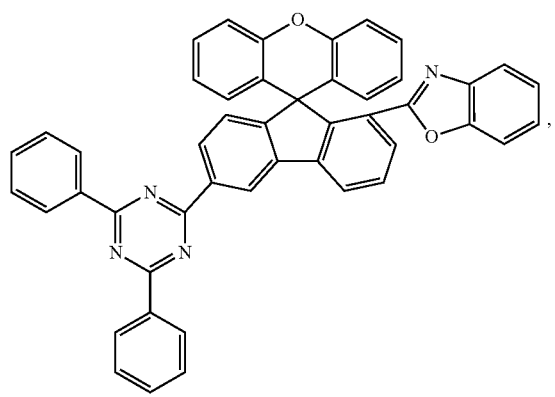
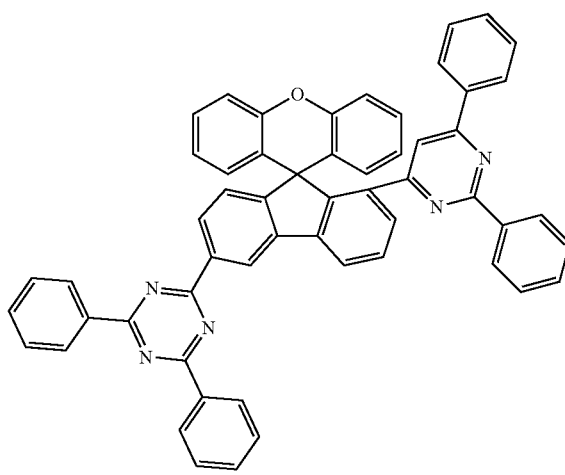
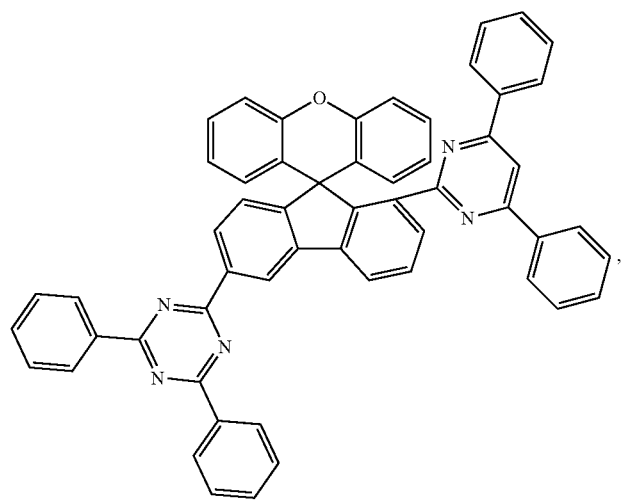

-continued
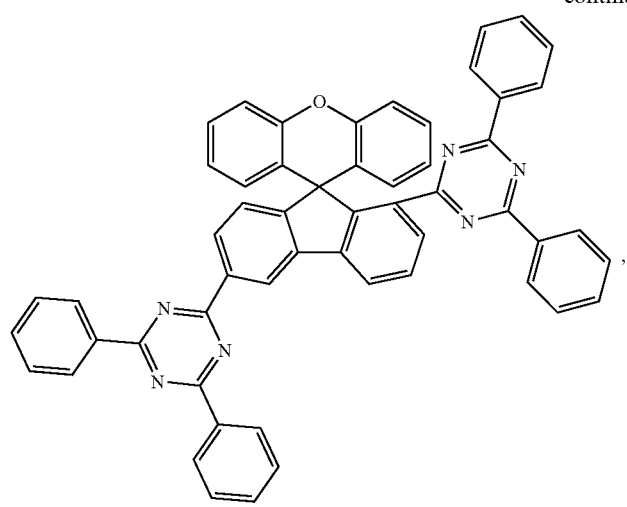
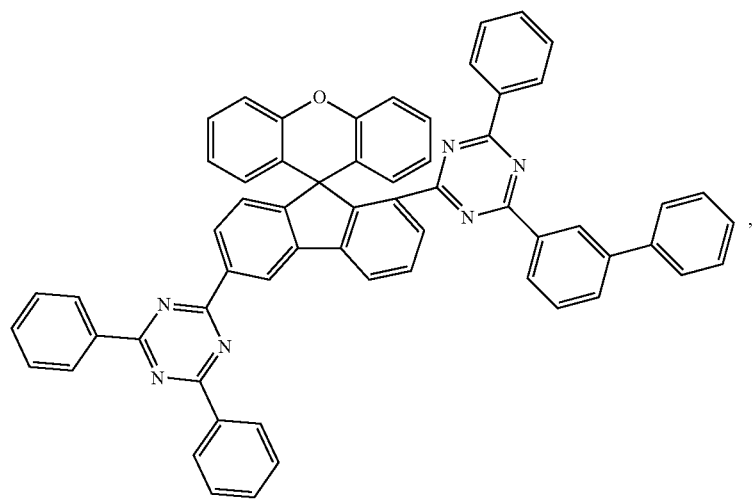
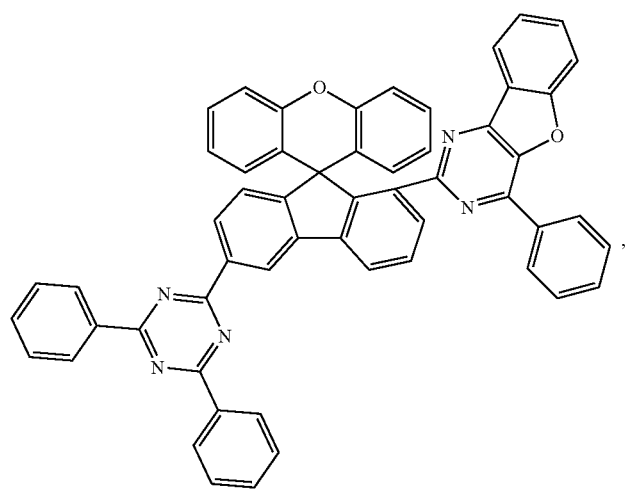

-continued
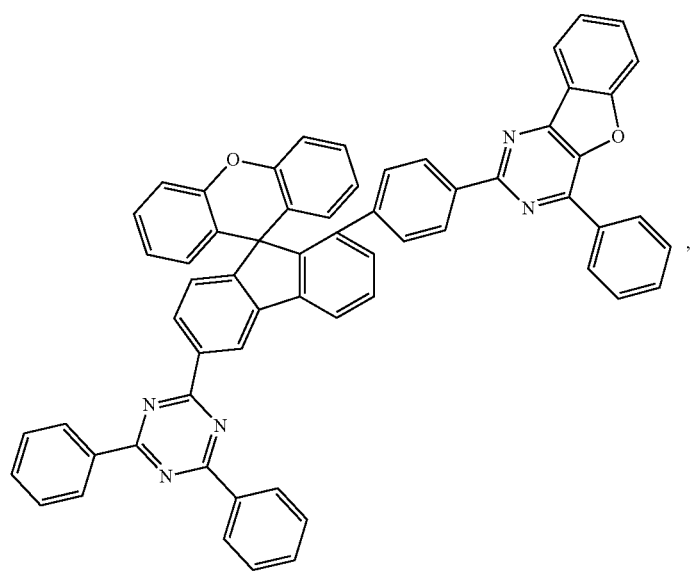
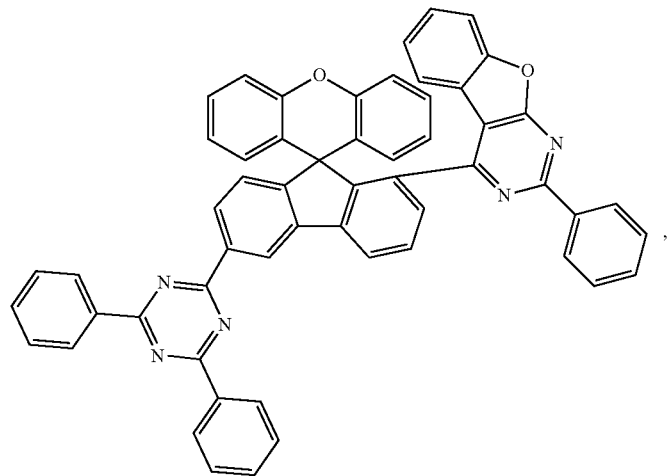
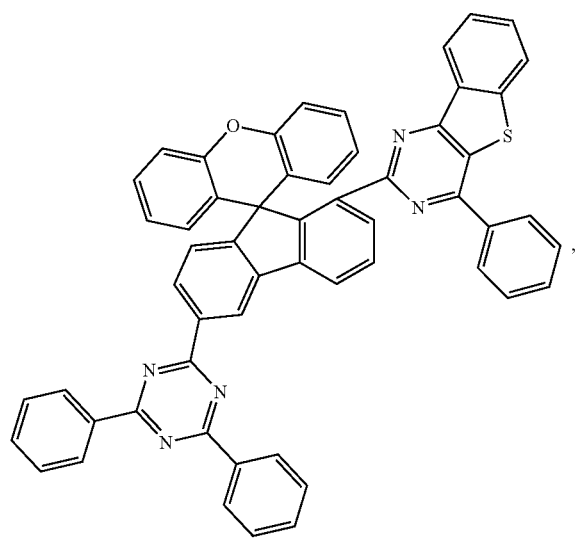

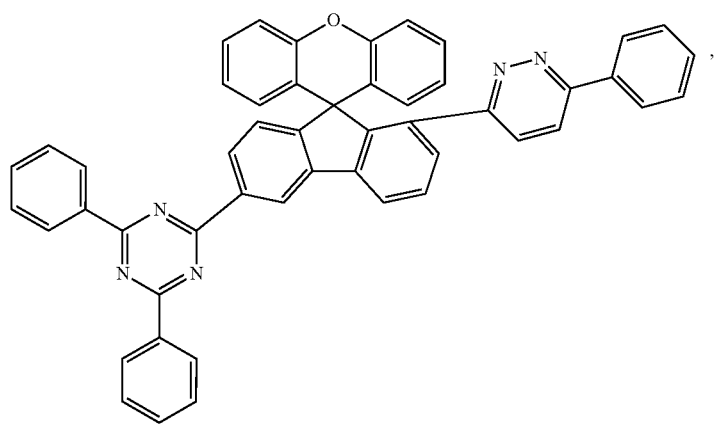
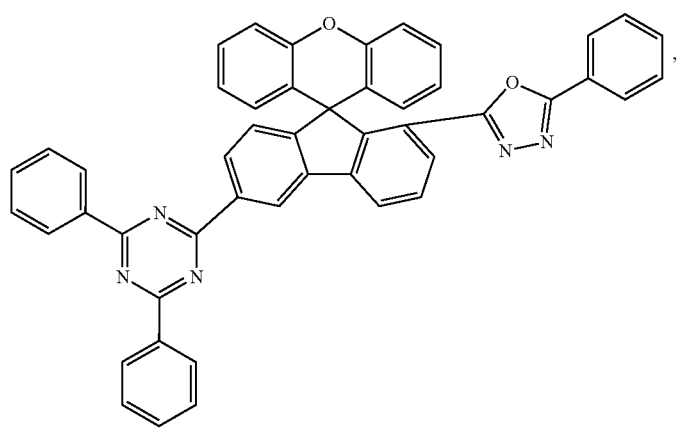
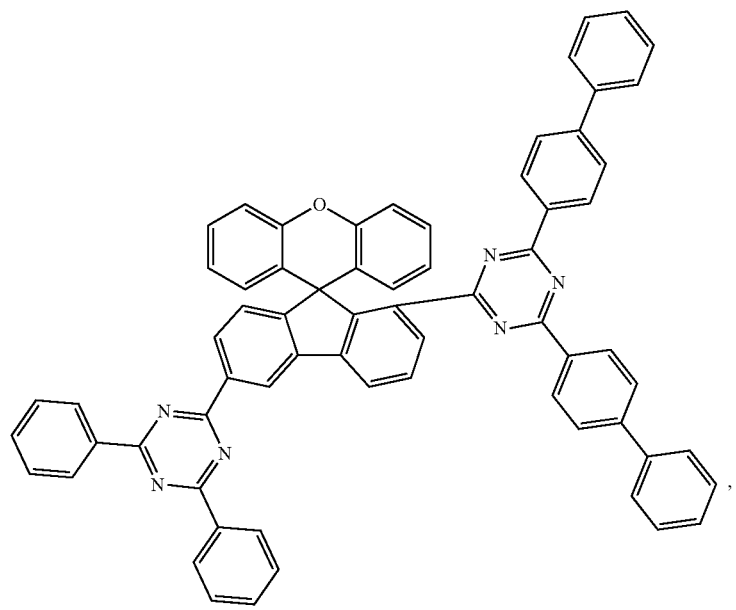

-continued
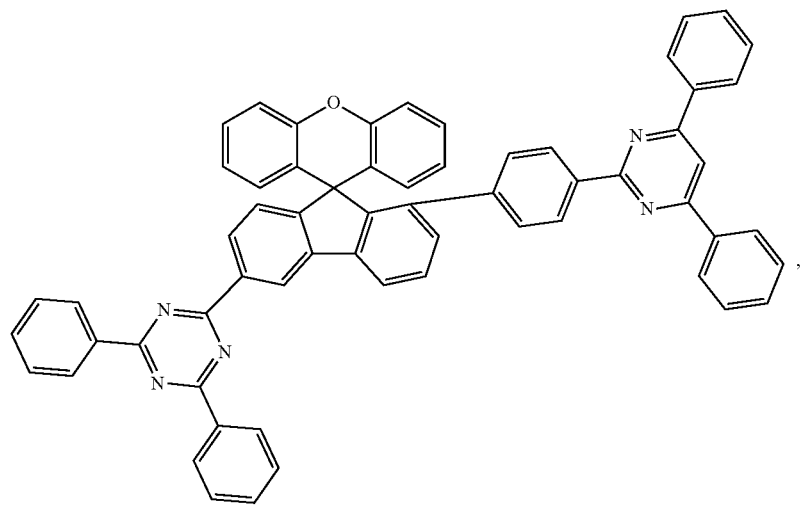
,
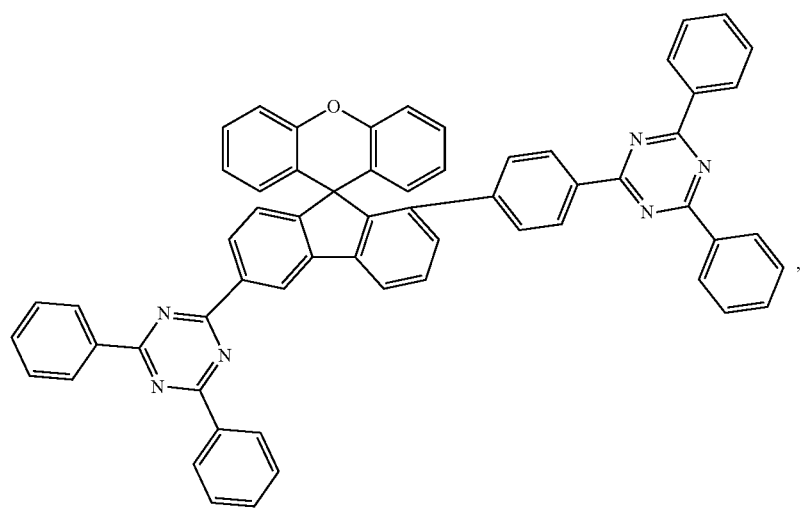
,

-continued
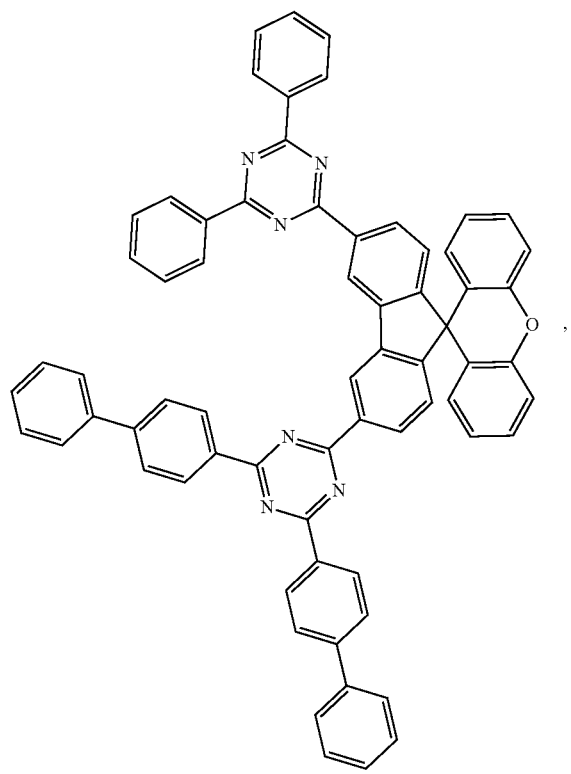
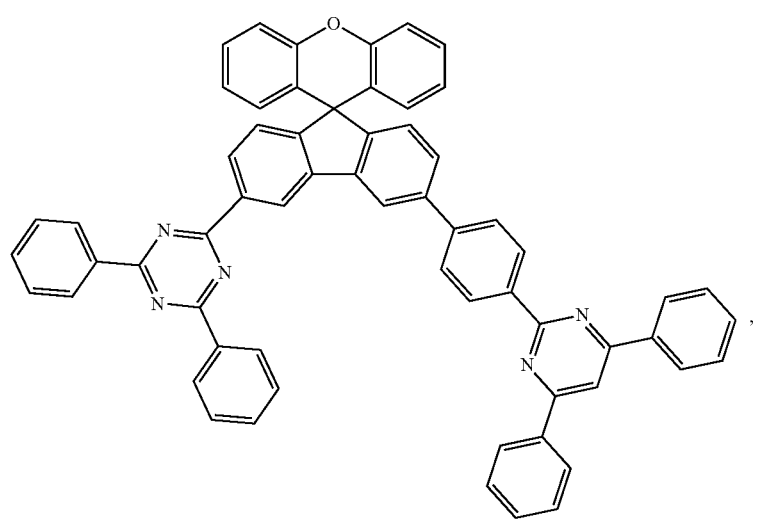

-continued
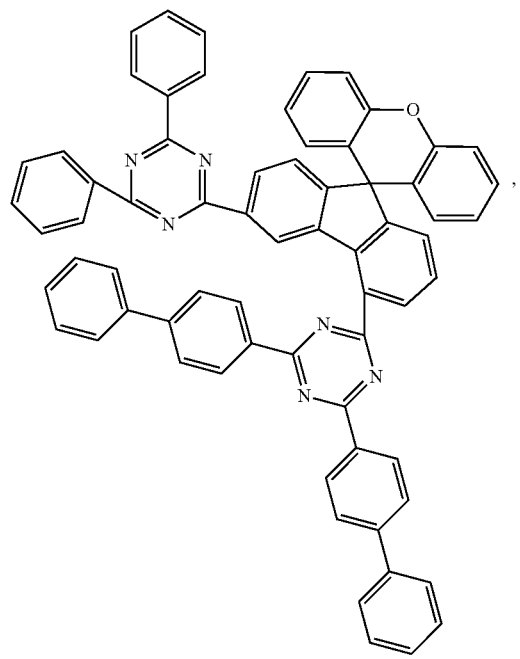
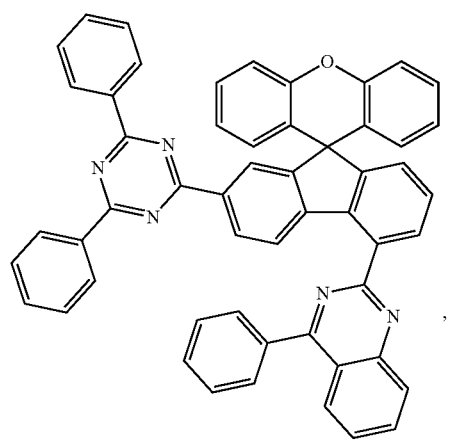
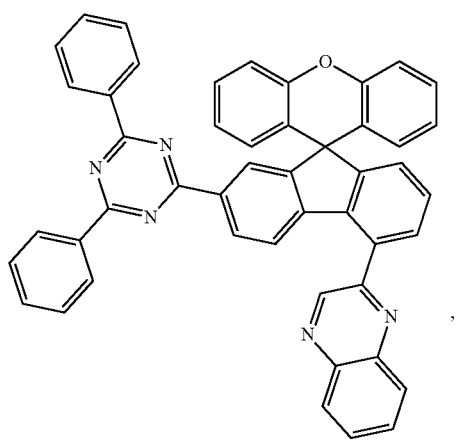
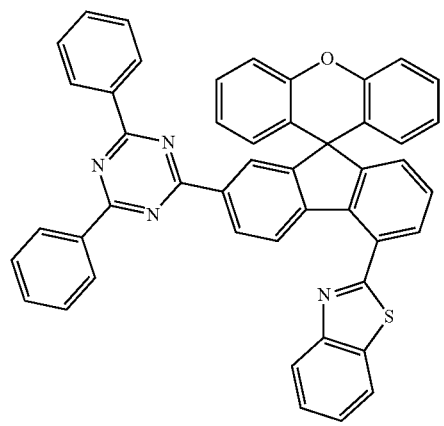
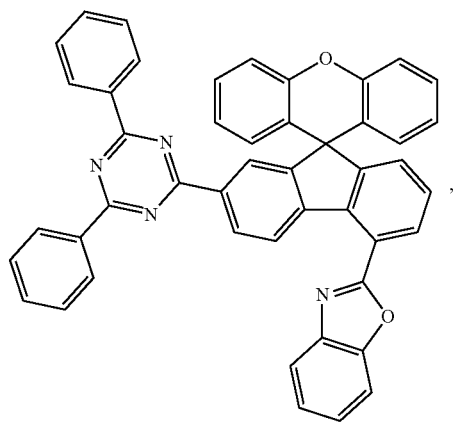

,
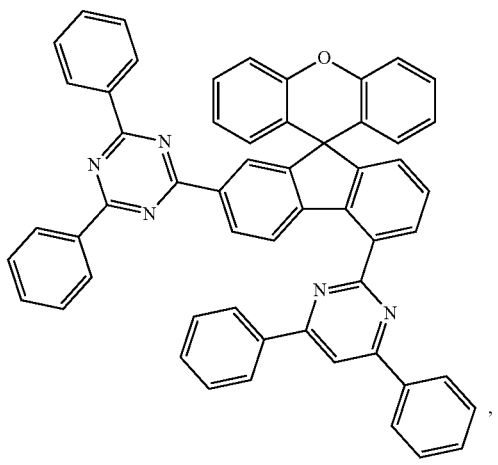
,
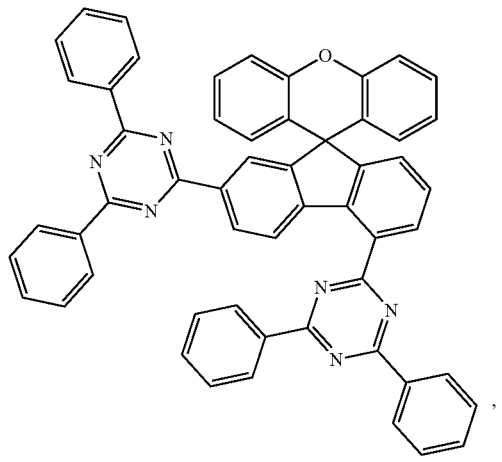
,
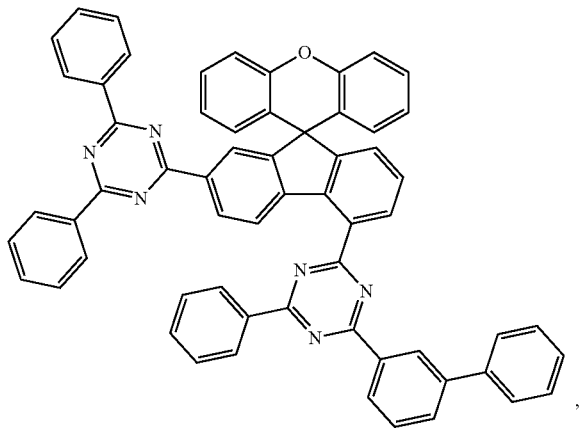
,
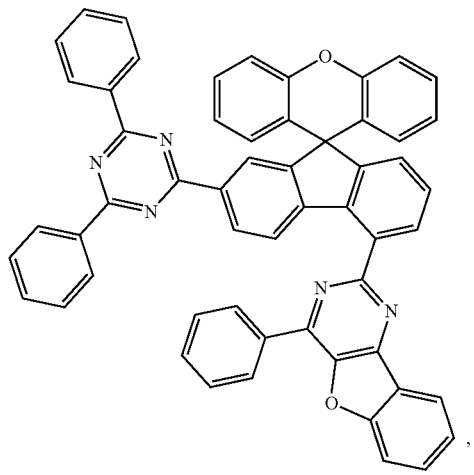
,
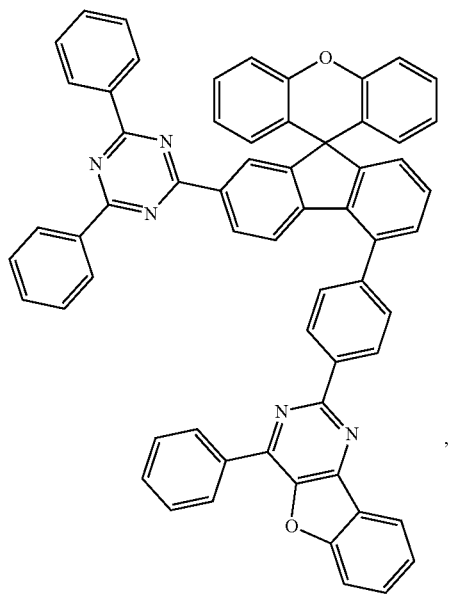
, 71
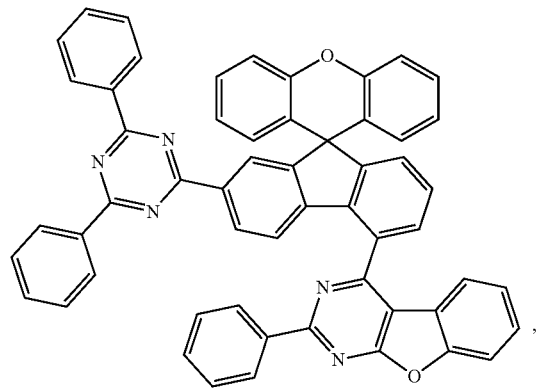
72
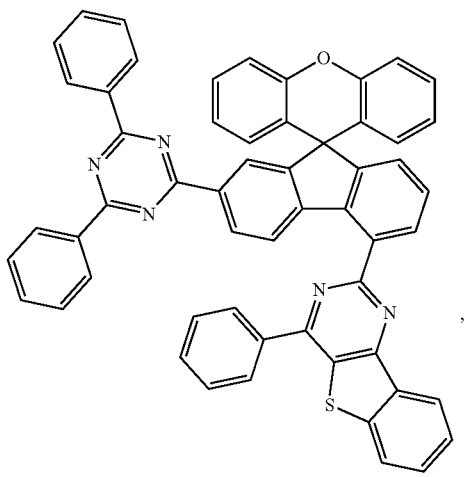
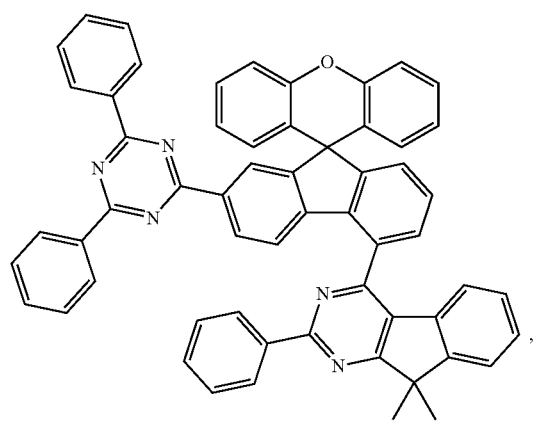
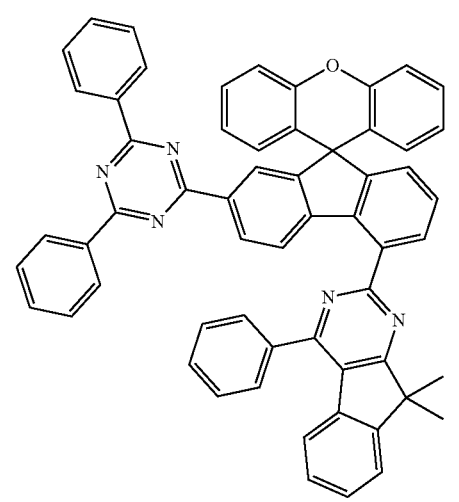
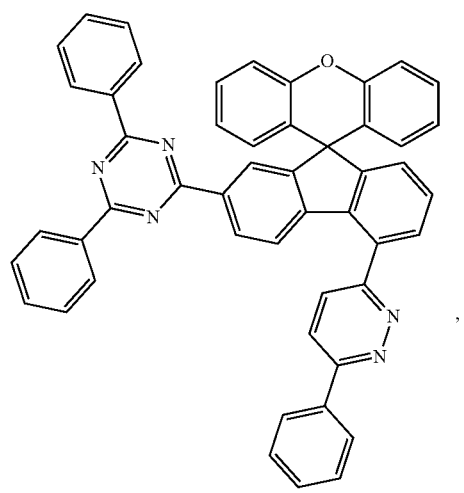
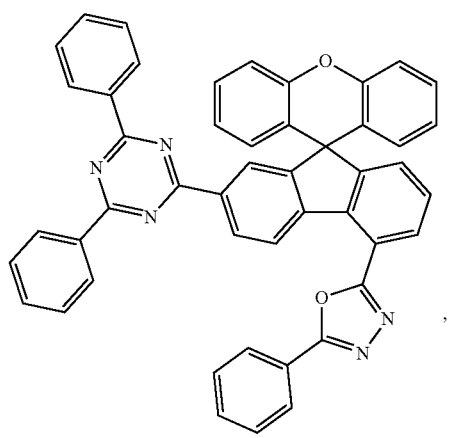

-continued
73
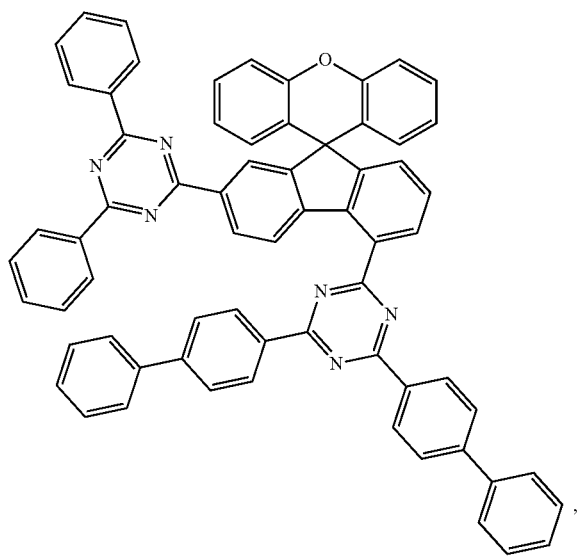
74
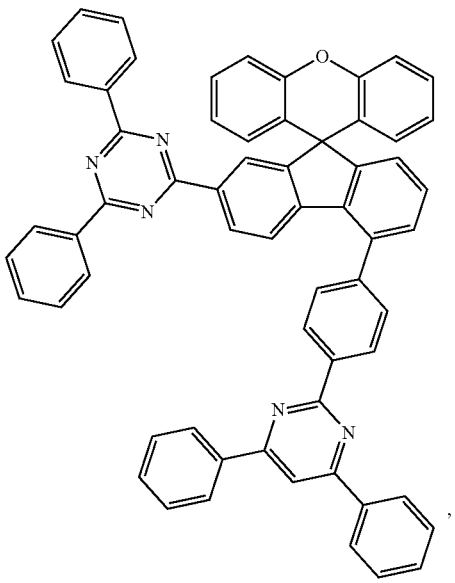
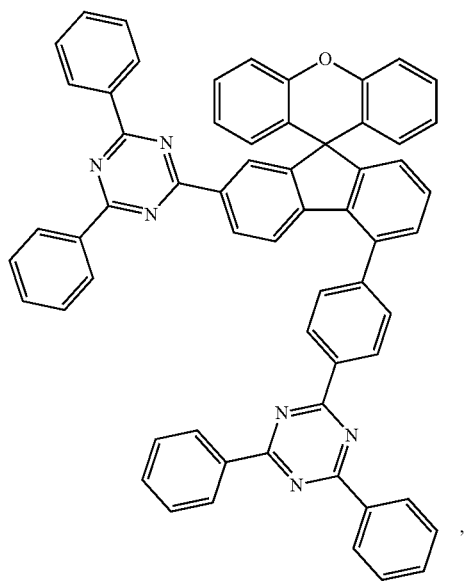
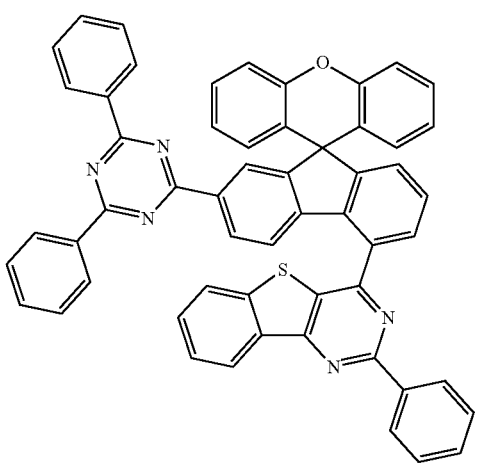
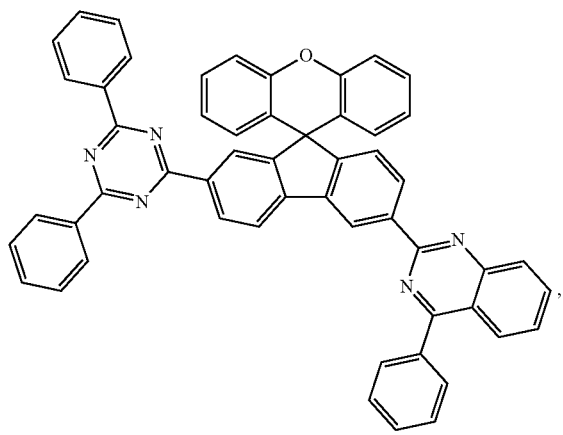
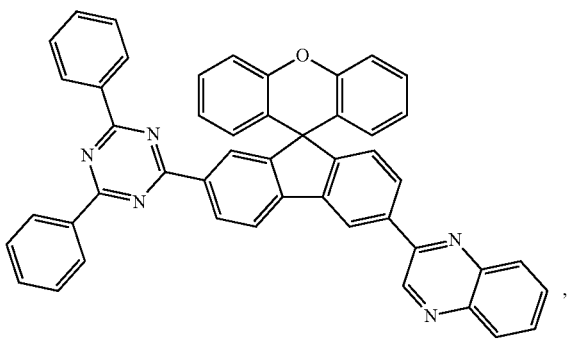

75
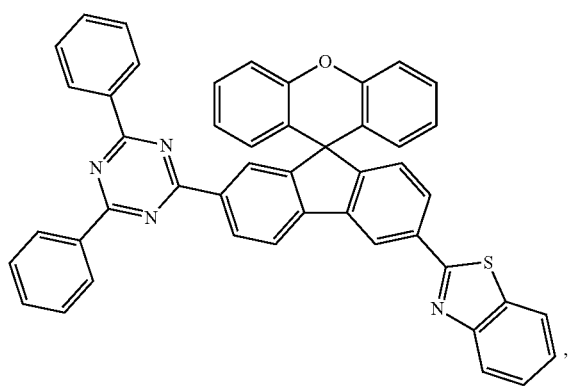
76
-continued
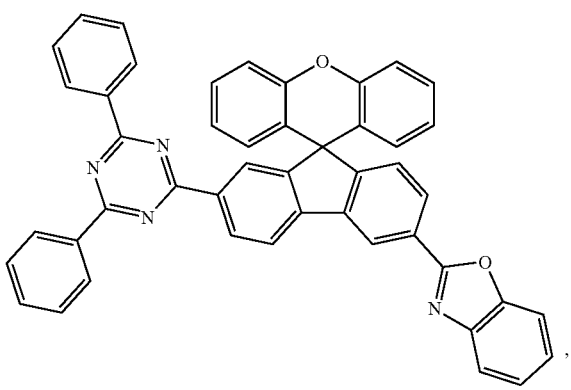
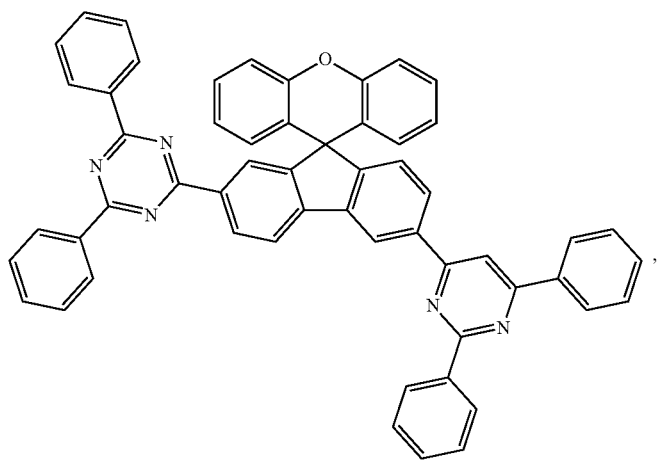
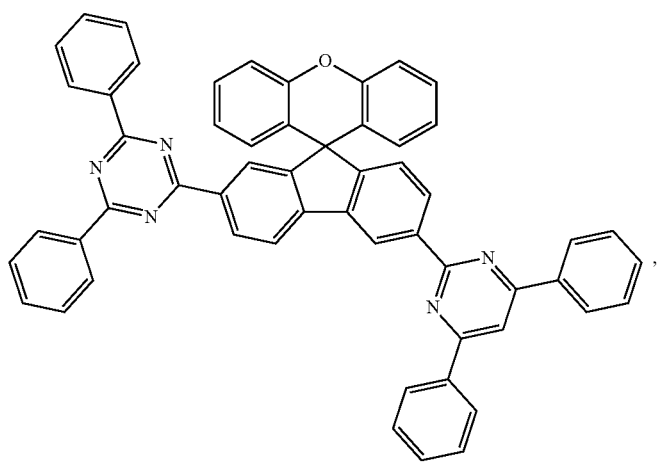

-continued
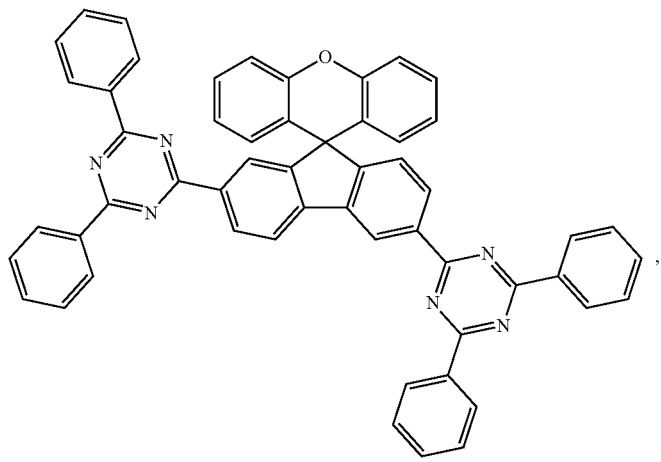
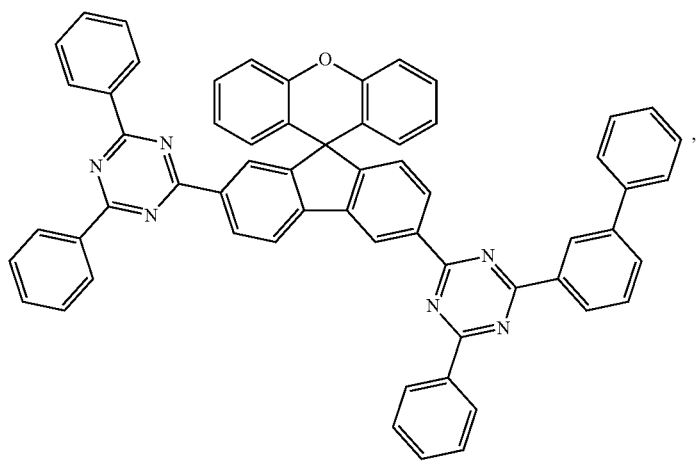
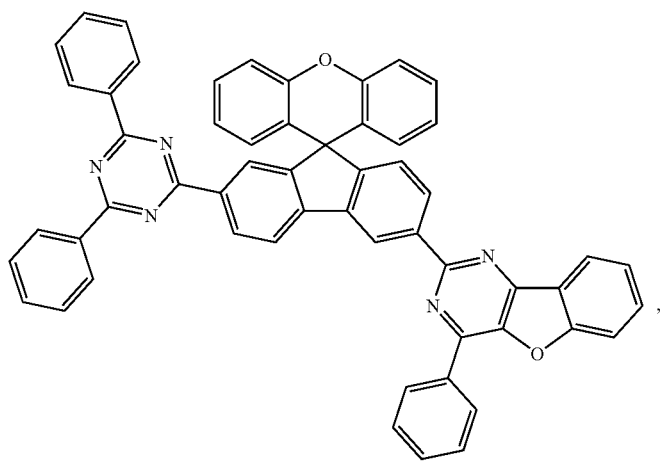

-continued
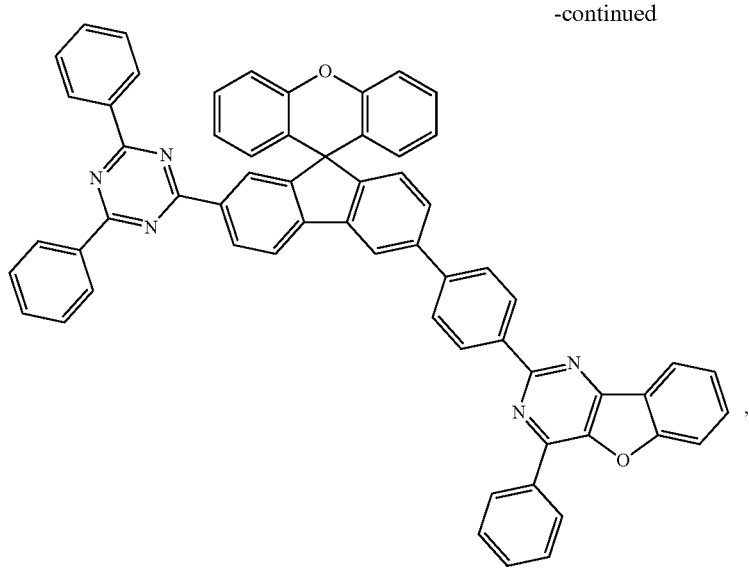
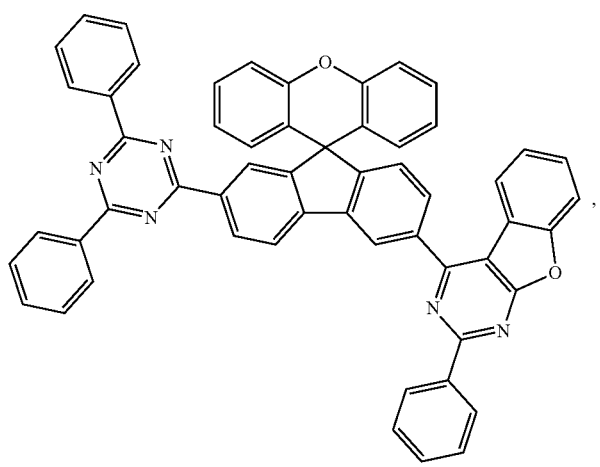
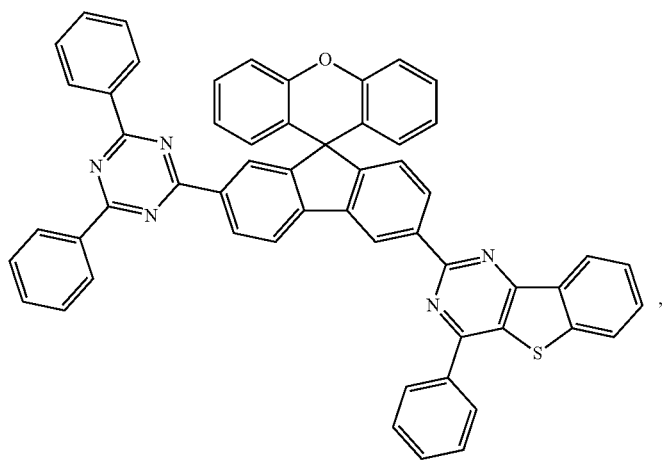

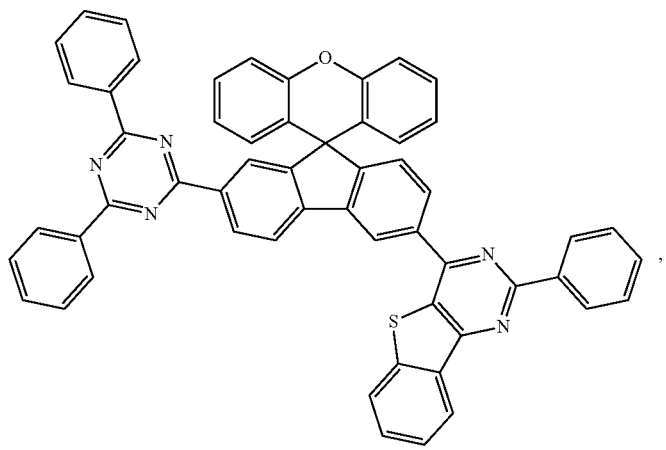

83
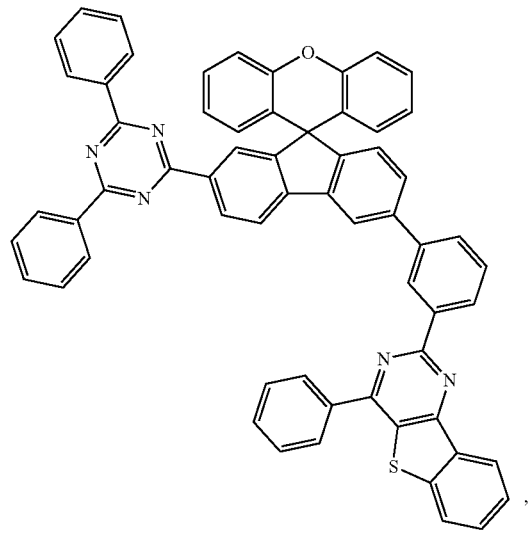
84
-continued
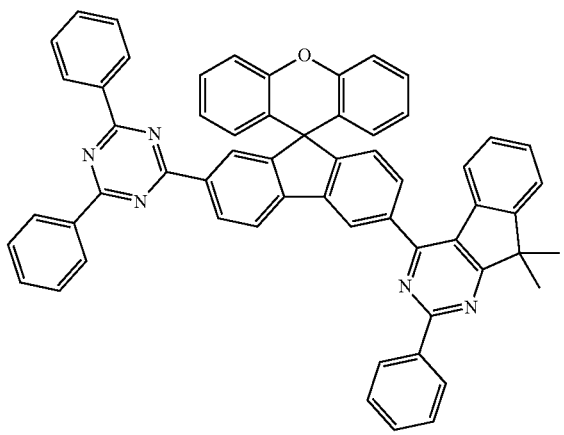
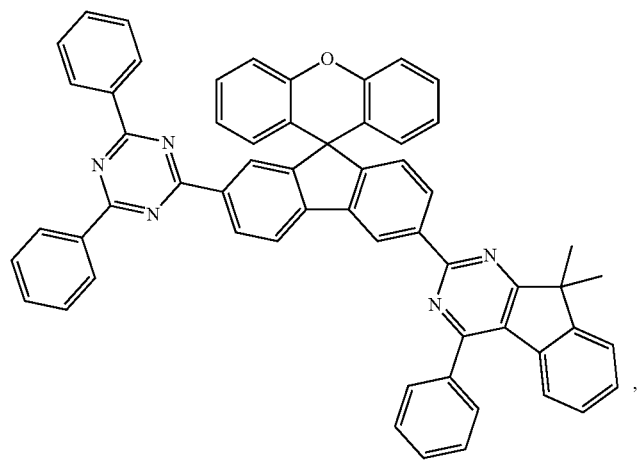
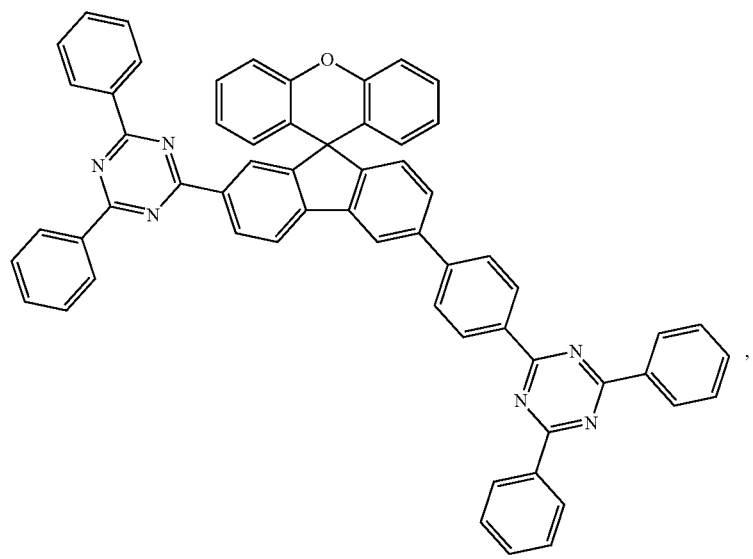 [SMILES: c1ccc(-c2nc(-c3ccccc3)nc(-c3ccc(-c4ccc5c(c4)-c4ccc(-c6nc(-c7ccccc7)nc(-c7ccccc7)n6)cc4C54c5ccccc5Oc5ccccc54)cc3)n2)cc1]

-continued
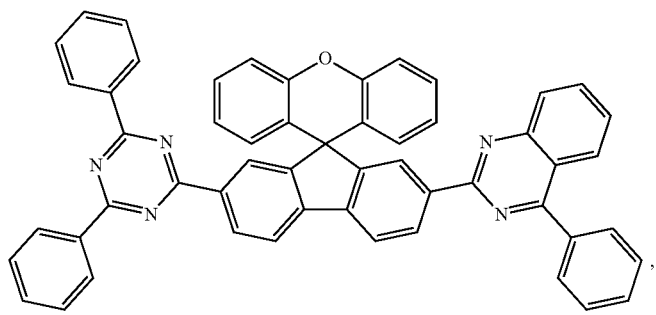
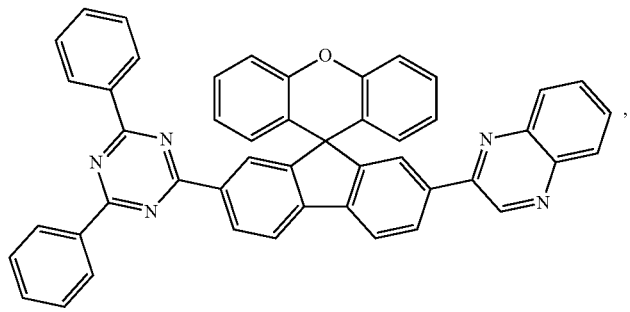
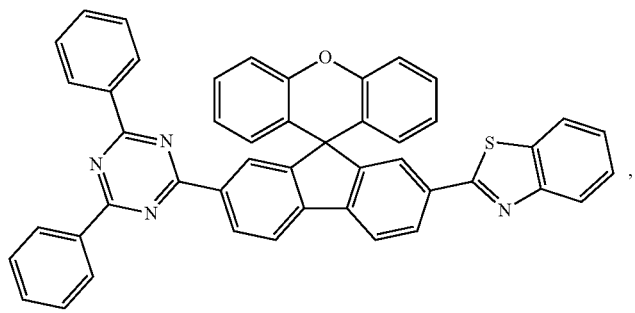
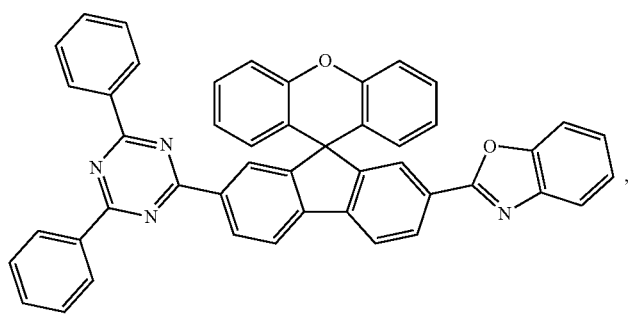
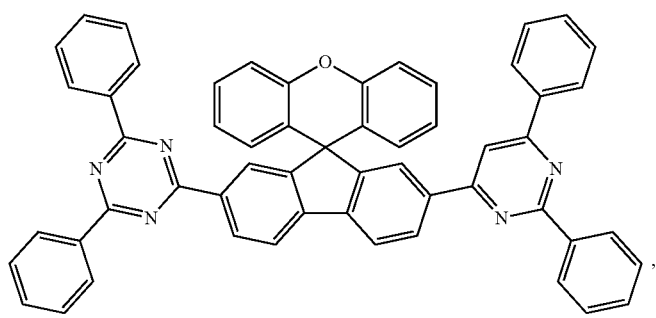

-continued
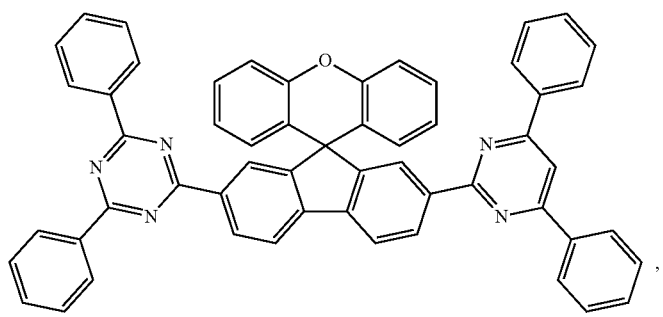,
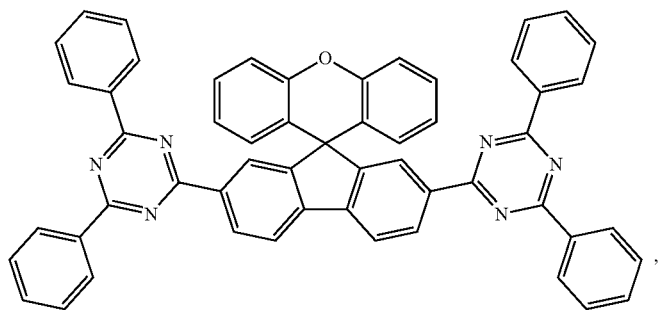,
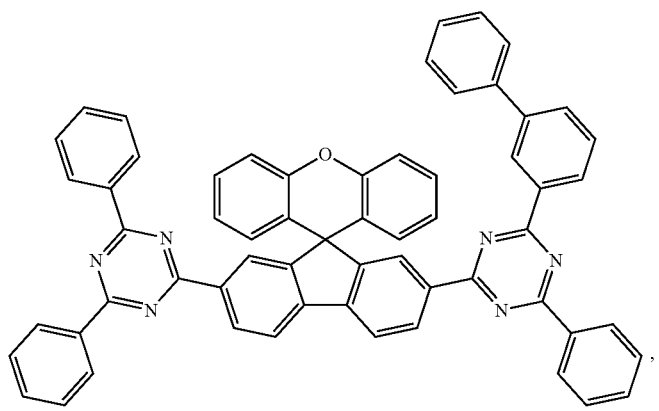,
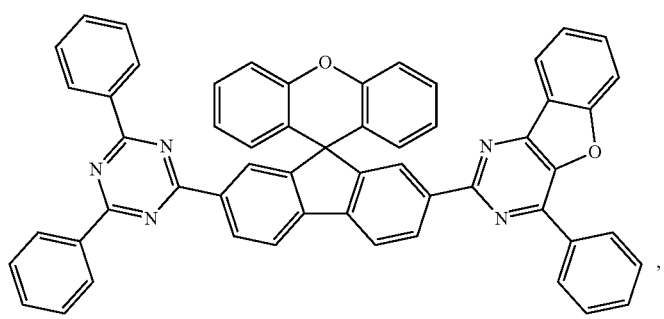,
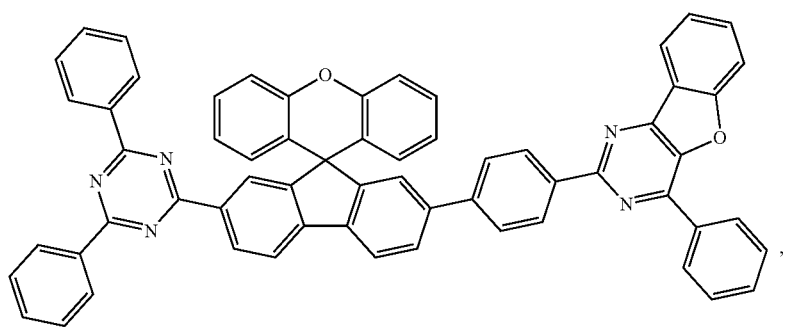,

-continued
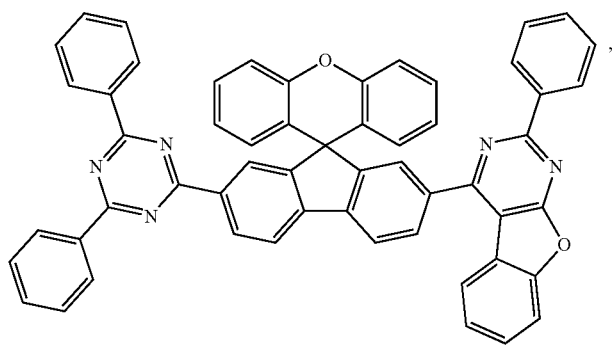
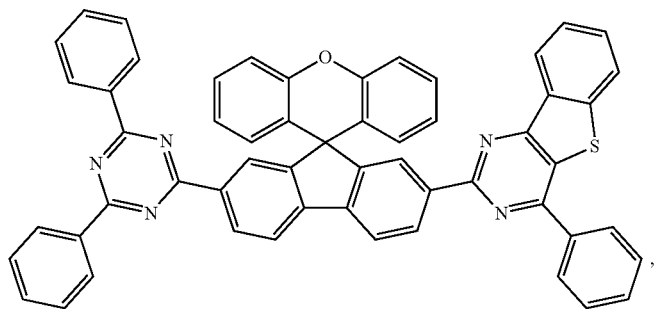
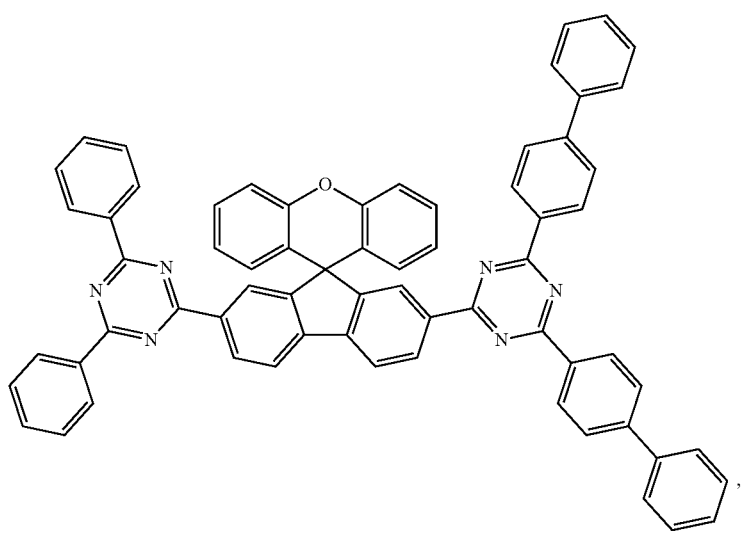
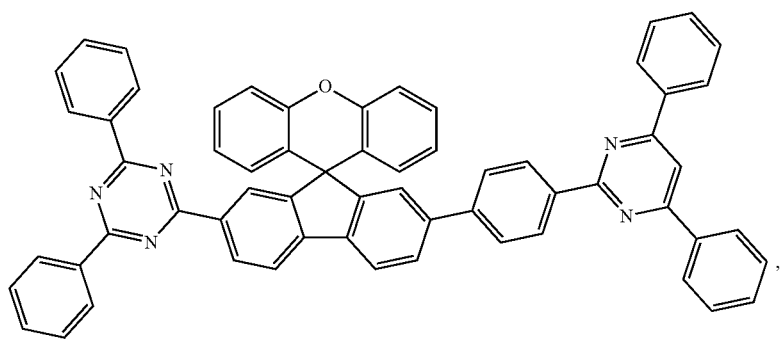

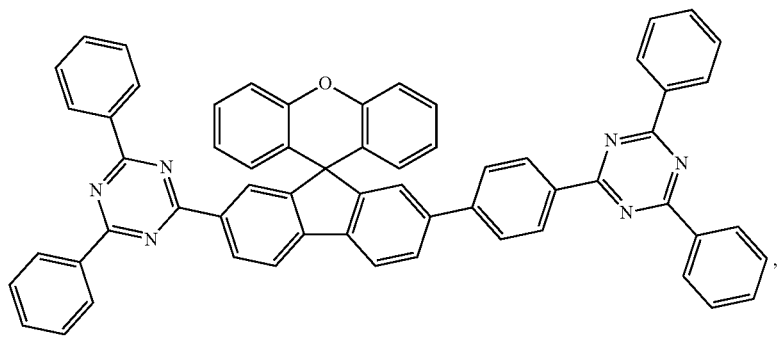
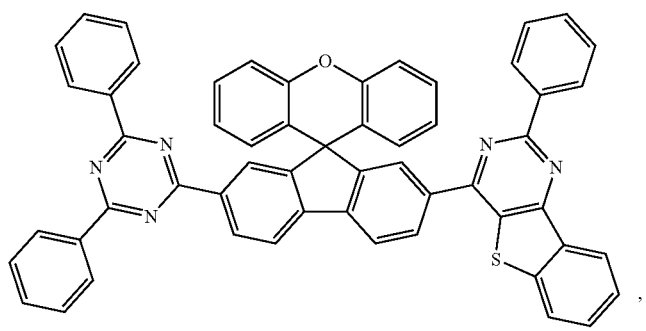
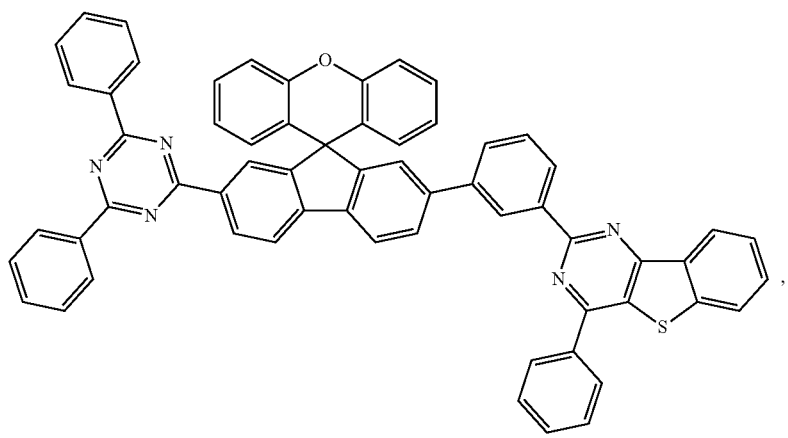
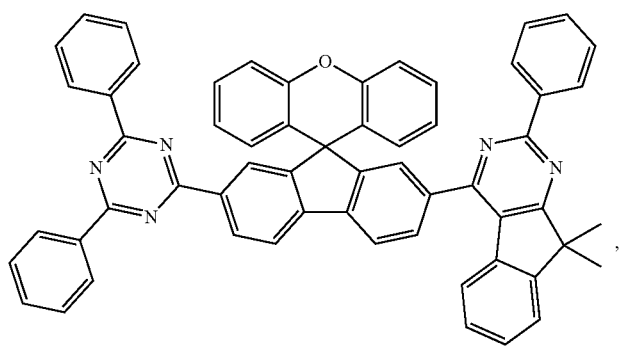

-continued
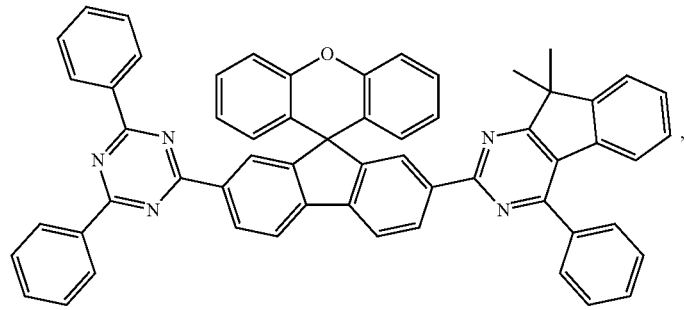
,
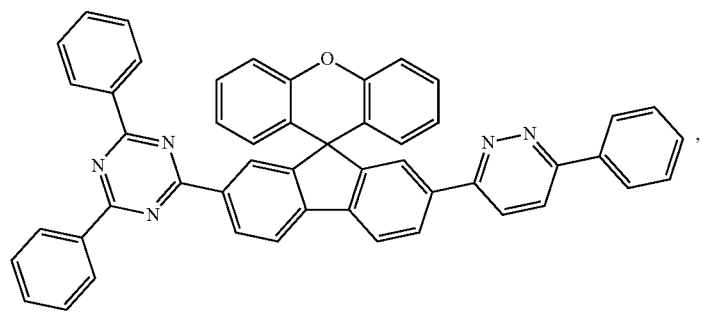
,
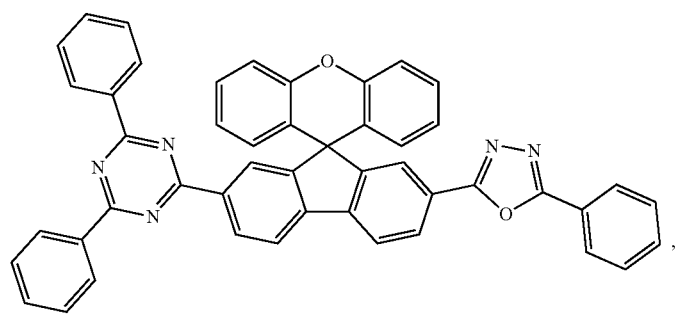
,
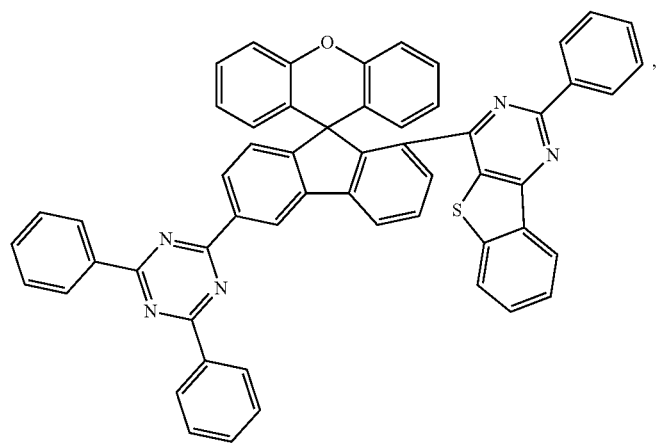
,

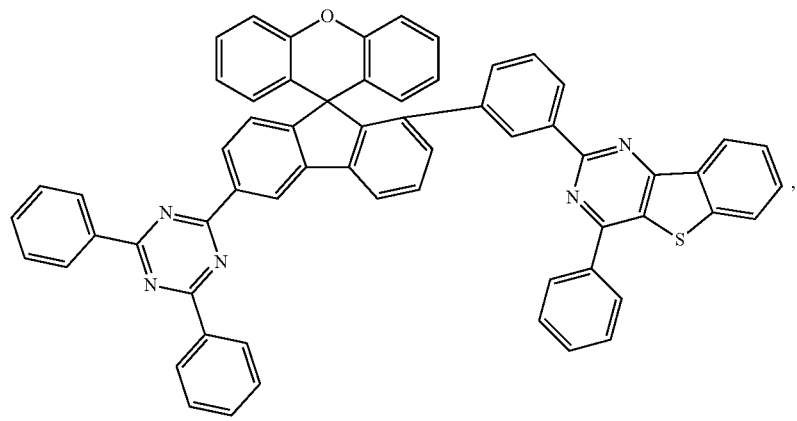
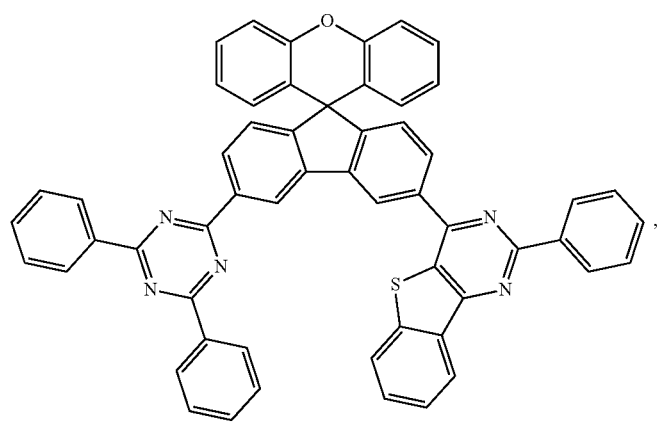
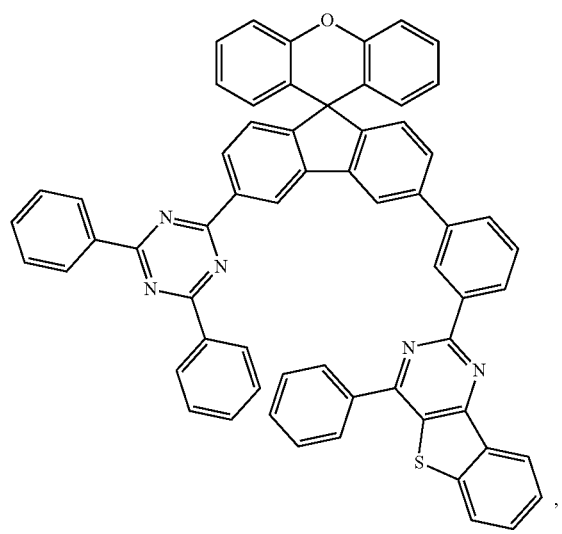

-continued
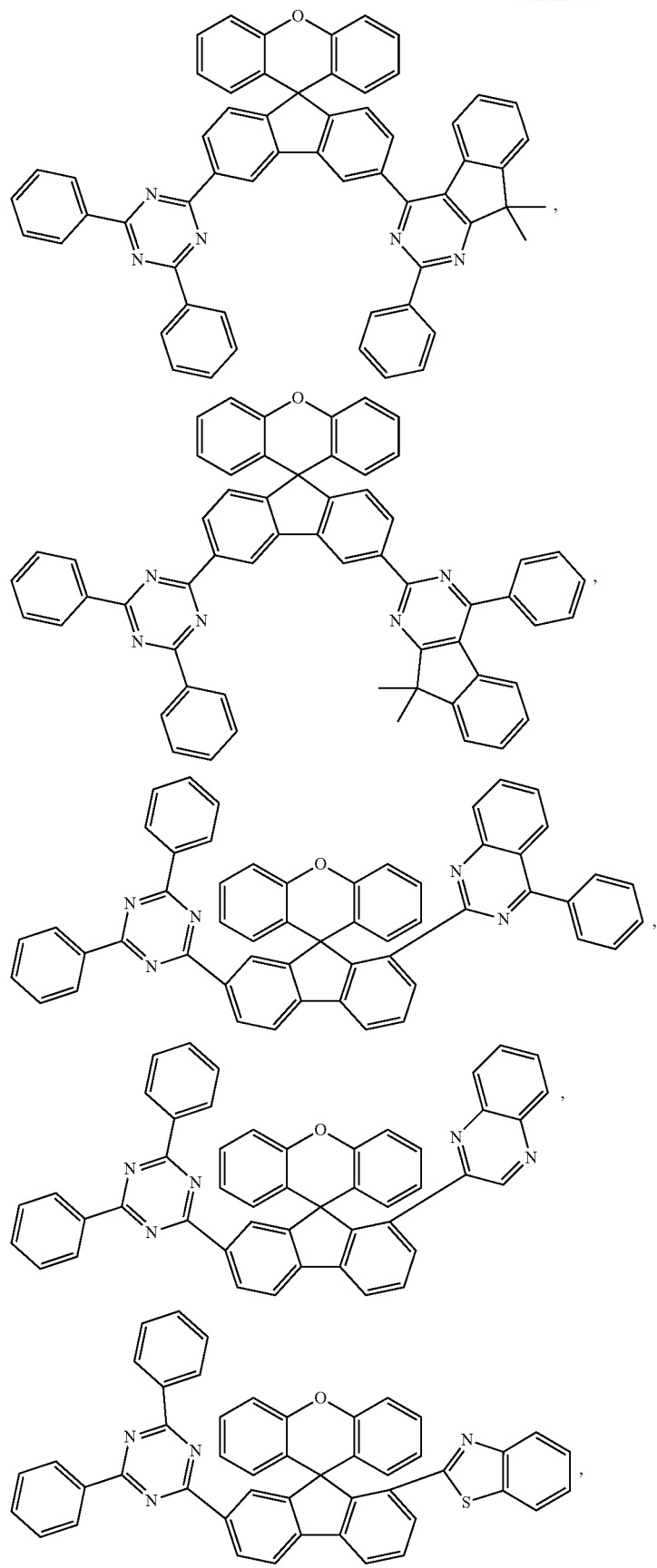

-continued
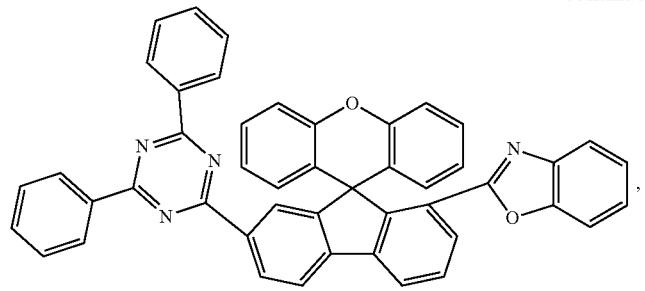
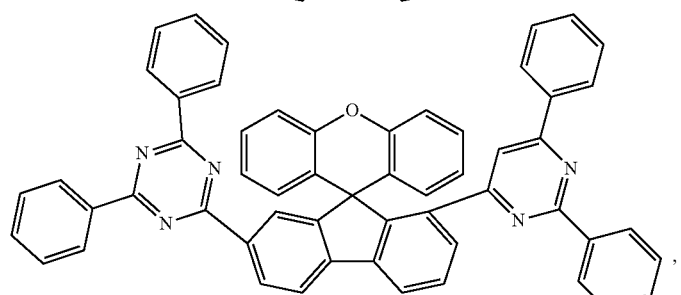
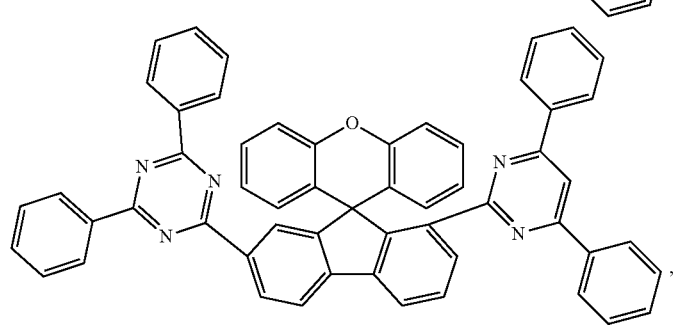
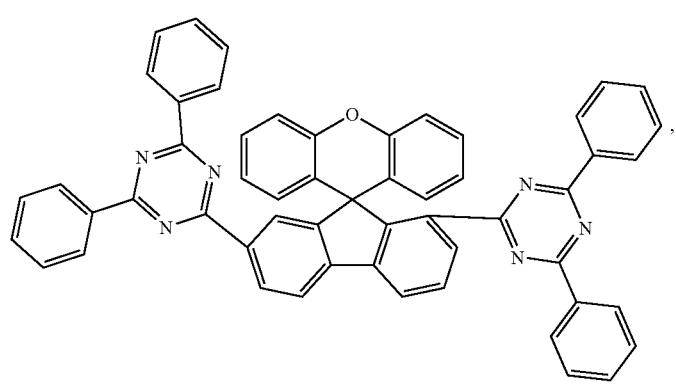
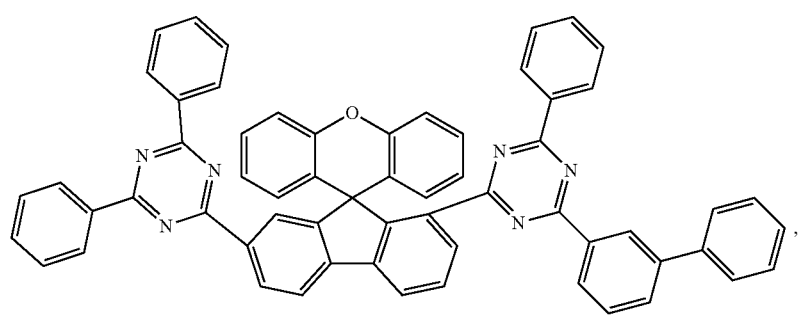

-continued
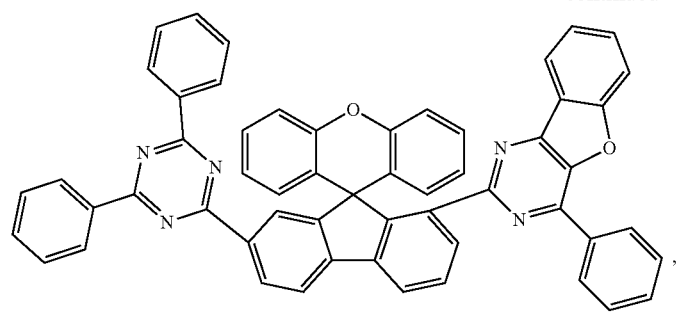
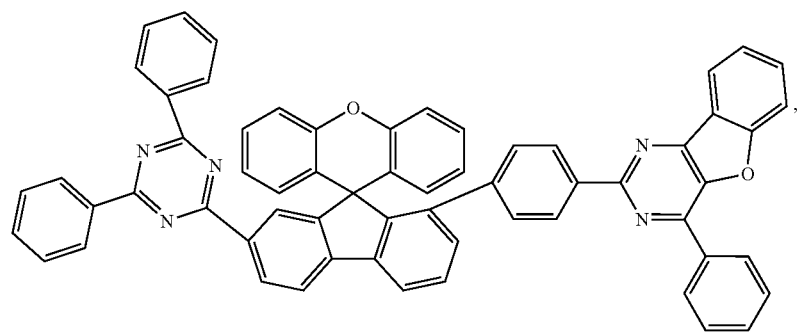
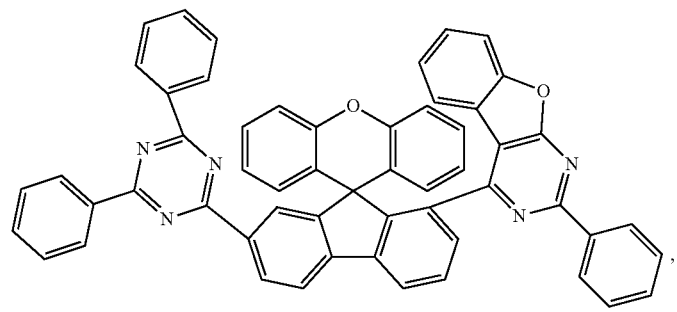
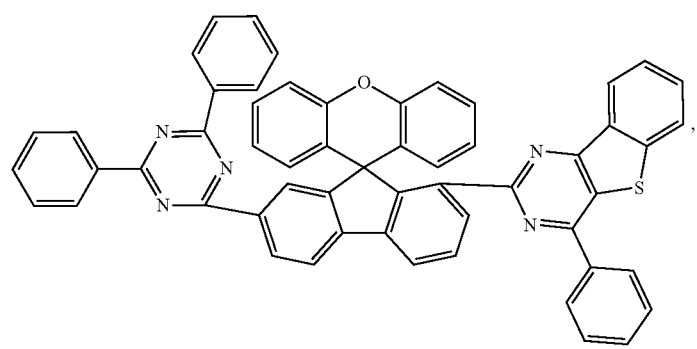

-continued
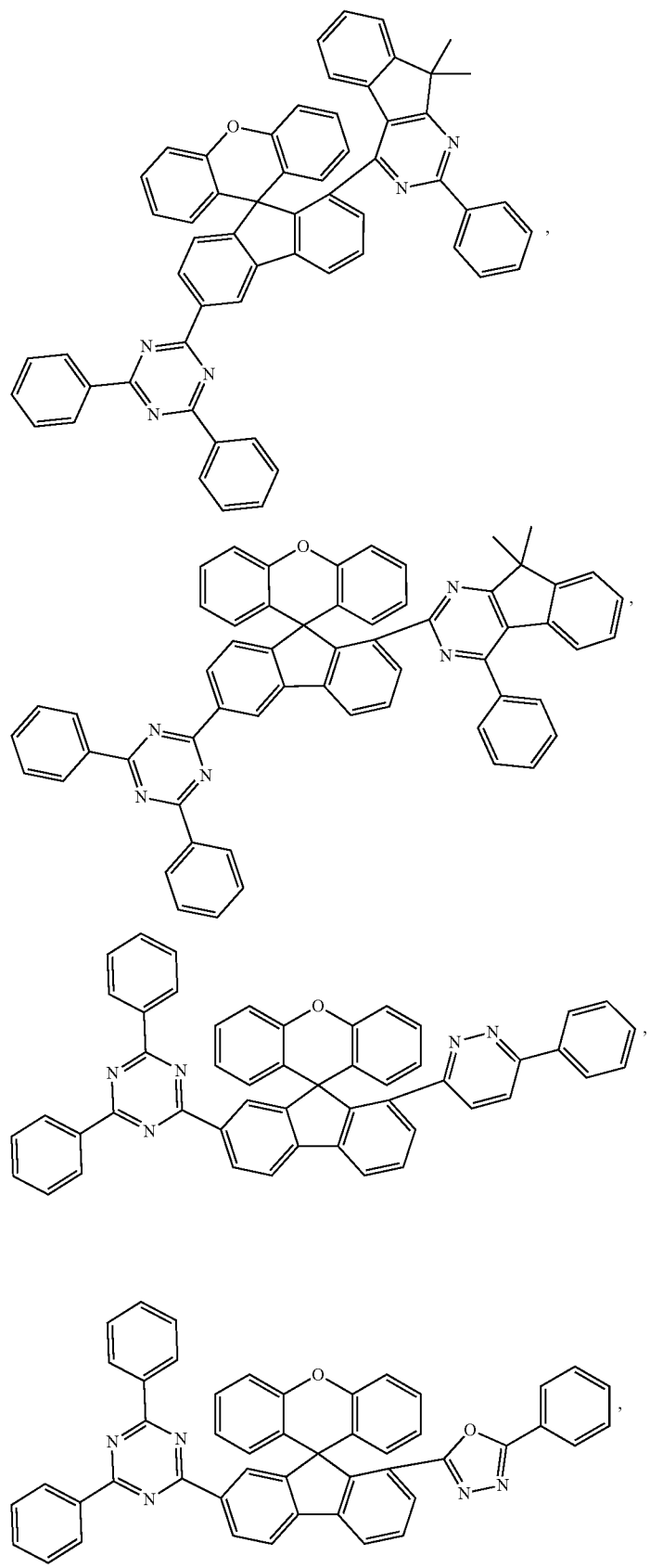

-continued
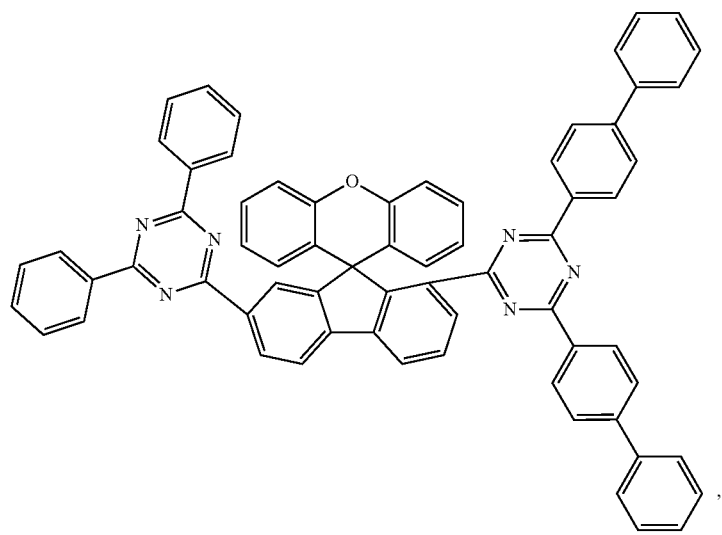
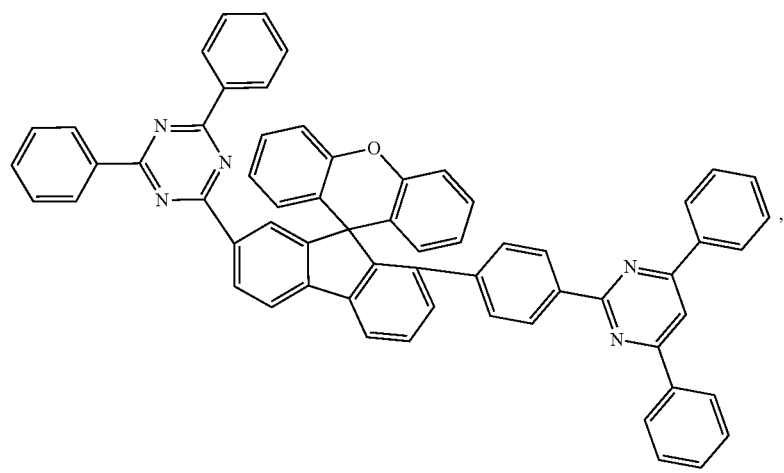
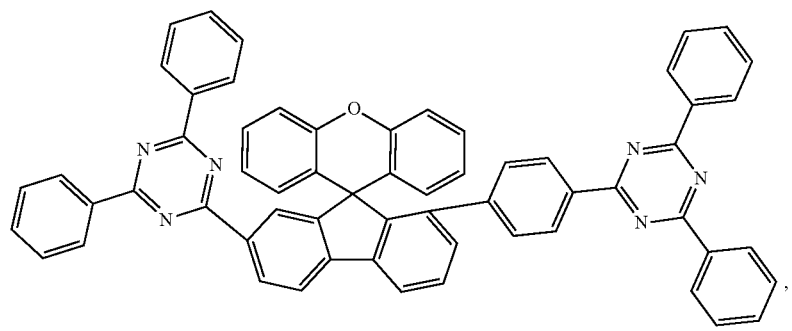
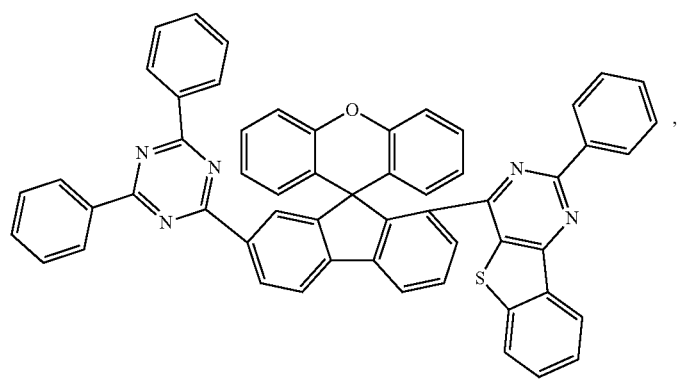

-continued
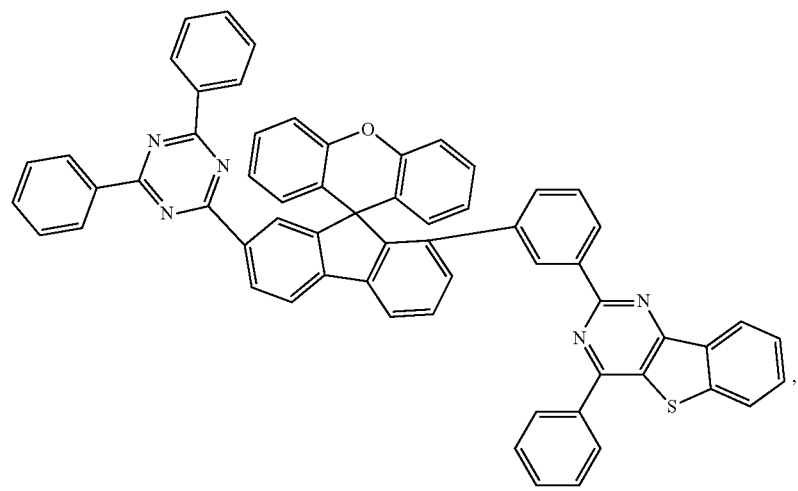
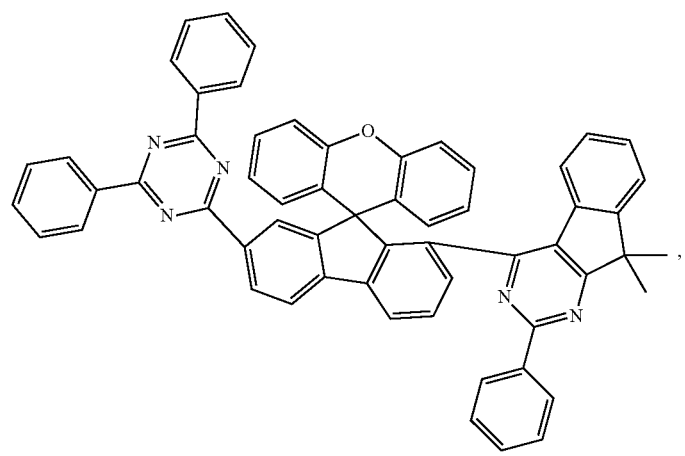
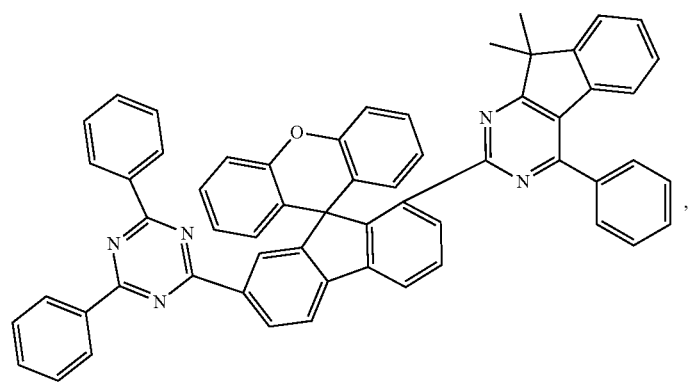

-continued
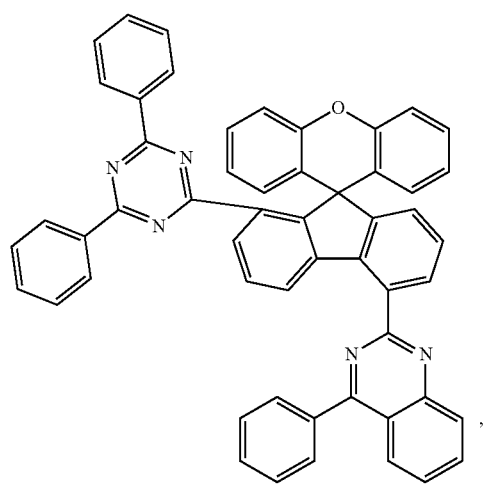
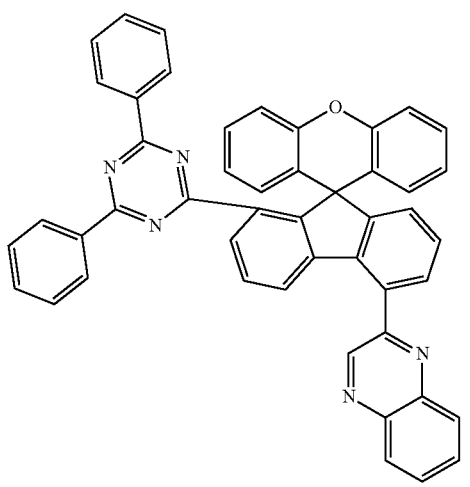
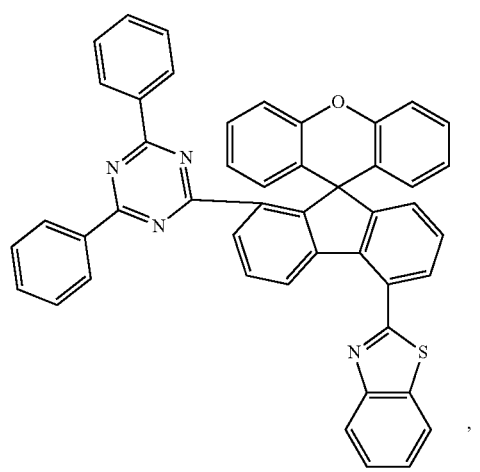
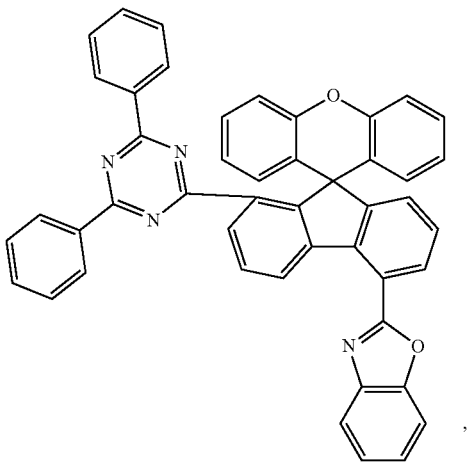
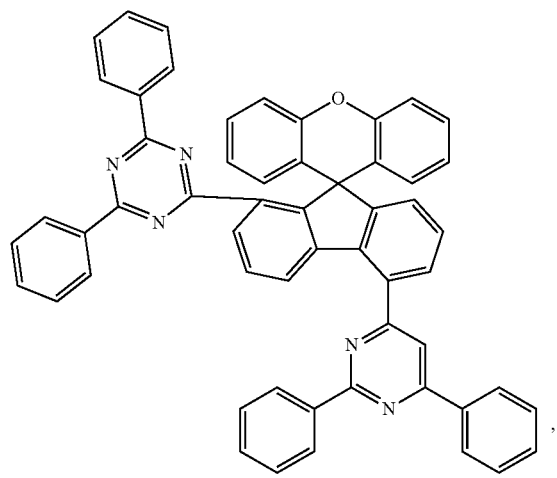
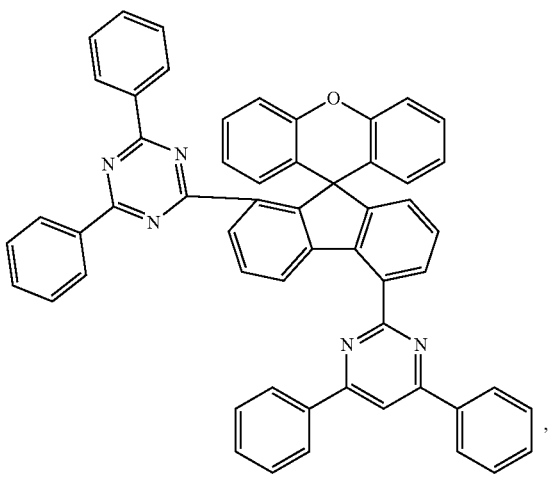

-continued
111
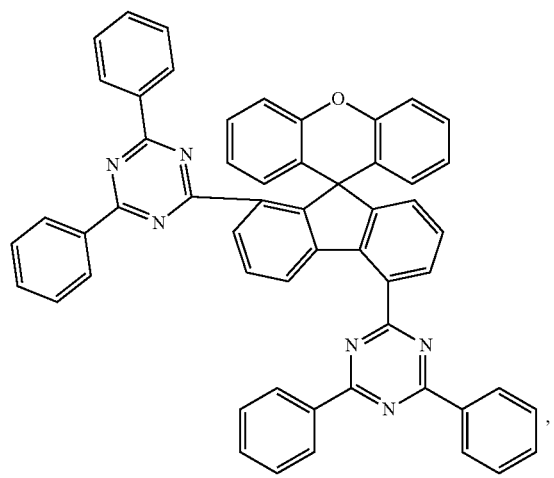
112
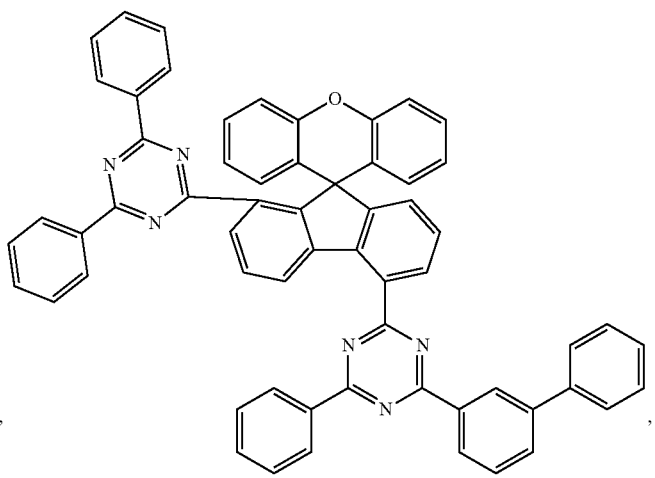
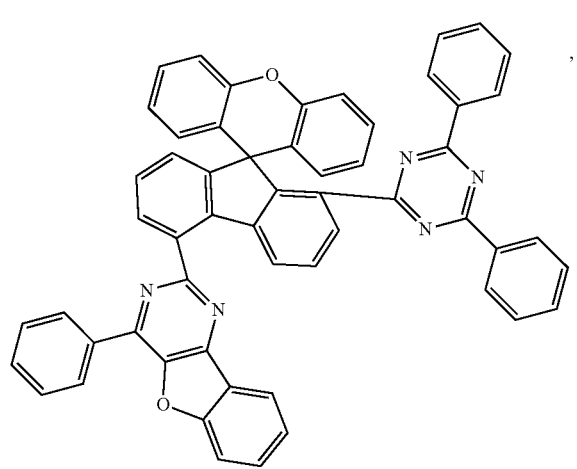
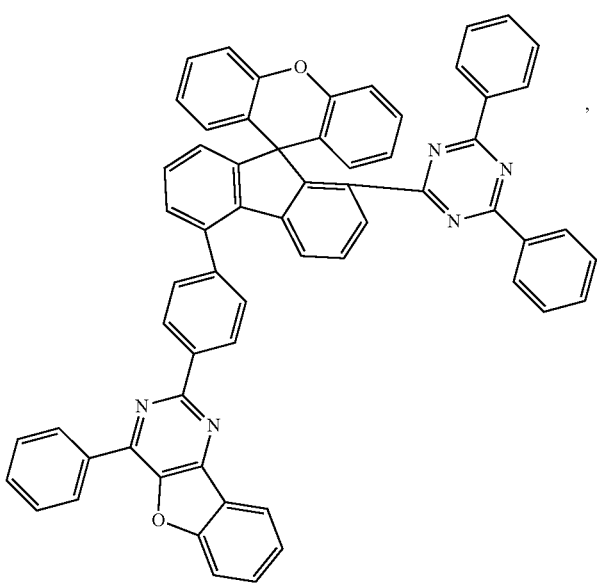
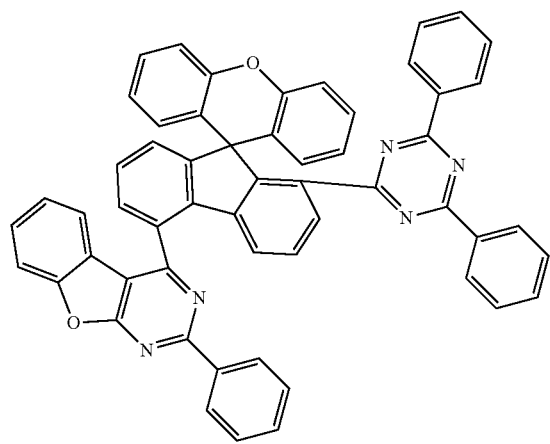
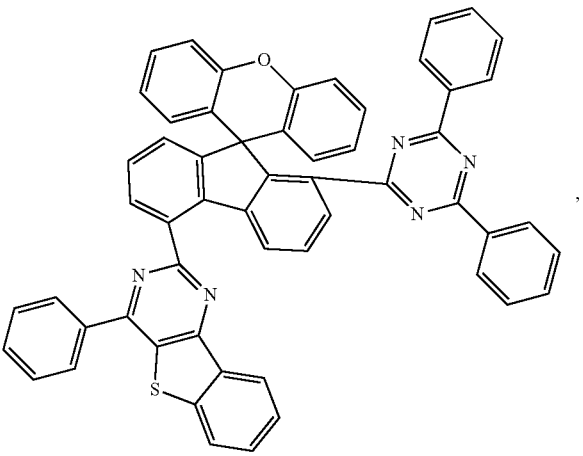

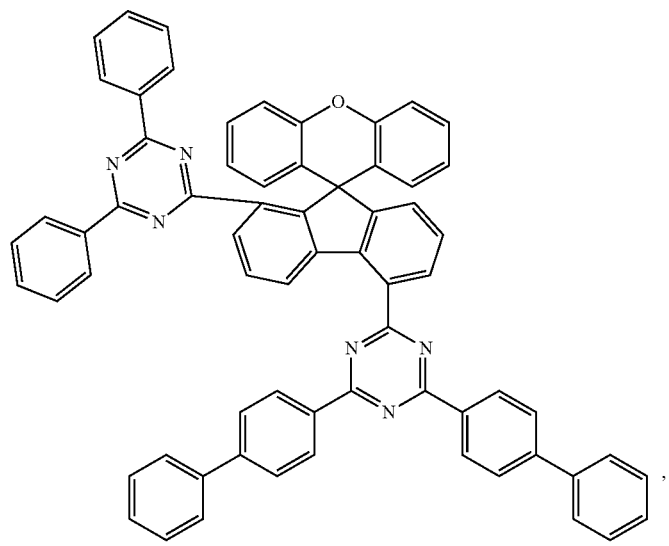
,
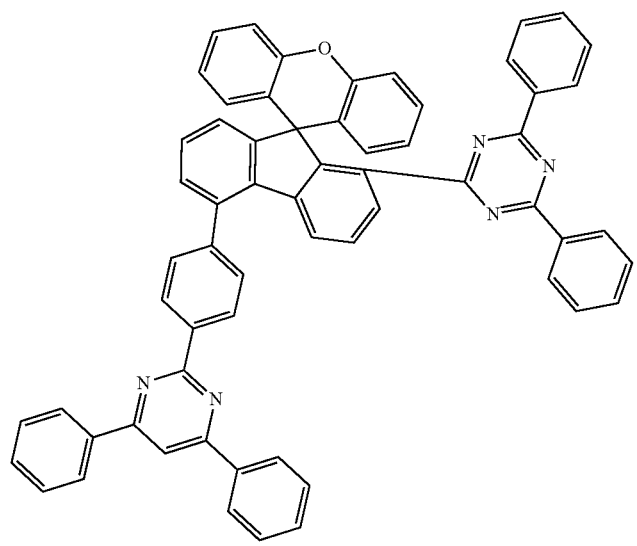
,
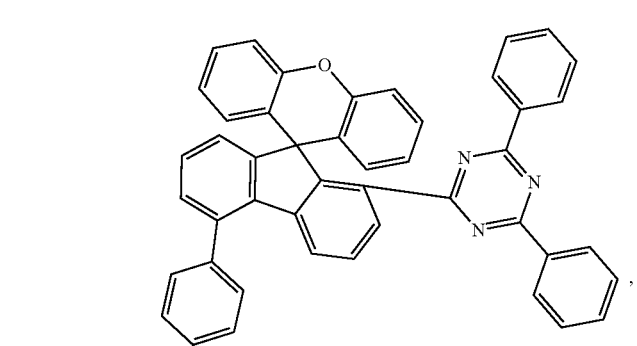
,
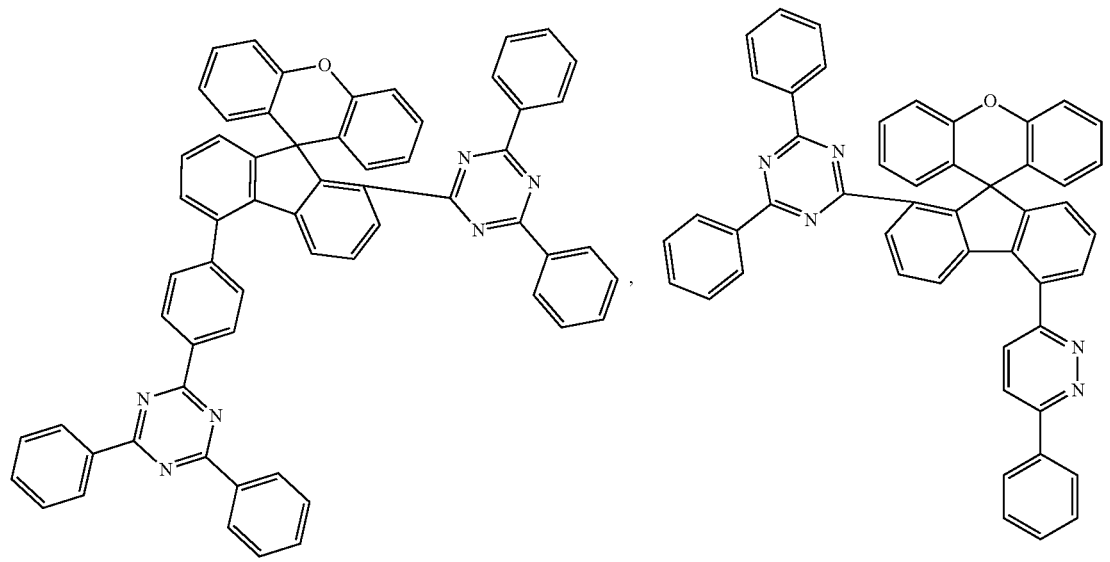
,

115
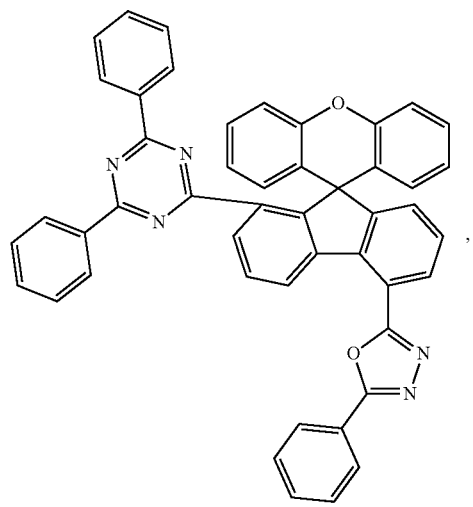
116
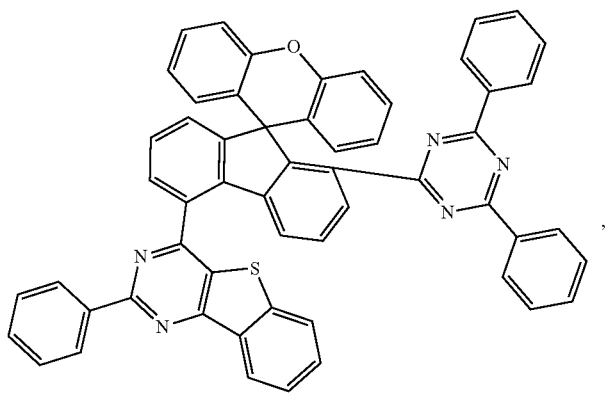
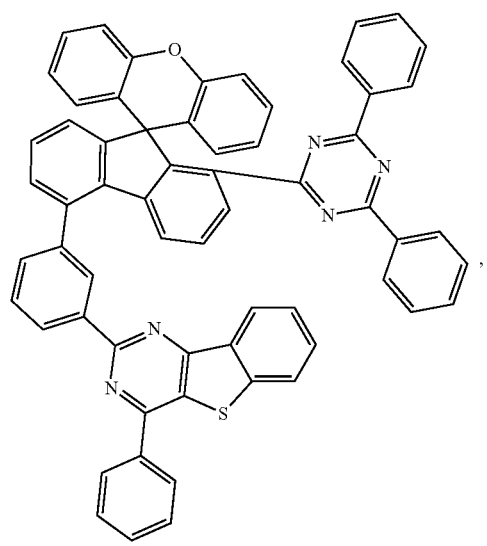
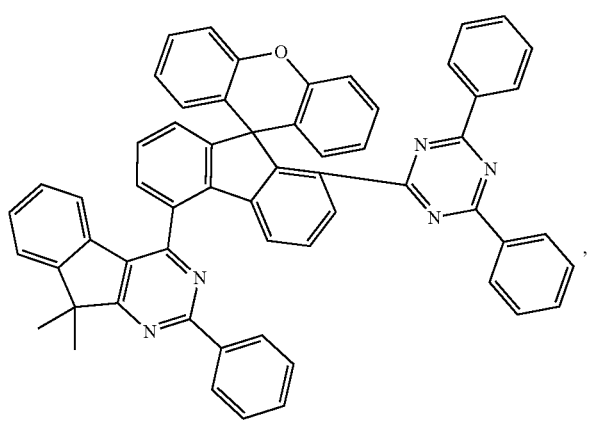
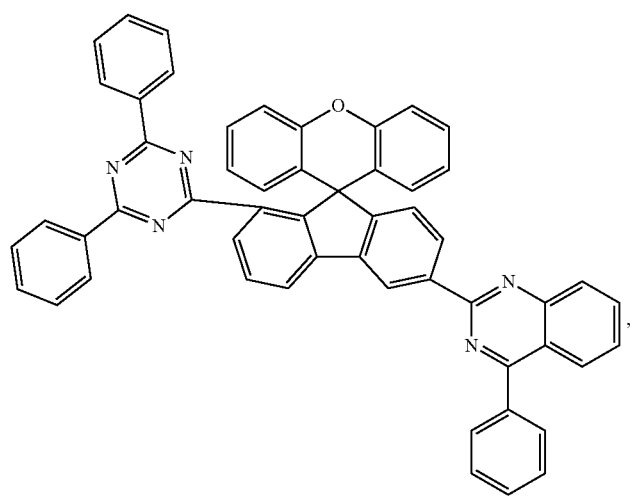

-continued
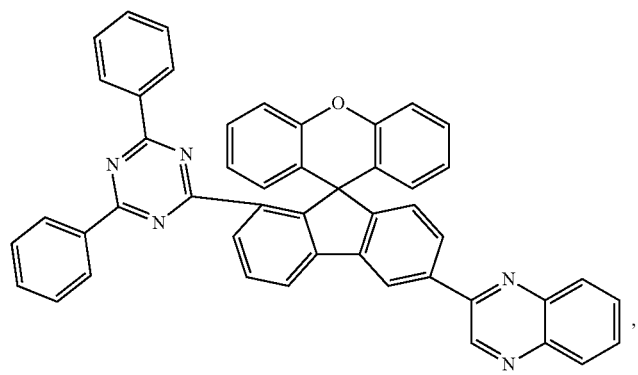
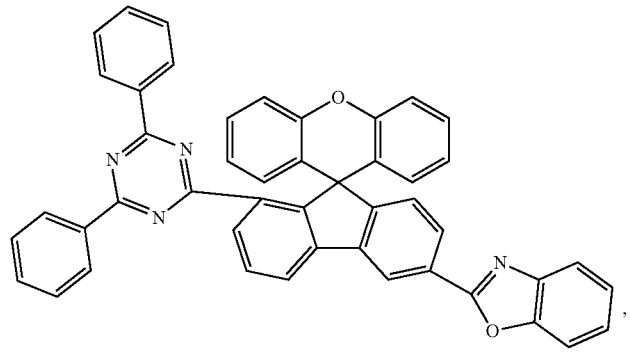
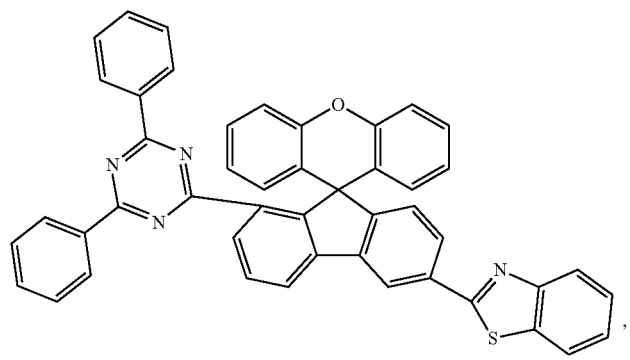
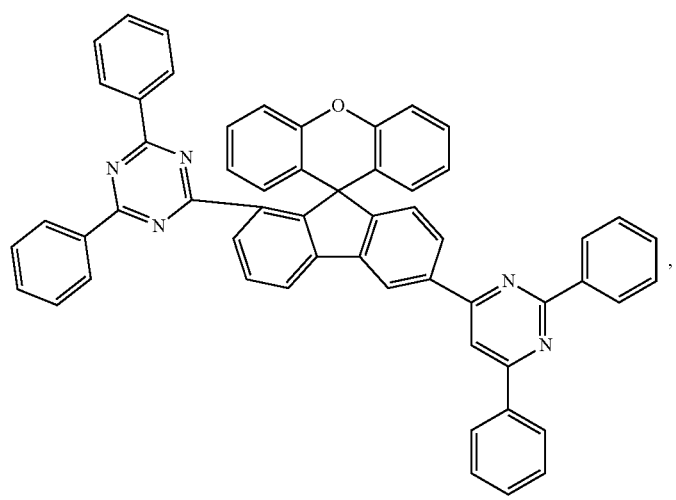

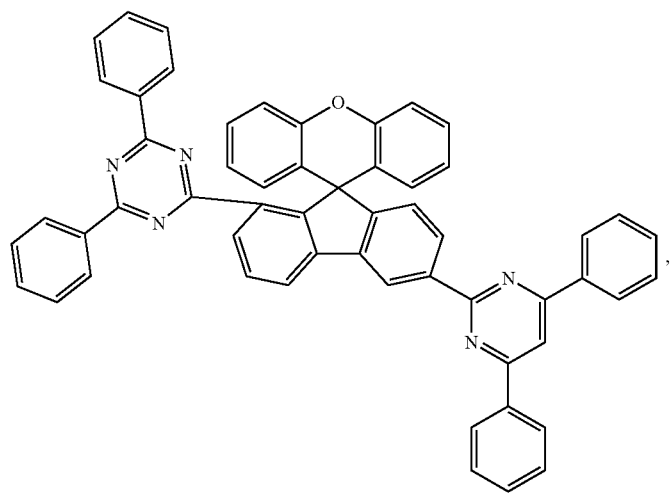,
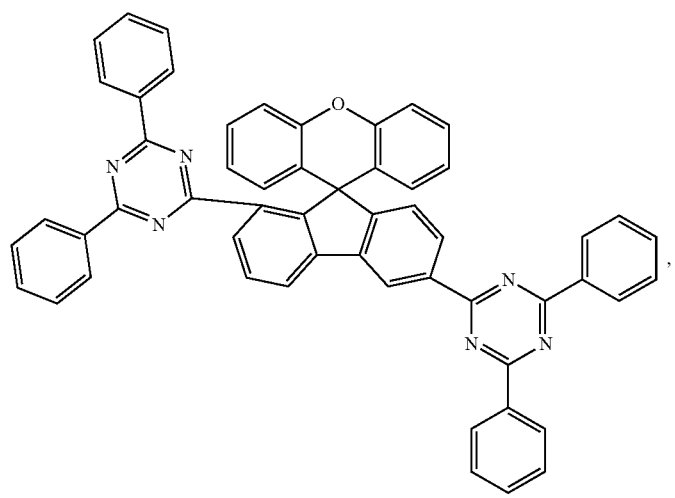,
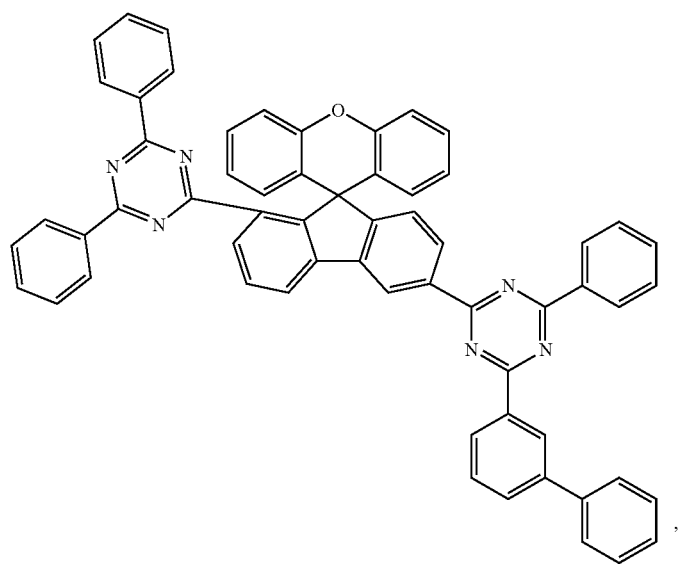 [SMILES: c1ccc(-c2cccc(-c3nc(-c4ccccc4)nc(-c4ccc5c(c4)-c4cccc(-c6nc(-c7ccccc7)nc(-c7ccccc7)n6)c4C54c5ccccc5Oc5ccccc54)n3)c2)cc1],

-continued
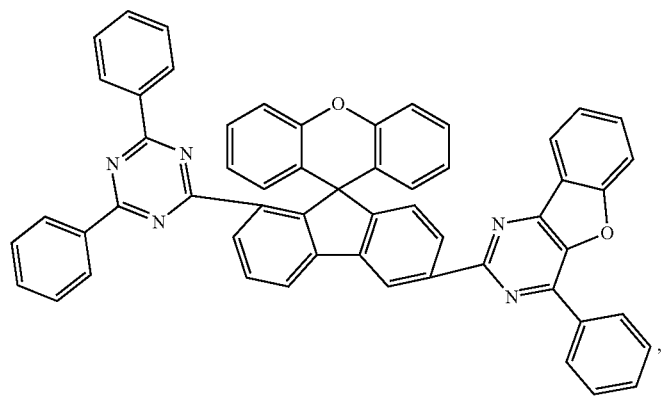
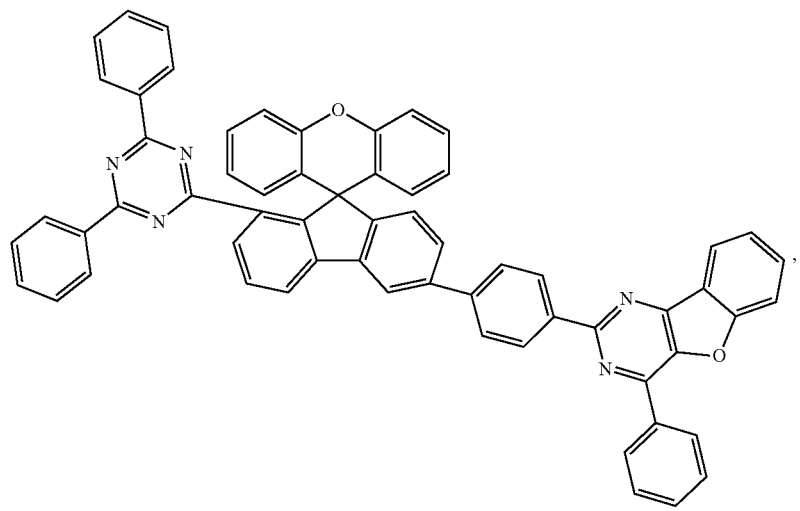
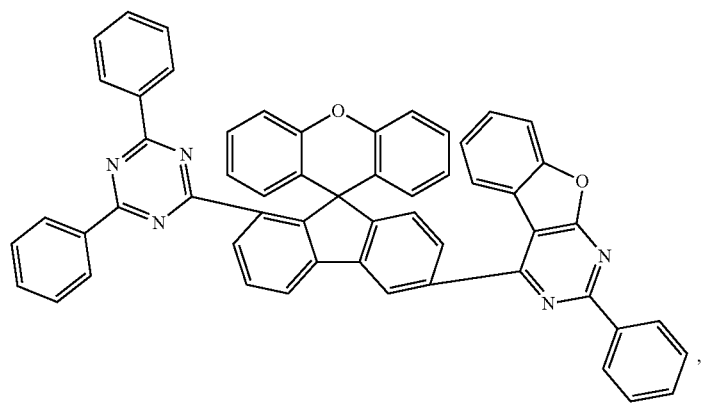
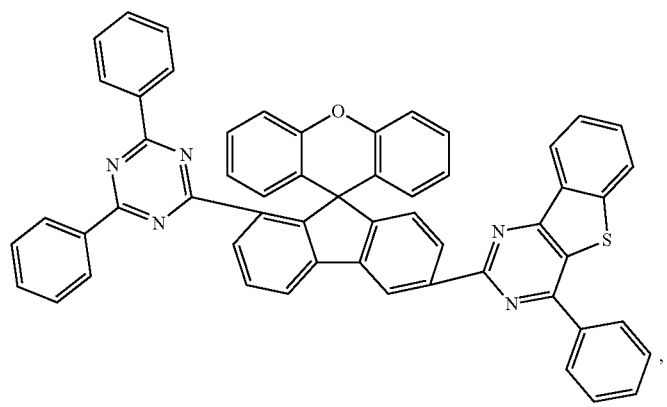

-continued
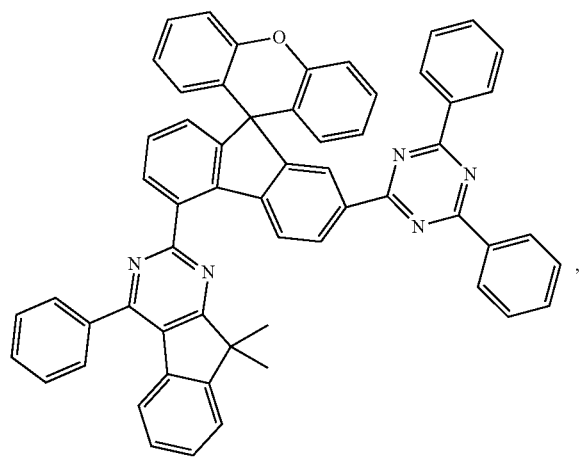
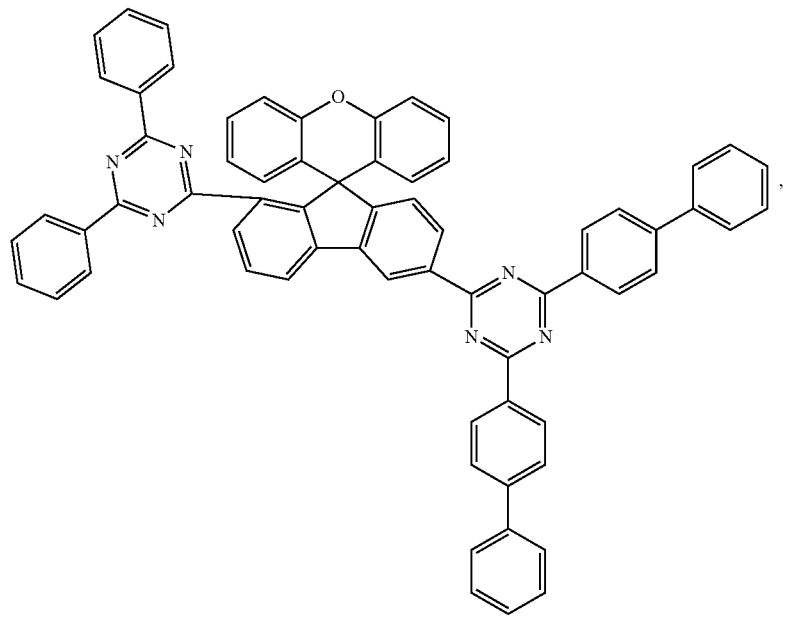
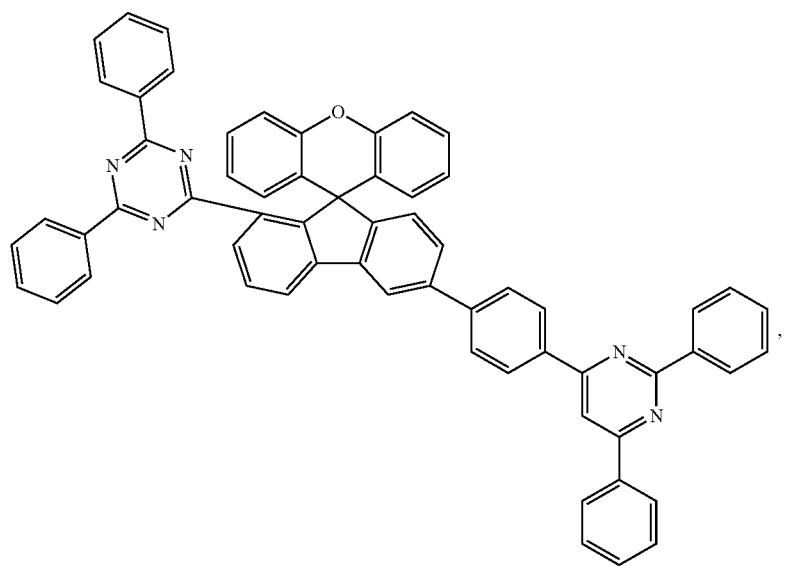

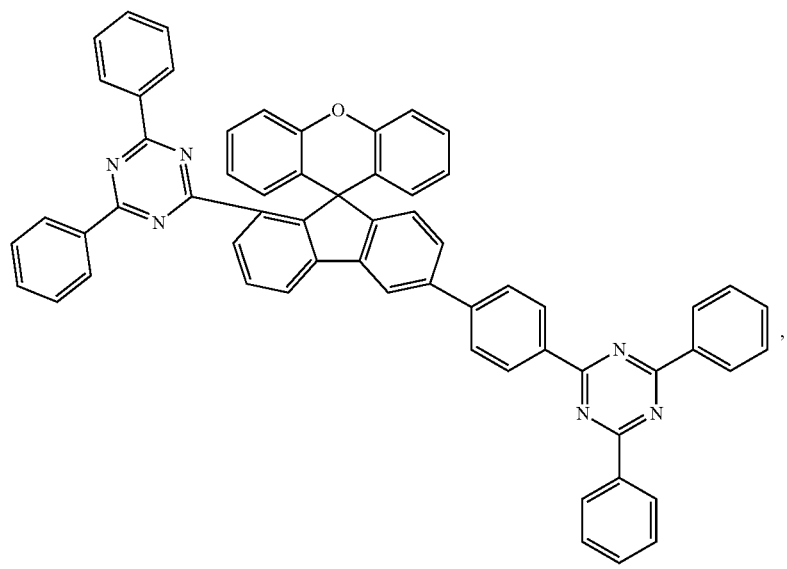
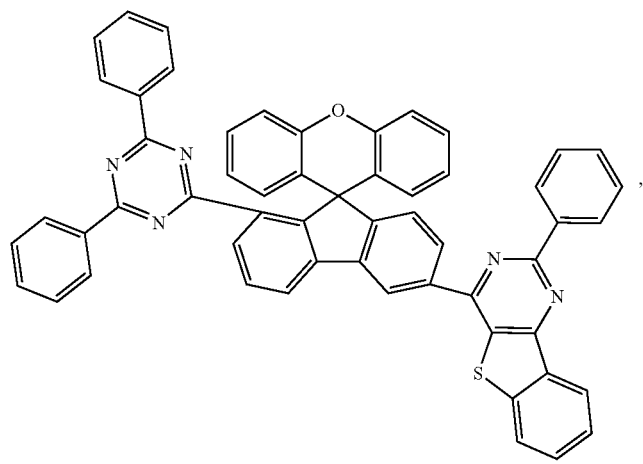
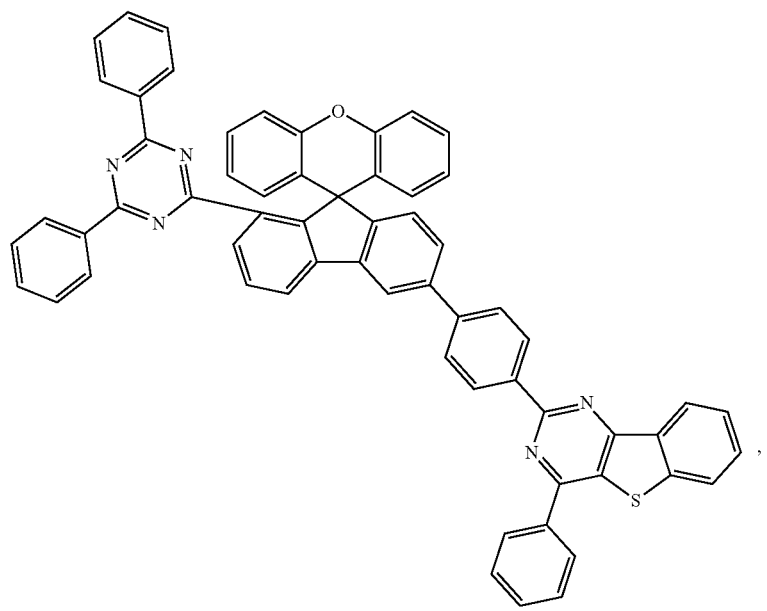

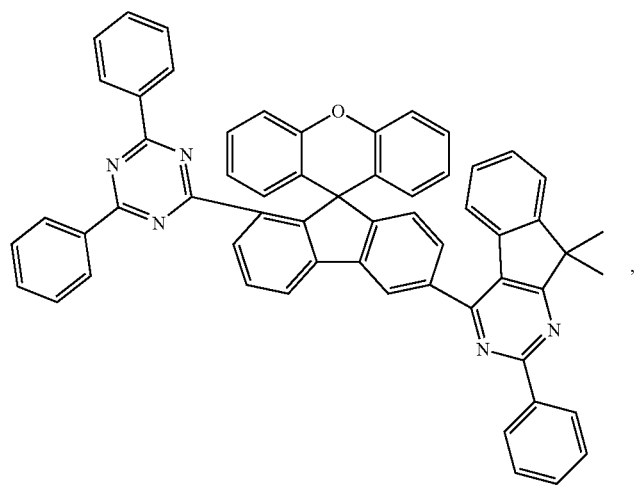
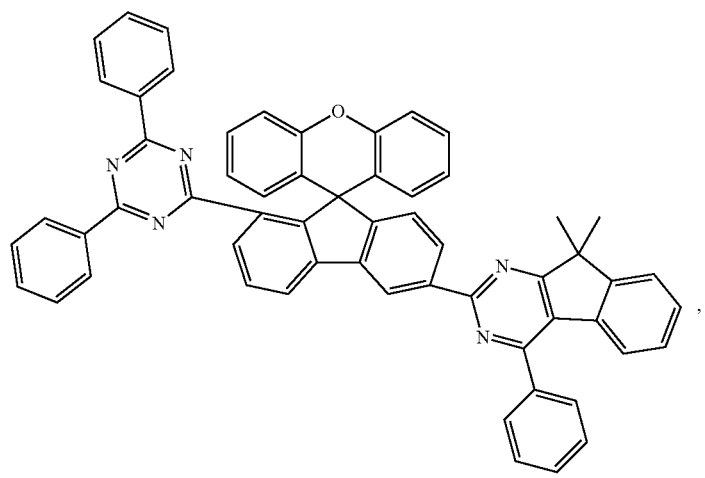
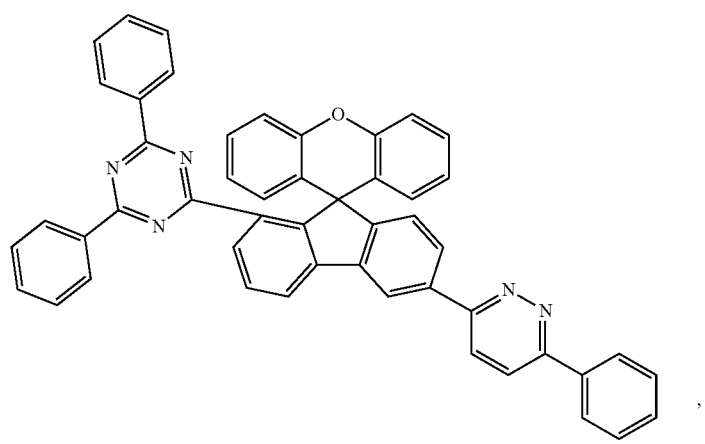

-continued
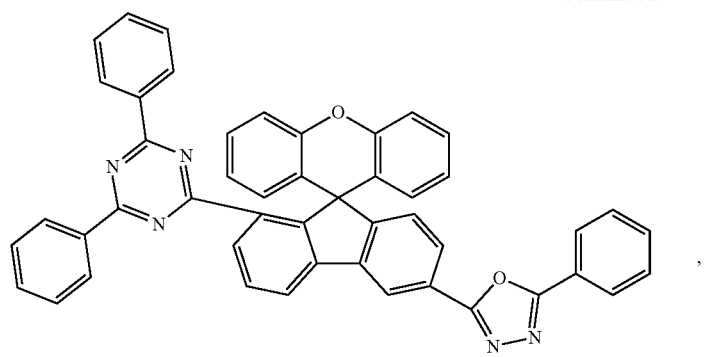
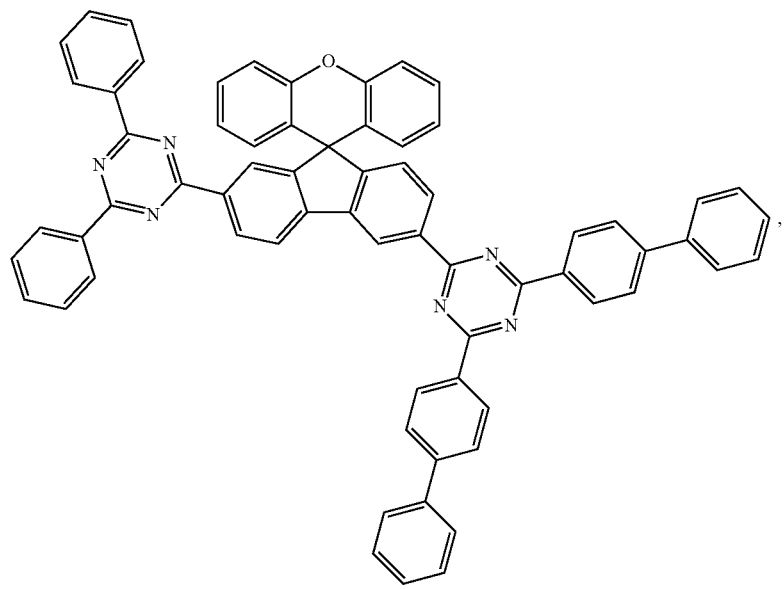
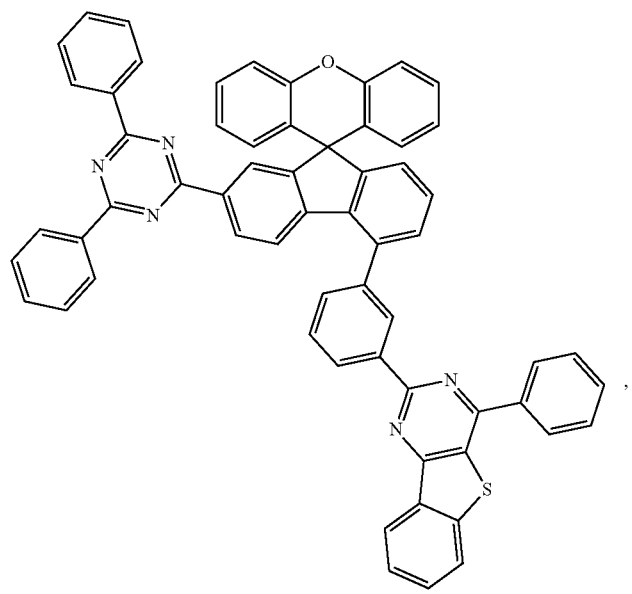

-continued
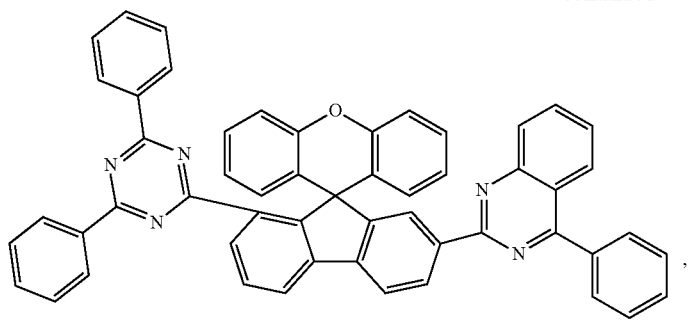
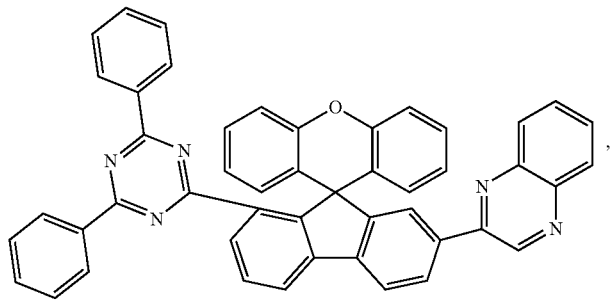
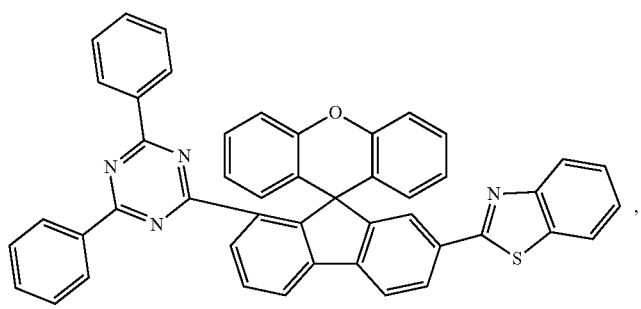
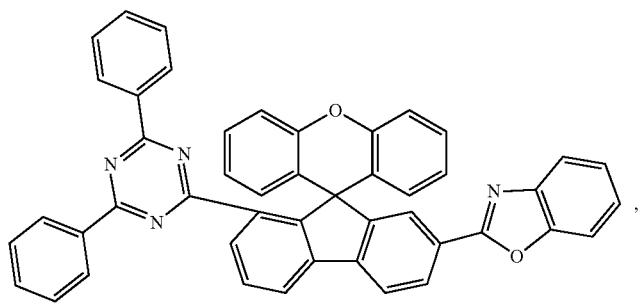
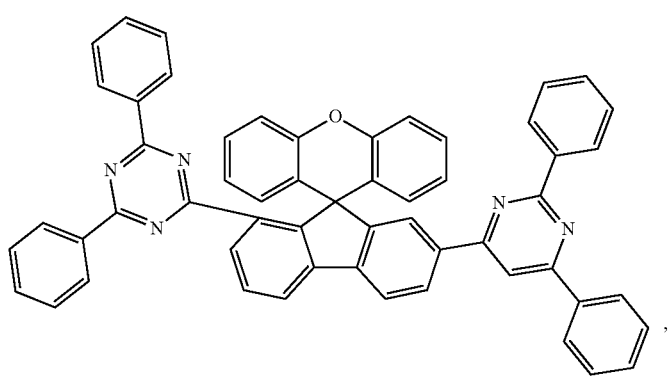

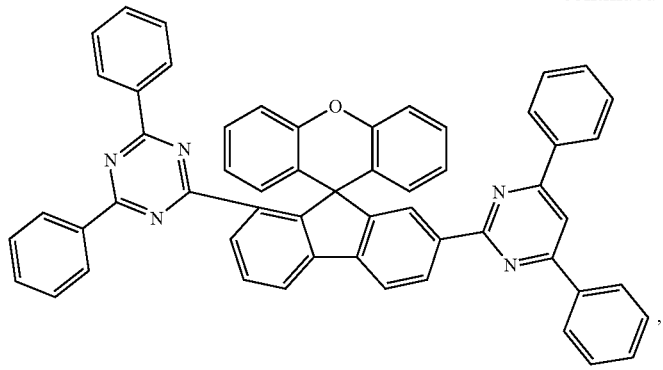
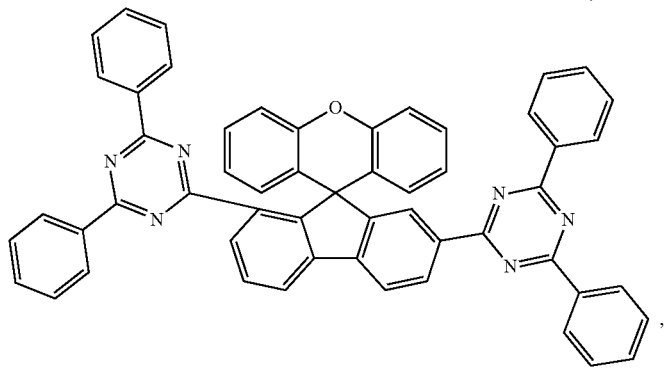
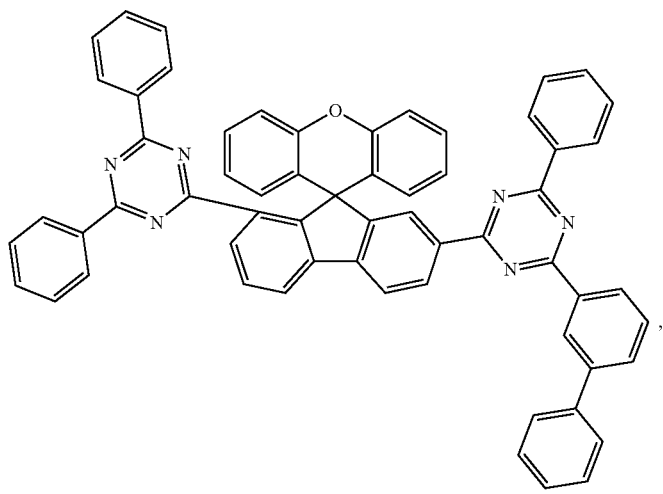
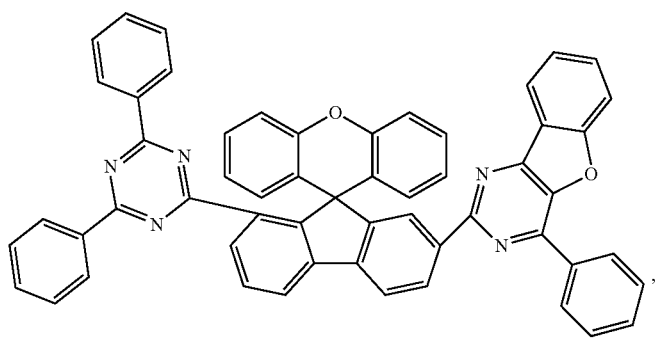

-continued
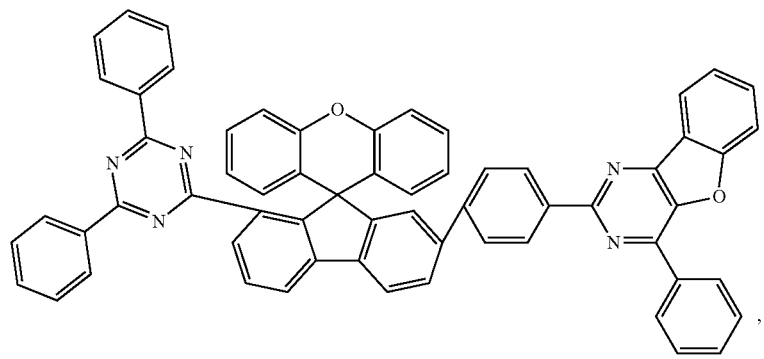
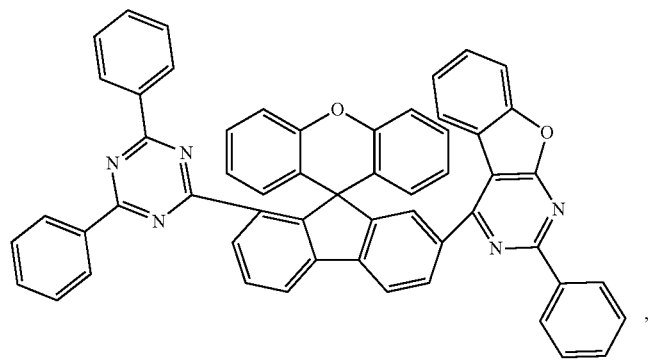
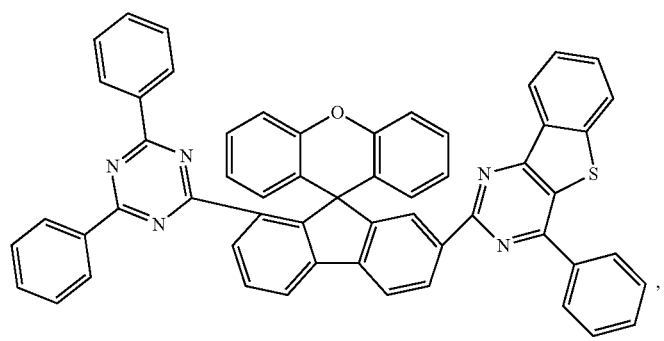
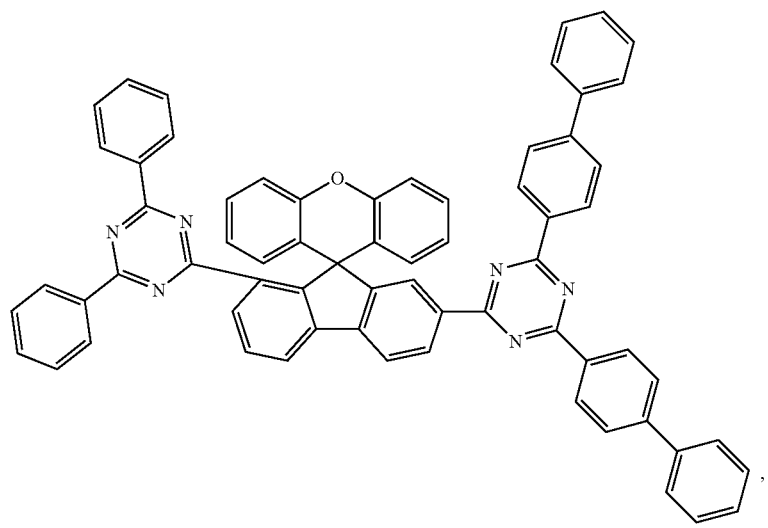

-continued
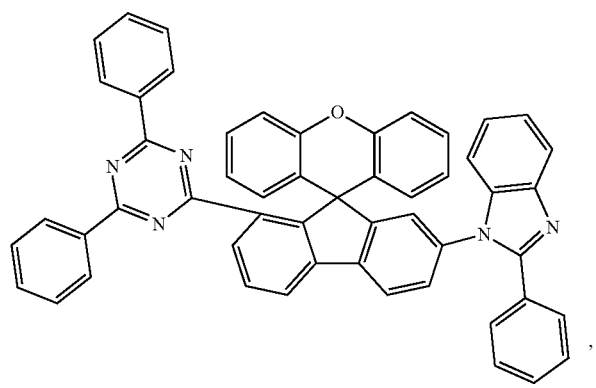,
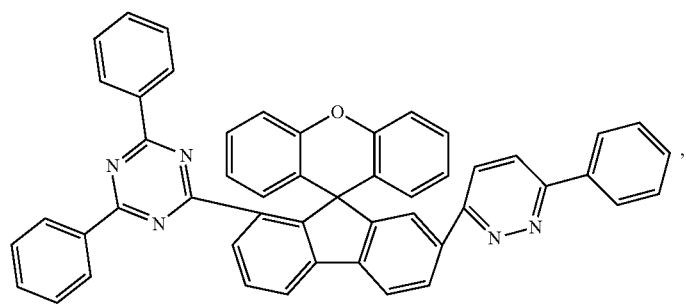,
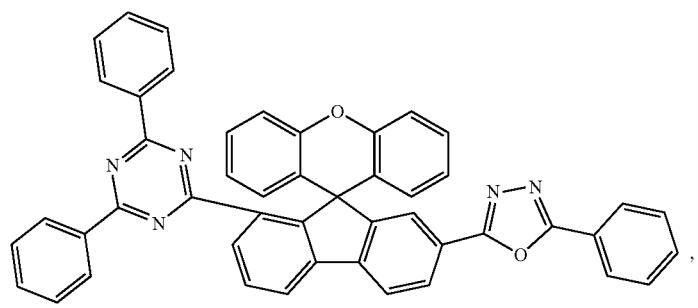,
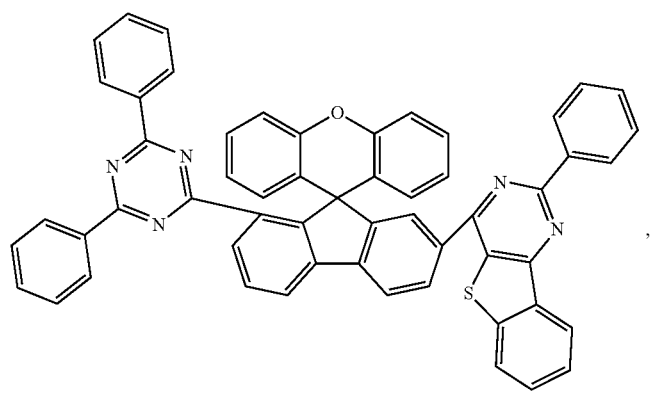,

-continued
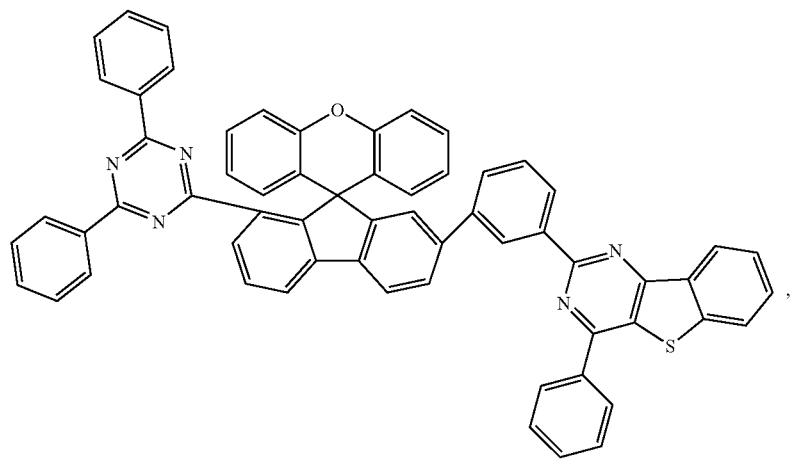
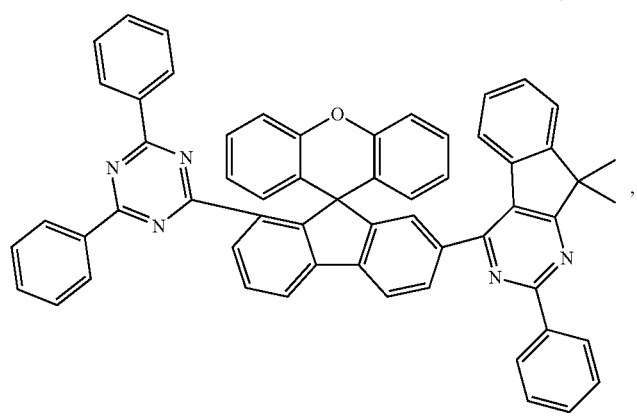
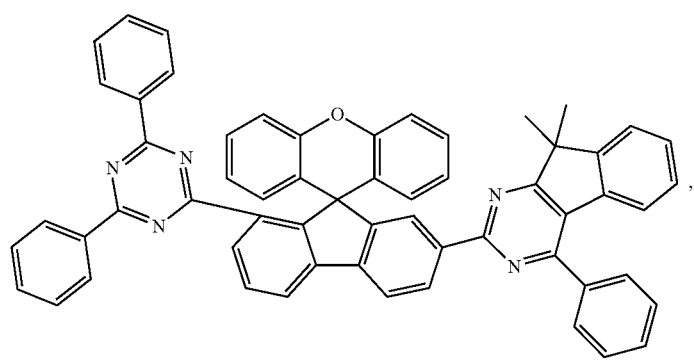
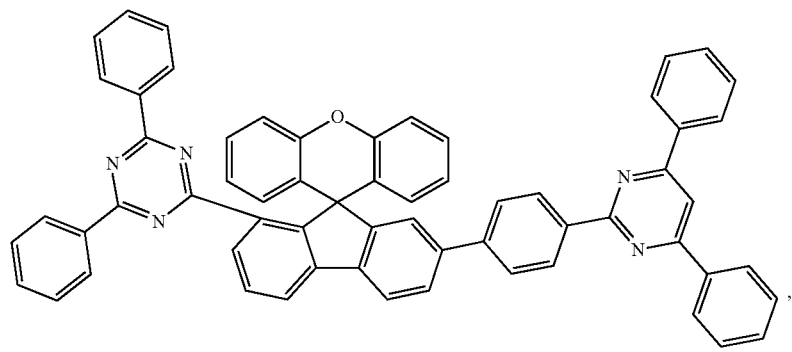

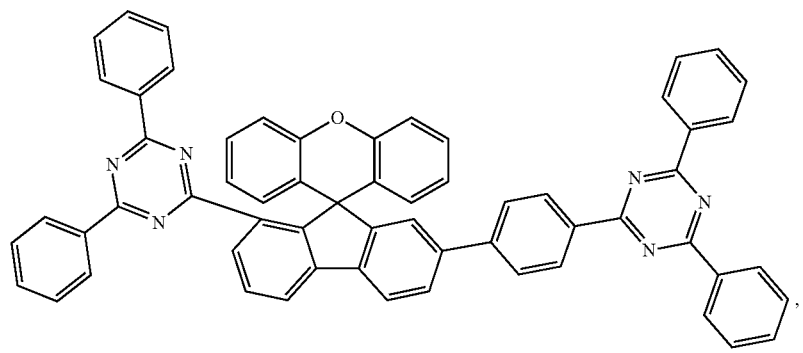,
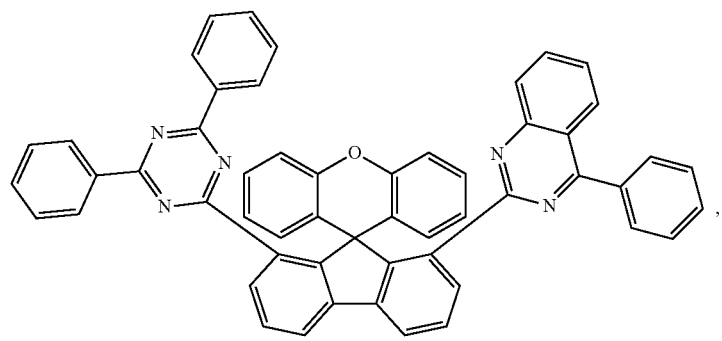,
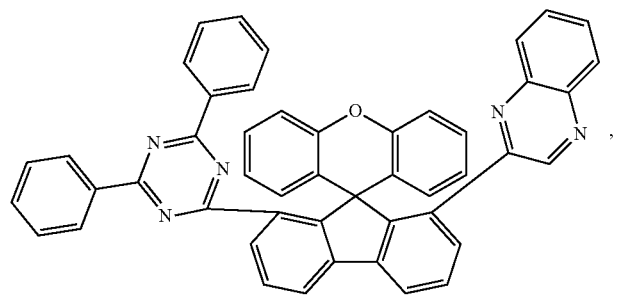,
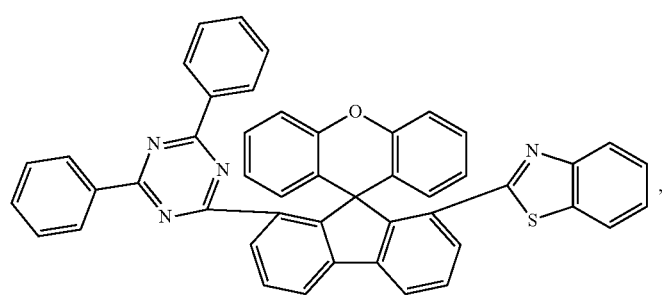,
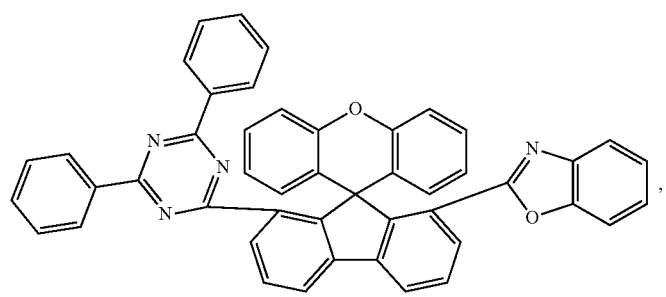,

-continued
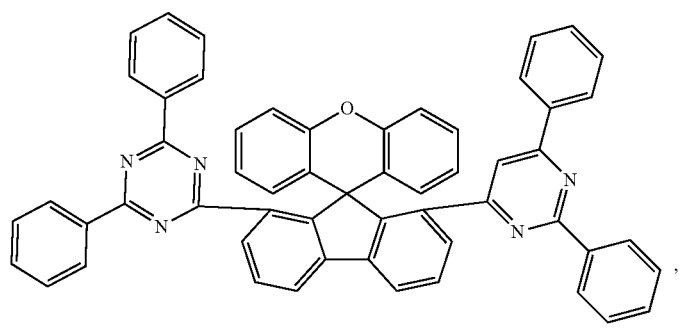
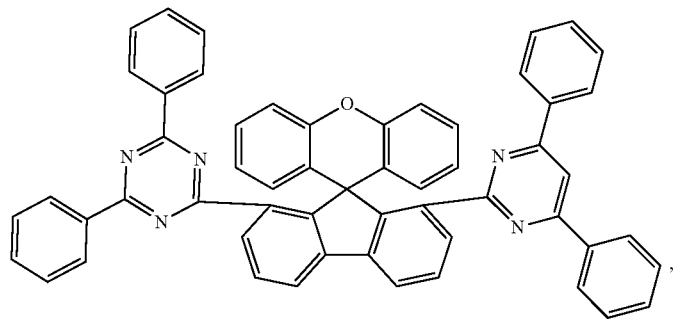
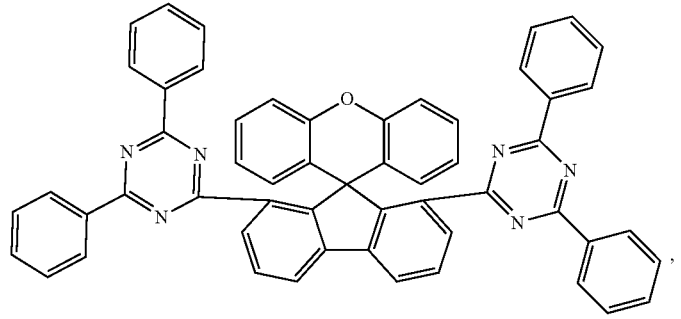
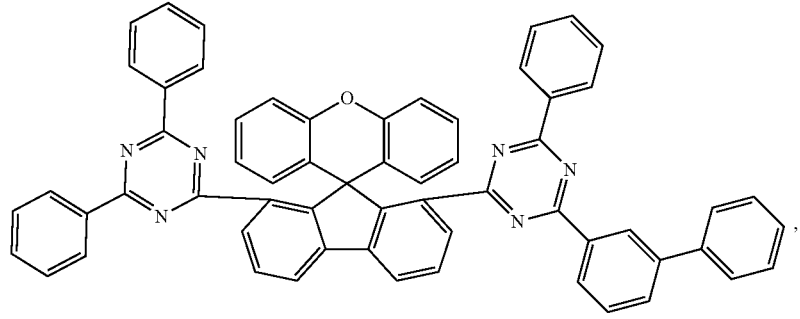
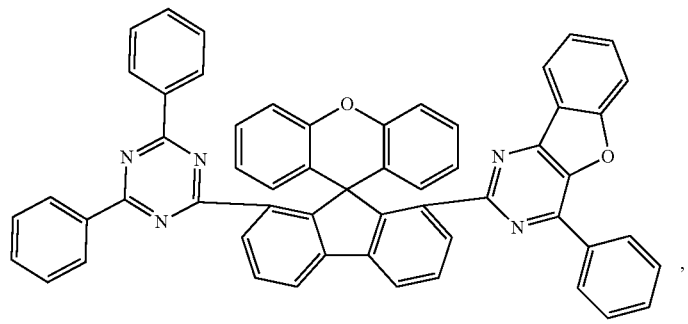

-continued
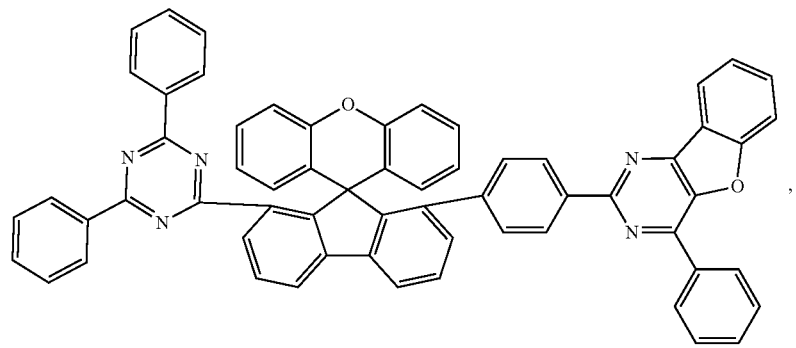
,
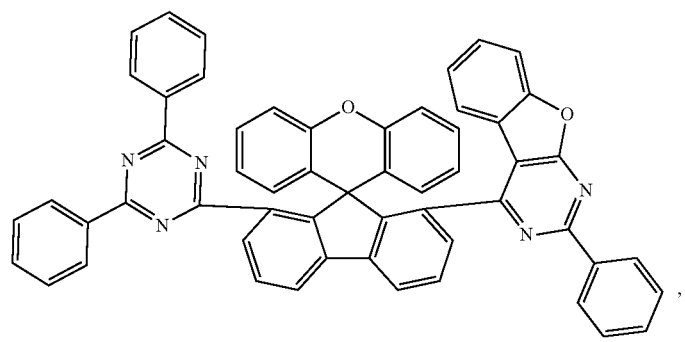
,
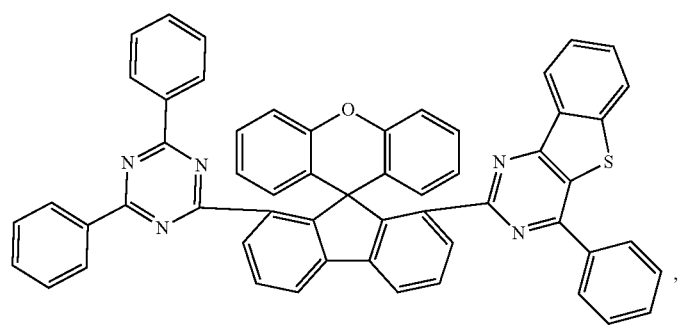
,
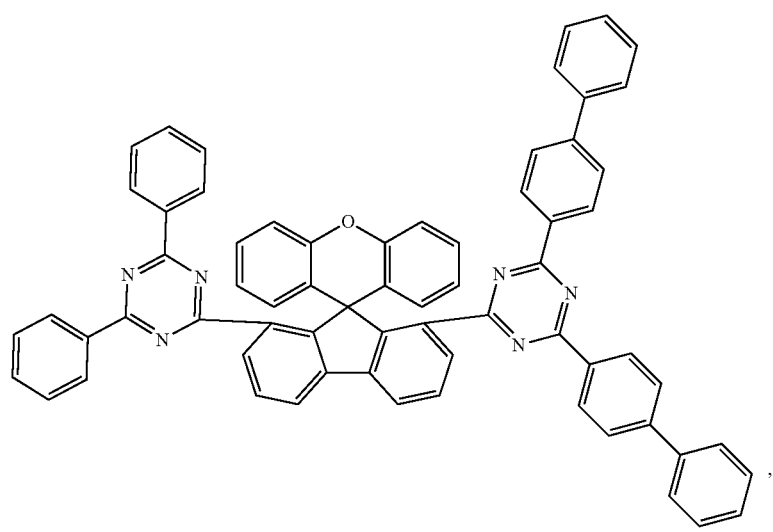
,

-continued
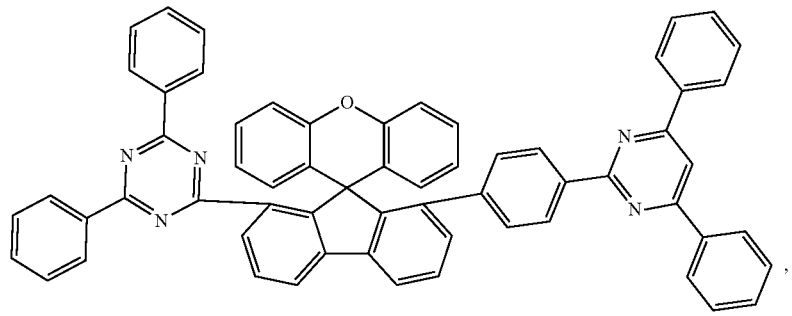
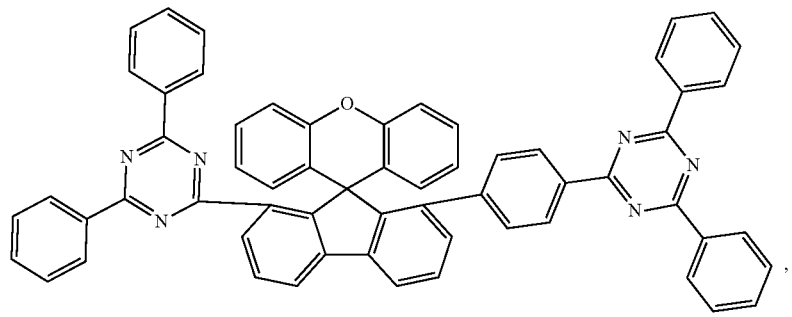
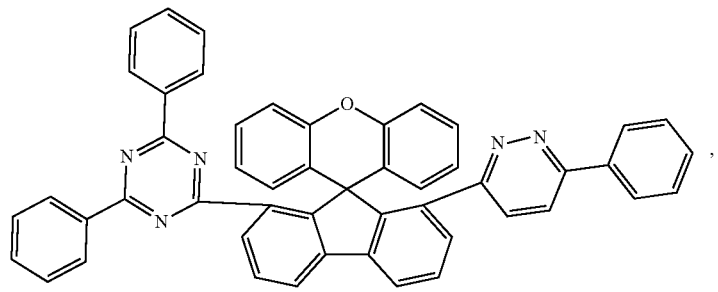
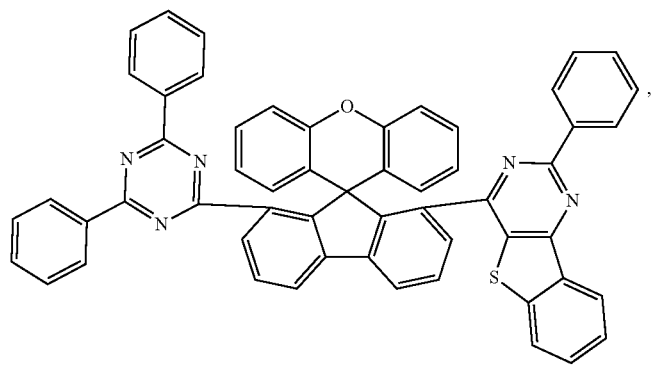
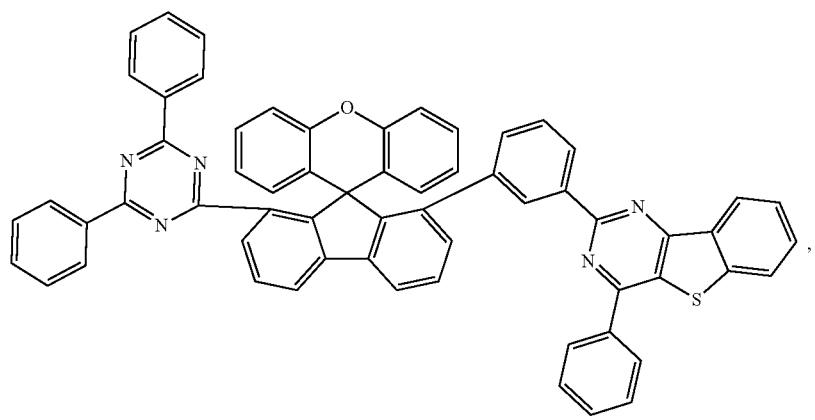

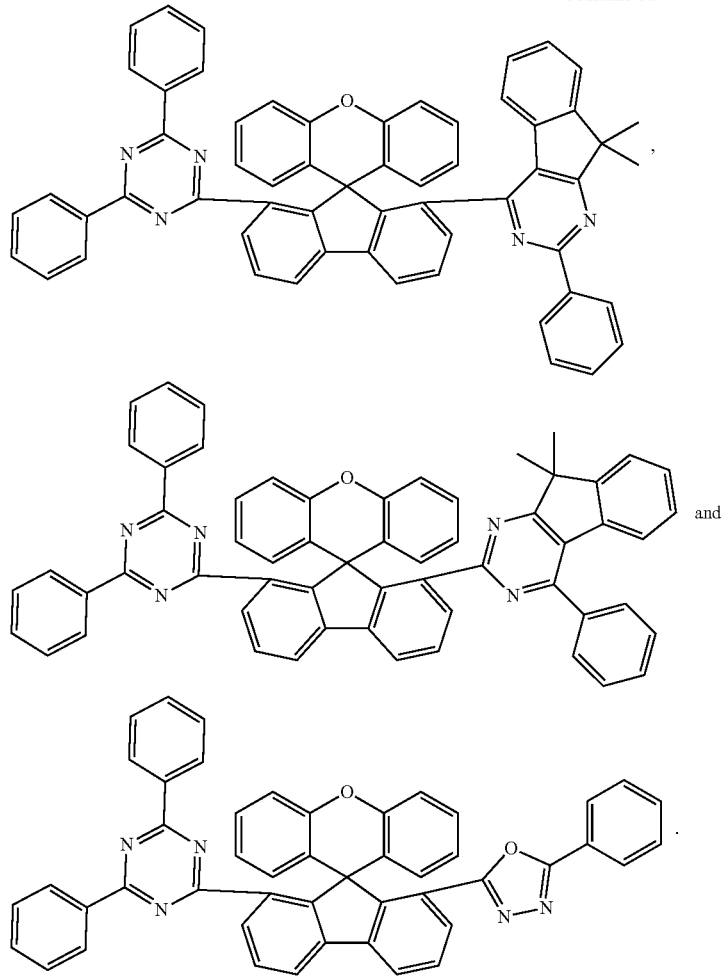

FIG. 1 illustrates an organic light emitting device according to an embodiment of the present specification. Referring to FIG. 1, the embodiment of the present specification provides an organic light emitting device including: a first electrode 101; a second electrode 301 facing the first electrode 101; and at least one organic material layer 201 interposed between the first electrode 101 and the second electrode 301, wherein the at least one organic material layer 201 contains the compound of Chemical Formula 1.

The organic material layer of the organic light emitting device according to the present specification can have a single layer structure, or a multiple layer structure in which two or more organic material layers are laminated. For example, the organic light emitting device according to the present specification can have, as the organic material layer, a structure including a hole injection layer, a hole transport layer, a light emitting layer, an electron transport layer, an electron injection layer, an electron blocking layer, an electron transport-aid layer or the like. However, the structure of the organic light emitting device is not limited thereto and can include a smaller number of organic layers.

According to an embodiment of the present specification, the organic material layer includes a hole injection layer, a hole transport layer or a hole injection/transport layer, and the hole injection layer, the hole transport layer, or the hole injection/transport layer can contain the compound of Chemical Formula 1.

According to another embodiment, the organic material layer can include a light emitting layer, and the light emitting layer can contain the compound of Chemical Formula 1.

According to an embodiment of the present specification, the organic material layer can include an electron transport layer or an electron transport-aid layer, and the electron transport layer or the electron transport-aid layer can contain the compound of Chemical Formula 1.

According to an embodiment of the present specification, the organic material layer can include an electron blocking layer, and the electron blocking layer can contain the compound of Chemical Formula 1.

According to an embodiment of the present specification, the electron transport layer, the electron injection layer or an electron transport/injection layer can contain the compound of Chemical Formula 1.

According to another embodiment, the organic material layer can include a light emitting layer and an electron transport layer, and the electron transport layer can contain the compound of Chemical Formula 1.

According to another embodiment, the organic material layer can contain the compound as a host and can include another organic compound, a metal or a metal compound as a dopant.

According to another embodiment, the organic light emitting device can be a normal-type organic light emitting device having a structure in which an anode, at least one organic material layer and a cathode are laminated in this order on a substrate.

According to another embodiment, the organic light emitting device can be an inverted-type organic light emitting device having a structure in which a cathode, at least one organic material layer and an anode are laminated in this order on a substrate.

The organic light emitting device of the present specification can be manufactured using materials and methods well-known in the art, except that at least one organic material layer contains the compound of the present specification, that is, the compound of Chemical Formula 1.

When the organic light emitting device includes a plurality of organic material layers, the organic material layers can be formed with the same or different materials.

The organic light emitting device of the present specification can be manufactured using materials and methods well-known in the art, except that at least one organic material layer contains the compound of the present specification, that is, the compound represented by Chemical Formula 1.

For example, the organic light emitting device of the present specification can be manufactured by sequentially depositing a first electrode, an organic material layer and a second electrode on a substrate. At this time, the organic light emitting device can be manufactured by depositing a metal, an alloy thereof, or a metal oxide having conductivity, on the substrate using a physical vapor deposition (PVD) method such as sputtering or e-beam evaporation to form an anode, forming, on the anode, an organic material layer including a hole injection layer, a hole transport layer, a light emitting layer and an electron transport layer, and then depositing a material for a cathode thereon. Apart from this method, the organic light emitting device can be manufactured by sequentially depositing a cathode material, an organic material layer and an anode material on a substrate.

In addition, the compound of Chemical Formula 1 can be produced into the organic material layer not only by the vapor deposition method, but also by a solution application method, during the manufacture of the organic light emitting device. Here, the solution application method means spin coating, dip coating, doctor blading, inkjet printing, screen printing, spraying, roll coating or the like, but is not limited thereto.

Apart from such a method, the organic light emitting device can be manufactured by sequentially depositing a cathode material, an organic material layer and an anode material on a substrate (PCT Application Publication No. WO2003/012890), but the manufacturing method is not limited thereto.

According to an embodiment of the present specification, the first electrode can be an anode and the second electrode can be a cathode.

According to another embodiment, the first electrode can be a cathode and the second electrode can be an anode.

Generally, the anode material can be a material having a high work function to facilitate injection of holes into the organic material layer. Specifically, examples of the anode material that can be used in the present specification include, but are not limited to: metals such as vanadium, chromium, copper, zinc and gold, or alloys thereof; metal oxides such as zinc oxide, indium oxide, indium tin oxide (ITO) and indium zinc oxide (IZO); combinations of a metal with oxide such as ZnO:Al or SnO$_2$:Sb; conductive polymers such as poly(3-methylthiophene), poly[3,4-(ethylene-1,2-dioxy)thiophene] (PEDOT), polypyrrole and polyaniline; and the like.

Generally, the cathode material can be a material that has a low work function to facilitate injection of electrons into the organic material layer. Specific examples of the cathode material include, but are not limited to, metals such as magnesium, calcium, sodium, potassium, titanium, indium, yttrium, lithium, gadolinium, aluminum, silver, tin and lead, or alloys thereof; multilayer structure materials such as LiF/Al and LiO$_2$/Al; and the like.

The hole injection layer is a layer that injects holes from an electrode, and the hole injection material is preferably a compound that has an ability to transport holes, thus has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of an adjacent organic material layer. Specific examples of the hole injection material include, but are not limited to, metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like.

The hole transport layer is a layer that receives holes from a hole injection layer and transports the holes to a light emitting layer, and the hole transfer material is preferably a material that is capable of receiving holes from an anode or a hole injection layer, moving the holes to a light emitting layer and having high mobility for the holes. Specific examples of the hole transfer material include, but are not limited to, arylamine-based organic materials, conductive polymers, block copolymers having conjugated parts and non-conjugated parts together, and the like.

The light emitting material is a material that is capable of receiving holes and electrons from the hole transport layer and the electron transport layer, respectively, and emitting visible light by combination between the holes and electrons, and is preferably a material having excellent quantum efficiency for fluorescence or phosphorescence. Specific examples thereof include, but are not limited thereto, 8-hydroxyquinoline aluminum complexes (Alq$_3$); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)-based polymers; spiro compounds; polyfluorene, rubrene, and the like.

The light emitting layer can include a host material and a dopant material. The host material includes a fused aromatic ring derivative, a heteroring-containing compound or the like. Specifically, examples of the fused aromatic ring derivative include, but are not limited to, anthracene derivatives, pyrene derivatives, naphthalene derivatives, pentacene derivatives, phenanthrene compounds, fluoranthene compounds and the like, and examples of the heteroring-containing compound include, but are not limited to, carbazole derivatives, dibenzofuran derivatives, ladder-type furan compounds, pyrimidine derivatives and the like.

The dopant material includes an aromatic amine derivative, a styrylamine compound, a boron complex, a fluoranthene compound, a metal complex or the like. Specifically, the aromatic amine derivative is a fused aromatic ring derivative having a substituted or unsubstituted arylamino group and includes arylamino group-containing pyrene, anthracene, chrysene and peryflanthene, and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, examples of the styrylamine compound include, but are not limited to, styrylamine, styryldiamine, styryltriamine, styryltetramine and the like. In addition, examples of the metal complex include, but are not limited to, iridium complexes, platinum complexes and the like.

Specifically, an iridium-based complex used as a phosphorescent dopant can be represented below, but is not limited thereto.

Dp-1

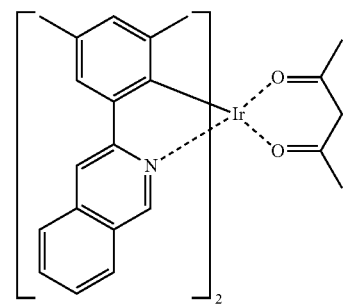

Dp-4

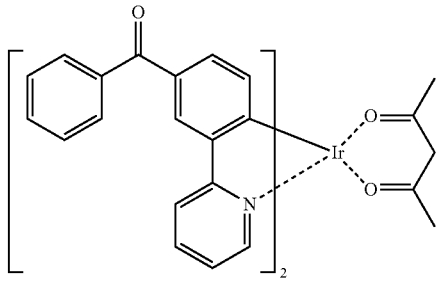

Dp-5

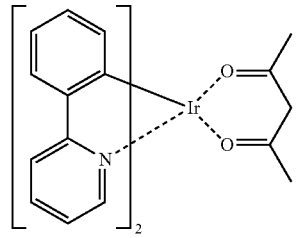

Dp-6

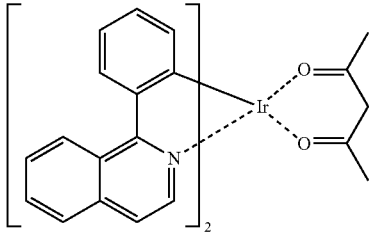

Dp-2

Dp-7

Dp-3

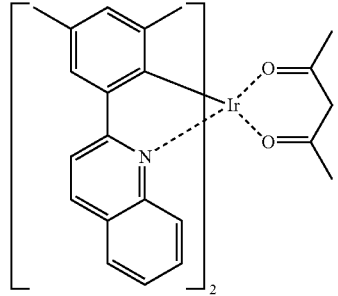

Dp-8

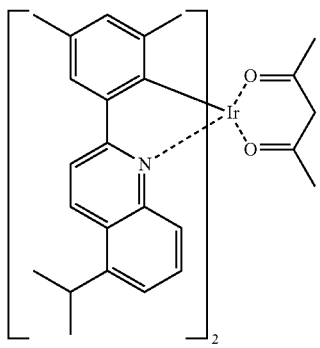

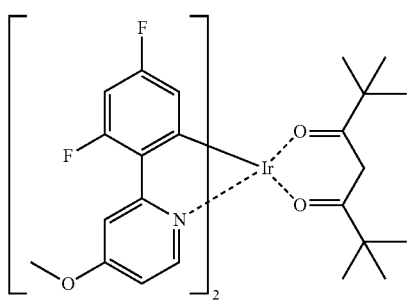
Dp-9
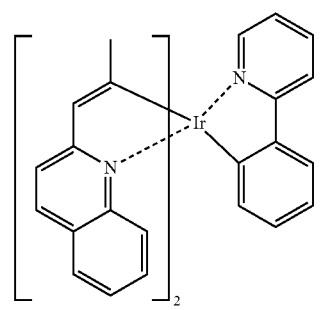
Dp-10
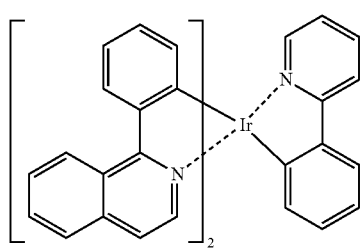
Dp-11
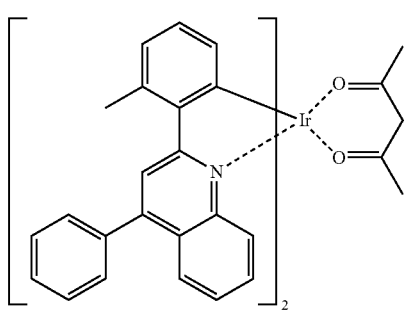
Dp-12
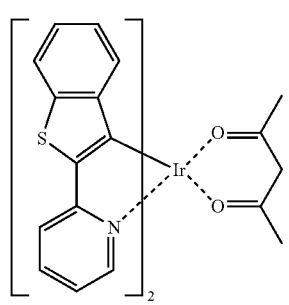
Dp-13
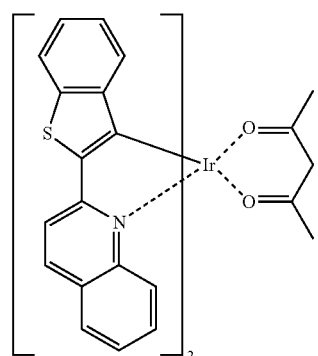
Dp-14
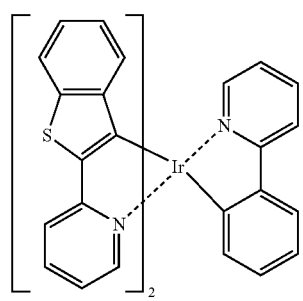
Dp-15
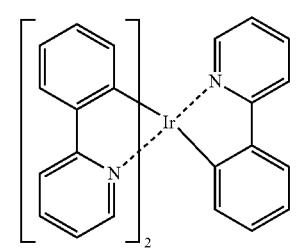
Dp-16
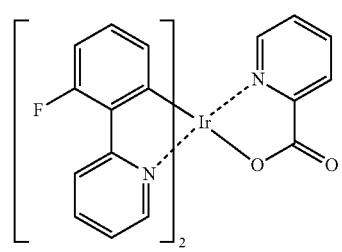
Dp-17
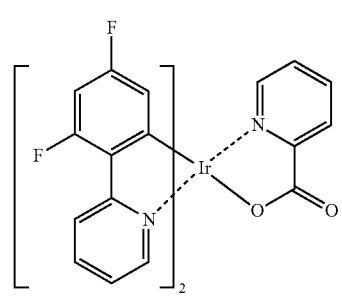
Dp-18

Dp-19
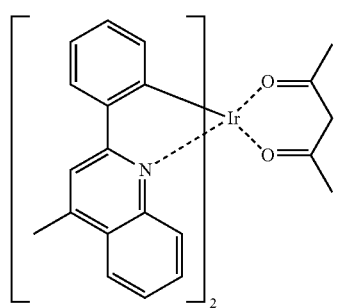
Dp-20
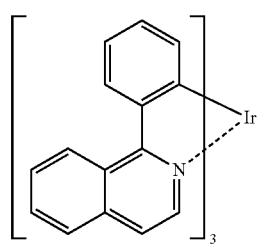
Dp-21
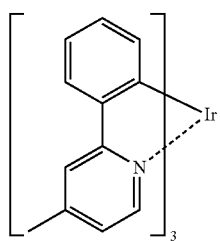
Dp-22
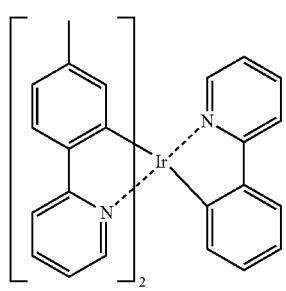
Dp-23
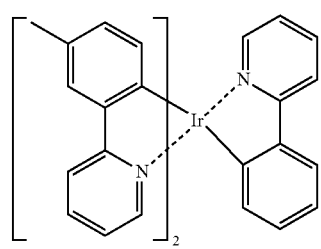
Dp-24
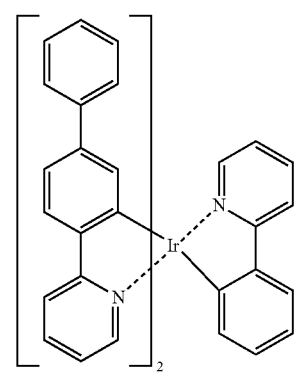
Dp-25
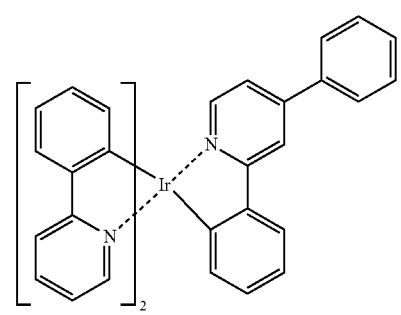
Dp-26
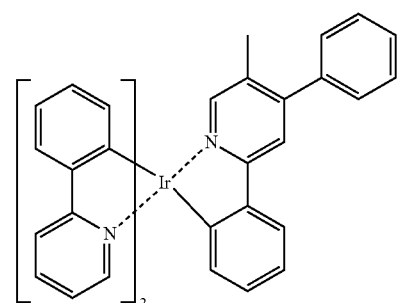
Dp-27
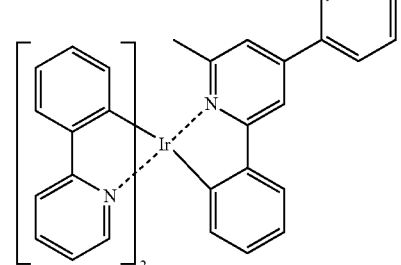
Dp-28
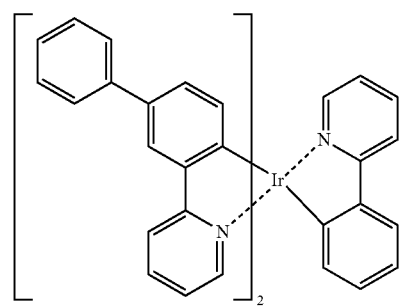

Dp-29
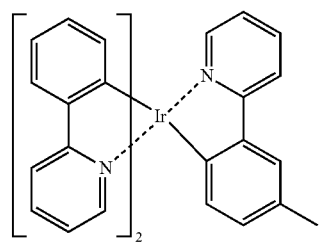
Dp-30
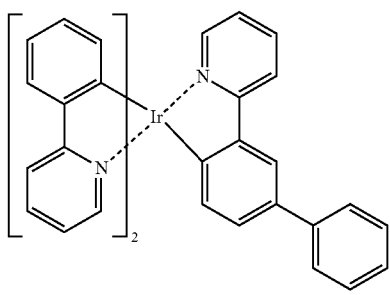
Dp-31
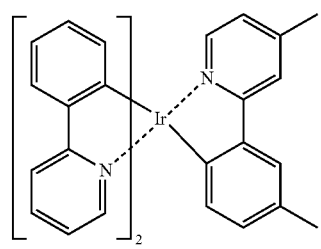
Dp-32
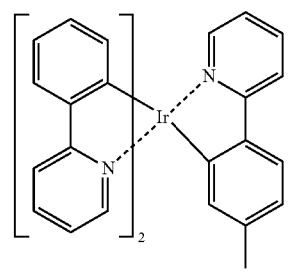
Dp-33
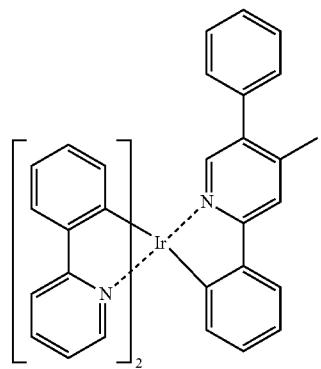
Dp-34
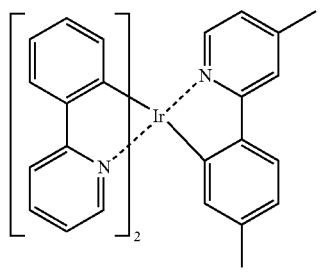
Dp-35
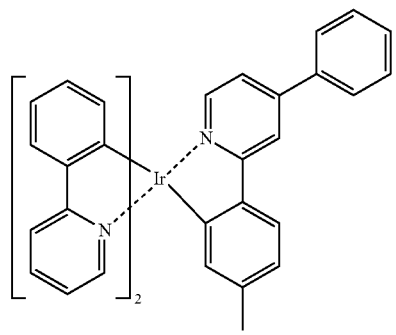
Dp-36
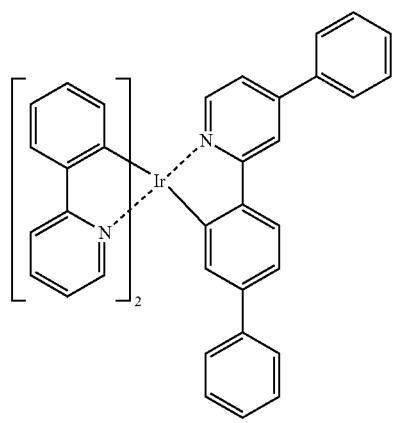
Dp-37
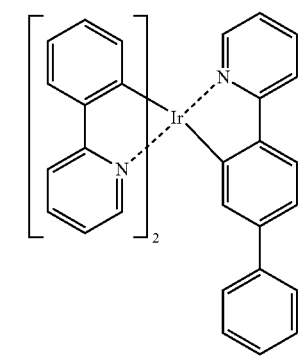

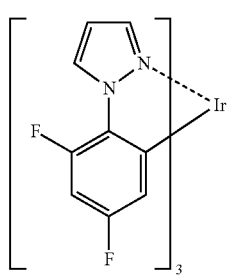

Dp-38

The electron transport layer is a layer that receives electrons from the electron injection layer and transports the electrons to the light emitting layer and the electron transport material is preferably a material that is capable of favorably receiving electrons from the cathode and transporting the electrons to the light emitting layer and has high mobility for electrons. Specifically, examples of the electron transport material include, but are not limited to: Al complexes of 8-hydroxyquinoline; complexes including Alq$_3$; organic radical compounds; hydroxyflavone-metal complexes and the like. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transport electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specifically, examples of the electron injection material include, but are not limited to, fluorenone, anthraquinodimethane, diphenoquinone, thiopyran dioxide, oxazole, oxadiazole, triazole, imidazole, perylene tetracarboxylic acid, fluorenylidene methane, anthrone and the like, and derivatives thereof, metal complex compounds, nitrogen-containing 5-membered ring derivatives, and the like.

Examples of the metal complex compound include, but are not limited to, 8-hydroxy-quinolinato lithium, bis(8-hydroxy-quinolinato)zinc, bis(8-hydroxyquinolinato)-copper, bis(8-hydroxyquinolinato)manganese, tris(8-hydroxyquinolinato)-aluminum, tris(2-methyl-8-hydroxyquinolinato)aluminum, tris(8-hydroxyquinolinato) gallium, bis(10-hydroxybenzo[h]quinolinato)-beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)-aluminum, bis(2-methyl-8-quinolinato)(2-naphtholato)gallium and the like. More specifically, the metal complex compound can include Ir(ppy)$_3$ (tris[2-phenylpyridine]iridium), which is a green dopant compound, or the like.

The organic light emitting device according to the present specification can be a top-emission type, a bottom-emission type or a dual-emission type depending on the materials used.

In an embodiment of the present specification, the compound of Chemical Formula 1 can be included not only in the organic light emitting device, but also, in an organic solar cell or an organic transistor.

Hereinafter, embodiments of the present specification will be exemplified with reference to examples. However, the examples according to the present specification are provided only for illustration of the present specification and should not be construed as limiting the scope of the present specification.

Preparation Example 1

Preparation Example 1-1: Synthesis of Intermediate Compound 1h

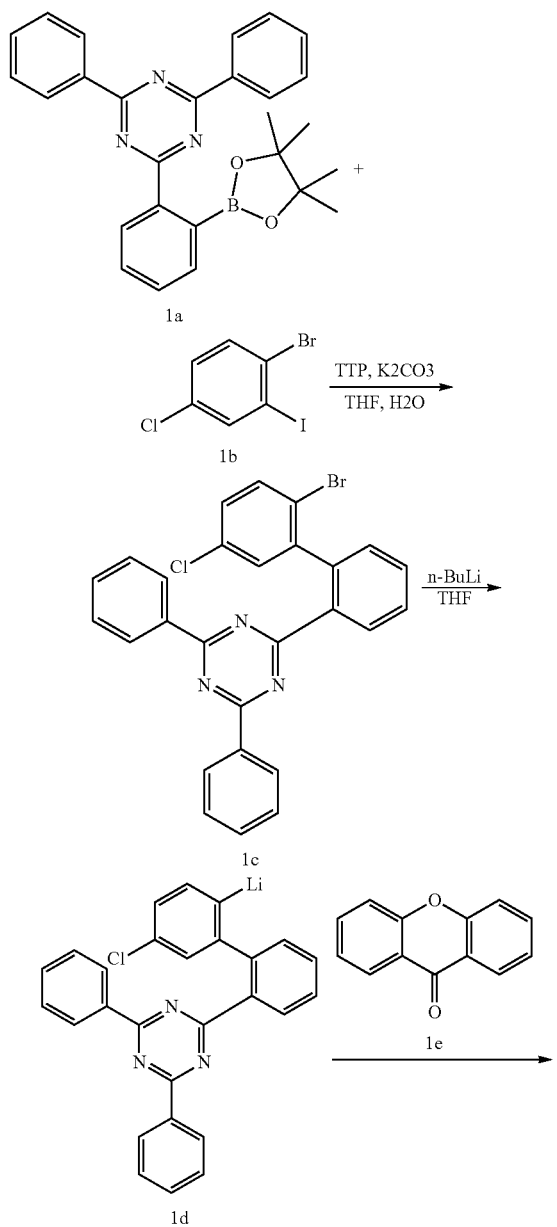

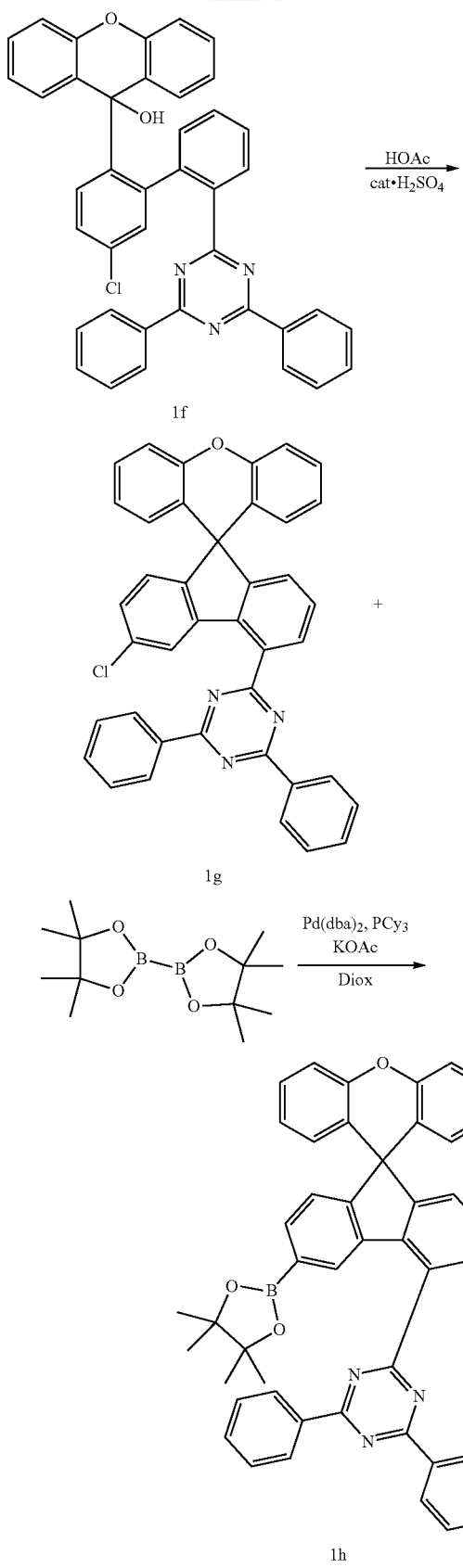

1) Preparation of Chemical Formula 1C

Under a nitrogen atmosphere, Chemical Formula 1a (80 g, 184 mmol) and Chemical Formula 1b (58 g, 184 mmol) were added to 550 ml of tetrahydrofuran and a solution of potassium carbonate (76 g, 552 mmol) in water was added thereto while stirring. Then, tetrakis(triphenylphosphine) palladium (0) (6.3 g, 5 mmol) was slowly added thereto while heating under reflux. Then, reaction proceeded for about 9 hours and then finished. After reaction, the reaction solution was allowed to cool to room temperature, and an organic layer was separated and then distilled. Then, the distilled product was extracted with chloroform and water twice, and the organic layer was distilled under reduced pressure again and then purified by column chromatography (chloroform:hexane) to prepare Chemical Formula 1c (70 g, 77%).

2) Preparation of Chemical Formula 1g

Chemical Formula 1c (60.0 g, 120 mmol) was added to 1,000 ml of anhydrous tetrahydrofuran and cooled to −78° C. Then, n-butyllithium (58 mL, 144 mmol) was slowly dropwise added over 30 minutes while stirring, reacted for one hour, allowed to warm to room temperature and then reacted for one hour. After reaction, the reaction solution was cooled to −78° C. and then Chemical Formula 1e (23.6 g, 120 mmol) as a solid was added thereto portionwise. After the reaction solution was slowly warmed and reacted for 2 hours, water was added to end the reaction, an aqueous layer and an organic layer were separated, and the organic layer was then distilled under reduced pressure to obtain Chemical Formula 1f. The compound of Chemical Formula 1f was added to 500 ml of acetic acid, one or two drops of sulfuric acid as a catalyst was added while stirring, and reflux was then conducted. After reaction for 2 hours, the produced solid was filtered, the filtrate was dissolved in chloroform again, neutralized with water saturated with calcium carbonate and extracted, and the organic layer was then dried over magnesium sulfate. Then, the organic layer was distilled under reduced pressure and recrystallized with ethanol. The produced solid was filtered and dried to prepare Chemical Formula 1g (41 g, 57%).

3) Preparation of Chemical Formula 1h

Under a nitrogen atmosphere, Chemical Formula 1g (41 g, 69 mmol), bis(pinacolato)diboron (17.4 g, 69 mmol) and potassium acetate (24 g, 240 mmol) were mixed, the resulting mixture was added to 410 ml of dioxane and the mixture was heated while stirring. Bis(dibenzylideneacetone)palladium (1.1 g, 2 mmol) and tricyclohexylphosphine (1.1 g, 4 mmol) were added thereto under reflux, followed by heating and stirring for 13 hours. After completion of reaction, the reaction solution was allowed to cool to room temperature and then filtered. Water was added to the filtrate, the mixture was extracted with chloroform, and the organic layer was dried over anhydrous magnesium sulfate. After distillation under reduced pressure, re-crystallization was conducted with ethanol to prepare Chemical Formula 1h (33 g, 72%).

Preparation Example 1-2: Synthesis of Compound 1

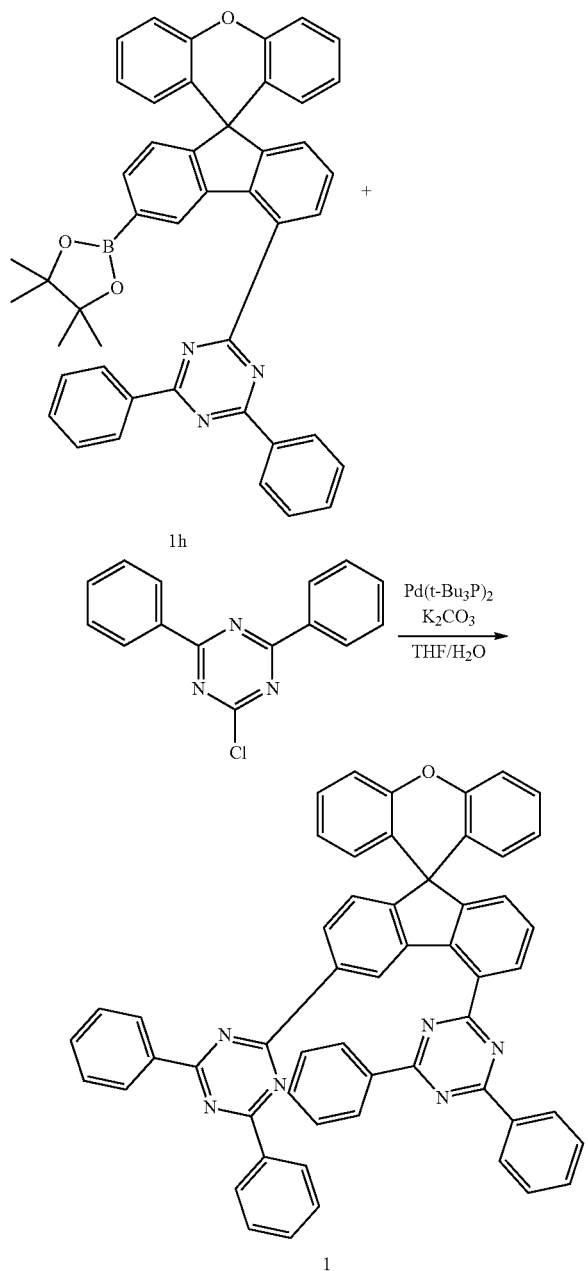

1) Preparation of Compound 1

Under a nitrogen atmosphere, Chemical Formula 1h (10 g, 15 mmol) and 2-chloro-4,6-diphenyl-1,3,5-triazine (3.8 g, 15 mmol) were added to 100 ml of tetrahydrofuran, followed by stirring and refluxing. Then, a solution of potassium carbonate (6 g, 44 mmol) in 30 ml of water was added to the reaction solution, stirring was thoroughly conducted, and then bis(tri-t-butylphosphine)palladium (0) (0.5 g, 0.4 mmol) was added thereto. After reaction for 3 hours, the reaction solution was allowed to cool to room temperature and filtered. The filtrate was extracted with chloroform and water, and the organic layer was dried with magnesium sulfate. Then, the organic layer was distilled under reduced pressure and then re-crystallized with a mix solution of tetrahydrofuran and ethyl acetate. The produced product was filtered and dried to prepare Compound 1 (7.0 g, 61%).

MS: [M+H]$^+$=795

Preparation Example 1-3: Synthesis of Compound 2

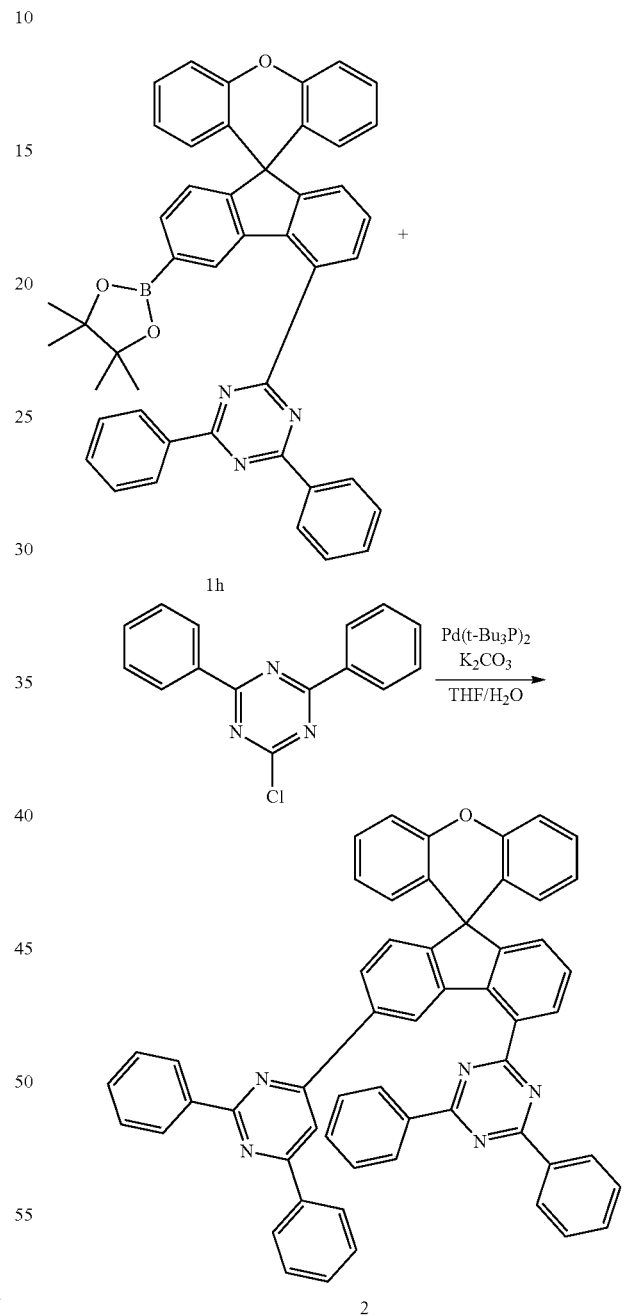

1) Preparation of Compound 2

Compound 2 (6.6 g, yield 57%) shown above was prepared in the same manner as in Compound 1, except that 4-chloro-2,6-diphenylpyrimidine was used instead of 2-chloro-4,6-diphenyl-1,3,5-triazine.

MS: [M+H]$^+$=794

Preparation Example 1-4: Synthesis of Compound 3

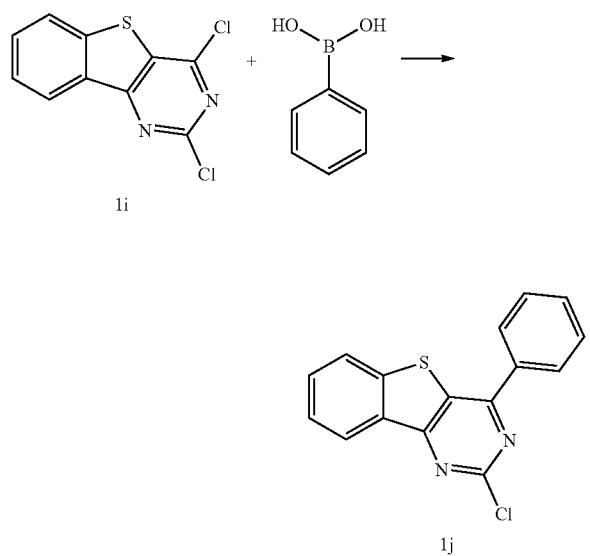

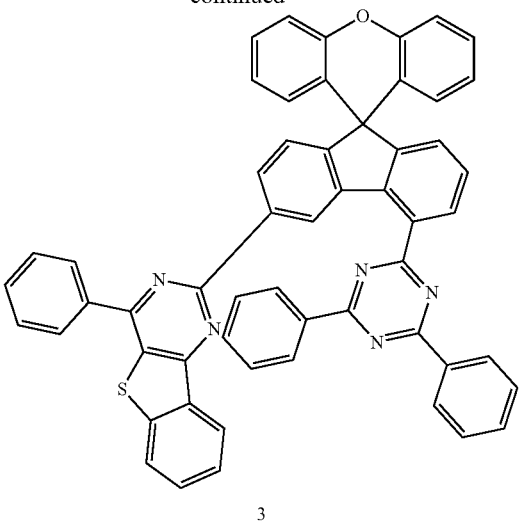

1) Preparation of Chemical Formula 1j

Under a nitrogen atmosphere, Chemical Formula 1i (13 g, 51 mmol) and phenylboronic acid (6.2 g, 51 mmol) were dissolved in 150 mL of tetrahydrofuran, a 1.5M aqueous potassium carbonate solution (100 mL) was added to the resulting solution, tetrakis-(triphenylphosphine)palladium (0.59 g, 0.51 mmol) was added thereto and heating was conducted while stirring for 7 hours. The reaction solution was allowed to cool to room temperature, the aqueous layer was separated and removed, dried over anhydrous magnesium sulfate and concentrated under reduced pressure, recrystallized with chloroform and ethanol, and then dried to prepare the titled Chemical Formula 1j (12.5 g, yield 82%).

2) Preparation of Compound 3

Compound 3 (8.5 g, yield 71%) shown above was prepared in the same manner as in Compound 1, except that Chemical Formula 1j was used instead of 2-chloro-4,6-diphenyl-1,3,5-triazine.

MS: $[M+H]^+ = 824$

Preparation Example 2

Preparation Example 2-1: Synthesis of Intermediate Compound 2h

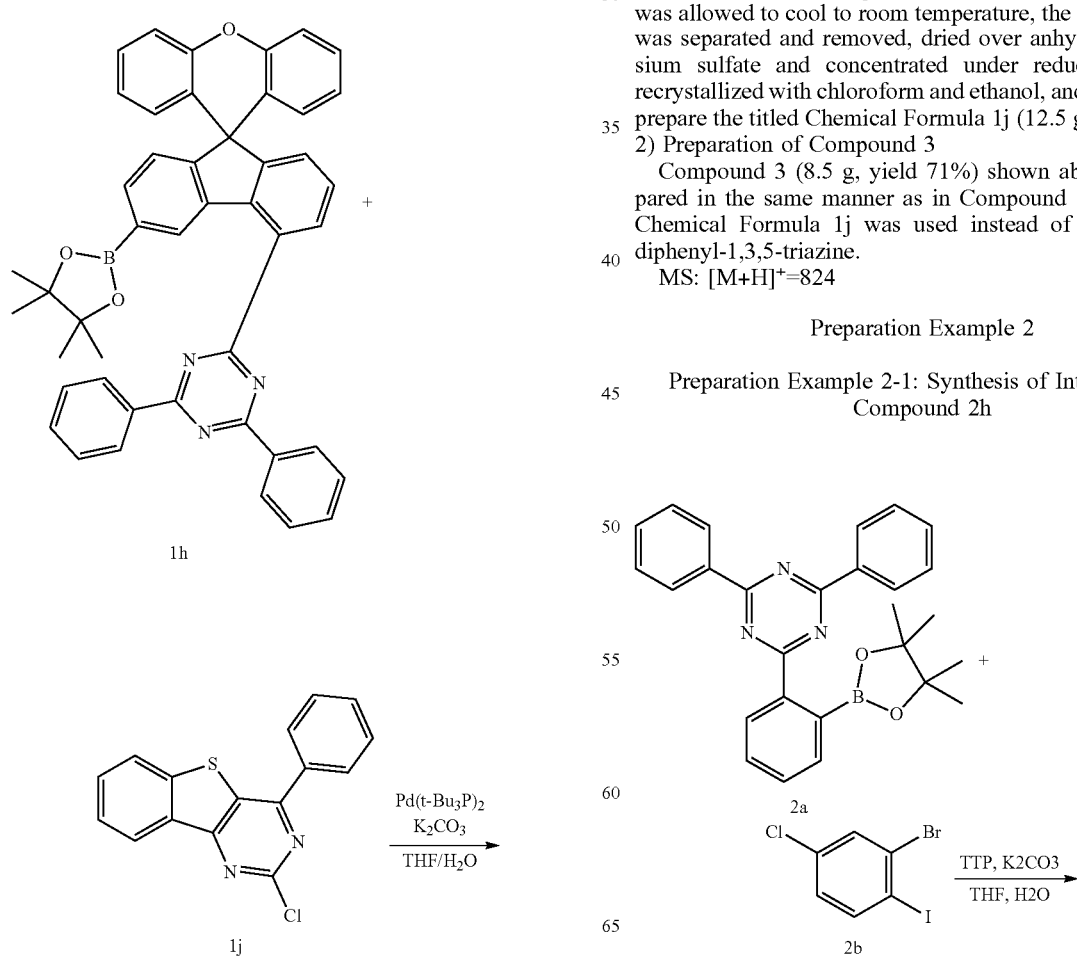

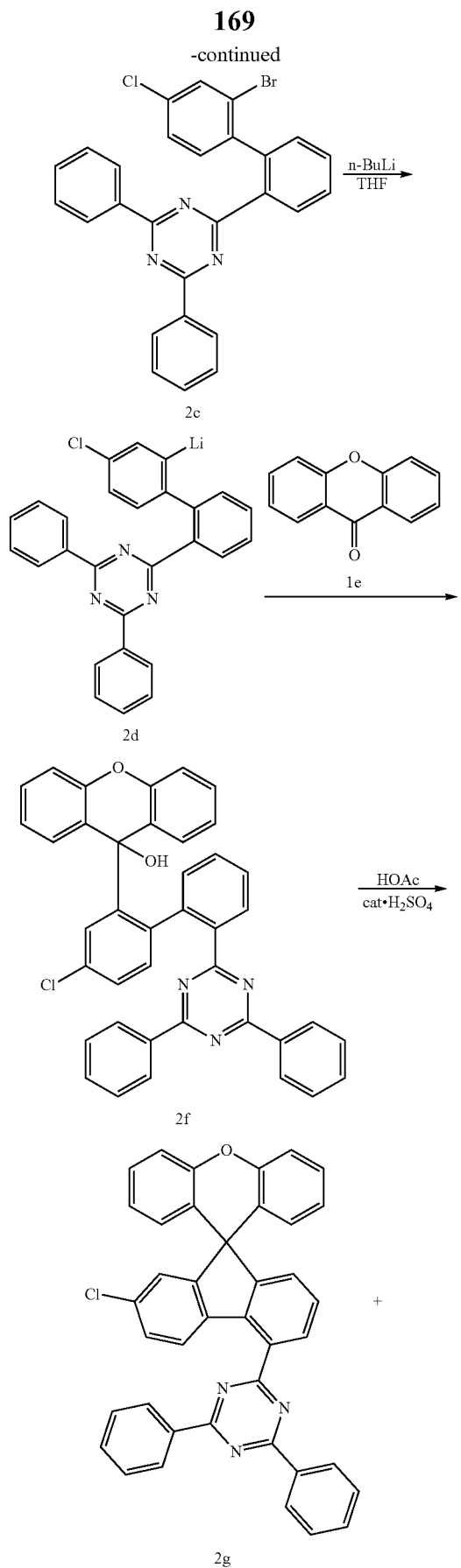

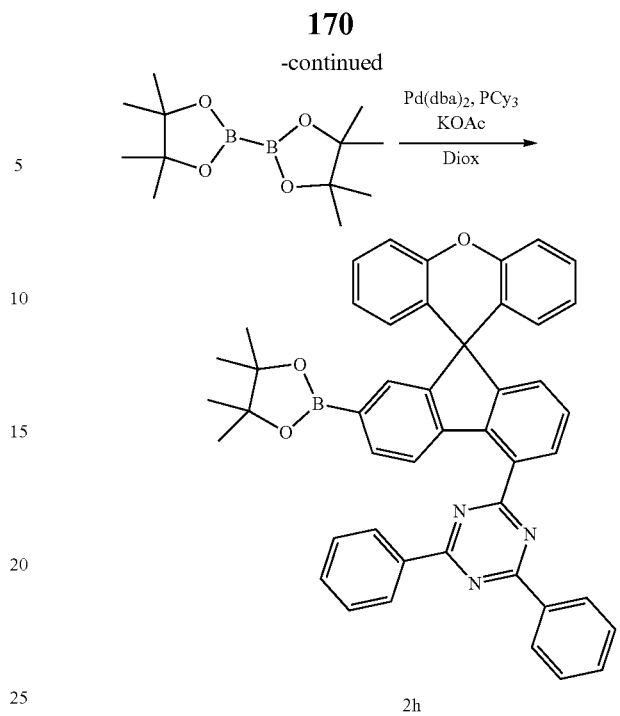

1) Preparation of Chemical Formula 2c

Under a nitrogen atmosphere, Chemical Formula 2a (80 g, 184 mmol) and Chemical Formula 2b (58 g, 184 mmol) were added to 550 ml of tetrahydrofuran and a solution of potassium carbonate (76 g, 552 mmol) in water was added thereto while stirring. Then, tetrakis(triphenylphosphine) palladium (0) (6.3 g, 5 mmol) was slowly added thereto while heating under reflux. Then, the reaction proceeded for about 9 hours and then finished. After reaction, the reaction solution was allowed to cool to room temperature and an organic layer was separated and then distilled. Then, the distilled product was extracted with chloroform and water twice, and the organic layer was distilled under reduced pressure and then purified by column chromatography (chloroform:hexane) to prepare Chemical Formula 2c (65 g, 71%).

2) Preparation of Chemical Formula 2g

Chemical Formula 2c (60.0 g, 120 mmol) was added to 1,000 ml of anhydrous tetrahydrofuran and cooled to −78° C. Then, n-butyllithium (58 mL, 144 mmol) was slowly dropwise added under stirring over 30 minutes, reacted for one hour, allowed to warm to room temperature and then reacted for one hour. After reaction, the reaction solution was cooled to −78° C. and then Chemical Formula 2e (23.6 g, 120 mmol) as a solid was added thereto portionwise. After the reaction solution was slowly warmed and reacted for 2 hours, water was added thereto to end the reaction, an aqueous layer and an organic layer were separated, and the organic layer was distilled under reduced pressure to obtain Chemical Formula 2f. The compound of Chemical Formula 2f was added to 500 ml of acetic acid, one or two drops of sulfuric acid as a catalyst was added while stirring and reflux was conducted. After reaction for 2 hours, the produced solid was filtered, the filtrate was dissolved in chloroform again, neutralized with water saturated with calcium carbonate and extracted, and the organic layer was then dried over magnesium sulfate. Then, the organic layer was distilled under reduced pressure and recrystallized with ethanol. The produced product was filtered and dried to prepare Chemical Formula 2g (45 g, 79%).

3) Preparation of Chemical Formula 2h

Under a nitrogen atmosphere, Chemical Formula 2g (45 g, 75 mmol), bis(pinacolato)diboron (21 g, 83 mmol) and potassium acetate (22 g, 226 mmol) were mixed, the resulting mixture was added to 410 ml of dioxane and the mixture was heated while stirring. Bis(dibenzylideneacetone)palladium (1.3 g, 2 mmol) and tricyclohexylphosphine (1.3 g, 4 mmol) were added under reflux, followed by heating and stirring for 10 hours. After completion of reaction, the reaction solution was allowed to cool to room temperature and then filtered. Water was added to the filtrate, the mixture was extracted with chloroform, and the organic layer was dried over anhydrous magnesium sulfate. After distillation under reduced pressure, re-crystallization was conducted with ethanol to prepare Chemical Formula 2h (41 g, 79%).

Preparation Example 2-2: Synthesis of Compound 4

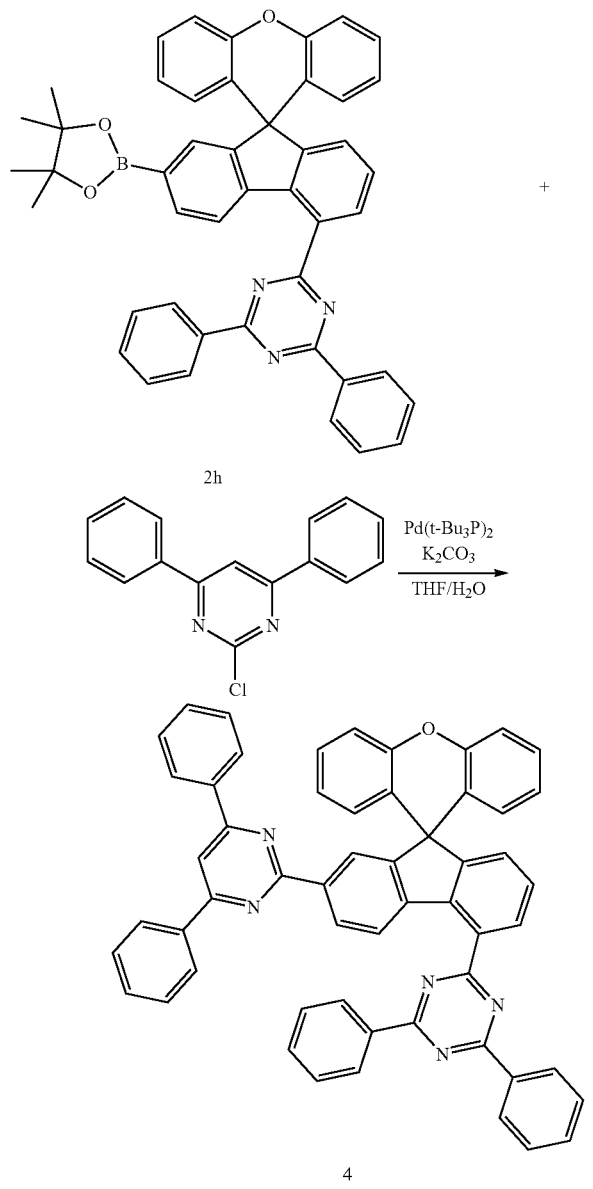

4

Compound 4 (6.9 g, yield 60%) shown above was prepared in the same manner as in Compound 1, except that Intermediate Compound 2h was used instead of Intermediate Compound 1h and 2-chloro-4,6-diphenylpyrimidine was used instead of 2-chloro-4,6-diphenyl-1,3,5-triazine.

MS: [M+H]$^+$=794

Preparation Example 2-3: Synthesis of Compound 5

5

Compound 5 (6.3 g, yield 62%) shown above was prepared in the same manner as Compound 1, except that Intermediate Compound 2h was used instead of Intermediate Compound 1h and 2-chlorobenzothiazole was used instead of 2-chloro-4,6-diphenyl-1,3,5-triazine.

MS: [M+H]$^+$=697

Preparation Example 2-4: Synthesis of Compound 6

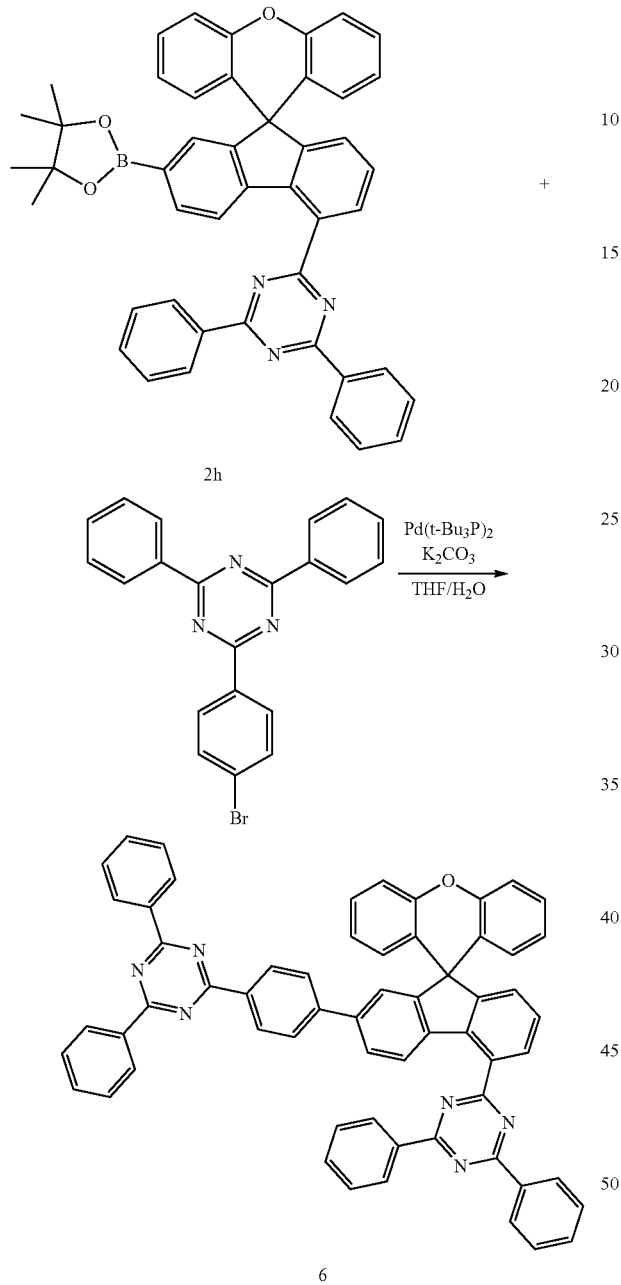

Compound 6 (9.5 g, yield 75%) shown above was prepared in the same manner as Compound 1, except that Intermediate Compound 2h was used instead of Intermediate Compound 1h and 2-(4-bromophenyl)-4,6-diphenyl-1,3,5-triazine was used instead of 2-chloro-4,6-diphenyl-1,3,5-triazine.

MS: [M+H]$^+$=871

Preparation Example 3

Preparation Example 3-1: Synthesis of Intermediate Compound 3h

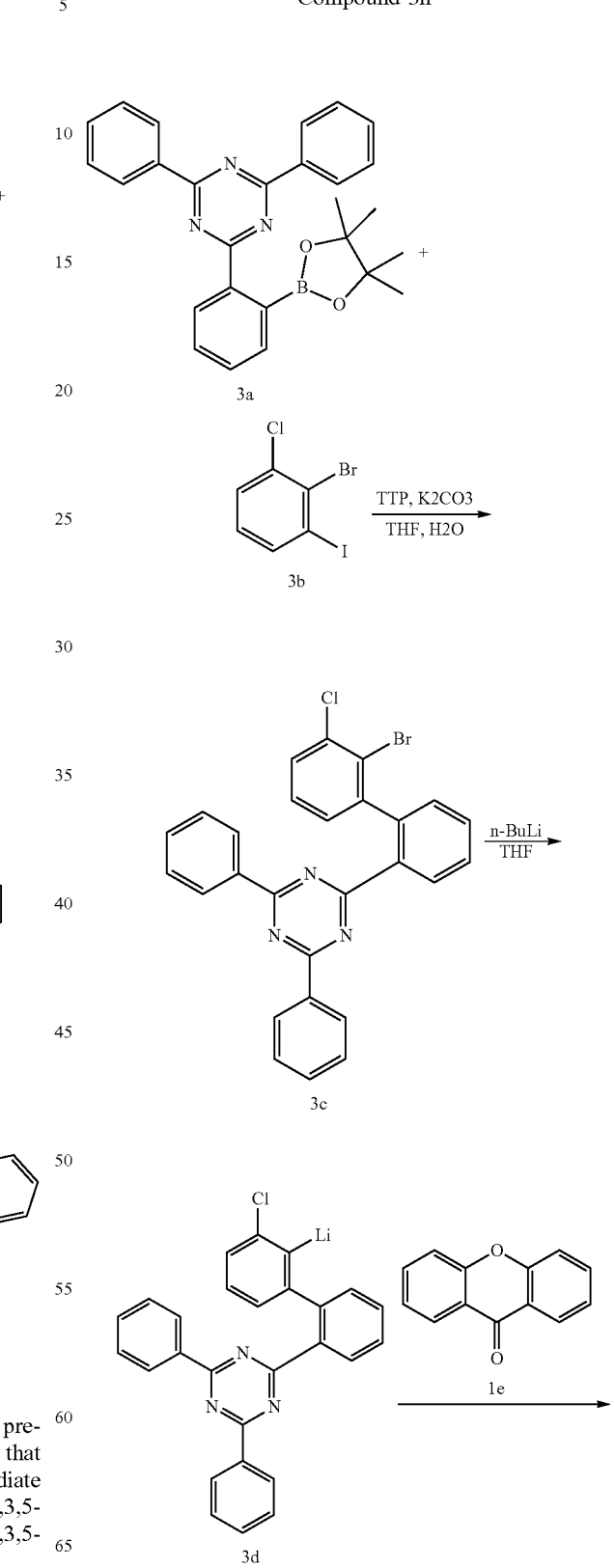

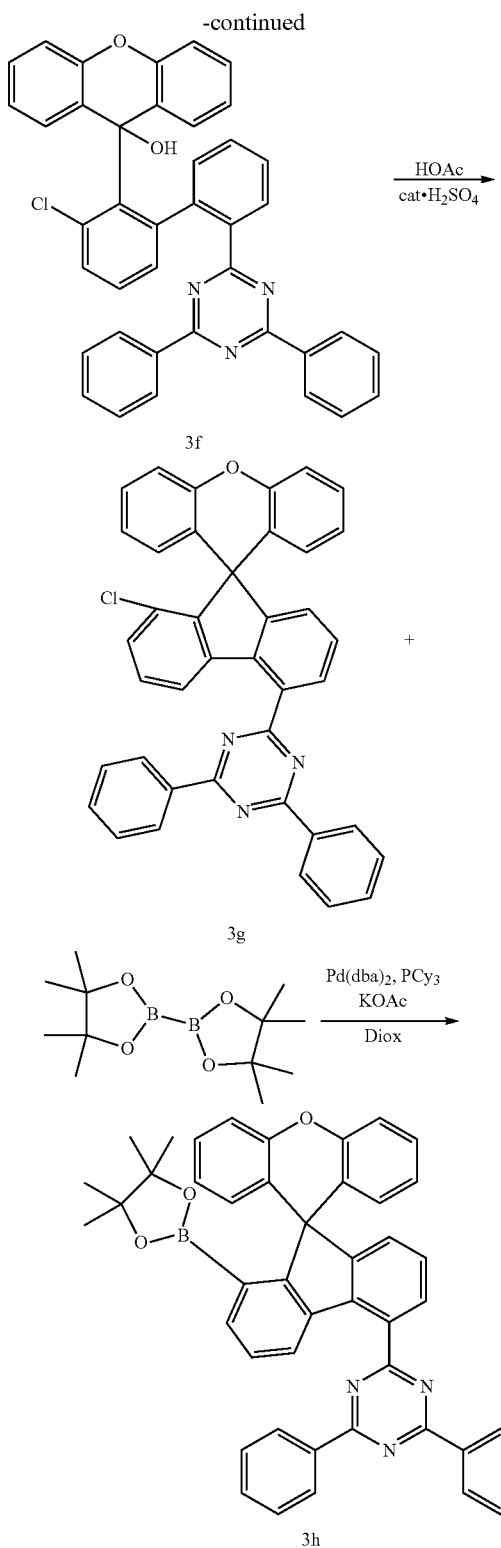

9 hours and then finished. After reaction, the reaction solution was allowed to cool to room temperature and an organic layer was separated and then distilled. Then, the distilled product was extracted with chloroform and water twice, and the organic layer was distilled under reduced pressure and then purified by column chromatography (chloroform:hexane) to prepare Chemical Formula 3c (46 g, 69%).

2) Preparation of Chemical Formula 3g

Chemical Formula 3c (30.0 g, 60 mmol) was added to 500 ml of anhydrous tetrahydrofuran and cooled to −78° C. Then, n-butyllithium (29 mL, 72 mmol) was slowly dropwise added over 30 minutes while stirring, reacted for one hour, allowed to warm to room temperature and then reacted for one hour. After reaction, the reaction solution was cooled to −78° C. and then Chemical Formula 1e (11.8 g, 60 mmol) as a solid was added thereto portionwise. After the reaction solution was slowly warmed and reacted for 2 hours, water was added thereto to end the reaction, an aqueous layer and an organic layer were separated, and the organic layer was distilled under reduced pressure to obtain Chemical Formula 3f. The compound of Chemical Formula 3f was added to 500 ml of acetic acid, one or two drops of sulfuric acid as a catalyst was added, while stirring, and reflux was conducted. After reaction for 2 hours, the produced solid was filtered, the filtrate was dissolved in chloroform again, neutralized with water saturated with calcium carbonate and extracted, and the organic layer was then dried over magnesium sulfate. Then, the organic layer was distilled under reduced pressure and recrystallized with ethanol. The produced product was filtered and dried to prepare Chemical Formula 3 g (21 g, 57%).

3) Preparation of Chemical Formula 3h

Under a nitrogen atmosphere, Chemical Formula 3g (20 g, 33 mmol), bis(pinacolato)diboron (9.4 g, 37 mmol) and potassium acetate (10 g, 100 mmol) were mixed, the resulting mixture was added to 200 ml of dioxane and the mixture was heated while stirring. Bis(dibenzylideneacetone)palladium (1.1 g, 2 mmol) and tricyclohexylphosphine (1.1 g, 4 mmol) were added under reflux, followed by heating and stirring for 13 hours. After completion of reaction, the reaction solution was allowed to cool to room temperature and then filtered. Water was added to the filtrate, the mixture was extracted with chloroform, and the organic layer was dried over anhydrous magnesium sulfate. After distillation under reduced pressure, re-crystallization was conducted with ethanol to prepare Chemical Formula 3h (14 g, 60%).

Preparation Example 3-2: Synthesis of Compound 7

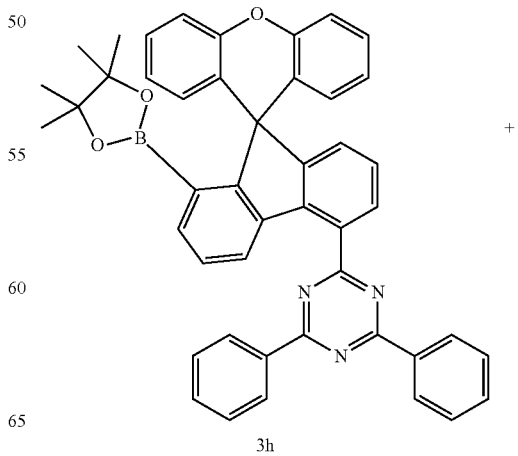

3h

1) Preparation of Chemical Formula 3c

Under a nitrogen atmosphere, Chemical Formula 3a (50 g, 115 mmol) and Chemical Formula 3b (36 g, 115 mmol) were added to 300 ml of tetrahydrofuran and a solution of potassium carbonate (48 g, 345 mmol in water) was added thereto while stirring. Then, tetrakis(triphenylphosphine)palladium (0) (4 g, 3 mmol) was slowly added thereto while heating under reflux. Then, the reaction proceeded for about

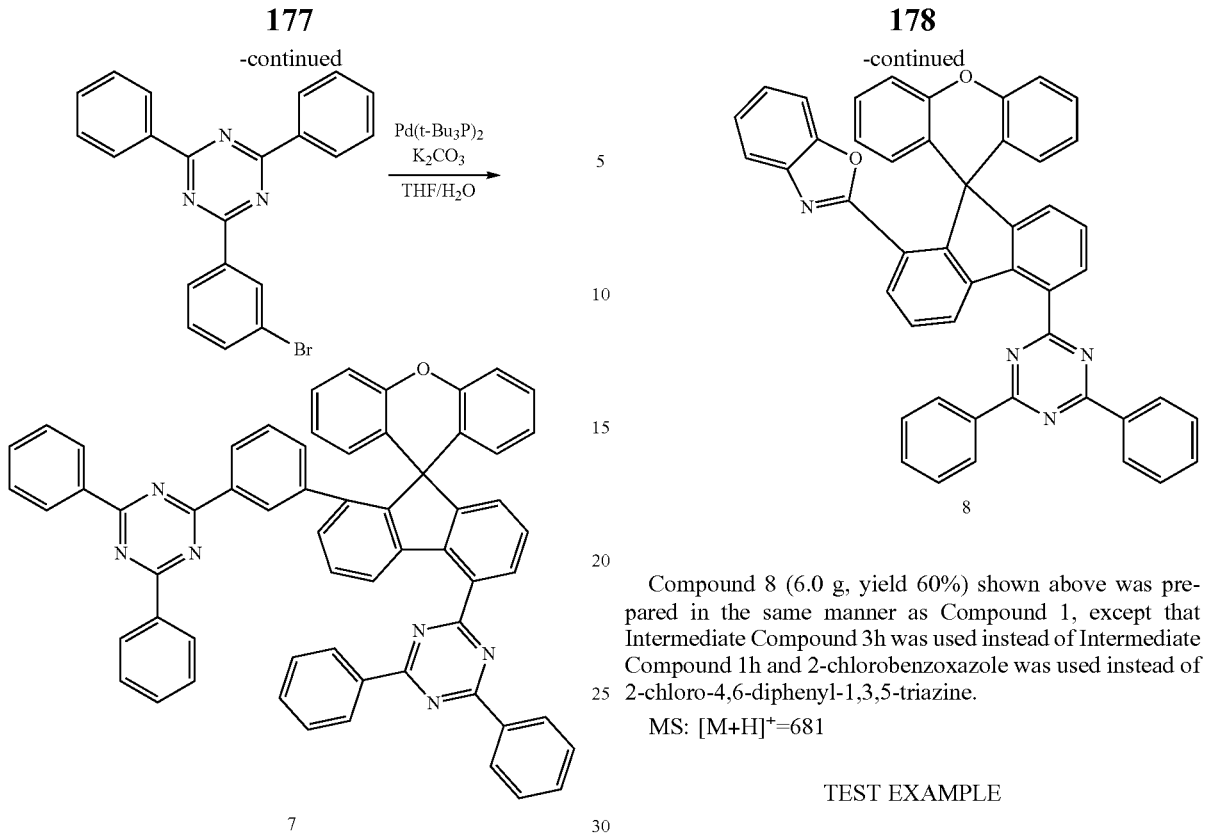

Compound 7 (9.5 g, yield 71%) shown above was prepared in the same manner as Compound 1, except that Intermediate Compound 3h was used instead of Intermediate Compound 1h and 2-(3-bromophenyl)-4,6-diphenyl-1,3,5-triazine was used instead of 2-chloro-4,6-diphenyl-1,3,5-triazine.

MS: [M+H]$^+$=871

Preparation Example 3-3: Synthesis of Compound 8

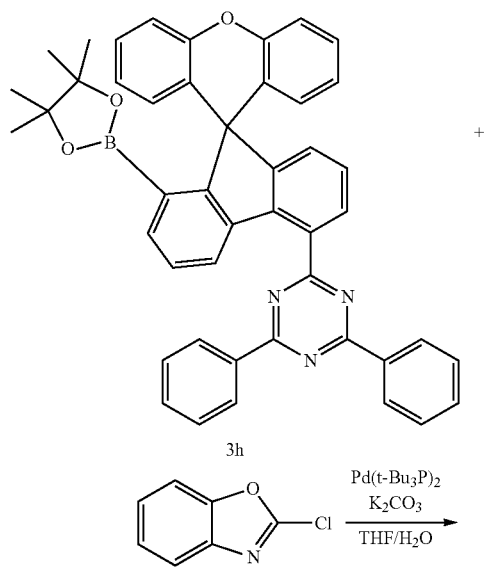

Compound 8 (6.0 g, yield 60%) shown above was prepared in the same manner as Compound 1, except that Intermediate Compound 3h was used instead of Intermediate Compound 1h and 2-chlorobenzoxazole was used instead of 2-chloro-4,6-diphenyl-1,3,5-triazine.

MS: [M+H]$^+$=681

TEST EXAMPLE

Test Example 1

A glass substrate coated to a thin thickness of 1,300 Å with ITO (indium tin oxide) was cleaned by ultrasonication with distilled water in which a dispersant was dissolved. The detergent used herein was a product commercially available from Fischer Co. and the distilled water used herein was distilled water secondarily filtered through a filter commercially available from Millipore Co. ITO was cleaned for 30 minutes and was then ultrasonically cleaned with distilled water repeatedly twice for 10 minutes. After cleaning with distilled water, ITO was subjected to ultrasonic cleaning with isopropyl alcohol, acetone and methanol solvents, dried and transported to a plasma cleaner. In addition, the substrate was cleaned with oxygen plasma for 5 minutes and transported to a vacuum deposition machine.

Compound HI-1 shown below was thermal-vacuum deposited to a thickness of 50 Å on the ITO transparent electrode thus prepared to form a hole injection layer. Compound HT-1 shown below was thermal-vacuum deposited to a thickness of 250 Å on the hole injection layer to form a hole transport layer, and Compound HT-2 shown below was vacuum-deposited to a thickness of 50 Å on the HT-1 deposition film to form an electron blocking layer. Compound 1 previously prepared in Example 1, Compound YGH-1 shown below and a phosphorescent dopant YGD-1 were co-deposited as materials for a light emitting layer on the HT-2 deposition film in a weight ratio of 44:44:12, to form a light emitting layer with a thickness of 400 Å. Compound ET-1 shown below was vacuum deposited to a thickness of 250 Å on the light emitting layer to foil an electron transport layer, Compound ET-2 shown below and Li were co-deposited in a weight ratio of 98:2 on the electron transport layer to form an electron injection layer with a thickness of 100 Å. Aluminum was deposited to a thickness of 1,000 Å on the electron injection layer to form a cathode.

HI-1
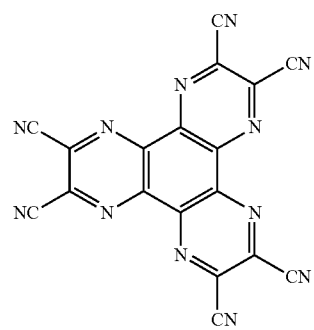
YGH-1
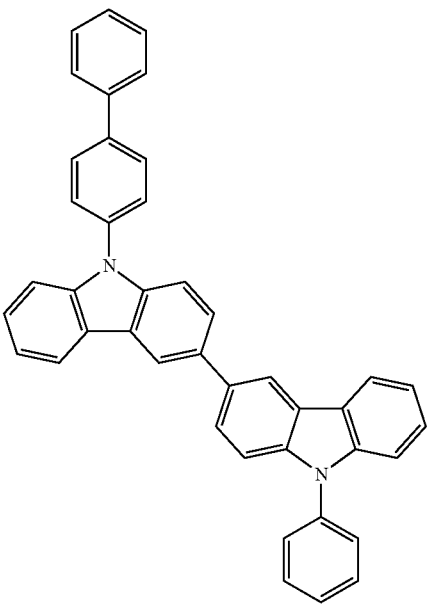
HT-1
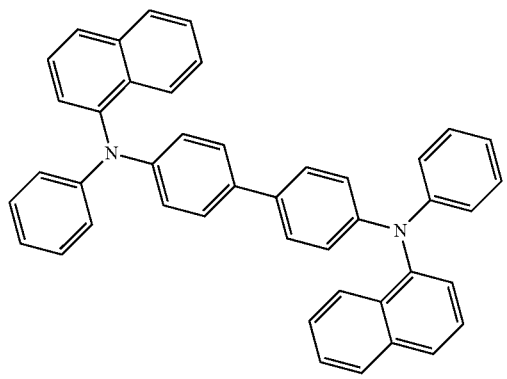
YGD-1
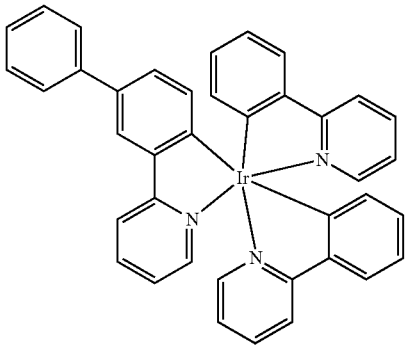
HT-2
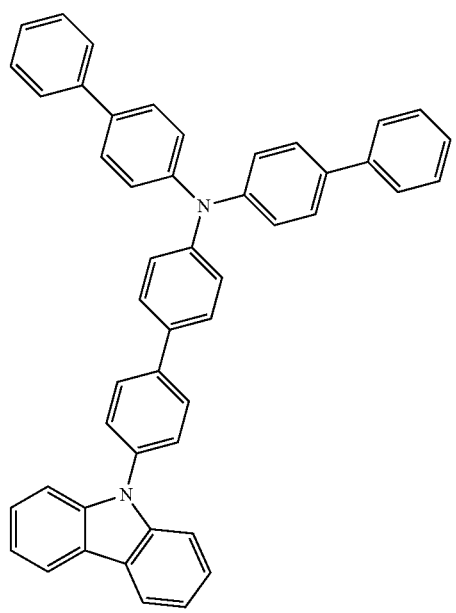
ET-1
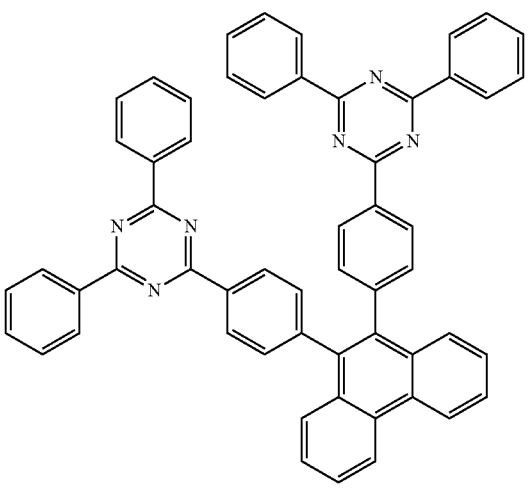

ET-2

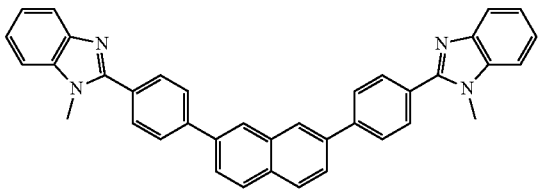

During the process, the deposition rate of the organic materials was maintained at 0.4 to 0.7 Å/sec, the deposition rate of aluminum was maintained at 2 Å/sec, and the vacuum level during deposition was maintained at $1 \times 10^{-7}$ to $5 \times 10^{-8}$ torr.

Test Examples 2 to 8

Organic light emitting devices were manufactured in the same manner as in Test Example 1 except that compounds shown in the following Table 1 were used instead of Compound 1 of Example 1.

Comparative Test Examples 1 to 3

Organic light emitting devices were manufactured in the same manner as in Test Example 1 except that compounds shown in the following Table 1 were used instead of Compound 1 of Example 1. Compounds C1 to C3 in the following Table 1 are shown below:

C1

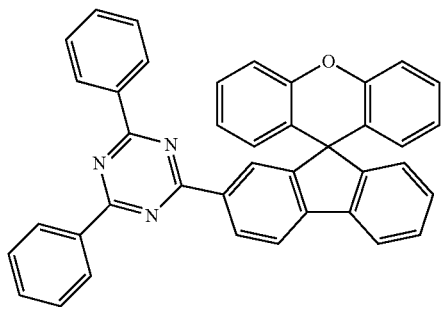

C2

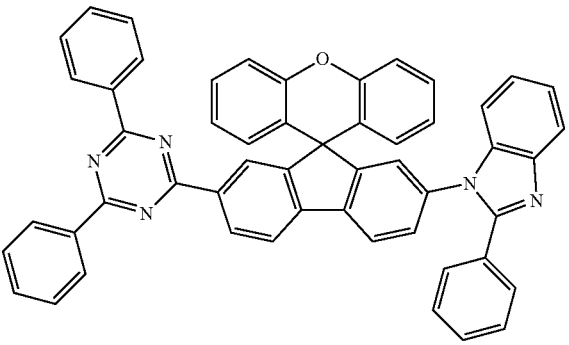

C3

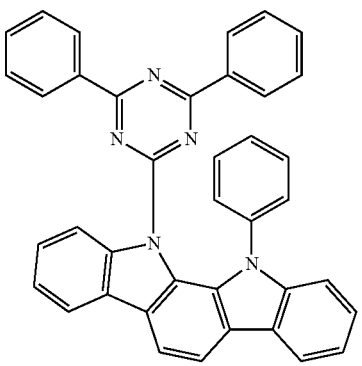

In the Test Examples and Comparative Test Examples, voltages and efficiencies of the organic light emitting devices were measured at a current density of 10 mA/cm², and lifetime was measured at a current density of 50 mA/cm². Results are shown in the following Table 1. Here, $LT_{95}$ means the time at which the present brightness corresponds to 95% of the initial brightness.

TABLE 1

|  | Compound | Voltage (V) (@10 mA/cm²) | Efficiency (Cd/A) (@10 mA/cm²) | Chromaticity coordinates (x, y) | Lifetime (h) ($LT_{95}$ at 50 mA/cm²) |
|---|---|---|---|---|---|
| Test Example 1 | Compound 1 | 3.8 | 78 | 0.45, 0.54 | 150 |
| Test Example 2 | Compound 2 | 3.9 | 77 | 0.46, 0.54 | 150 |
| Test Example 3 | Compound 3 | 3.6 | 75 | 0.45, 0.52 | 120 |
| Test Example 4 | Compound 4 | 3.9 | 77 | 0.45, 0.53 | 140 |
| Test Example 5 | Compound 5 | 4.0 | 73 | 0.46, 0.52 | 100 |
| Test Example 6 | Compound 6 | 3.8 | 79 | 0.46, 0.53 | 160 |
| Test Example 7 | Compound 7 | 3.8 | 79 | 0.46, 0.54 | 155 |
| Test Example 8 | Compound 8 | 4.0 | 72 | 0.45, 0.54 | 110 |
| Comparative Test Example 1 | C1 | 4.2 | 75 | 0.44, 0.55 | 30 |
| Comparative Test Example 2 | C2 | 4.3 | 71 | 0.46, 0.52 | 70 |
| Comparative Test Example 3 | C3 | 4.0 | 70 | 0.46, 0.53 | 90 |

As can be seen from Table 1 above, when the compounds according to the present specification are used as light emitting layer materials, excellent efficiency and lifetime are obtained, as compared to when the compounds according to Comparative Test Examples are used as light emitting layer materials. In particular, it can be seen that, when comparing the compounds of Test Examples 4, and 6 to 7 with the compound of Comparative Test Example 1, lifetime is about 4 times or more longer than the case of having one triazine or hetero-substituent. In addition, it can be seen that, when compared with the compound of Comparative Test Example 2, Compound 5 and Compound 8 having a benzoxazole substituent and a benzothiazole substituent, respectively, have improved efficiency and lifetime than Compound C2 having a benzoimidazole substituent.

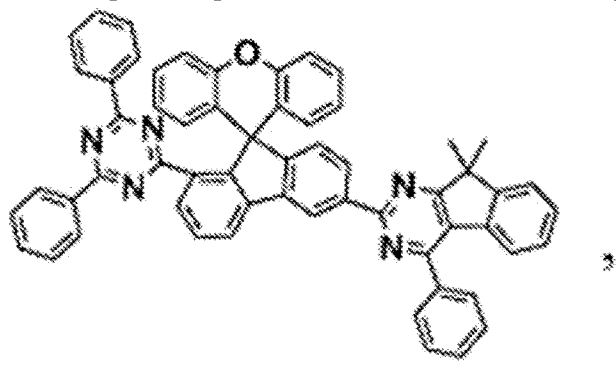

The invention claimed is:
1. A compound of Chemical Formula 1:

[Chemical Formula 1]

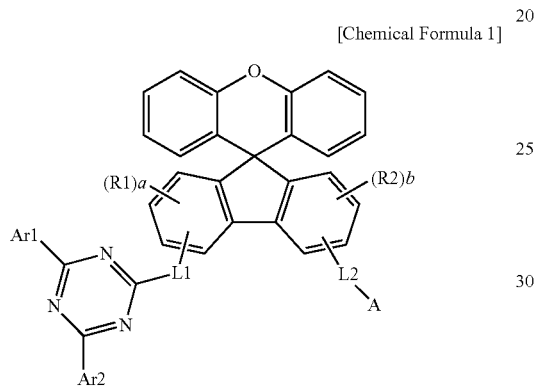

wherein:
R1 and R2 are each independently any one selected from the group consisting of hydrogen, deuterium, a halogen, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted aralkylamine group, a substituted or unsubstituted arylamine group, a substituted or unsubstituted arylphosphine group, a substituted or unsubstituted phosphine oxide group, a substituted or unsubstituted aryl group, and a substituted or unsubstituted heterocyclic group including one or more of N, O, S, Si and Se atoms;
a and b are each independently an integer of 1 to 3;
L1 and L2 are each independently a direct bond or a substituted or unsubstituted arylene group;
Ar1 and Ar2 are each independently a substituted or unsubstituted aryl group or a substituted or unsubstituted heterocyclic group; and A is any one group selected from the following formulae:

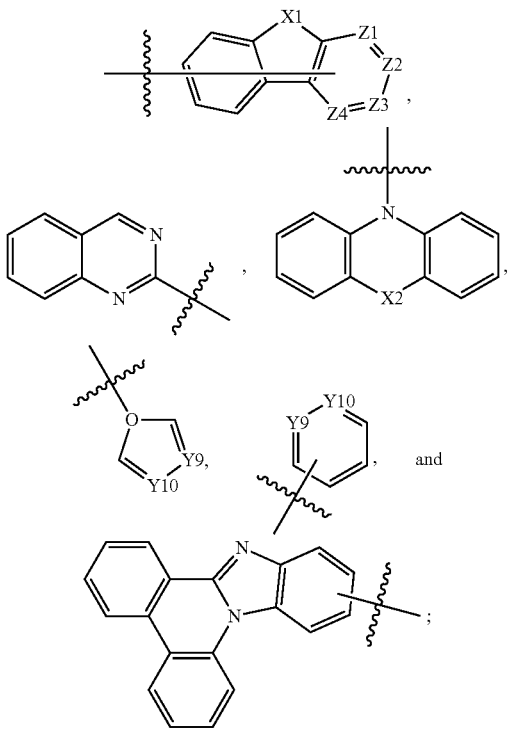

wherein:
X1 is O, S or CR3R4;
X2 is O, NR or S;
Y9 and Y10 are each independently N or CR5;
at least one of Y9 and Y10 is N; and
at least two of Z1 to Z4 are N and the others are C or CR6,
wherein R and R3 to R6 are each independently any one selected from the group consisting of hydrogen, deuterium, a halogen, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted aralkylamine group, a substituted or unsubstituted arylamine group, a substituted or unsubstituted arylphosphine group, a substituted or unsubstituted phosphine oxide group, a substituted or unsubstituted aryl group, and a substituted or unsubstituted heterocyclic group including one or more of N, O, S, Si and Se atoms; and
each A independently is unsubstituted or substituted with a substituted or unsubstituted alkyl group, a substituted or unsubstituted aryl group, or a substituted or unsubstituted heterocyclic group.

2. The compound of claim 1, wherein Chemical Formula 1 is a compound of any one of the following Chemical Formulae 2 to 5:

[Chemical Formula 2]

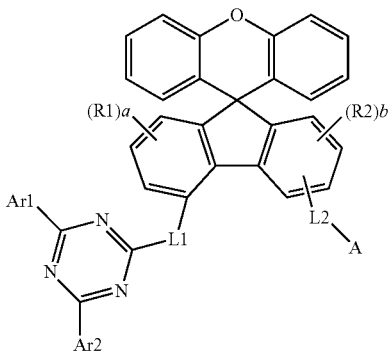

[Chemical Formula 3]

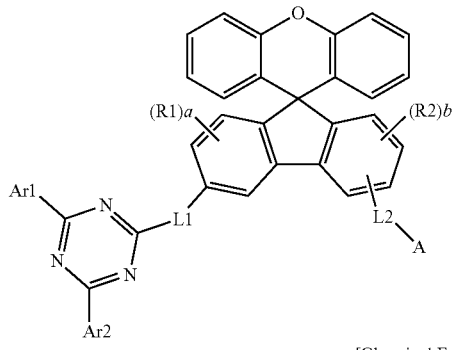

[Chemical Formula 4]

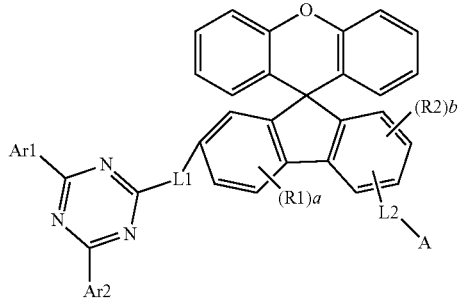

[Chemical Formula 5]

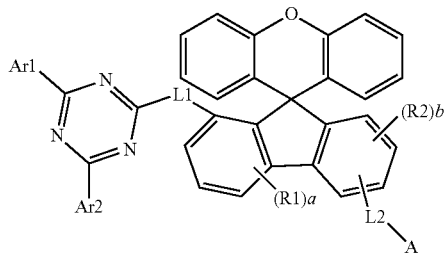

wherein:
R1 and R2 are each independently any one selected from the group consisting of hydrogen, deuterium, a halogen, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted aralkylamine group, a substituted or unsubstituted arylamine group, a substituted or unsubstituted arylphosphine group, a substituted or unsubstituted phosphine oxide group, a substituted or unsubstituted aryl group, and a substituted or unsubstituted heterocyclic group including one or more of N, O, S, Si and Se atoms;

a and b are each independently an integer of 1 to 3;

L1 and L2 are each independently a direct bond or a substituted or unsubstituted arylene group;

Ar1 and Ar2 are each independently a substituted or unsubstituted aryl group or a substituted or unsubstituted heterocyclic group; and A is any one group selected from the following formulae:

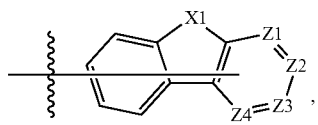

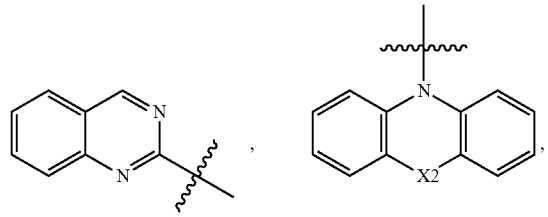

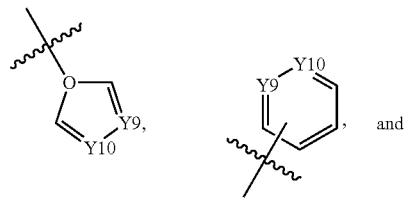, and

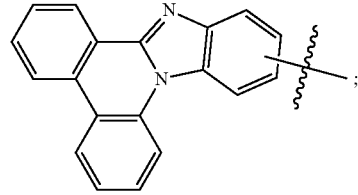;

wherein:
X1 is O, S or CR3R4;
X2 is O, NR or S;
Y9 and Y10 are each independently N or CR5;
at least one of Y9 and Y10 is N; and
at least two of Z1 to Z4 are N and the others are C or CR6, wherein R and R3 to R6 are each independently any one selected from the group consisting of hydrogen, deuterium a halogen, a nitrile group, a nitro group, a hydroxyl group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted aralkylamine group, a substituted or unsubstituted arylamine group, a substituted or unsubstituted arylphosphine group, a substituted or unsubstituted phosphine oxide group, a substituted or unsubstituted aryl group, and a substituted or unsubstituted heterocyclic group including one or more of N, O, S, Si and Se atoms; and each A independently is unsubstituted or substituted with a substituted or unsubstituted alkyl group, a substituted or unsubstituted aryl group, or a substituted or unsubstituted heterocyclic group.

3. The compound of claim 1, wherein A is a substituent selected from among the following formulae:

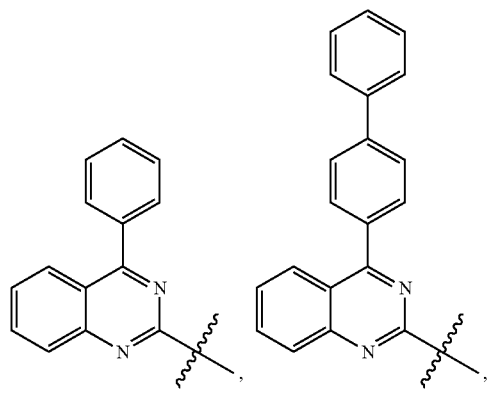

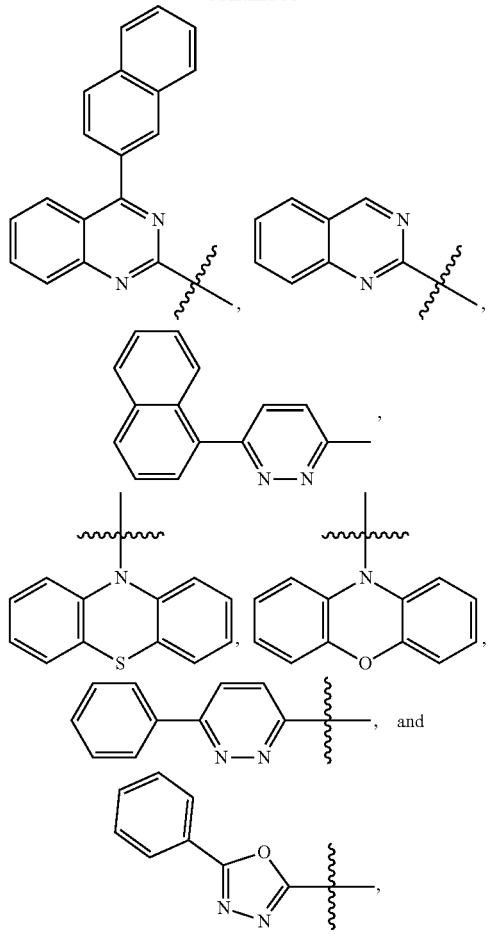

4. The compound of claim 1, wherein R1 to R6 are hydrogen.

5. The compound of claim 1, wherein the compound of Chemical Formula 1 is any one selected from among the following compounds:

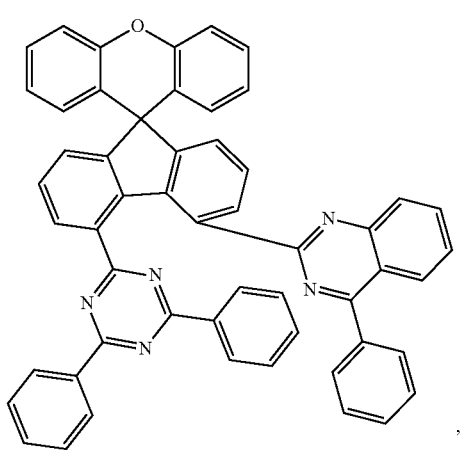

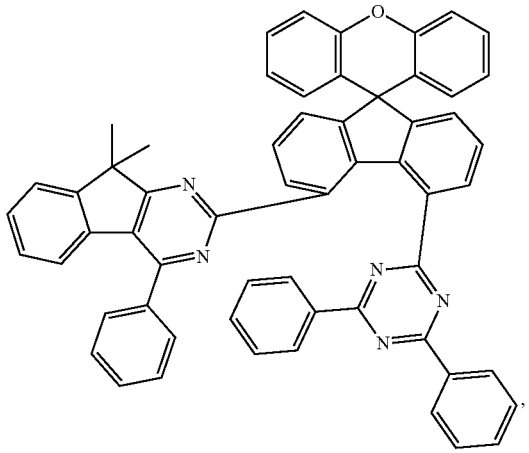

-continued
189
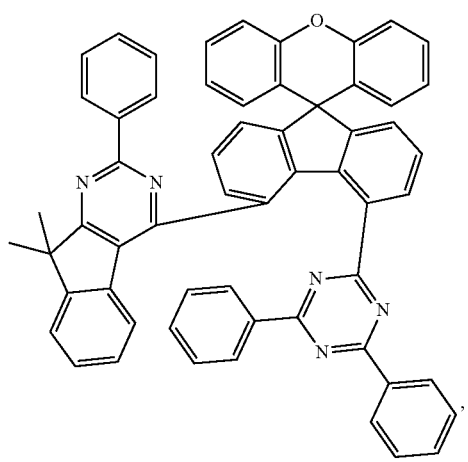
190
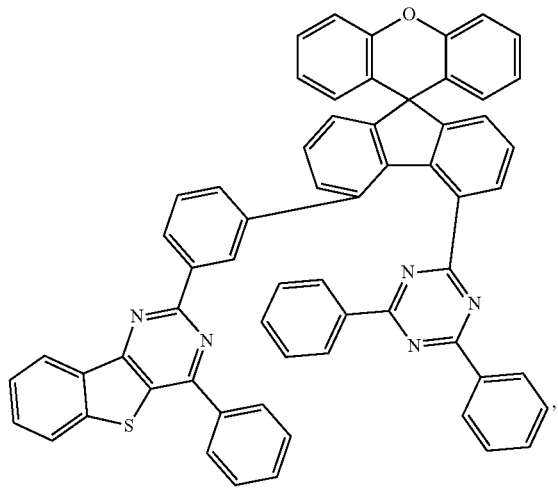
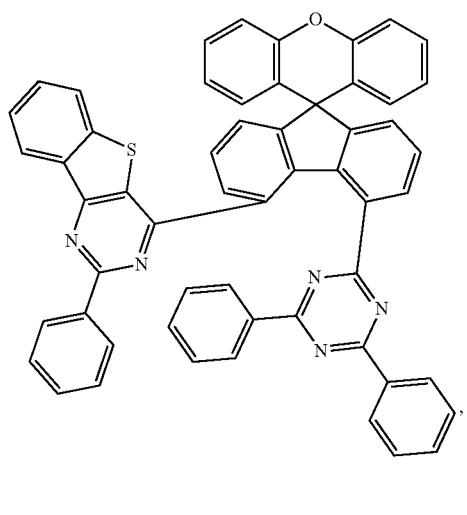
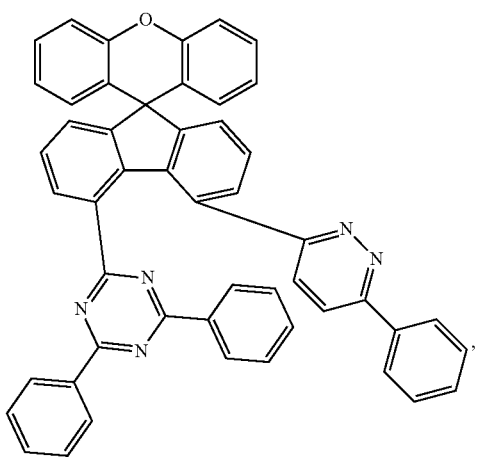
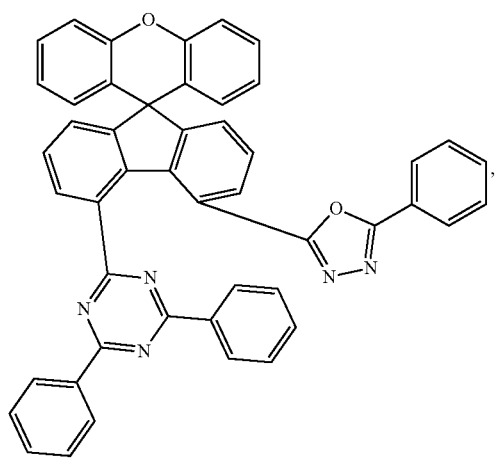
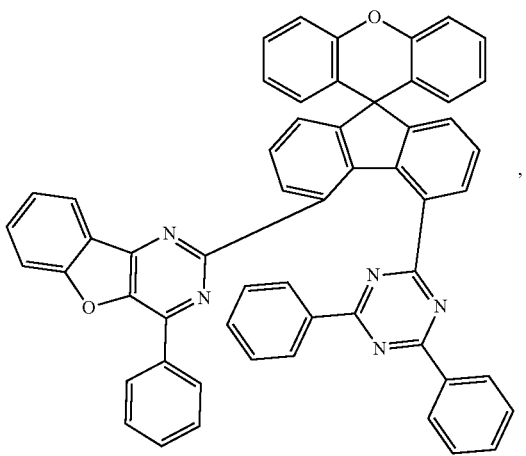

191 192
-continued
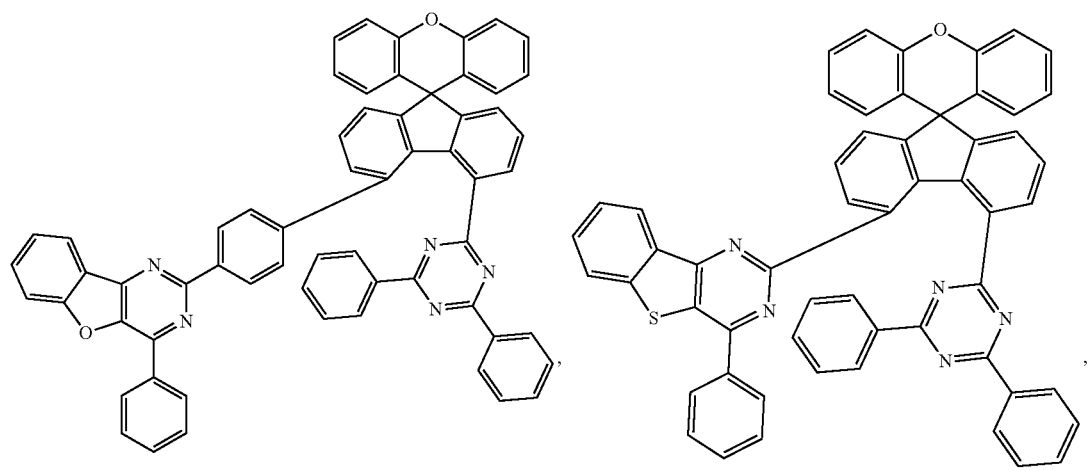
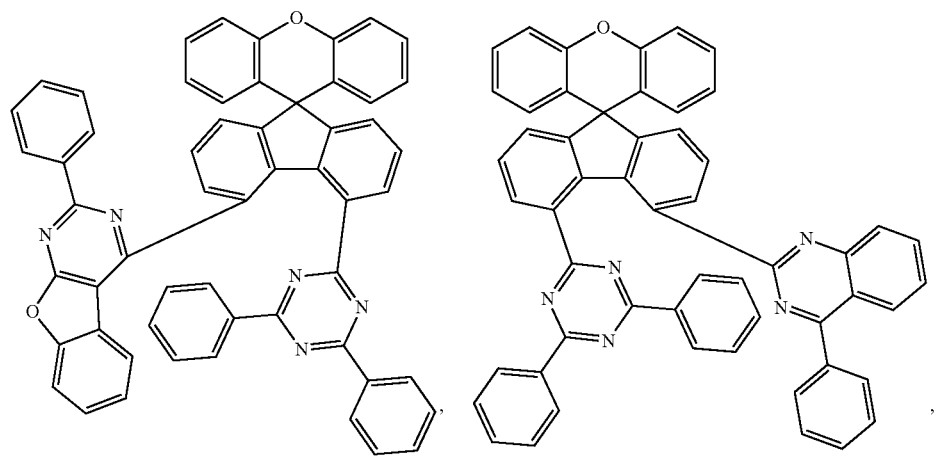
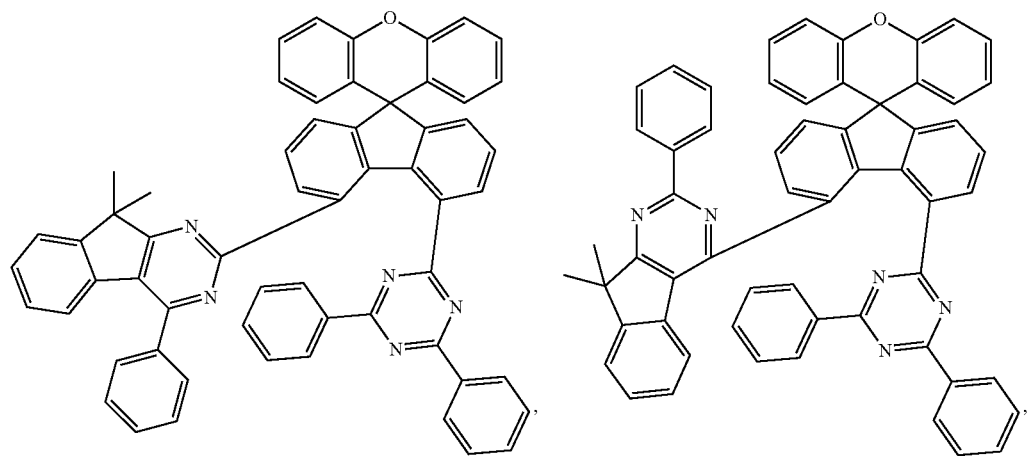

-continued
193
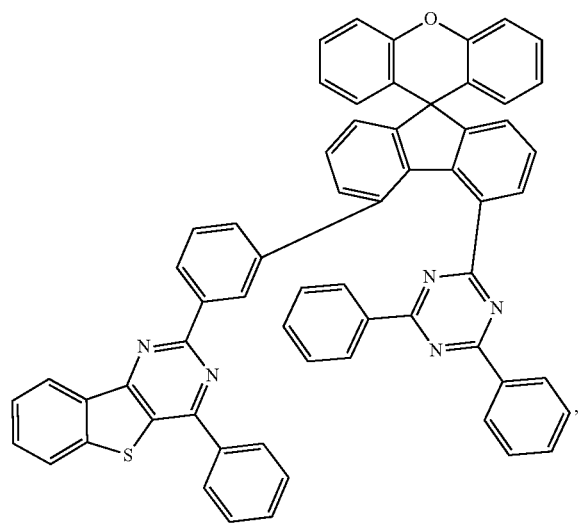
194
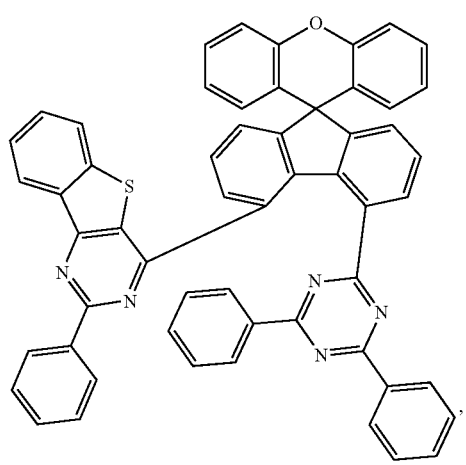
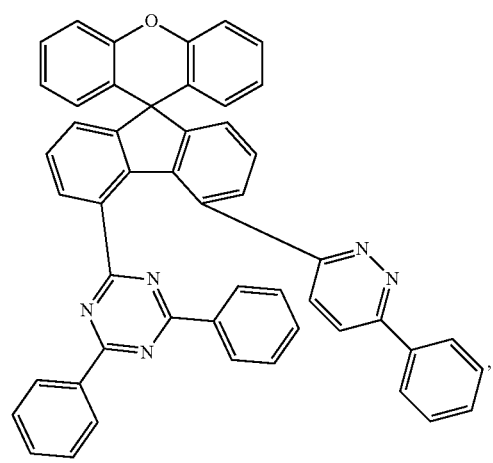
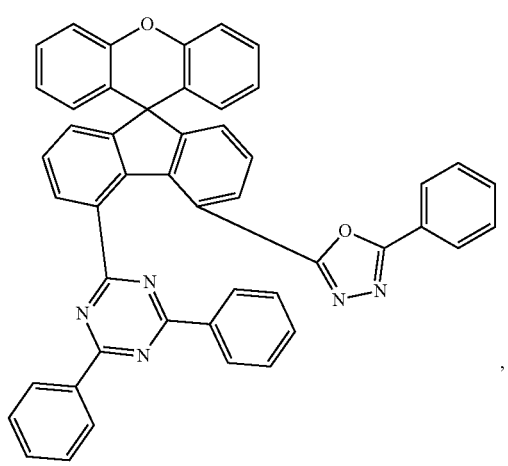
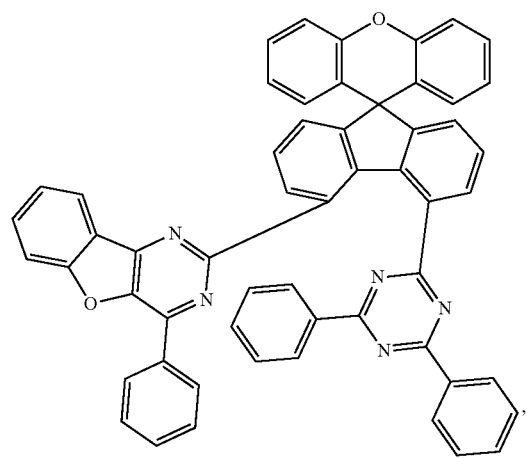
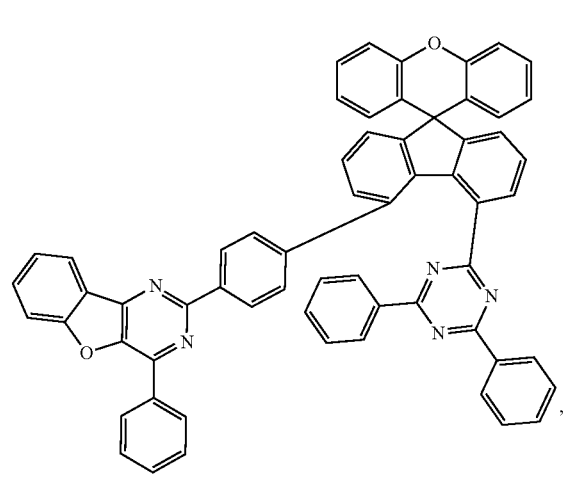

195 196
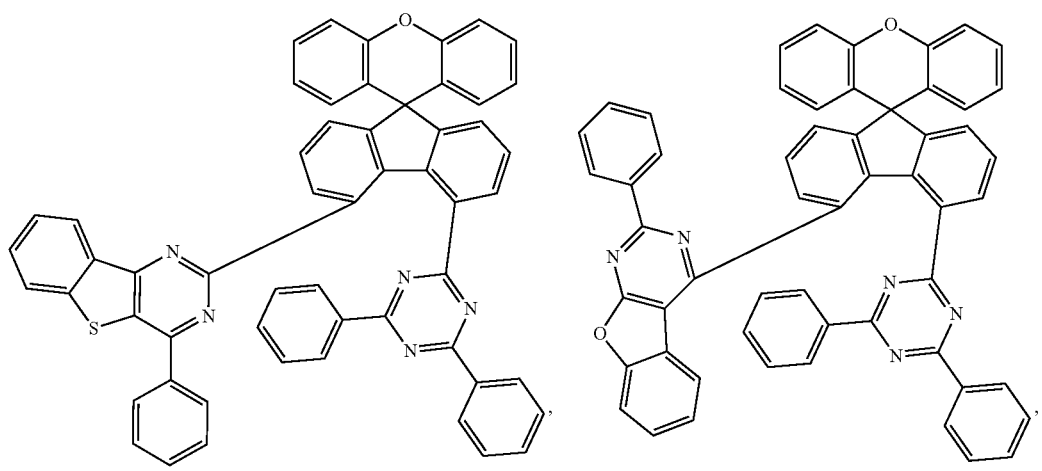
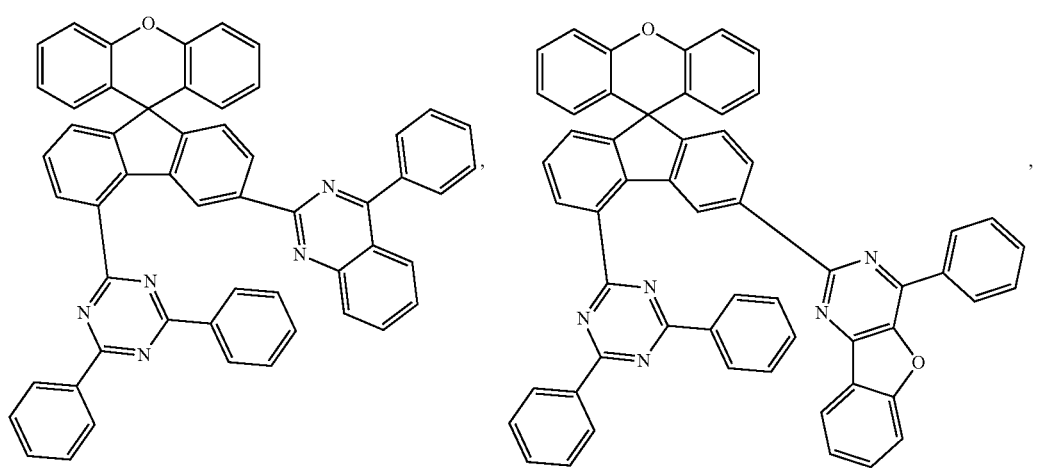
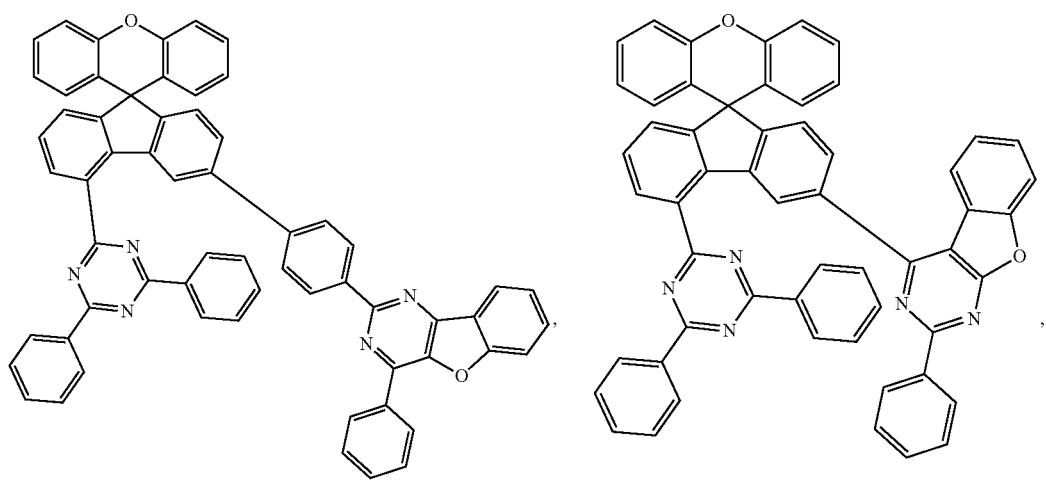

-continued
197
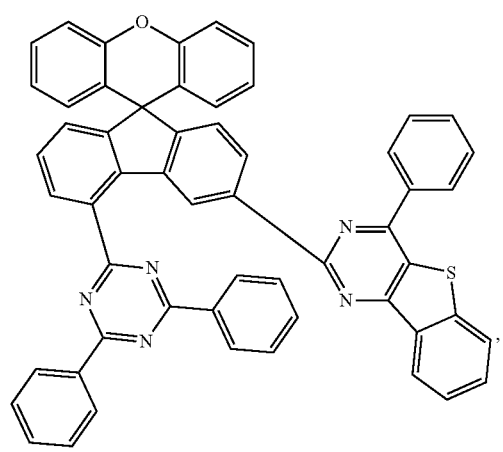
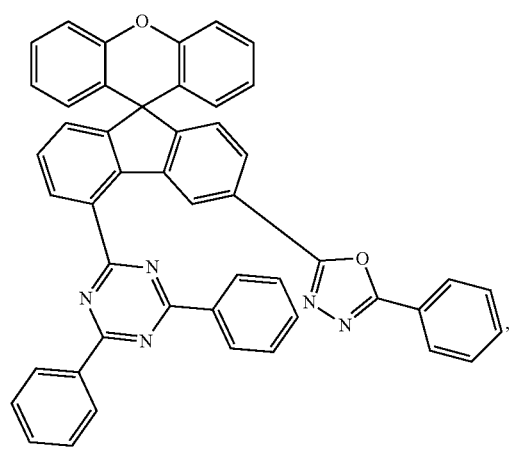
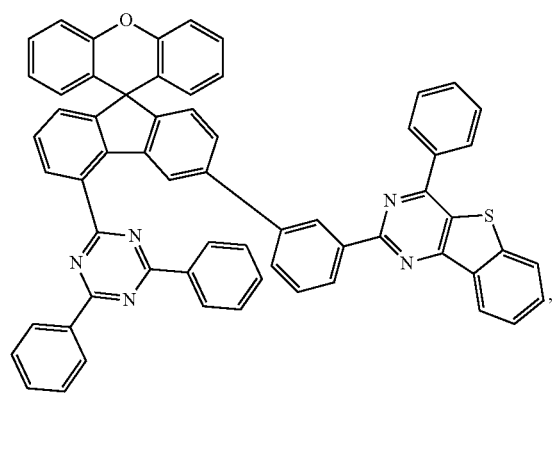
198
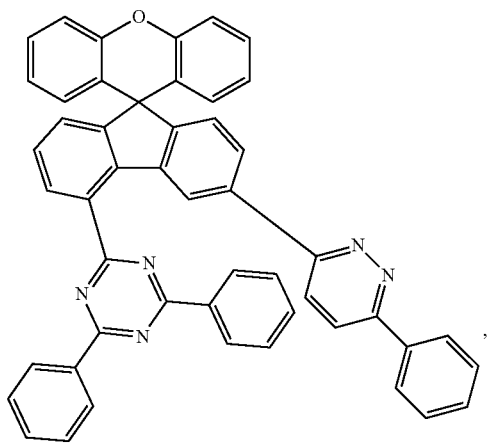
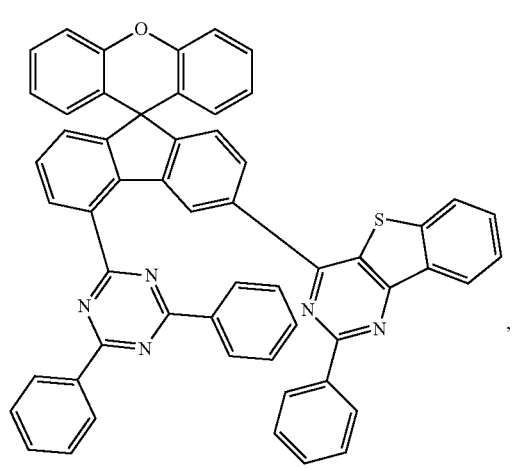
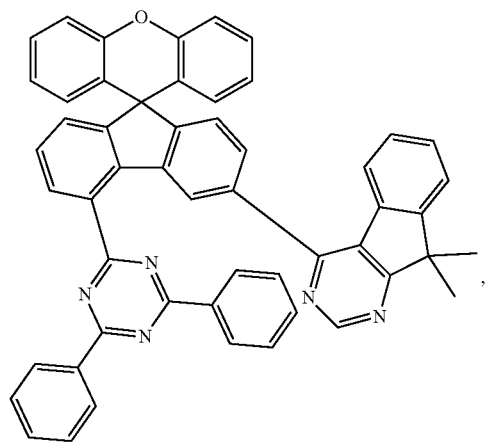

-continued
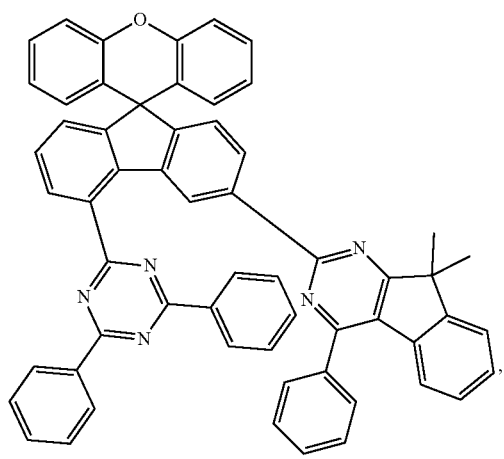
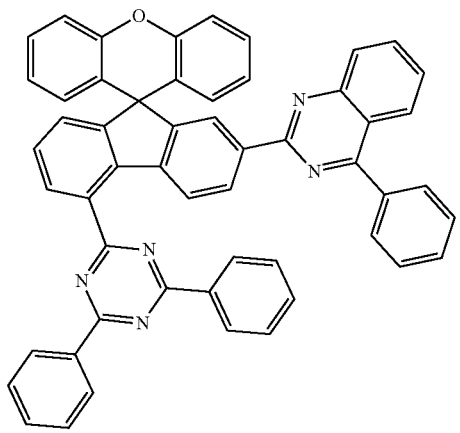
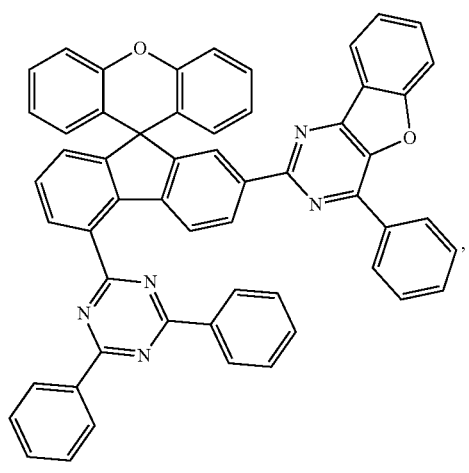
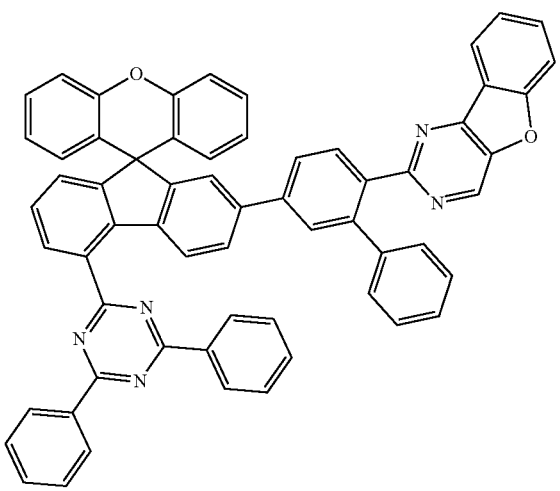
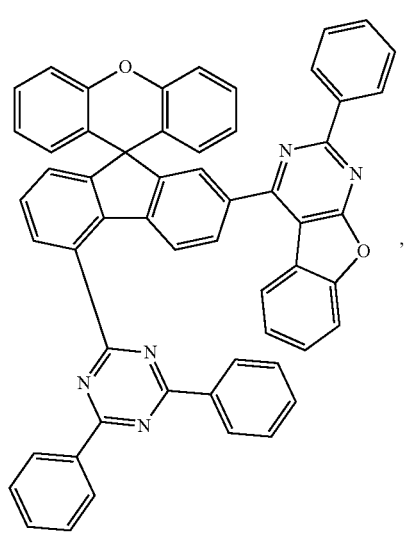
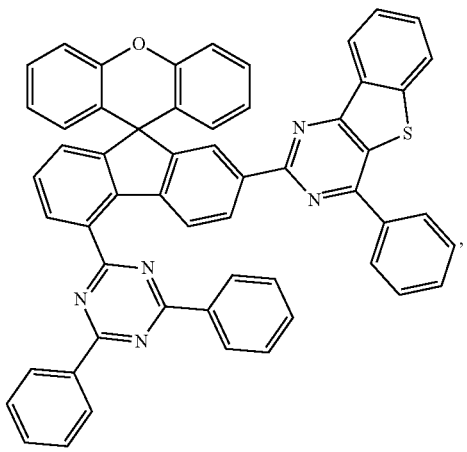

-continued
201
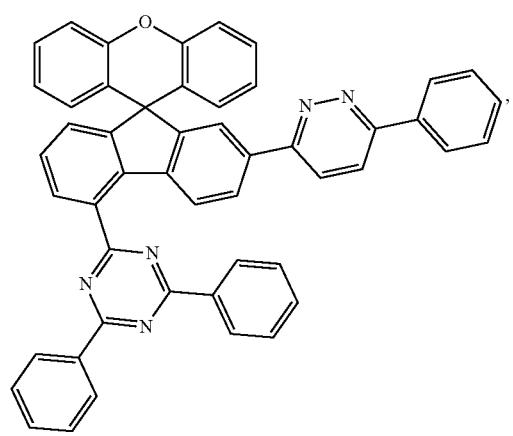
202
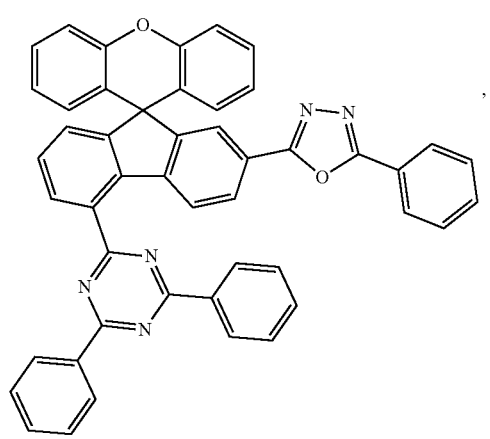
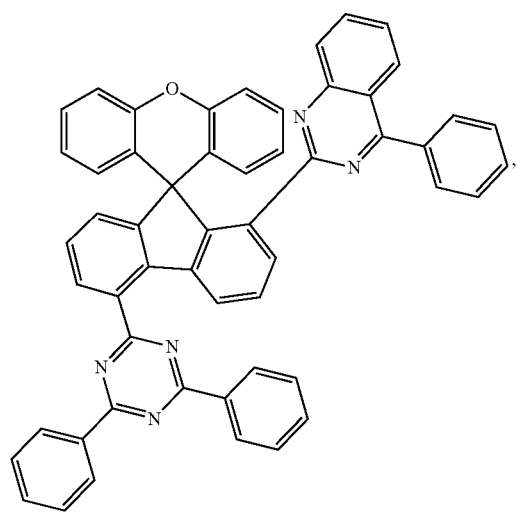
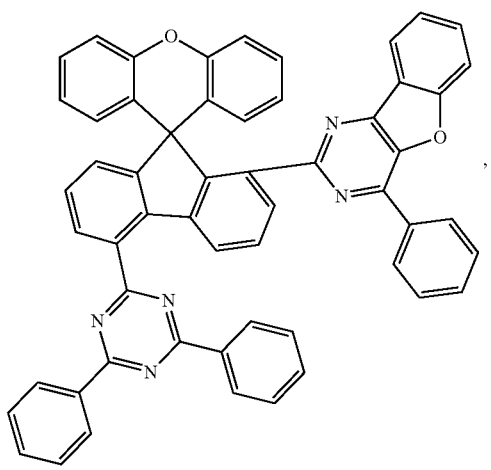
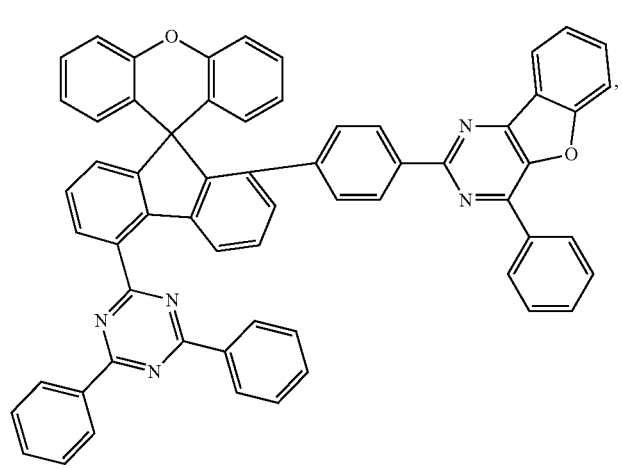
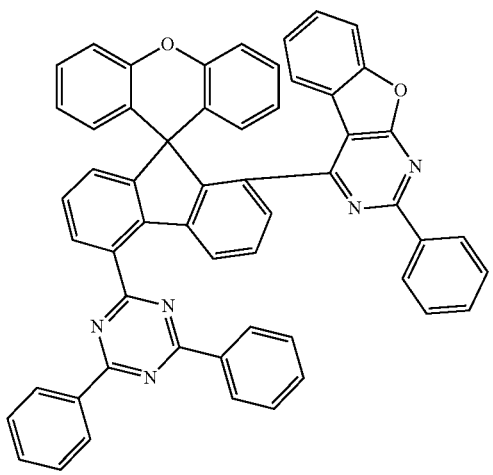

-continued
203
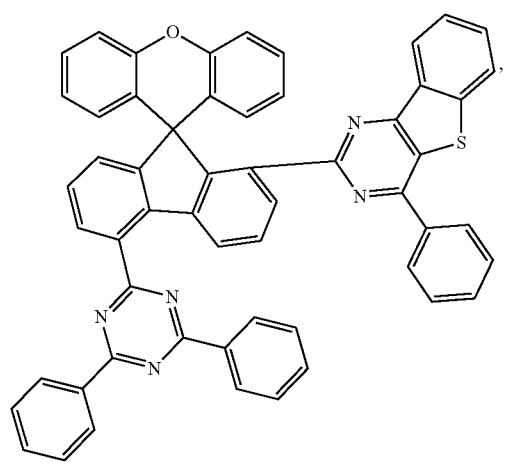
204
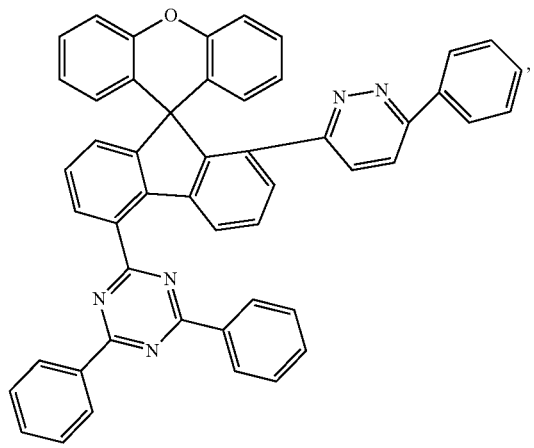
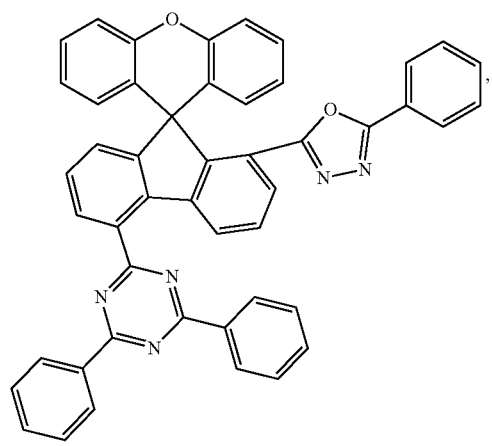
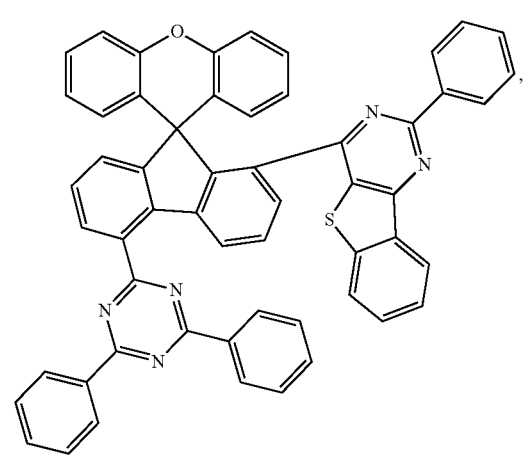
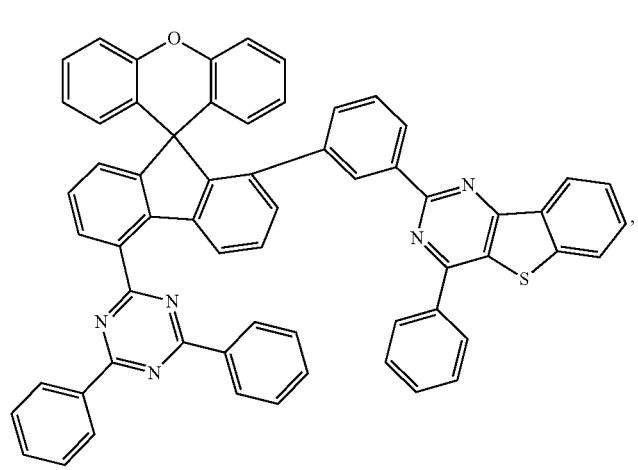
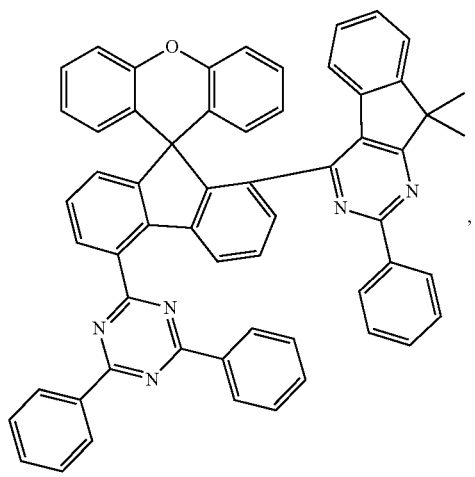

205
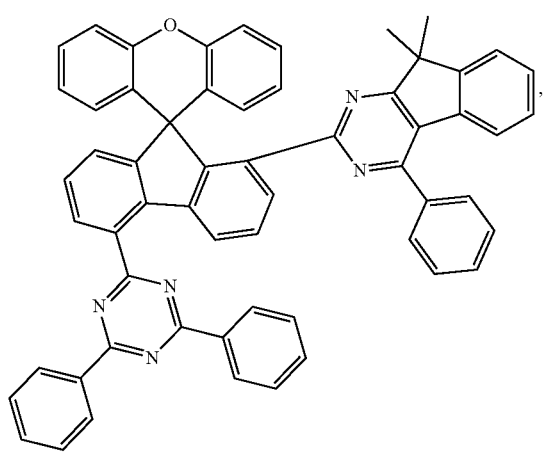
206
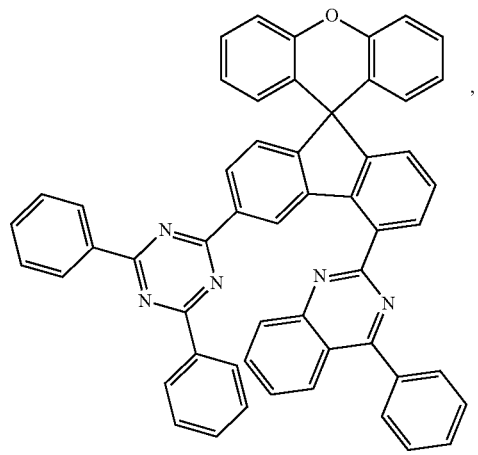
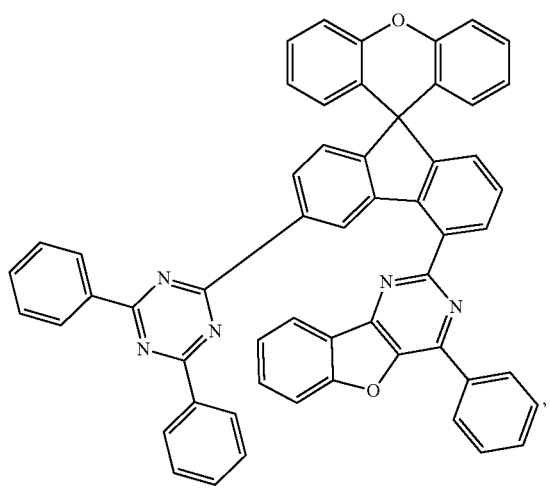
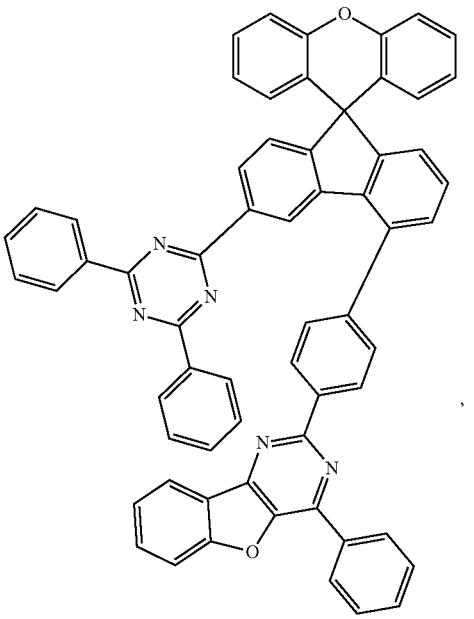
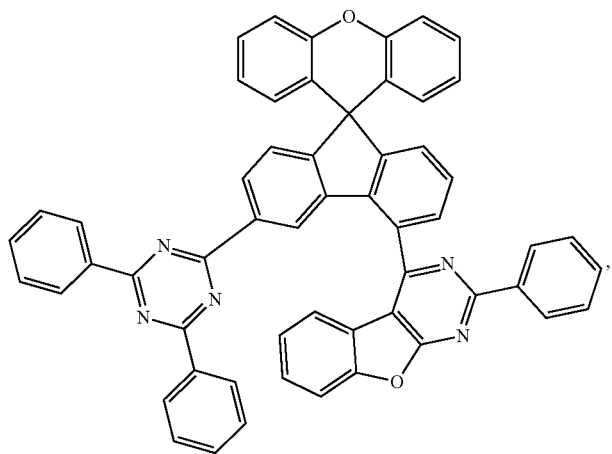

207
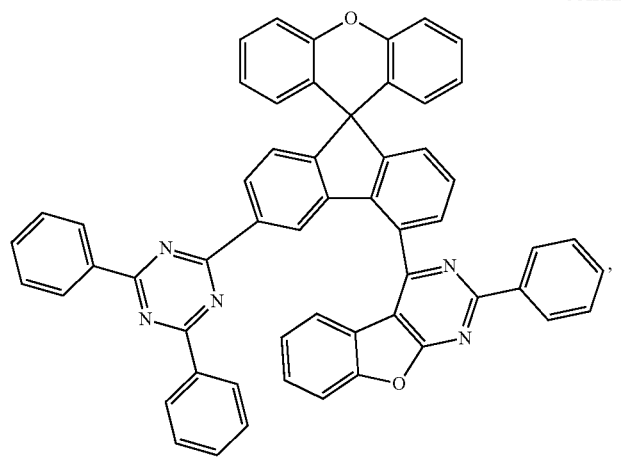,
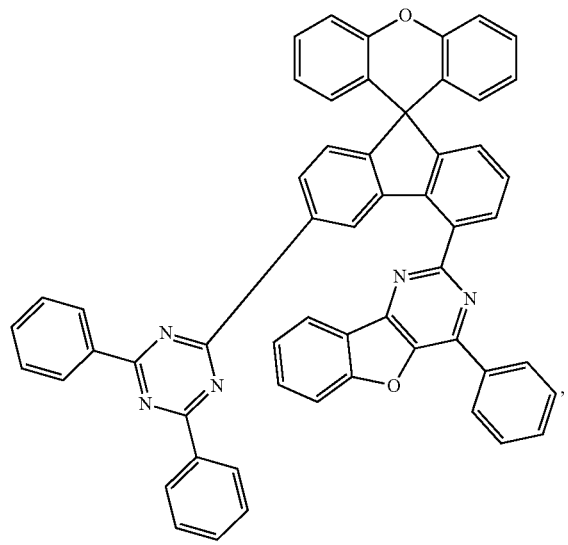,
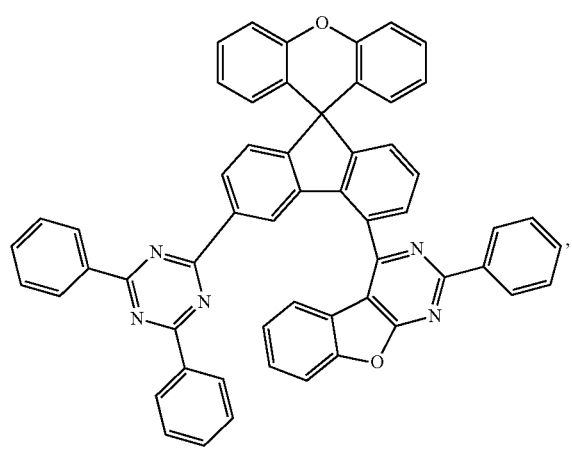,
208
-continued
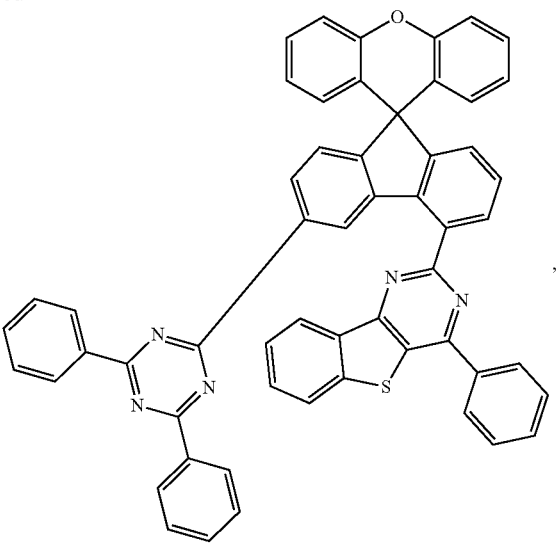,
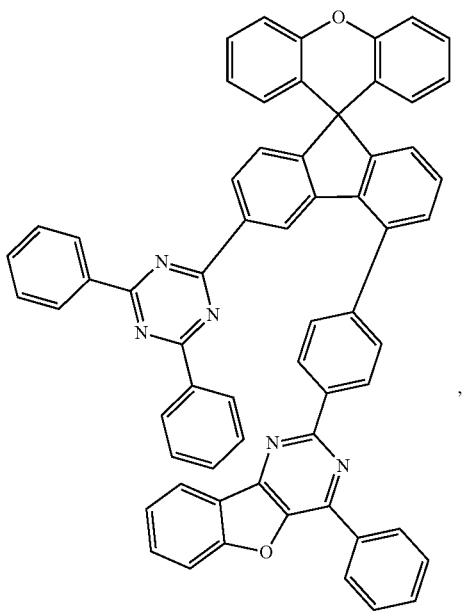,
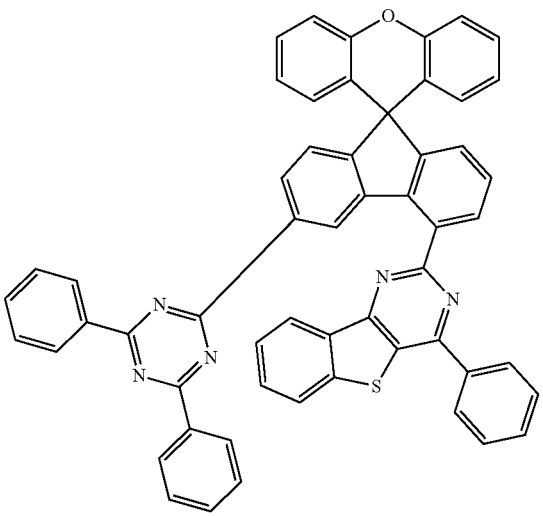, -continued
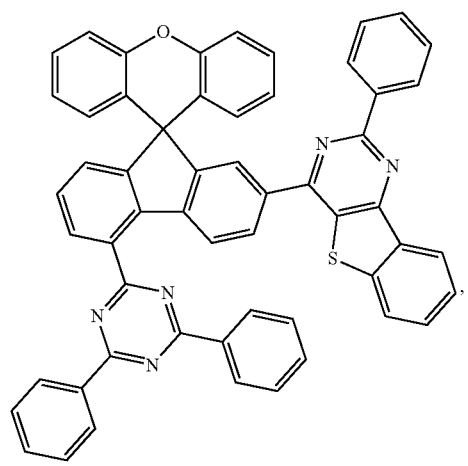
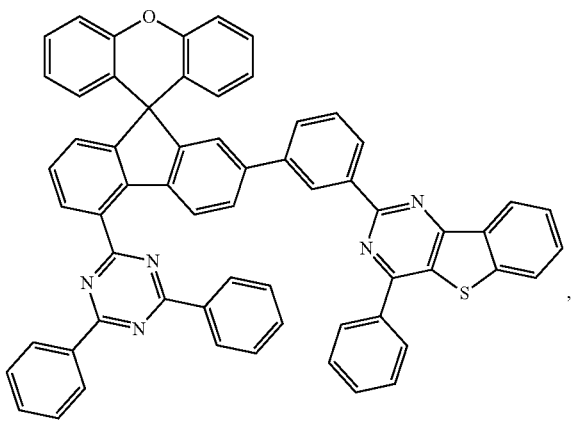
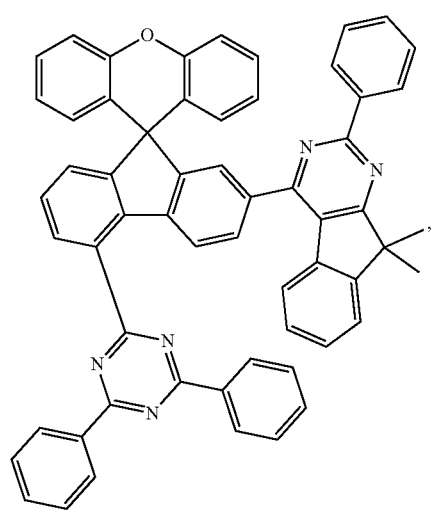
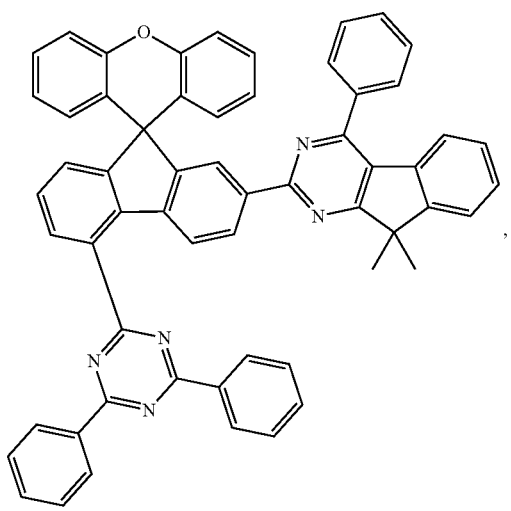
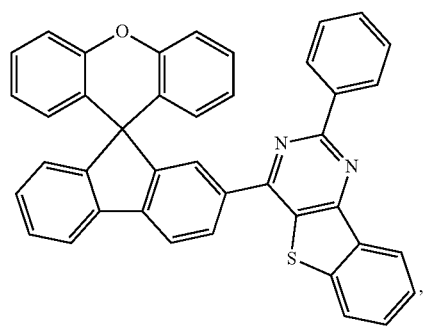
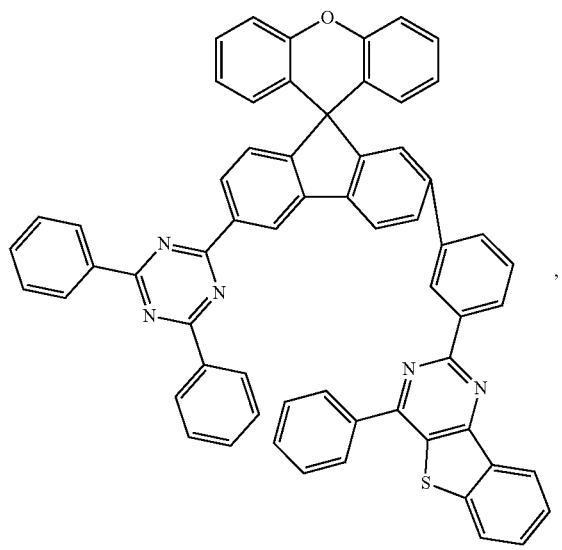

211 212
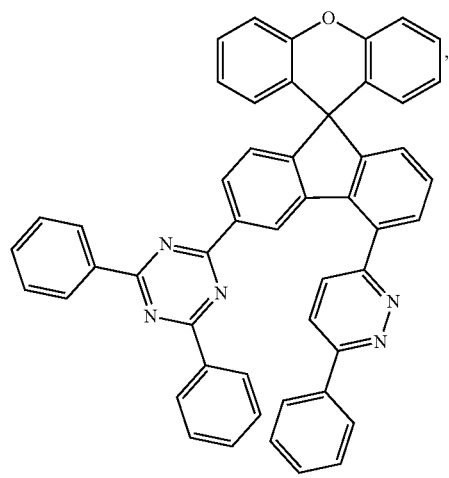 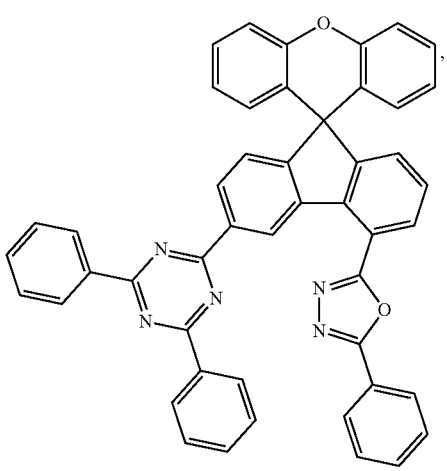
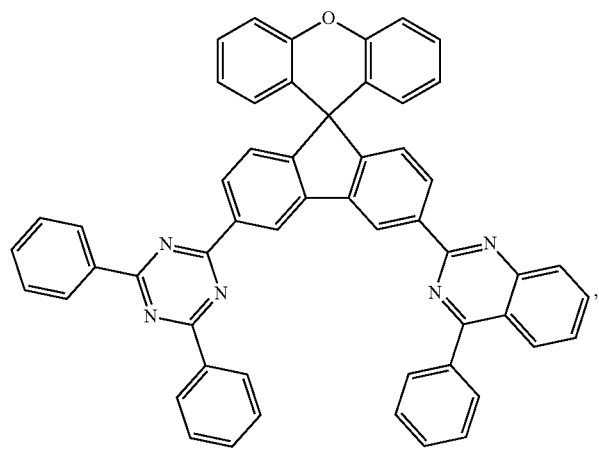
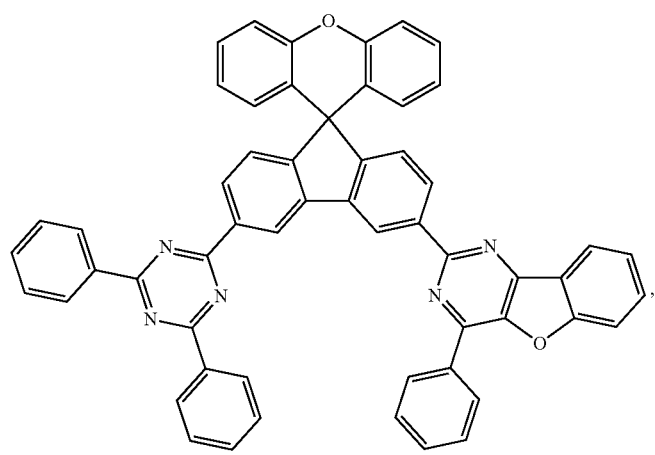

-continued

-continued
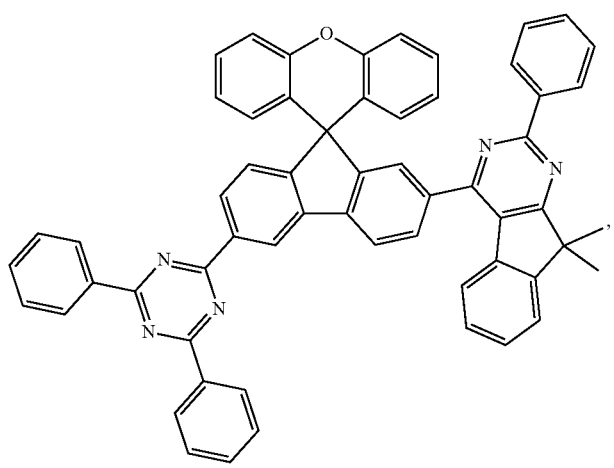
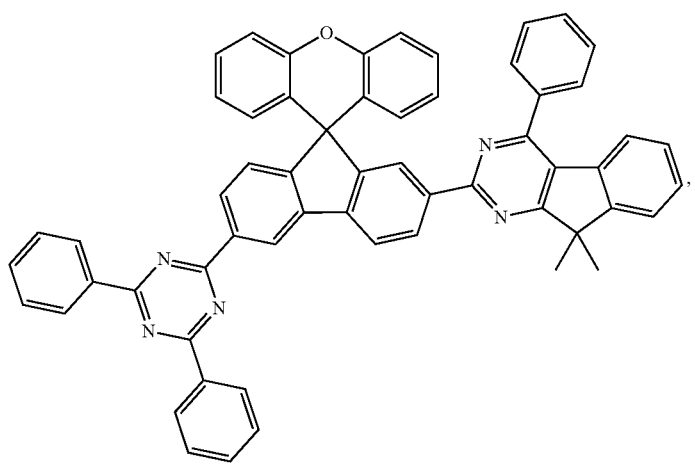
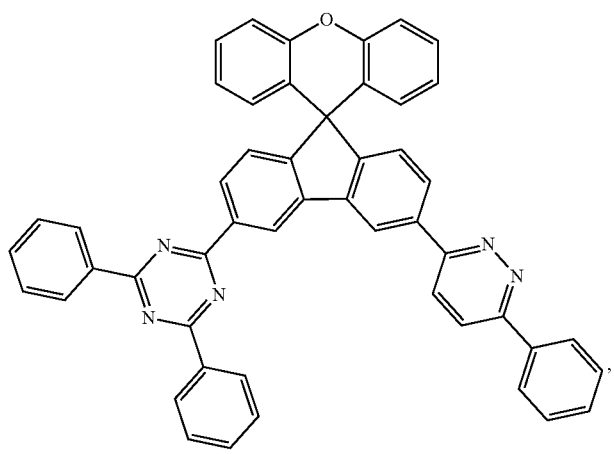

217 218
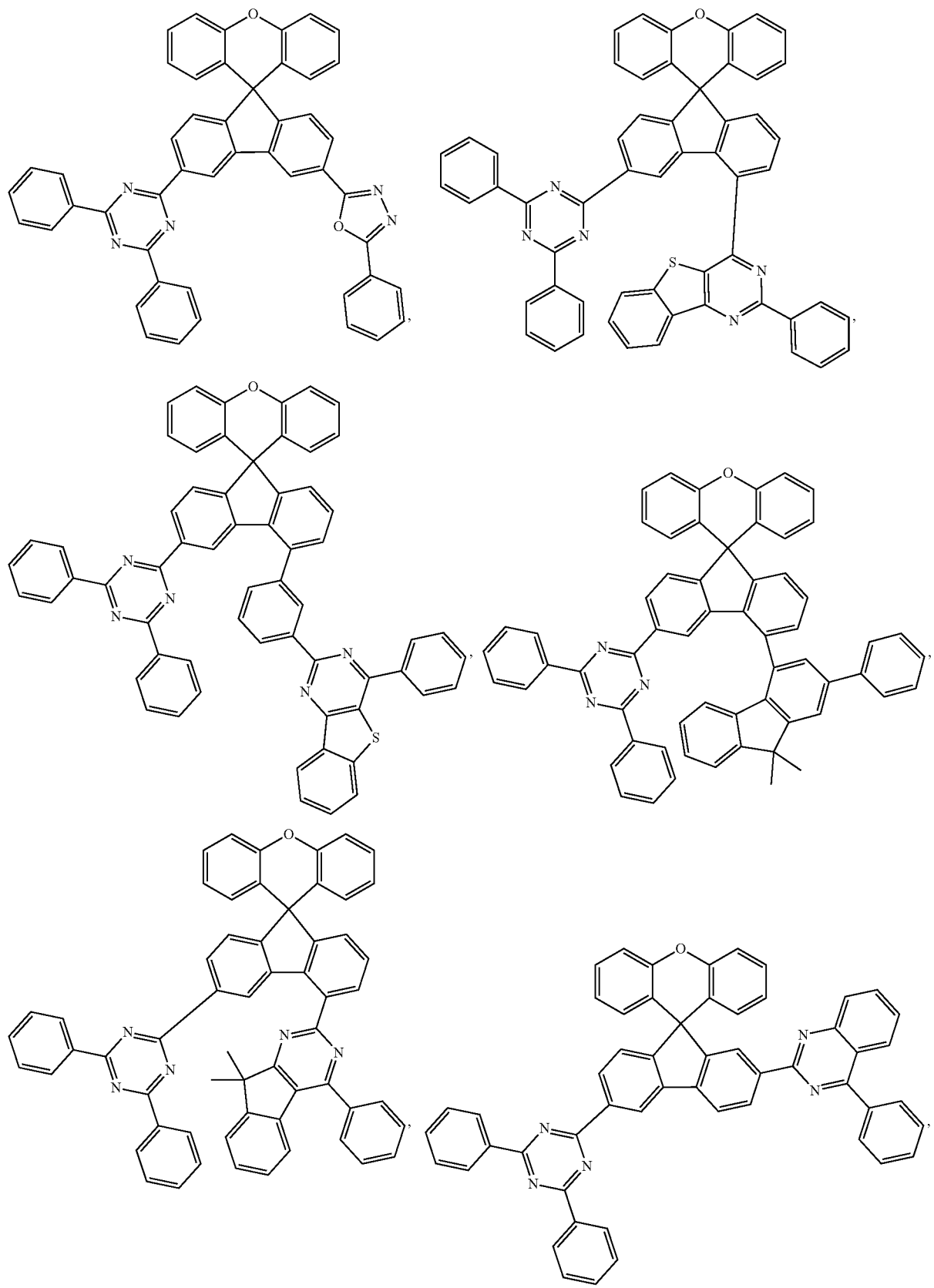
-continued

-continued
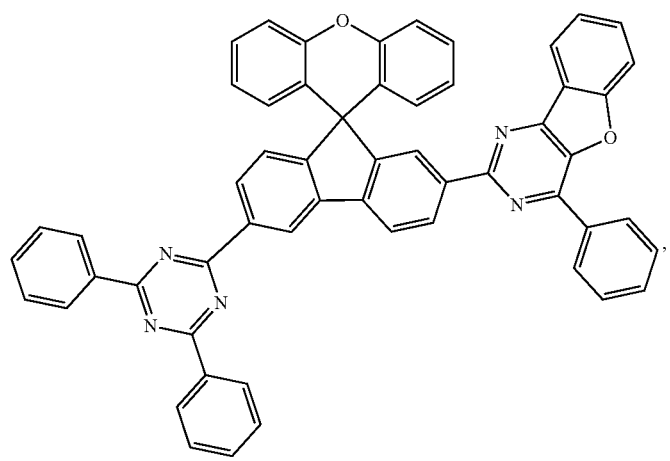
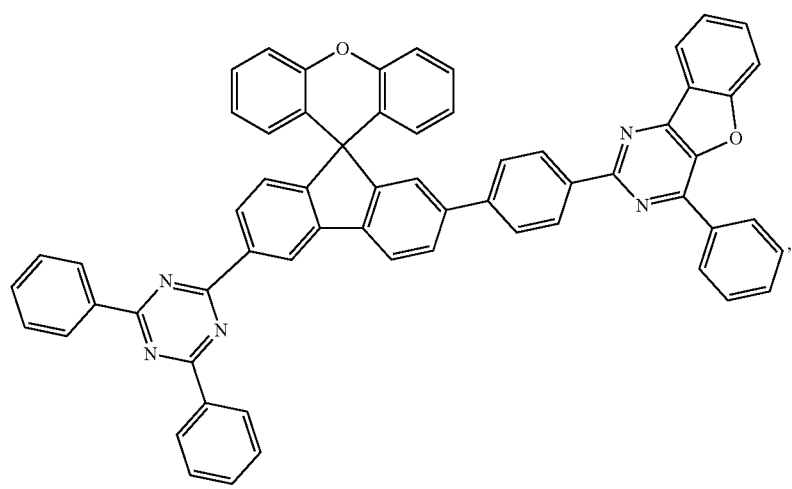
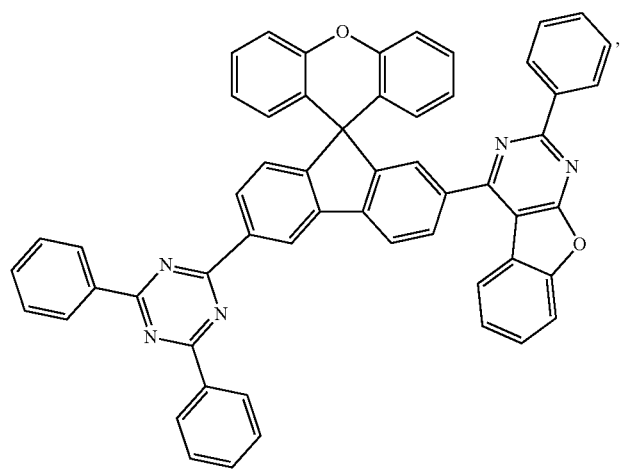

-continued
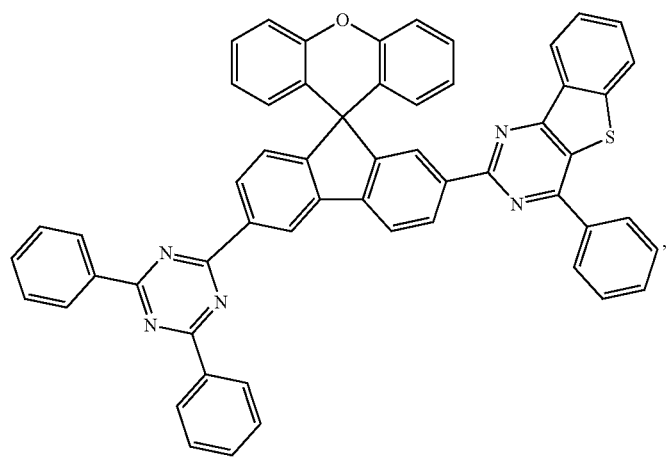
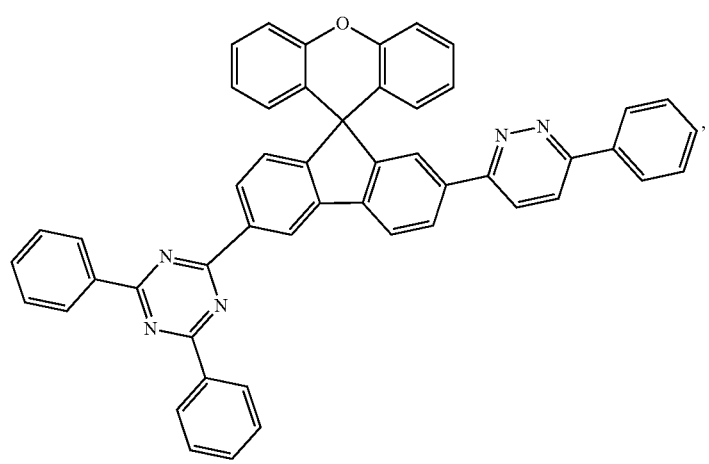
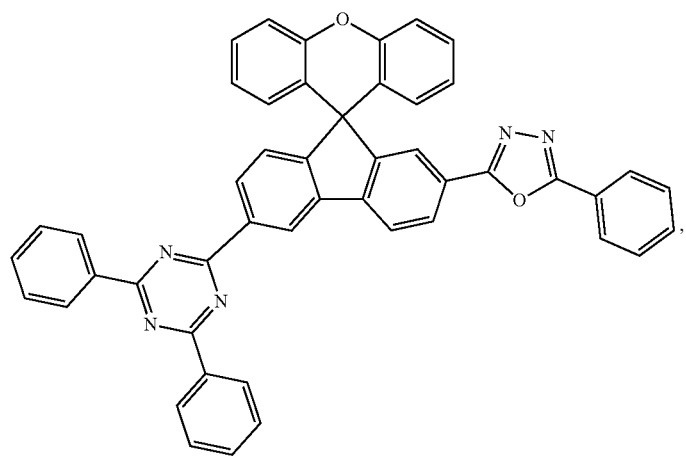 [SMILES: c1ccc(-c2nc(-c3ccccc3)nc(-c3ccc4c(c3)-c3ccc(-c5nnc(-c6ccccc6)o5)cc3C43c4ccccc4Oc4ccccc43)n2)cc1]

223
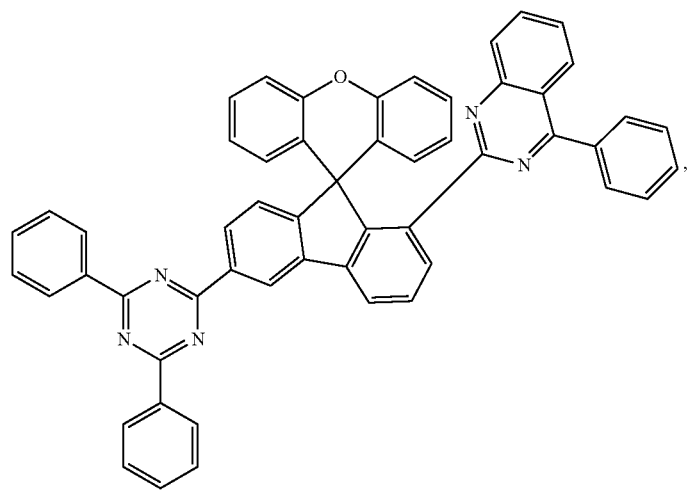
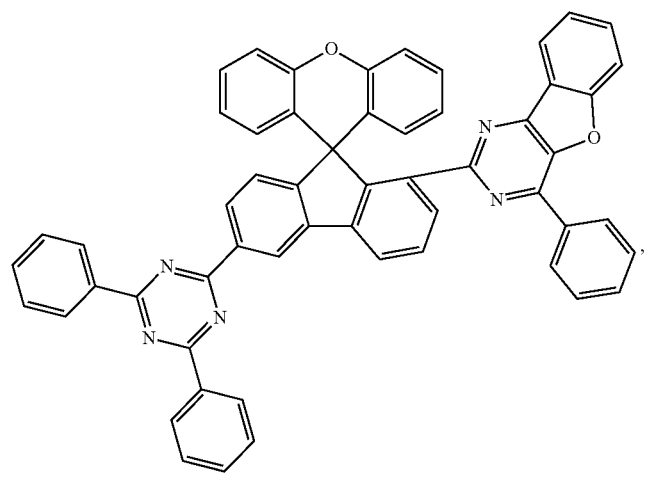
224
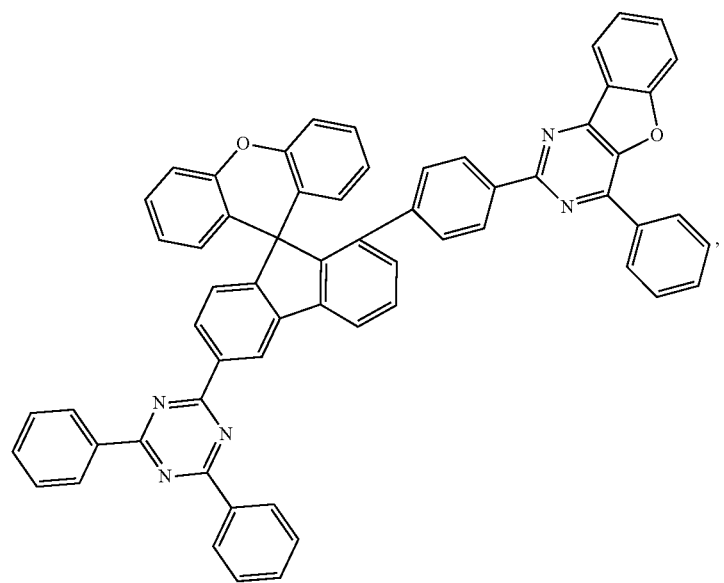

-continued
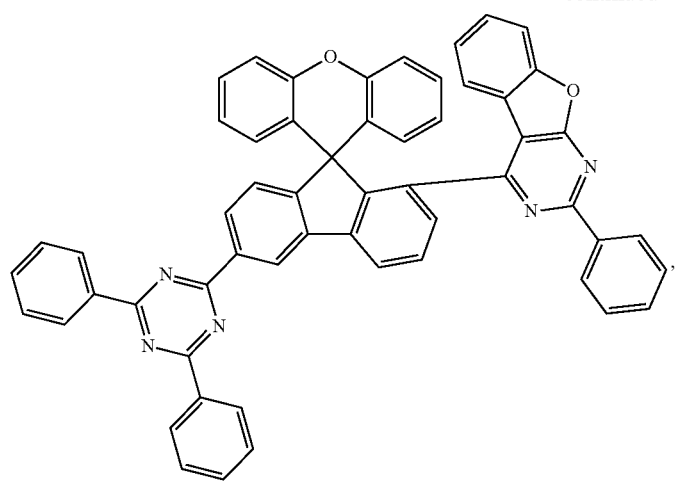 [SMILES: c1ccc(-c2nc(-c3ccccc3)nc(-c3ccc4c(c3)-c3cccc(-c5nc(-c6ccccc6)nc6oc7ccccc7c56)c3C43c4ccccc4Oc4ccccc43)n2)cc1]
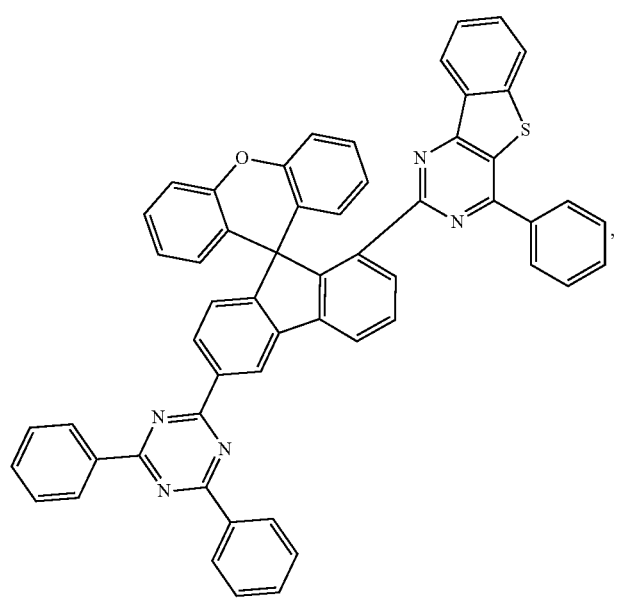
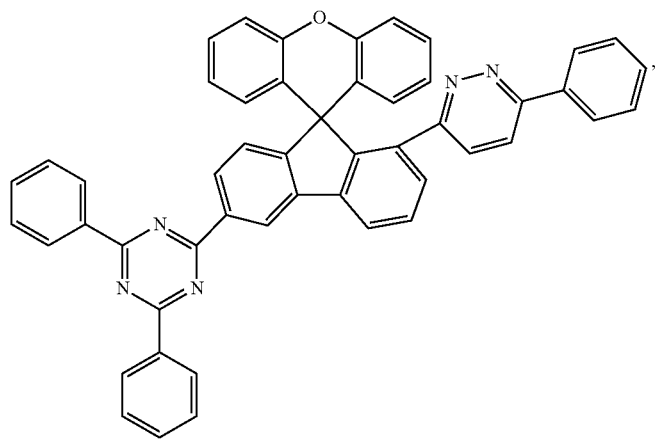

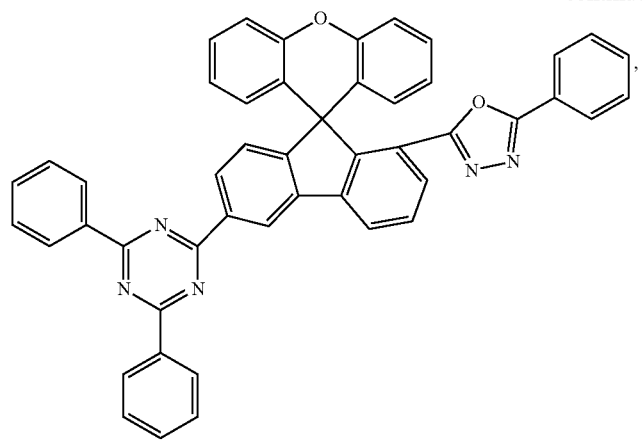
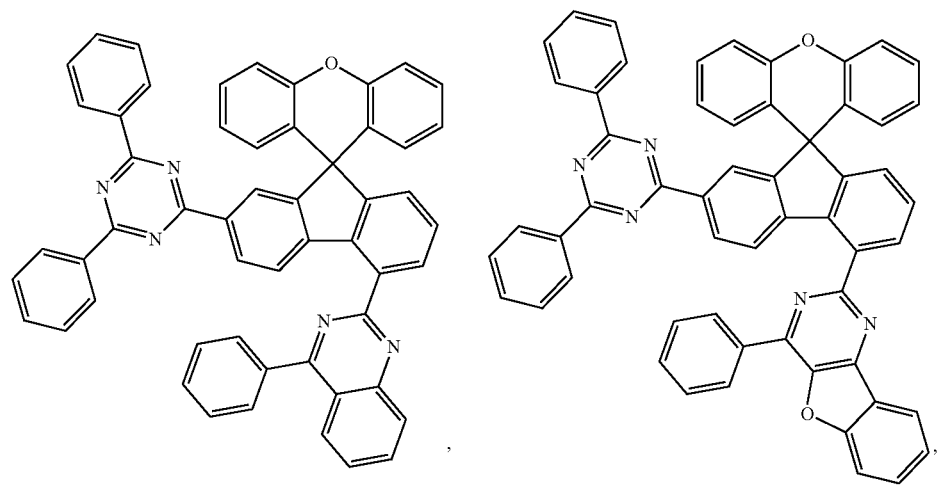
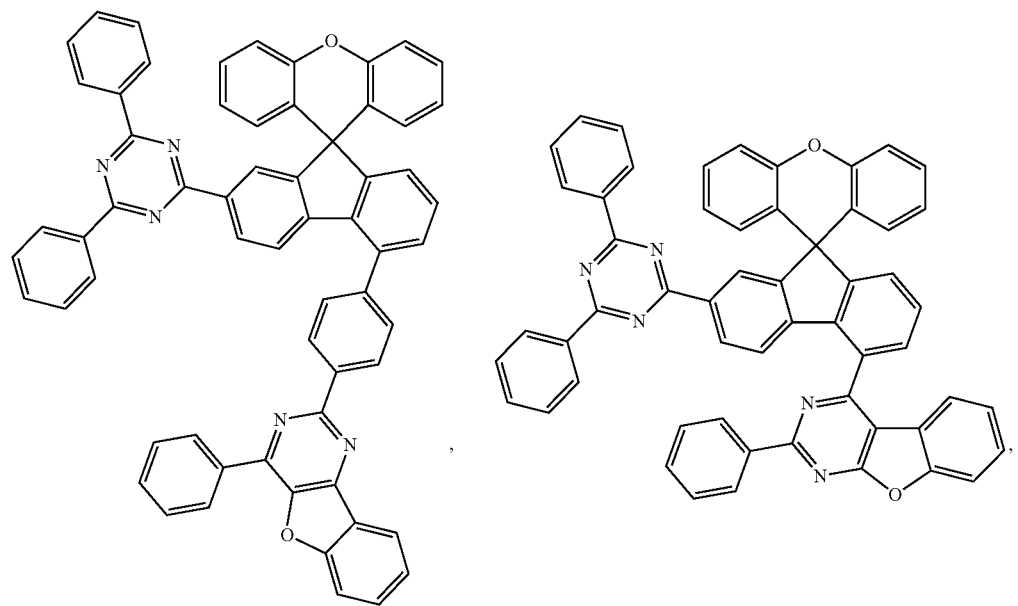

-continued
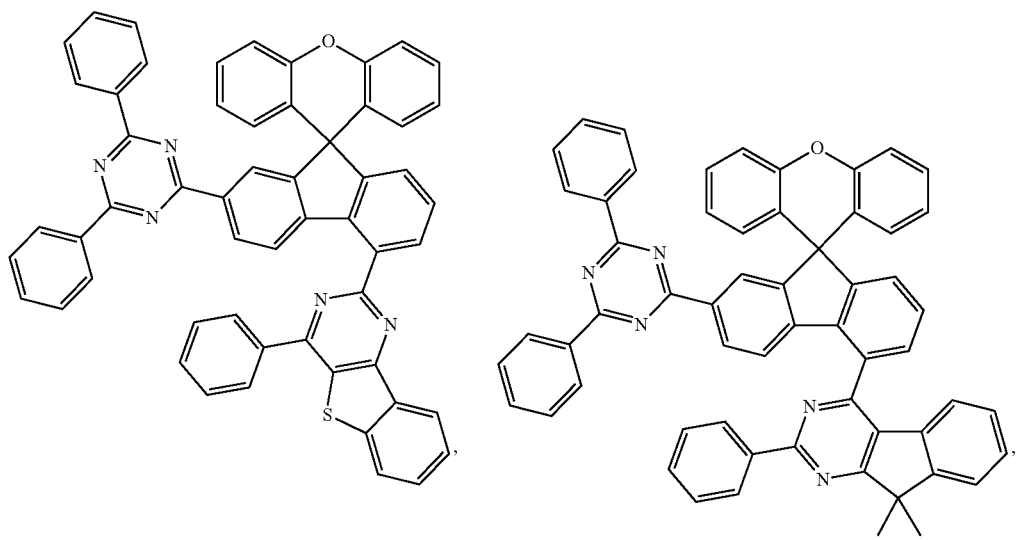 [SMILES: c1ccc(-c2nc(-c3ccccc3)nc(-c3ccc4c(c3)C3(c5ccccc5Oc5ccccc53)c3cccc(-c5nc(-c6ccccc6)c6sc7ccccc7c6n5)c3-4)n2)cc1 ; CC1(C)c2ccccc2-c2c(-c3cccc4c3-c3ccc(-c5nc(-c6ccccc6)nc(-c6ccccc6)n5)cc3C43c4ccccc4Oc4ccccc43)nc(-c3ccccc3)nc21]
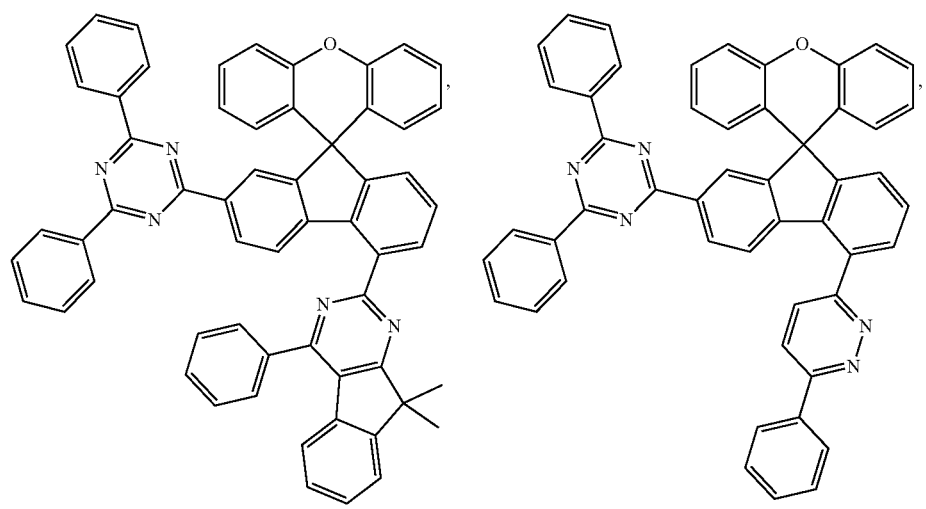
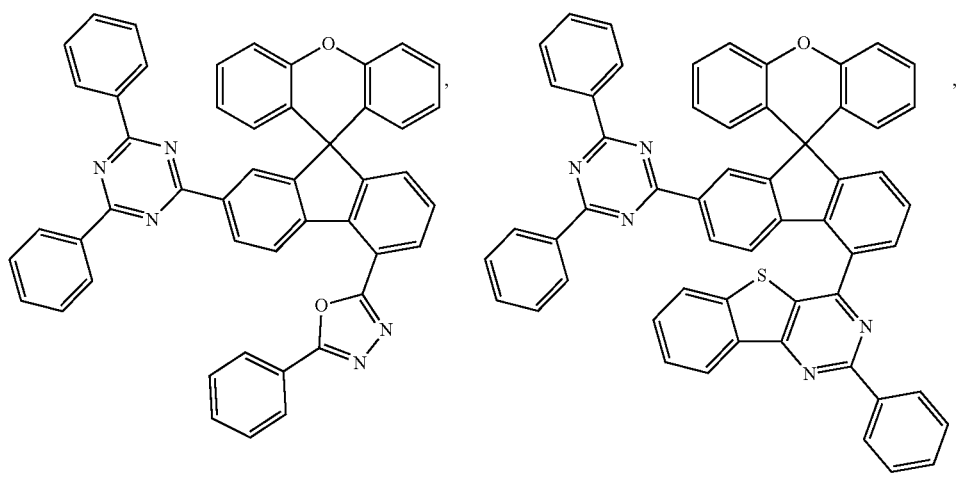

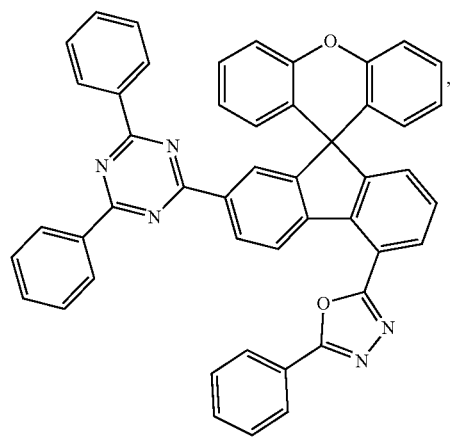
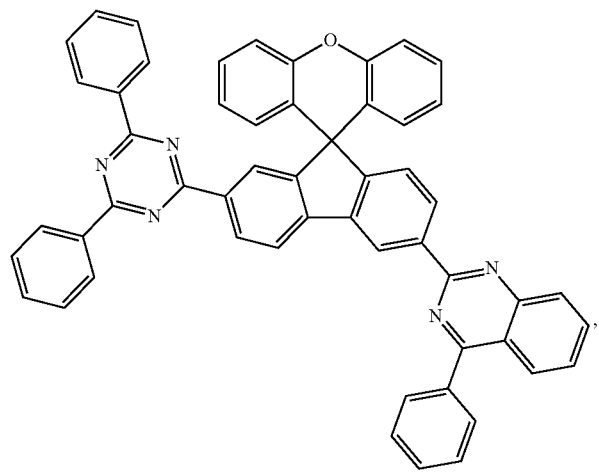
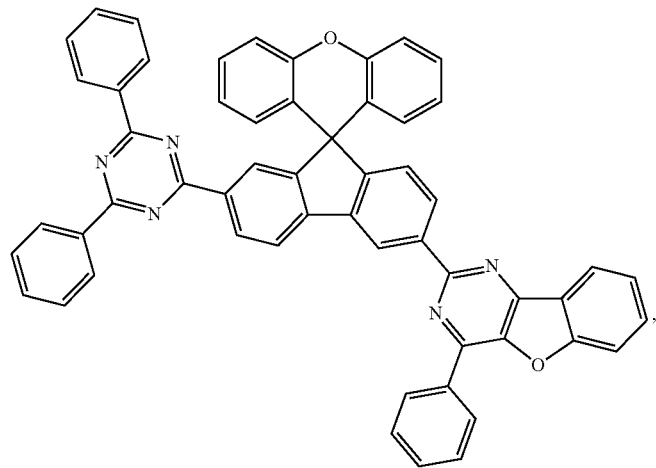

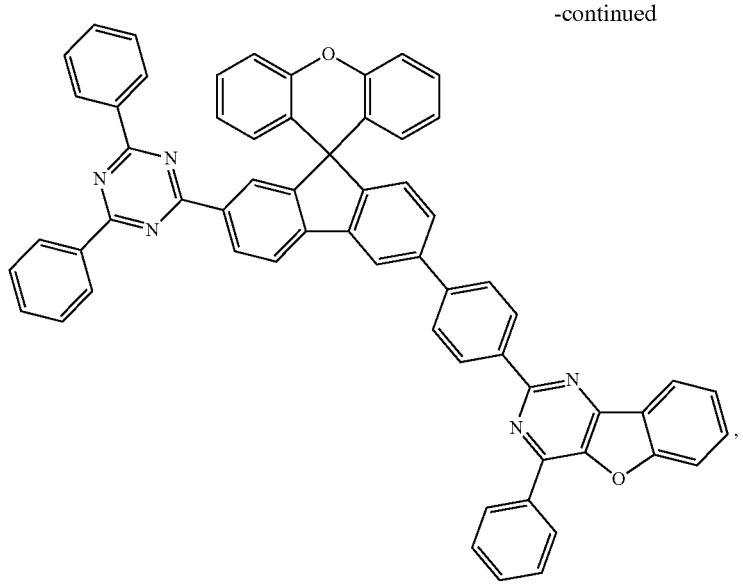
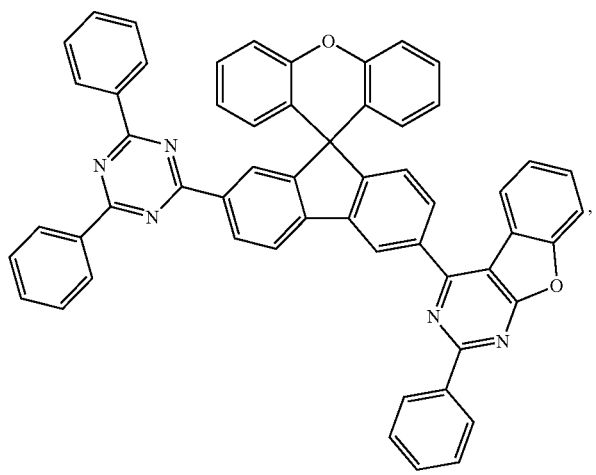
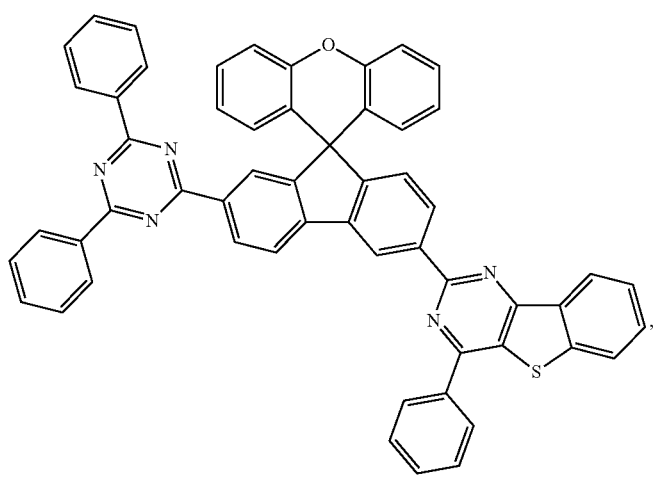

-continued
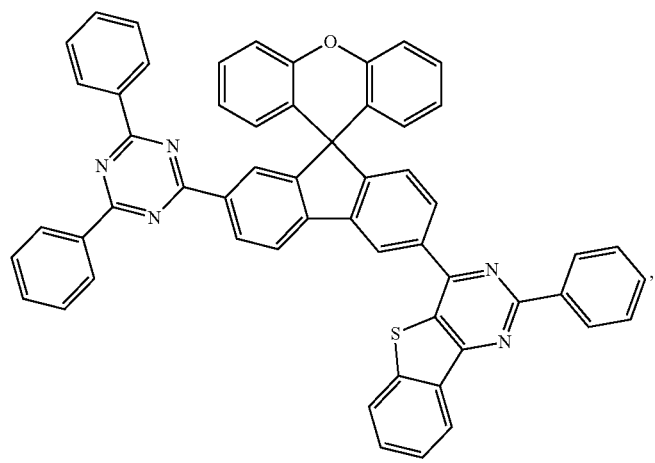
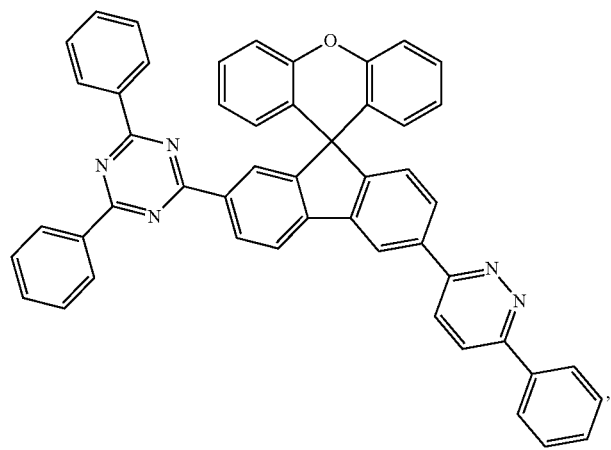
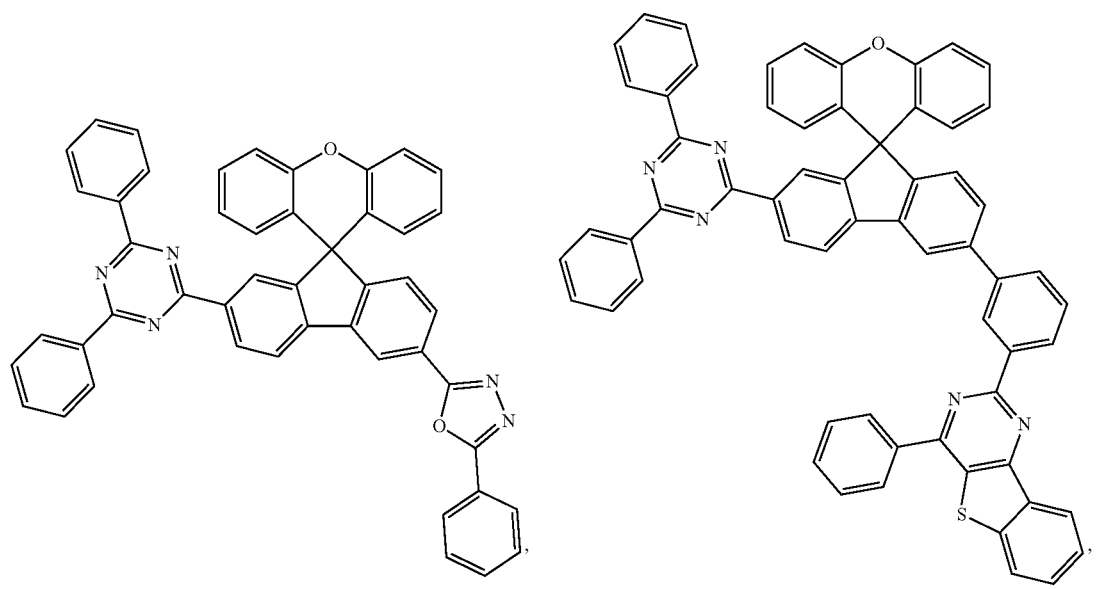

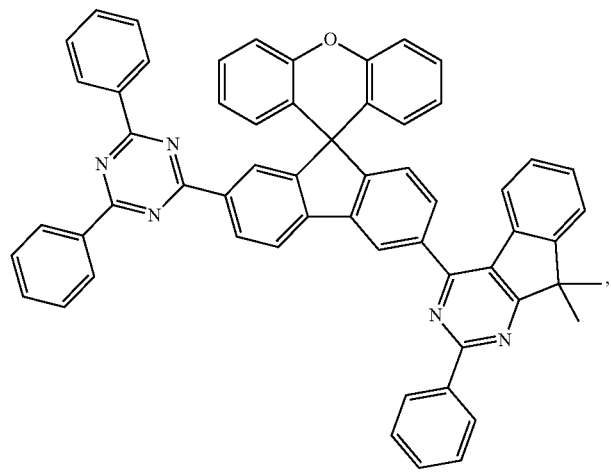
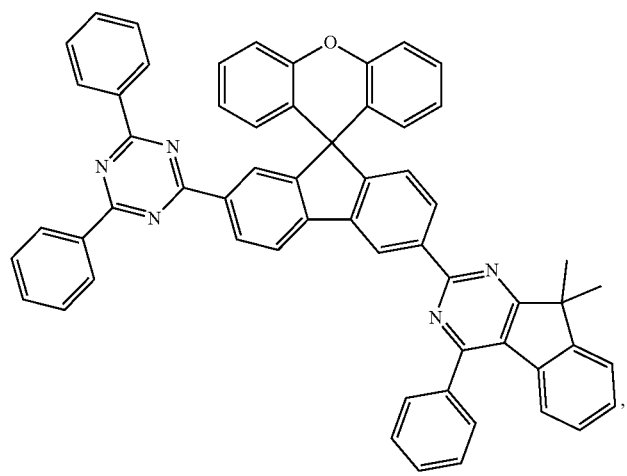
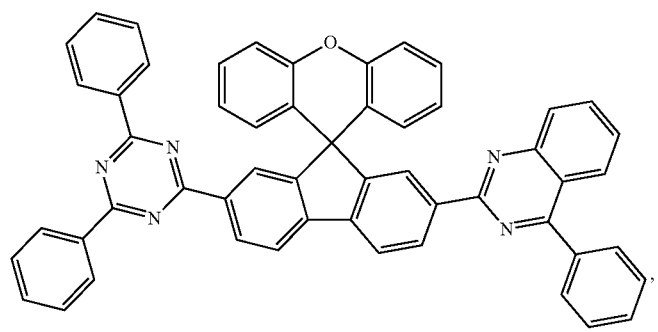
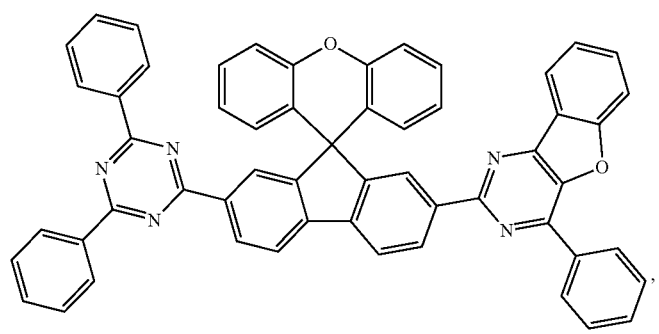

-continued
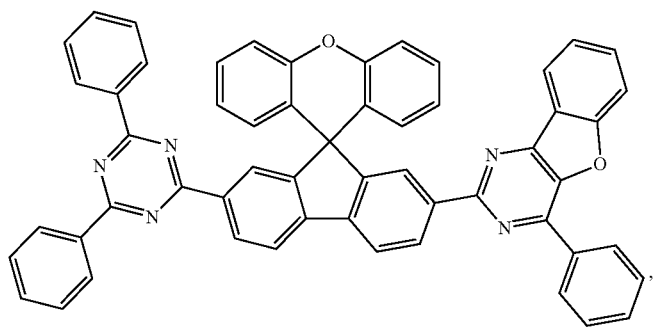
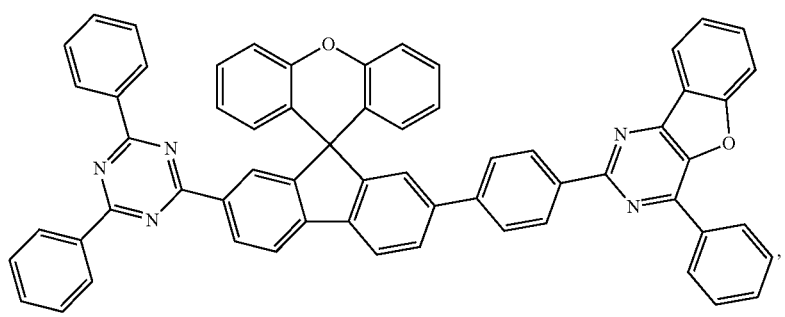
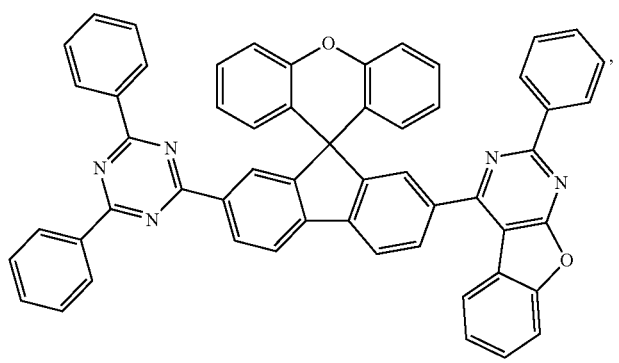
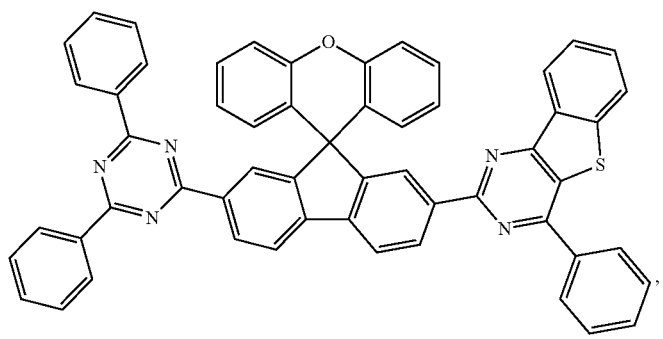
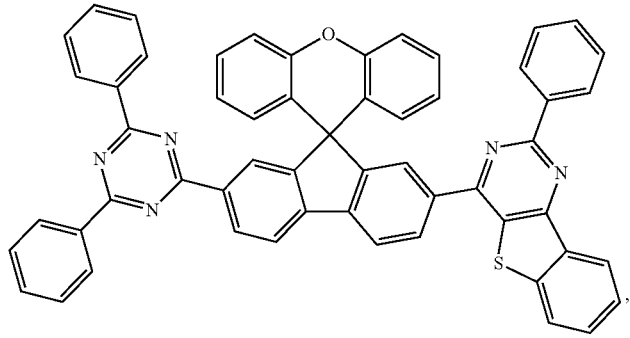

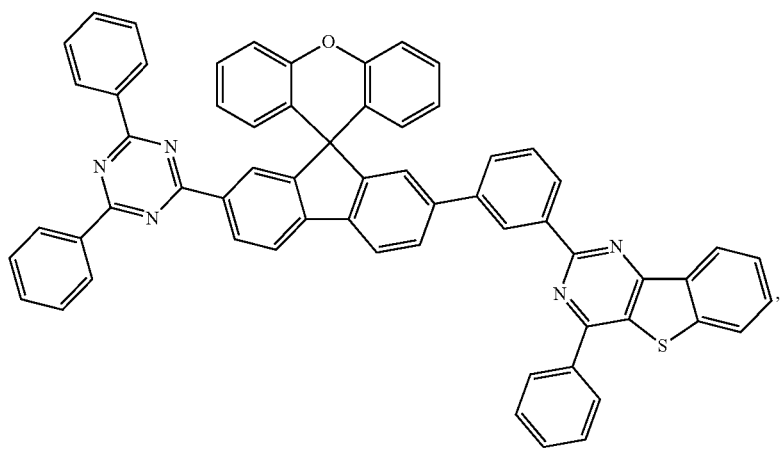
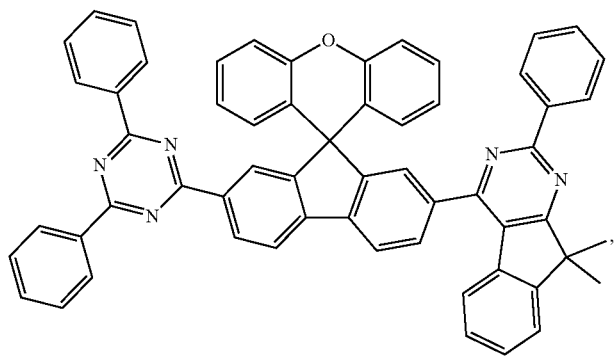
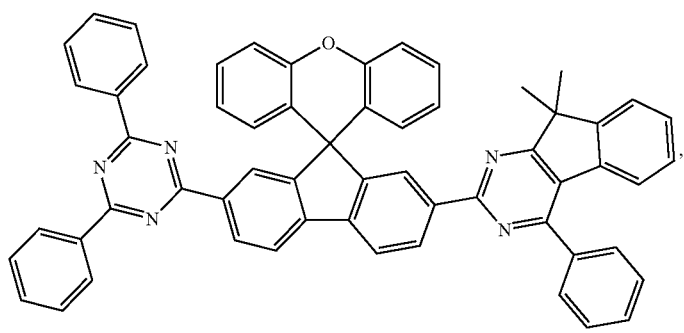
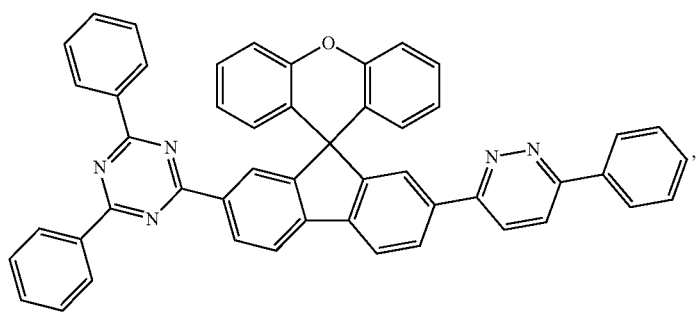

-continued
243
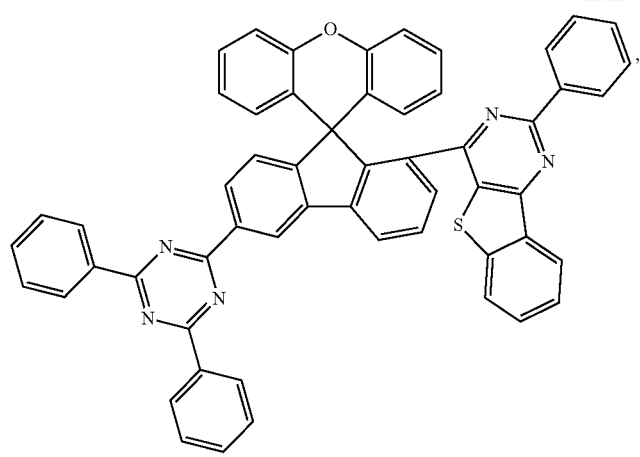
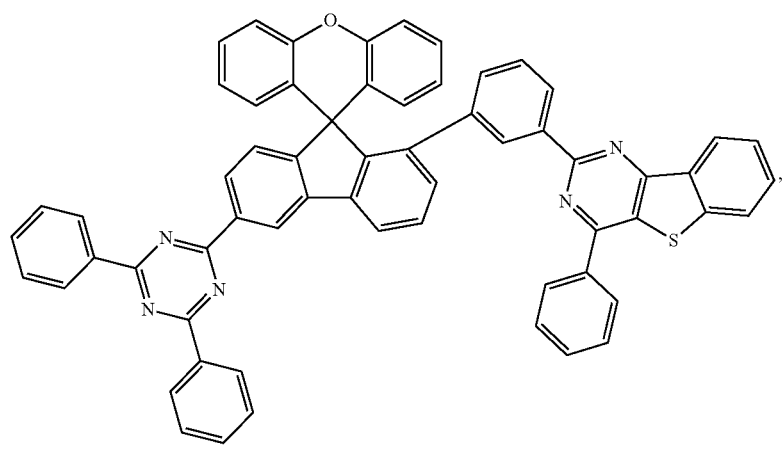
244
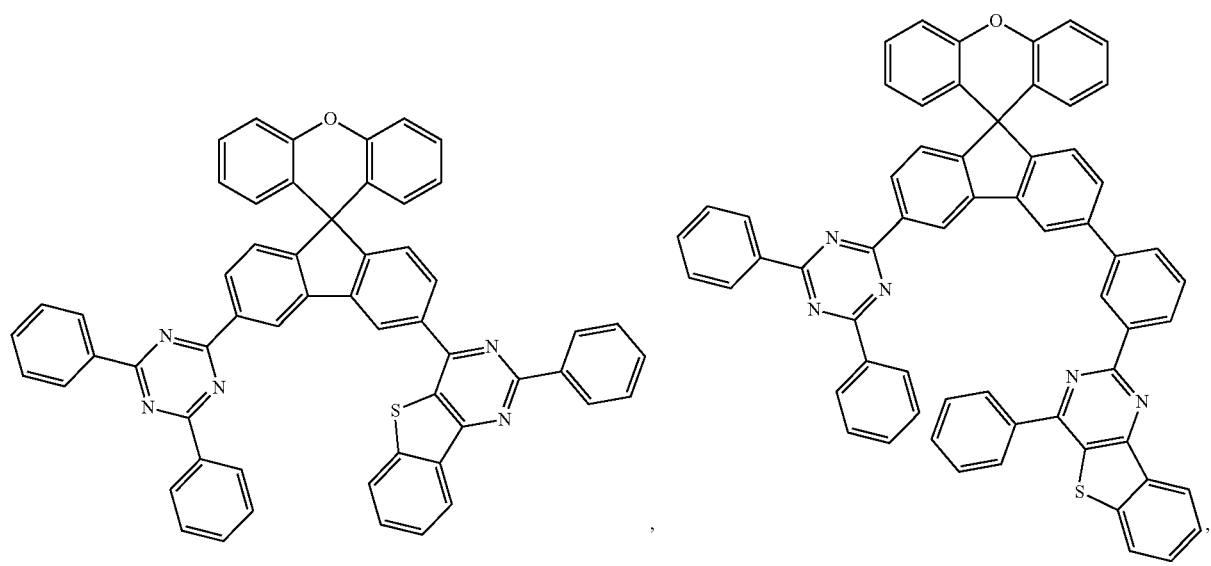

-continued
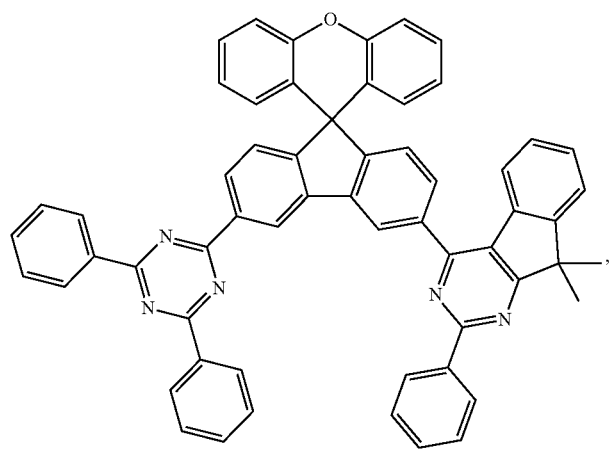
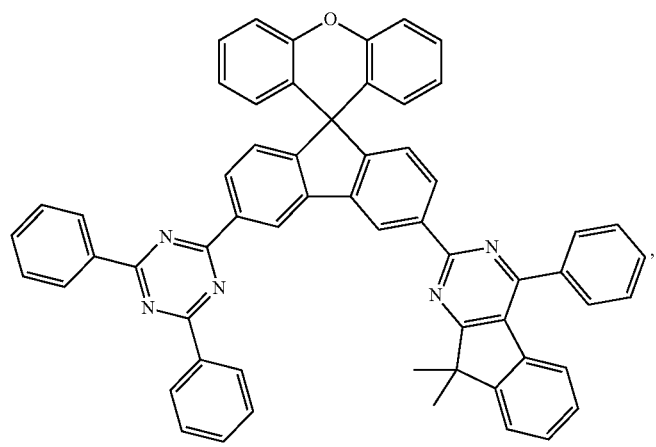
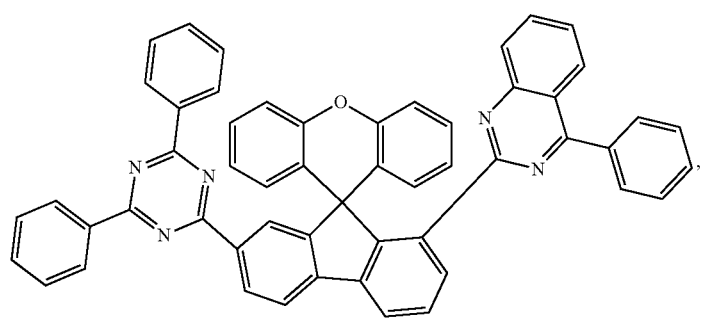
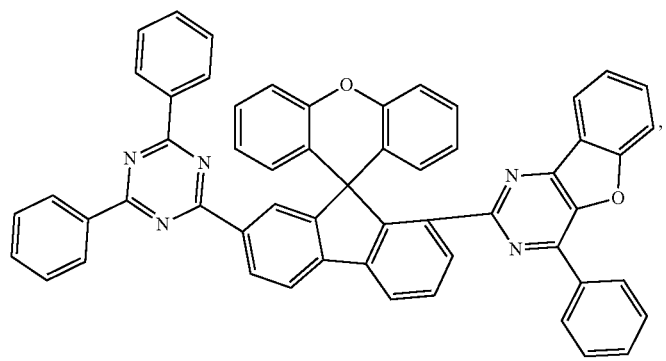

-continued
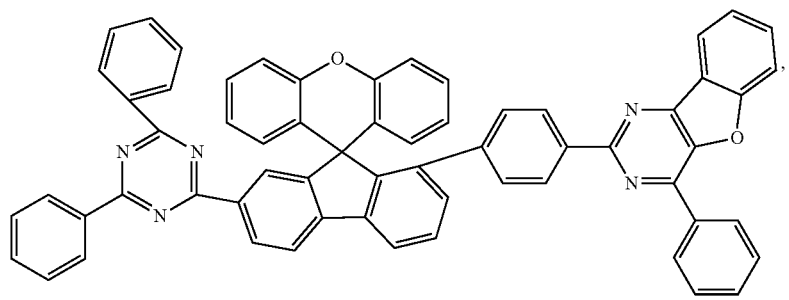
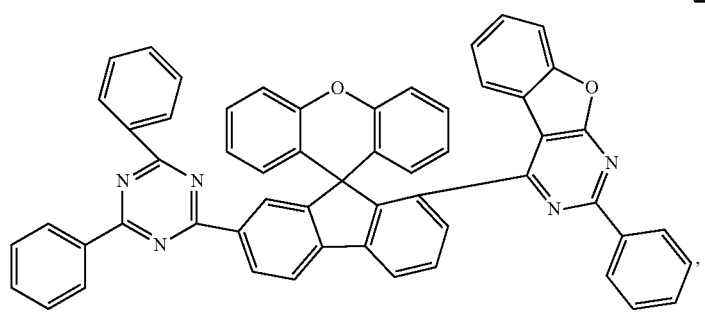
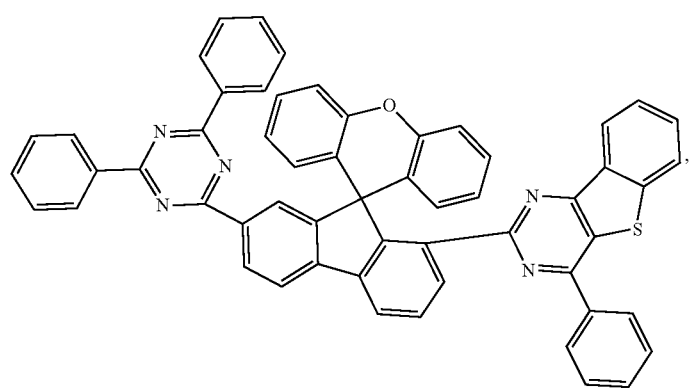
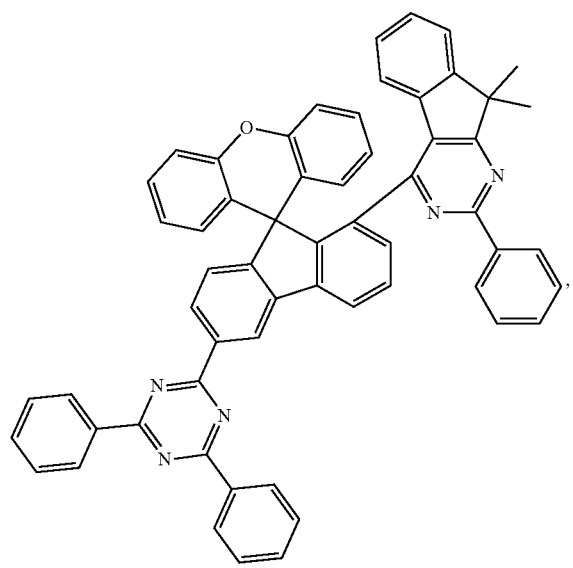

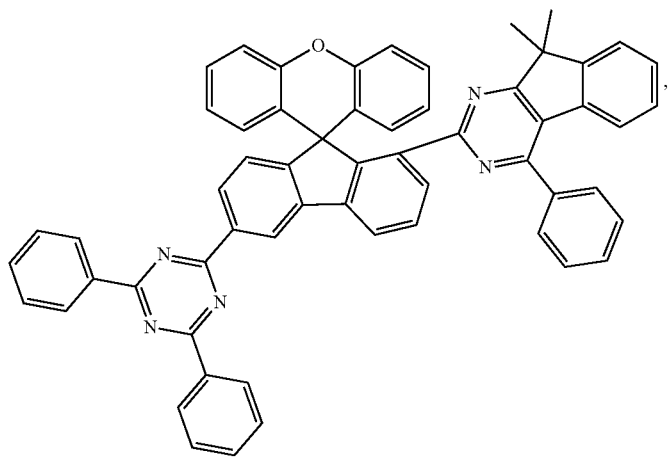
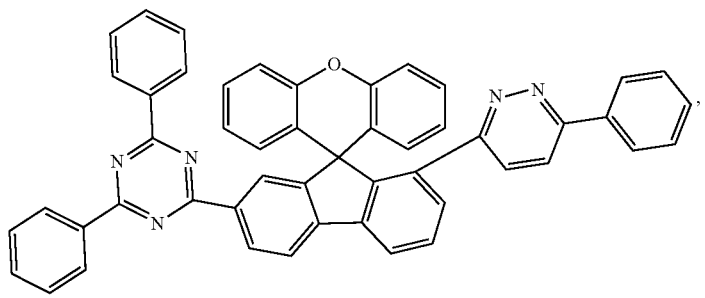
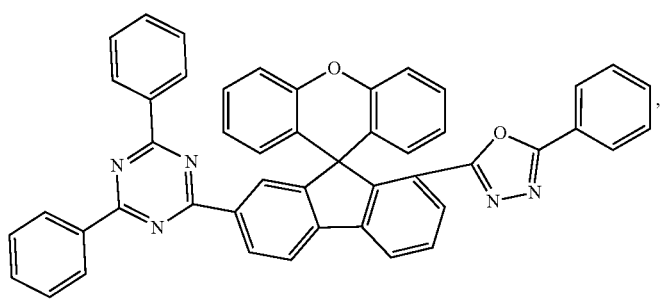
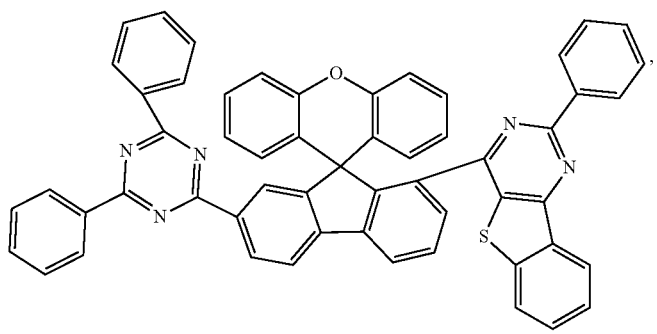

-continued
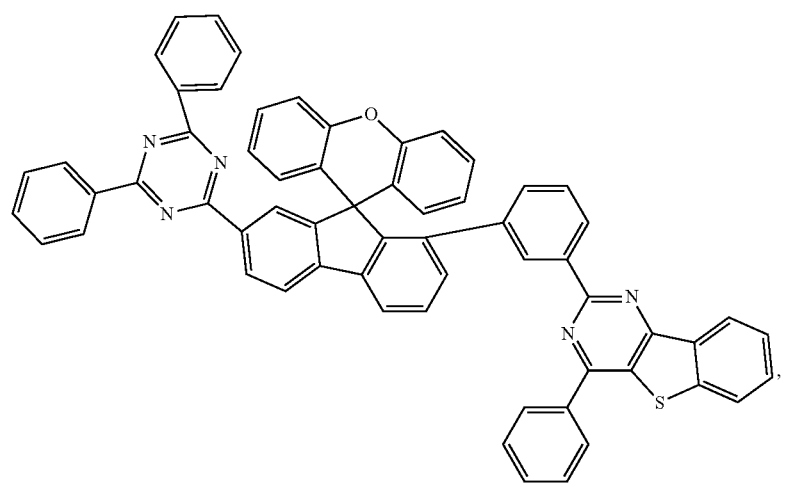
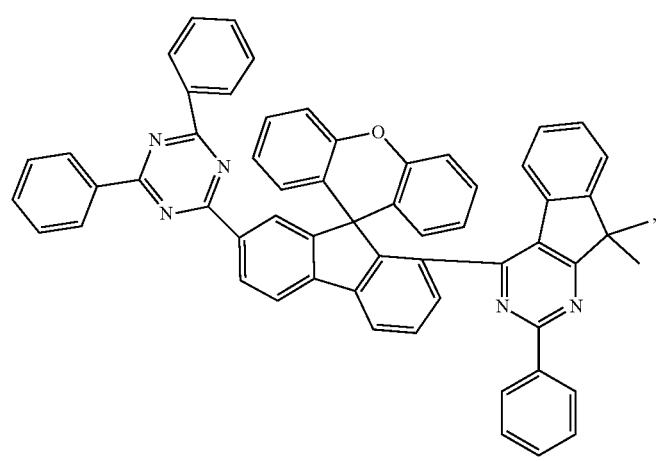
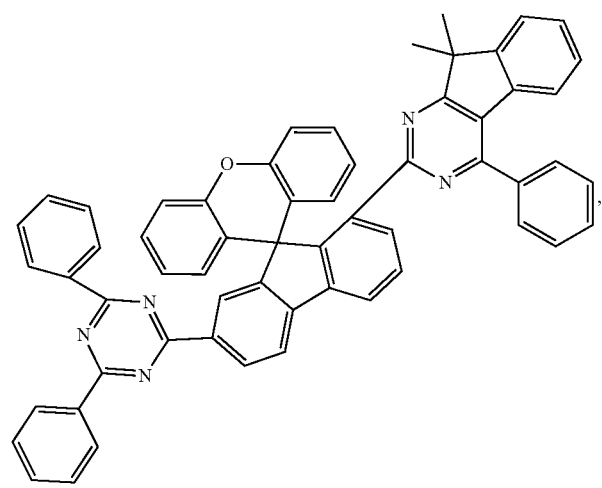

253                                     254
-continued
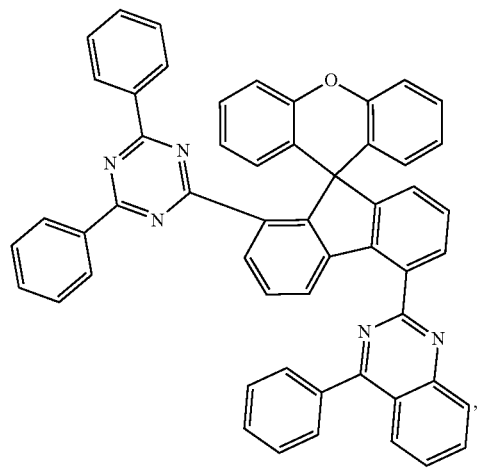
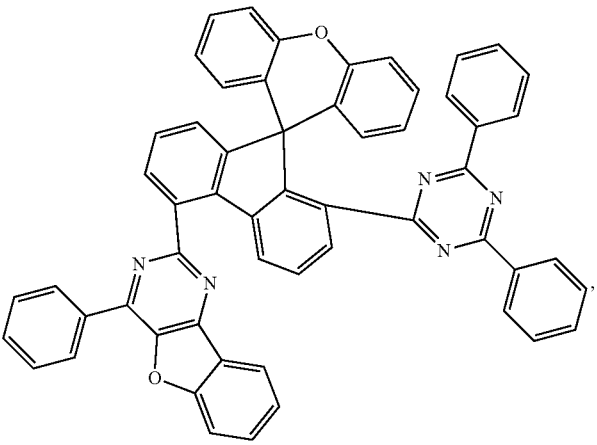
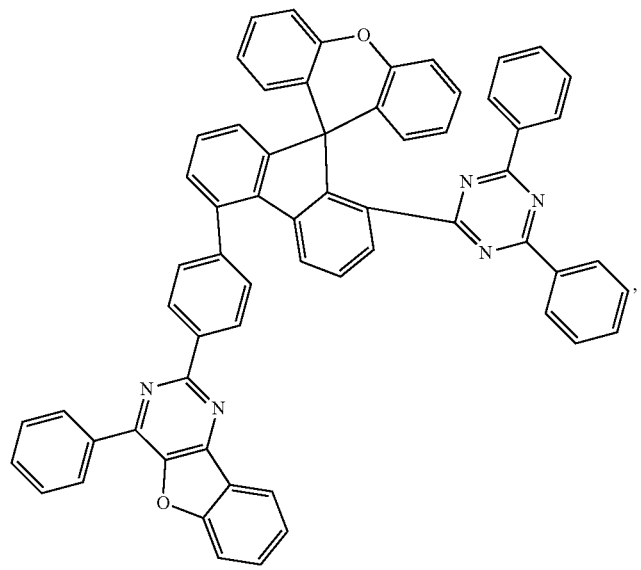
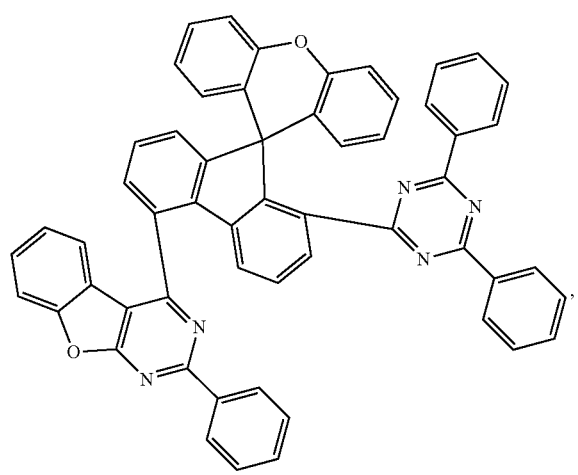
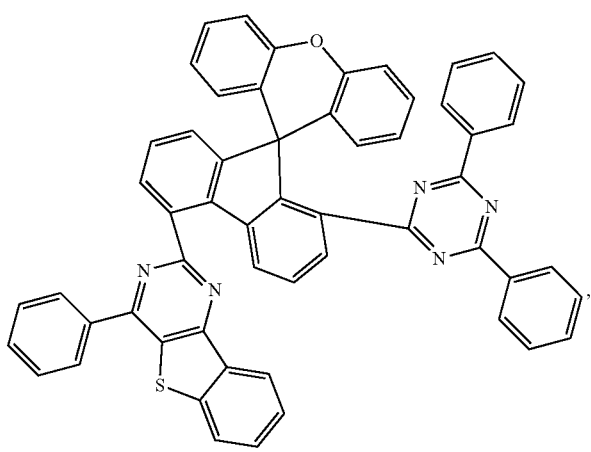

255 256
-continued
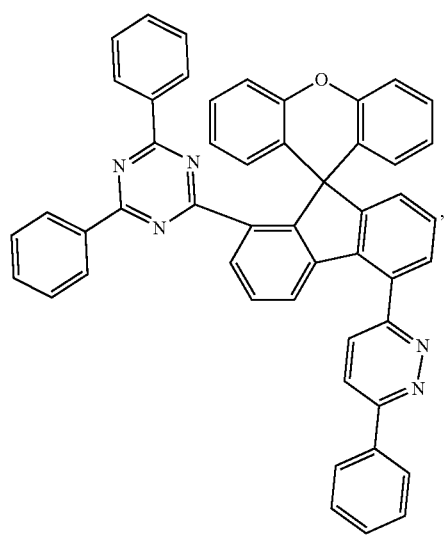
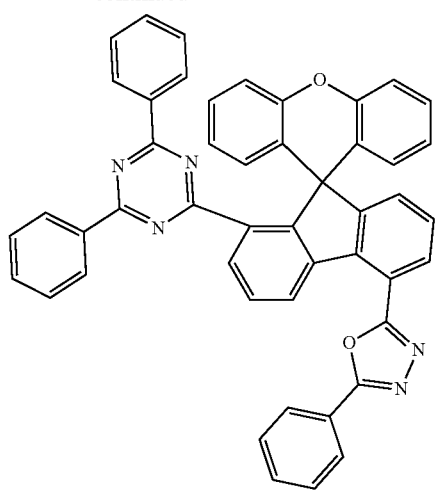
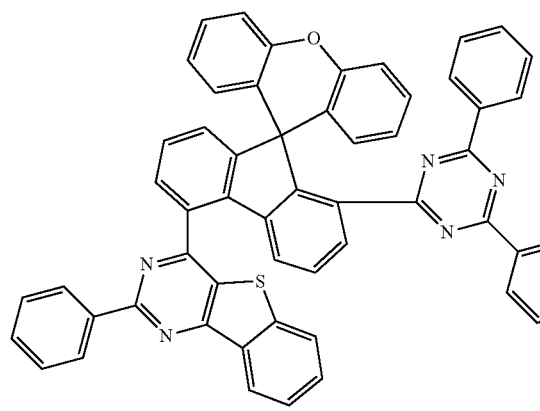
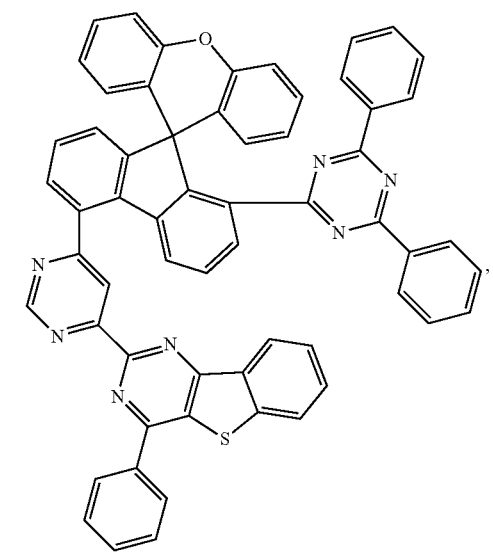
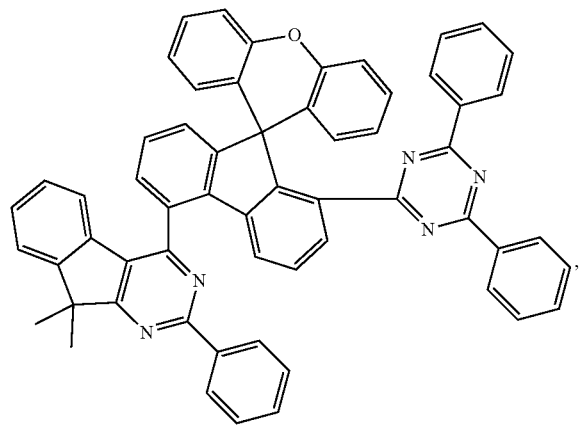
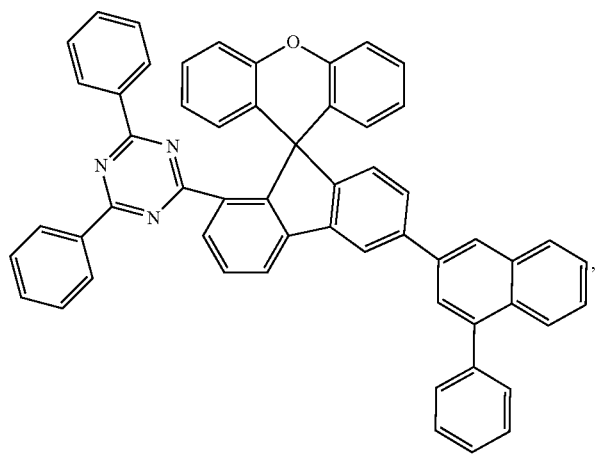

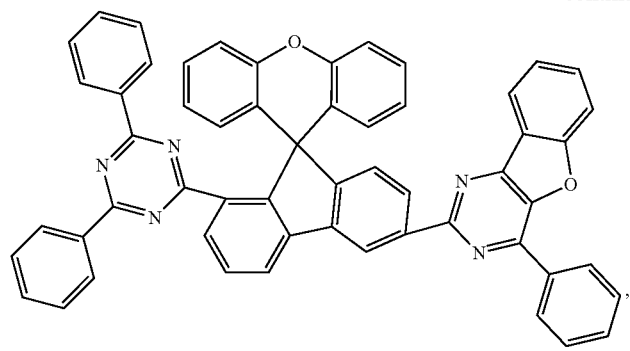
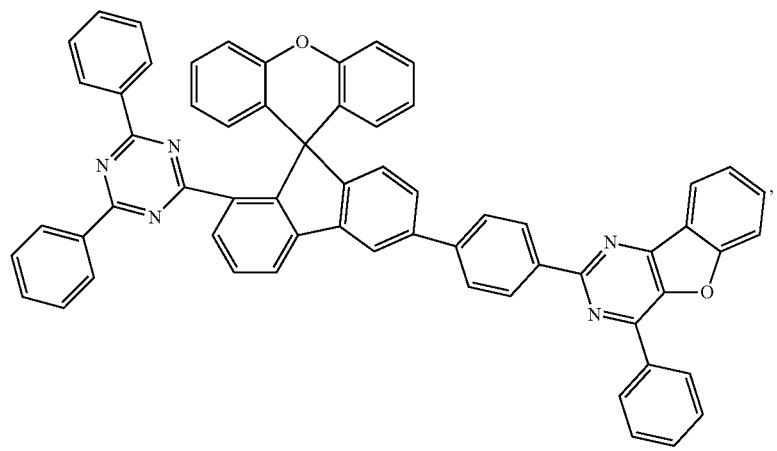
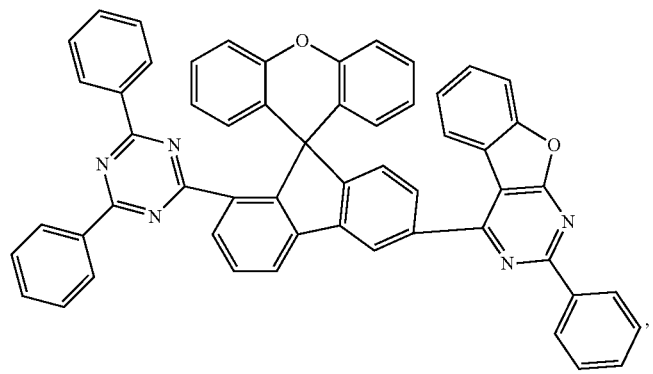
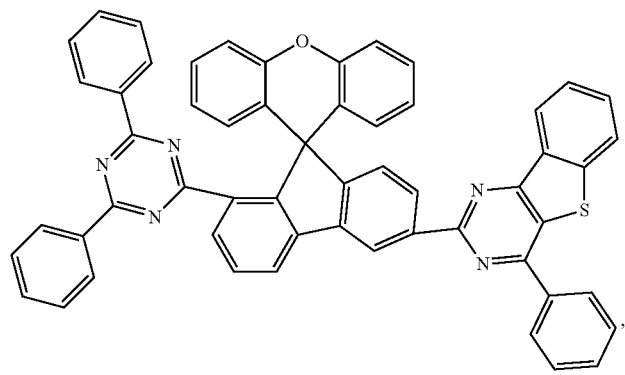

-continued
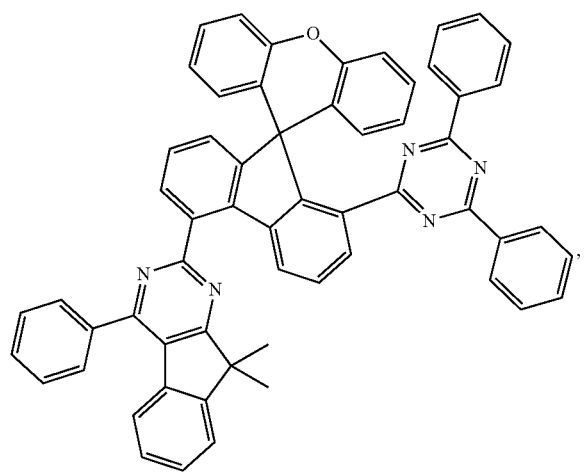
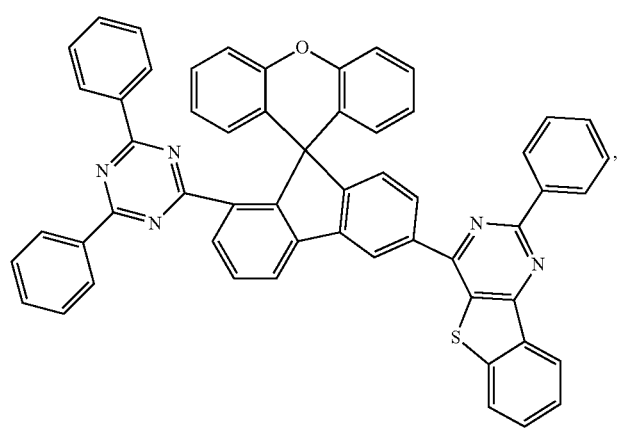
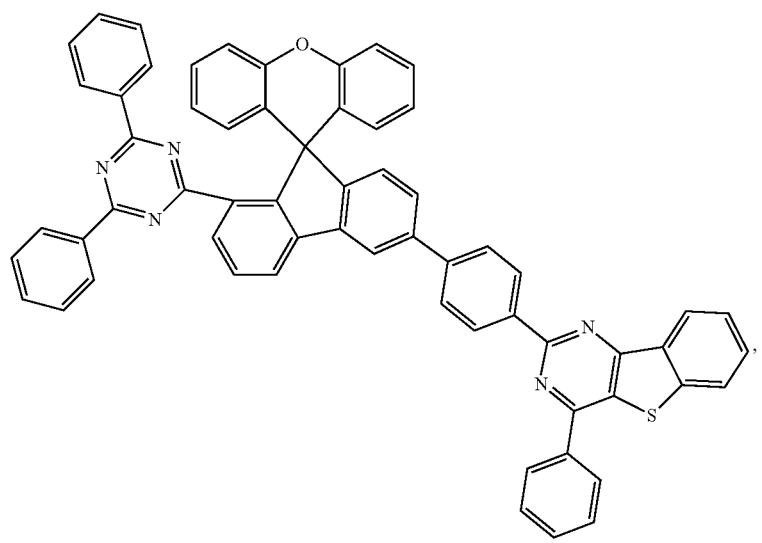

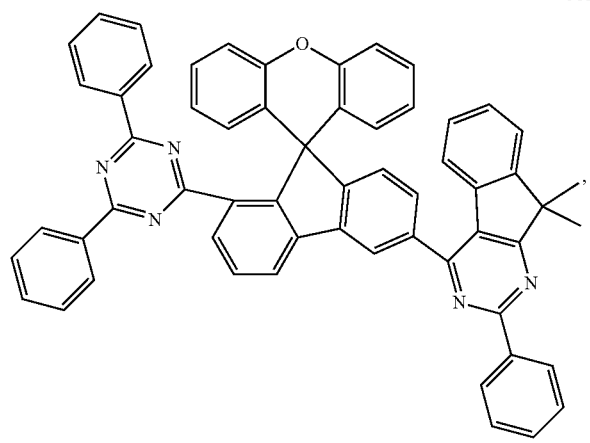
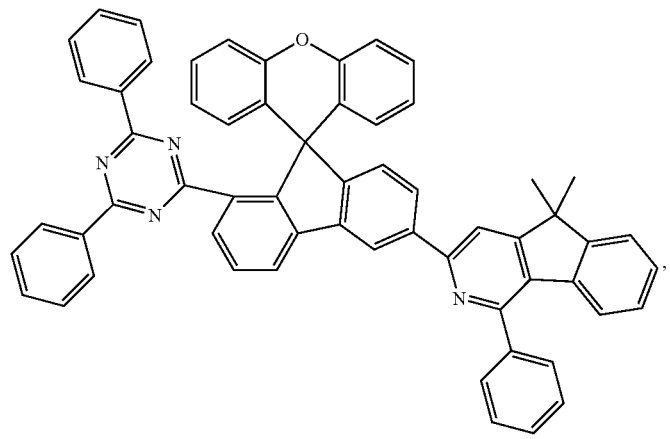
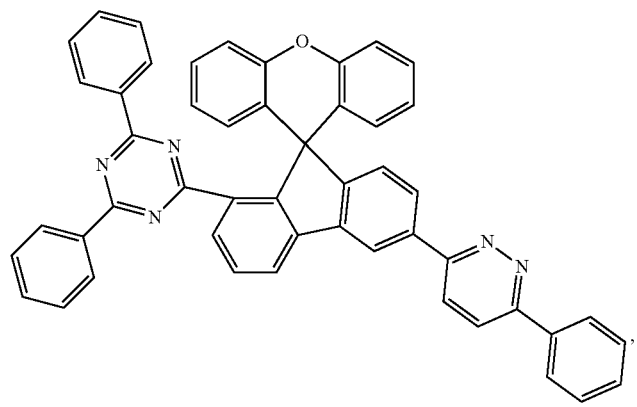
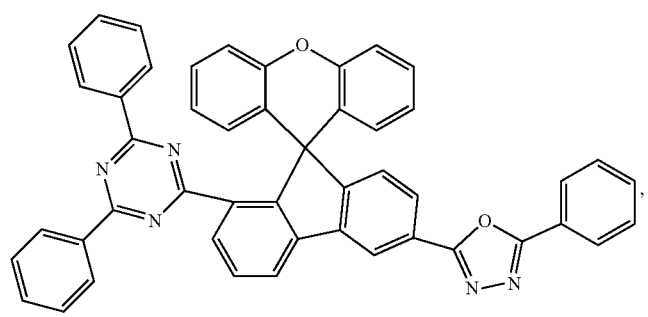

-continued
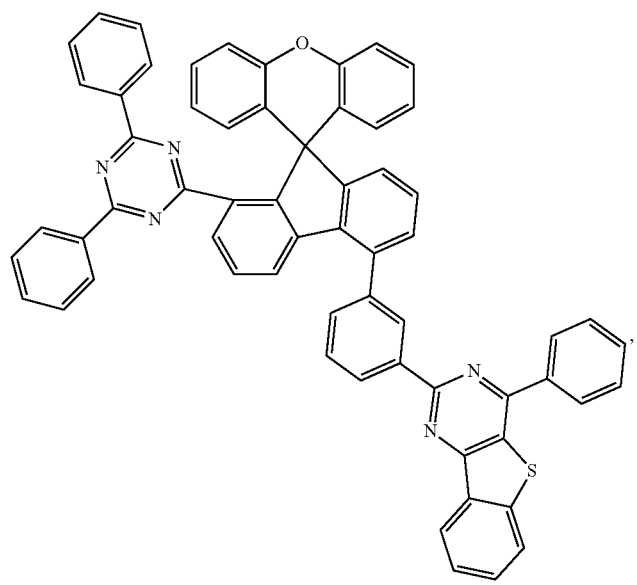
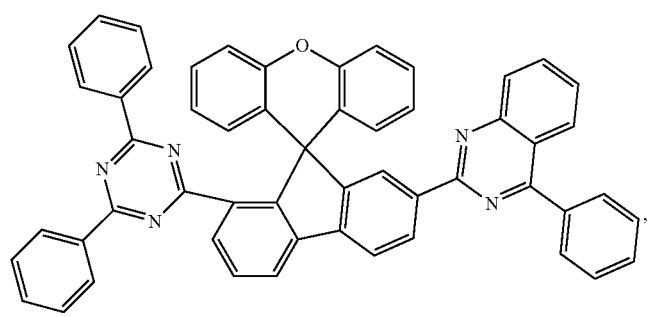
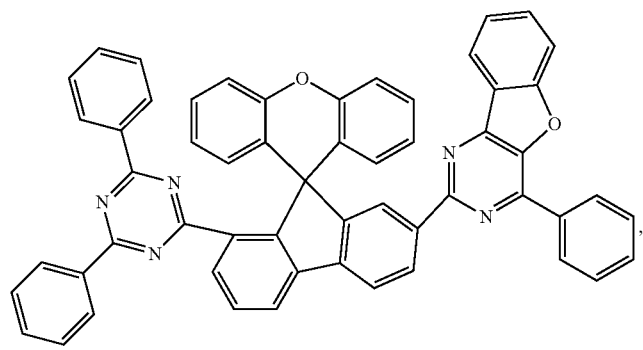
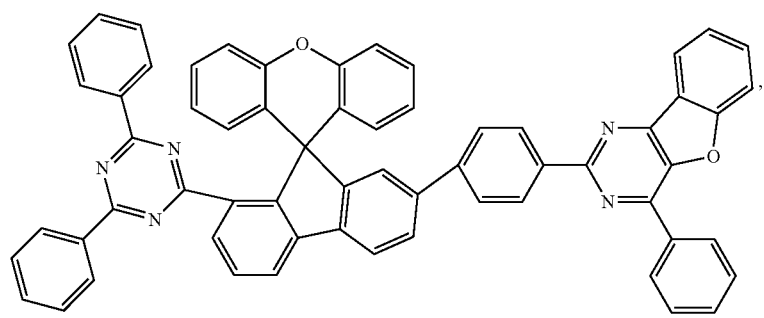

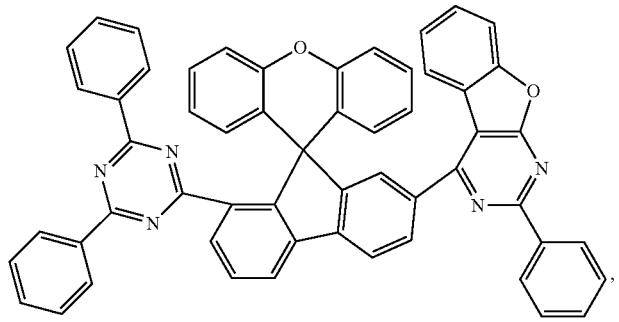
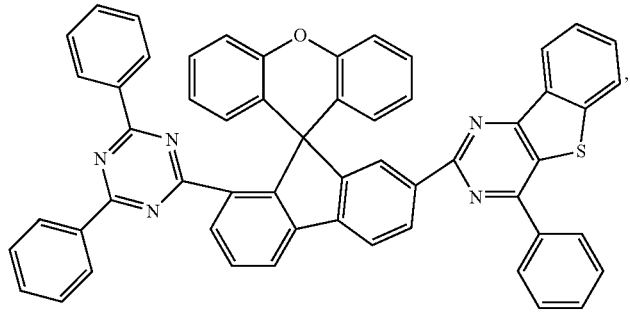
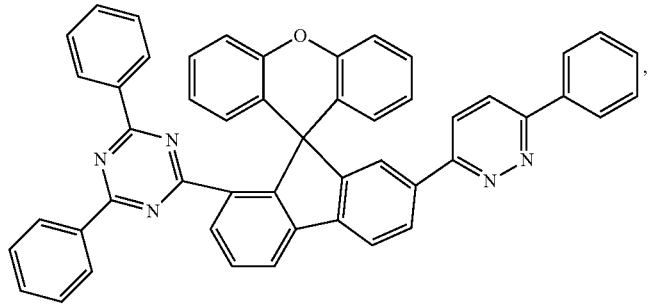
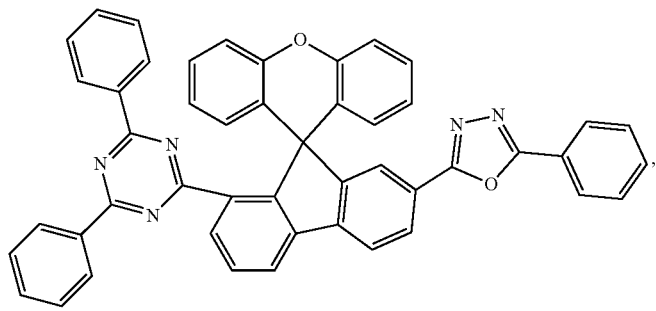
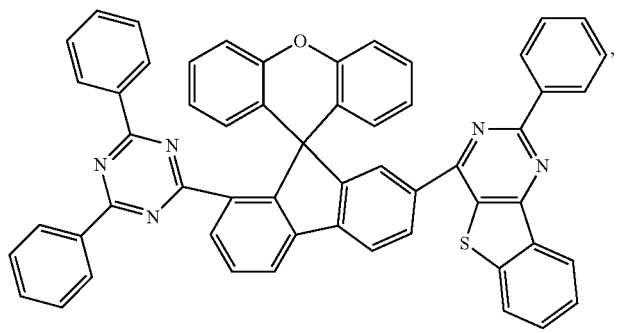

-continued
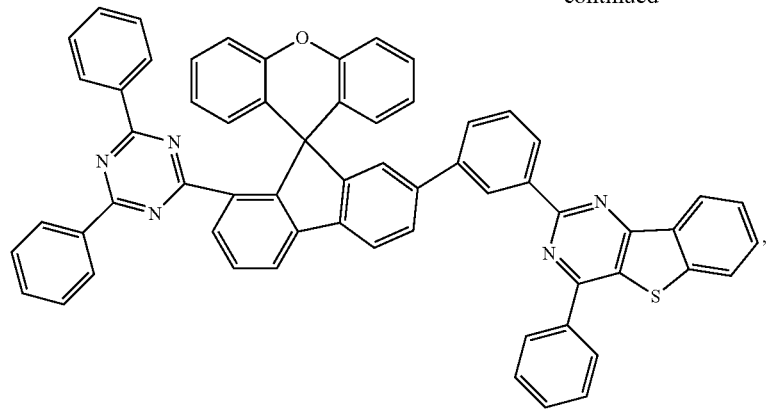
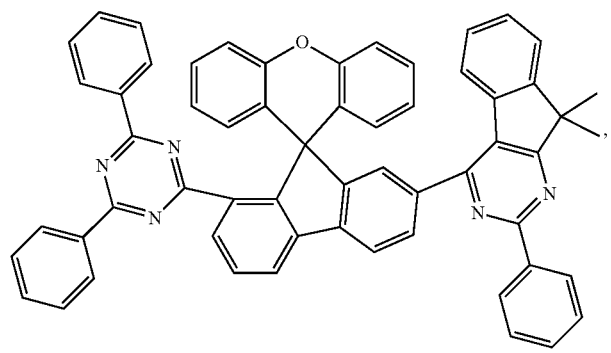
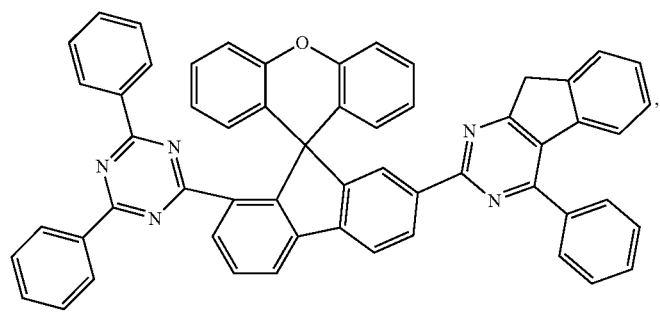
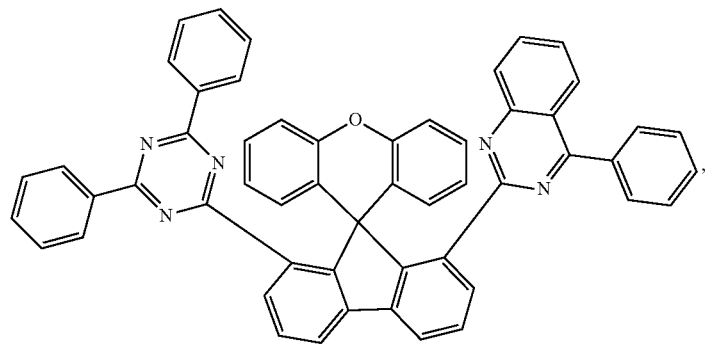

-continued
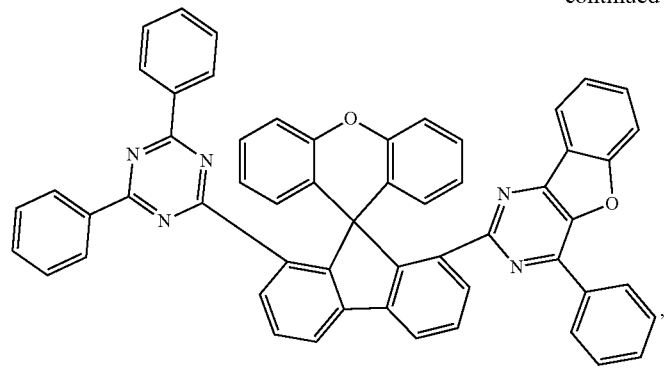
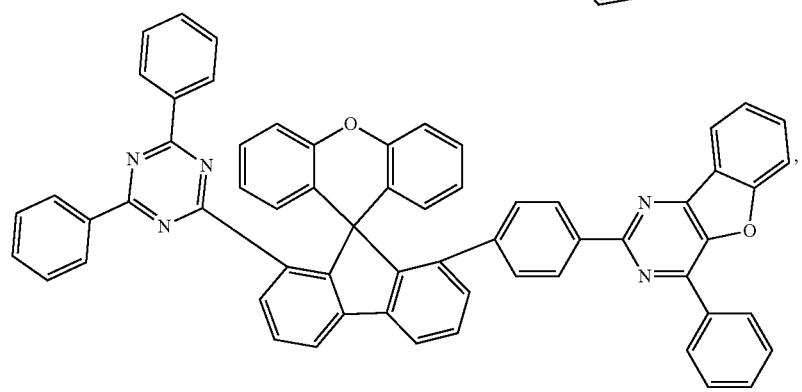
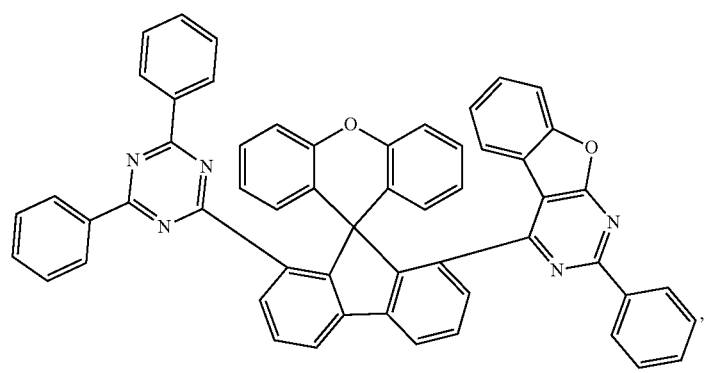
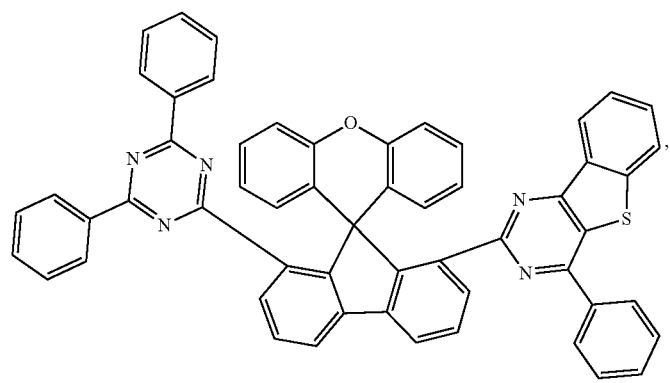

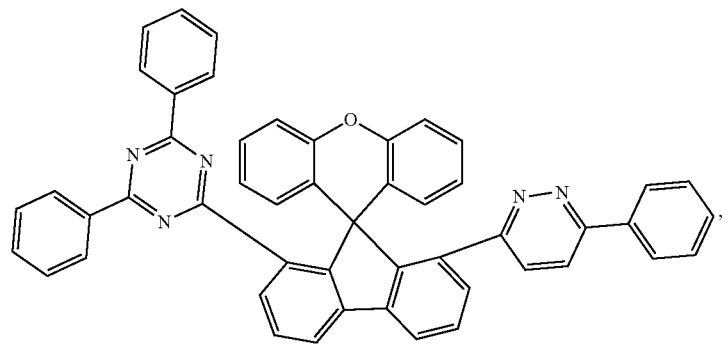
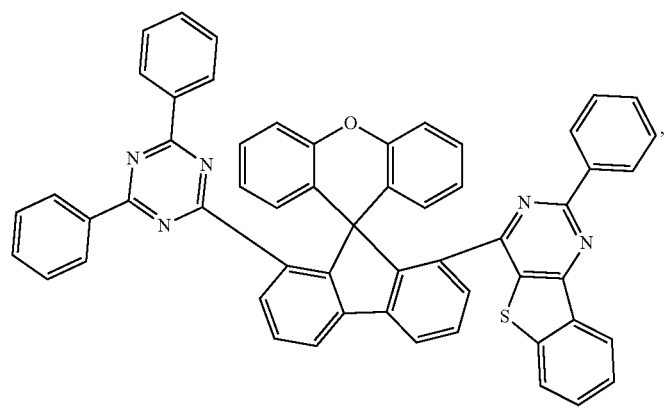
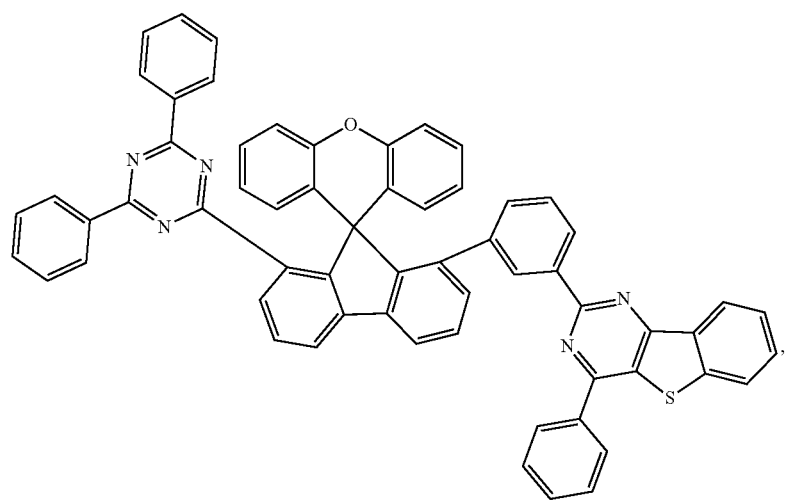
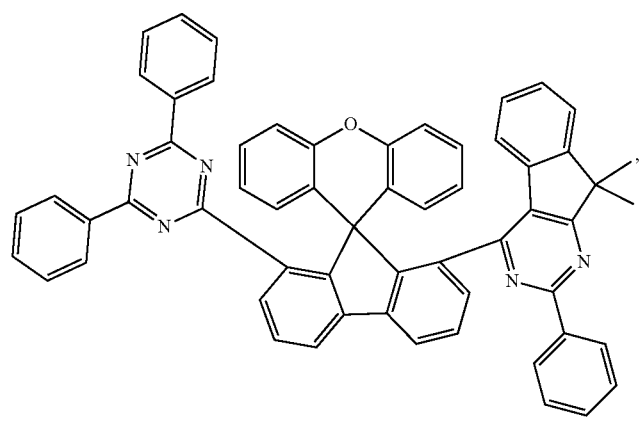

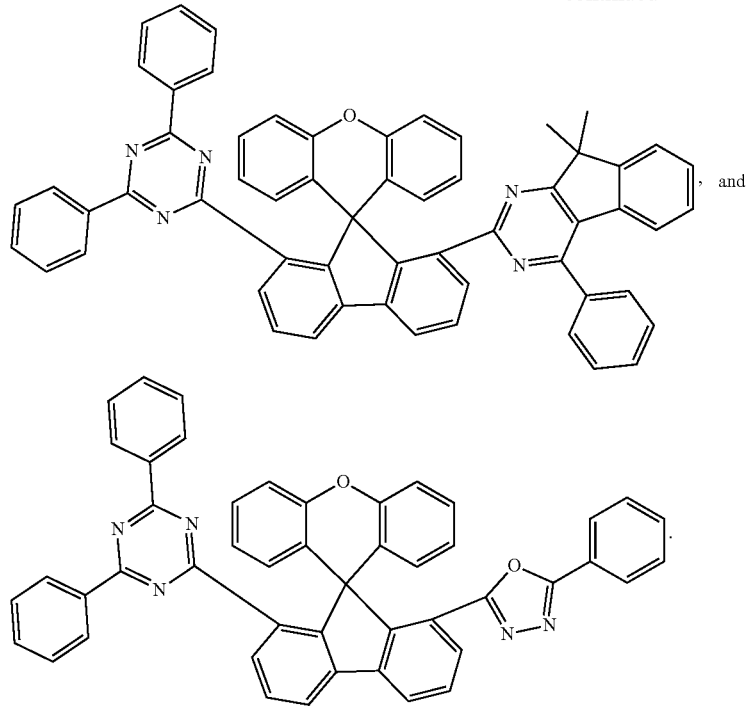

6. An organic light emitting device comprising:
a first electrode;
a second electrode facing the first electrode; and
at least one organic material layer interposed between the first electrode and the second electrode,
wherein the at least one organic material layer comprises the compound of claim 1.

7. The organic light emitting device of claim 6, wherein the organic material layer comprises a hole transport layer, wherein the hole transport layer comprises the compound.

8. The organic light emitting device of claim 6, wherein the organic material layer comprises a hole injection layer, wherein the hole injection layer comprises the compound.

9. The organic light emitting device of claim 6, wherein the organic material layer comprises an electron blocking layer, wherein the electron blocking layer comprises the compound.

10. The organic light emitting device of claim 6, wherein the organic material layer comprises a hole injection/transport layer, wherein the hole injection/transport layer comprises the compound.

11. The organic light emitting device of claim 6, wherein the organic material layer comprises a light emitting layer, wherein the light emitting layer comprises the compound as a host for the light emitting layer.

12. The organic light emitting device of claim 6, wherein the organic material layer comprises the compound as a host, and comprises another organic compound, a metal or a metal compound as a dopant.

* * * * *

UNITED STATES PATENT AND TRADEMARK OFFICE
CERTIFICATE OF CORRECTION

PATENT NO. : 11,641,778 B2  
APPLICATION NO. : 16/486773  
DATED : May 2, 2023  
INVENTOR(S) : Jungha Lee et al.

Page 1 of 3

It is certified that error appears in the above-identified patent and that said Letters Patent is hereby corrected as shown below:

In the Claims

In Claim 5, please replace the 2nd Chemical Structure appearing in Column 200 with:

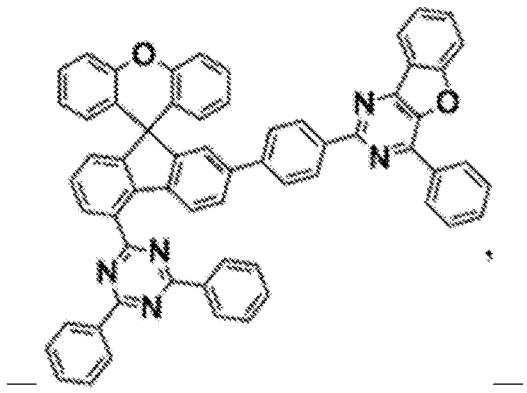

In Claim 5, please remove the 2nd Chemical Structure appearing in Column 208, which is a duplicate Chemical Structure:

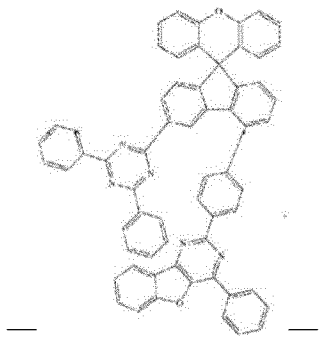

Signed and Sealed this  
Twentieth Day of June, 2023

Katherine Kelly Vidal  
*Director of the United States Patent and Trademark Office*

In Claim 5, please replace the 3rd Chemical Structure appearing in Column 209 with:
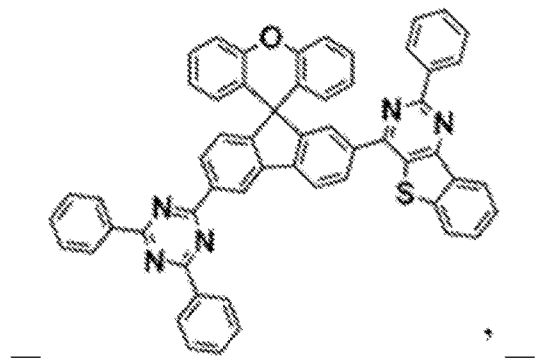
In Claim 5, please remove the 1st Chemical Structure appearing at Column 231, which is a duplicate Chemical Structure:
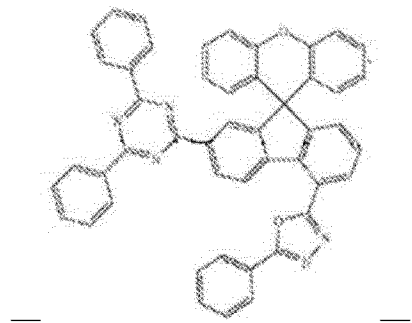
In Claim 5, before the 1st Chemical Structure in Column 243, please insert the following Chemical Structure:
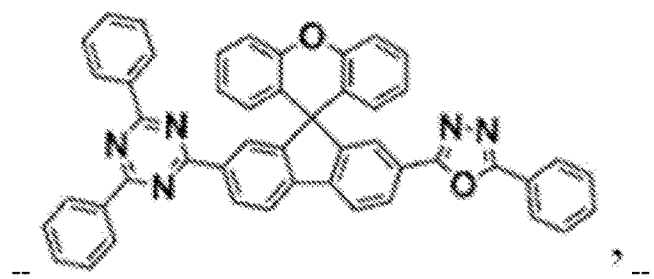

CERTIFICATE OF CORRECTION (continued)
U.S. Pat. No. 11,641,778 B2

In Claim 5, please replace the 3rd Chemical Structure appearing in Column 256 with:

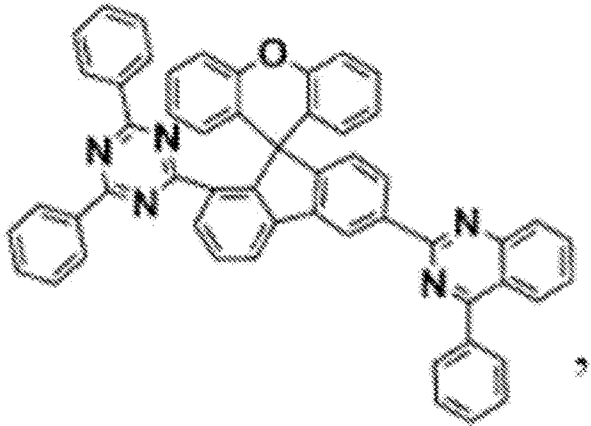

In Claim 5, please replace the 2nd Chemical Structure appearing in Column 261 with: